United States Patent
McVerry et al.

(10) Patent No.: US 11,807,701 B2
(45) Date of Patent: Nov. 7, 2023

(54) BIOFOULING RESISTANT COATINGS AND METHODS OF MAKING AND USING THE SAME

(71) Applicants: The Regents of the University of California, Oakland, CA (US); Hydrophilix, Inc., Los Angeles, CA (US)

(72) Inventors: Brian T. McVerry, Laguna Hills, CA (US); Ethan Rao, Venice, CA (US); Richard B. Kaner, Los Angeles, CA (US); Na He, Los Angeles, CA (US)

(73) Assignees: The Regents of the University of California, Oakland, CA (US); Silq Technologies Corporation, Los Angeles, CA (US)

( * ) Notice: Subject to any disclaimer, the term of this patent is extended or adjusted under 35 U.S.C. 154(b) by 432 days.

(21) Appl. No.: 16/892,980

(22) Filed: Jun. 4, 2020

(65) Prior Publication Data

US 2020/0385506 A1   Dec. 10, 2020

Related U.S. Application Data

(60) Provisional application No. 62/857,725, filed on Jun. 5, 2019.

(51) Int. Cl.

| C08F 220/34 | (2006.01) |
|---|---|
| C08F 220/30 | (2006.01) |
| C08F 293/00 | (2006.01) |
| C09D 153/00 | (2006.01) |
| A61L 29/08 | (2006.01) |

(Continued)

(52) U.S. Cl.
CPC .......... C08F 220/30 (2013.01); A61L 29/085 (2013.01); C08F 220/34 (2013.01); C08F 220/382 (2020.02); C08F 293/005 (2013.01); C09D 5/00 (2013.01); C09D 153/00 (2013.01);

(Continued)

(58) Field of Classification Search
CPC .. C08F 220/30; C08F 220/34; C08F 220/382; C08F 20/02; C08F 20/38
See application file for complete search history.

(56) References Cited

U.S. PATENT DOCUMENTS

| 3,796,314 A | 3/1974 | Kolek |
|---|---|---|
| 4,767,645 A | 8/1988 | Linder et al. |

(Continued)

FOREIGN PATENT DOCUMENTS

| CN | 1481928 A | 3/2004 |
|---|---|---|
| CN | 102067365 A | 5/2011 |

(Continued)

OTHER PUBLICATIONS

Extended European Search Report for EP Application No. 18876572.1 dated Jul. 9, 2021.

(Continued)

*Primary Examiner* — Amanda C. Walke
(74) *Attorney, Agent, or Firm* — Foley Hoag LLP; David P. Halstead

(57) ABSTRACT

Disclosed herein are compositions to use in biofouling-resistant coatings, biofouling-resistant coatings, methods of making biofouling-resistant coatings, biofouling-resistant devices, and methods of making biofouling-resistant devices.

14 Claims, 5 Drawing Sheets

(51) Int. Cl.
*C09D 5/00* (2006.01)
*C08F 220/38* (2006.01)

(52) U.S. Cl.
CPC ....... *A61L 2420/02* (2013.01); *C08F 2438/01* (2013.01)

(56) References Cited

U.S. PATENT DOCUMENTS

| | | | |
|---|---|---|---|
| 4,833,014 | A | 5/1989 | Linder et al. |
| 5,753,008 | A | 5/1998 | Friesen et al. |
| 7,670,720 | B1 | 3/2010 | Buerger et al. |
| 8,029,857 | B2 | 10/2011 | Hoek et al. |
| 8,132,677 | B2 | 3/2012 | Liu et al. |
| 8,530,269 | B2 | 9/2013 | Chua et al. |
| 8,550,256 | B1 * | 10/2013 | Diep ............... B01D 71/42 264/48 |
| 8,679,859 | B2 * | 3/2014 | Yan ................. C01B 32/19 977/734 |
| 9,662,617 | B2 | 5/2017 | Hoek et al. |
| 10,315,169 | B2 | 6/2019 | Hoek et al. |
| 10,629,880 | B2 | 4/2020 | McVerry et al. |
| 10,729,822 | B2 | 8/2020 | Kaner et al. |
| 11,084,002 | B2 | 8/2021 | Hoek et al. |
| 11,258,134 | B2 | 2/2022 | McVerry et al. |
| 11,541,153 | B2 | 1/2023 | Kaner et al. |
| 2002/0122872 | A1 | 9/2002 | Leukel et al. |
| 2005/0276419 | A1 | 12/2005 | Eggert et al. |
| 2006/0141273 | A1 | 6/2006 | Kino et al. |
| 2007/0254006 | A1 | 11/2007 | Loose et al. |
| 2008/0017512 | A1 | 1/2008 | Bordunov et al. |
| 2009/0155335 | A1 | 6/2009 | O'Shaughnessey et al. |
| 2009/0308804 | A1 | 12/2009 | Cohen et al. |
| 2010/0075101 | A1 | 3/2010 | Tang |
| 2011/0005997 | A1 | 1/2011 | Kurth et al. |
| 2011/0104573 | A1 | 5/2011 | Gogichev et al. |
| 2012/0201972 | A1 | 8/2012 | Hayashi et al. |
| 2012/0258313 | A1 | 10/2012 | Wen et al. |
| 2014/0206251 | A1 | 7/2014 | Stokes |
| 2014/0251897 | A1 | 9/2014 | Livingston et al. |
| 2015/0025168 | A1 | 1/2015 | Lienkamp et al. |
| 2016/0001236 | A1 | 1/2016 | Hoek et al. |
| 2016/0152008 | A1 | 6/2016 | Ogata et al. |
| 2017/0296986 | A1 | 10/2017 | Hoek et al. |
| 2017/0355799 | A1 | 12/2017 | Veiseh et al. |
| 2018/0021740 | A1 | 1/2018 | Hironaka et al. |
| 2018/0159106 | A1 | 6/2018 | McVerry et al. |
| 2019/0185776 | A1 | 6/2019 | Kuramoto et al. |
| 2020/0203692 | A1 | 6/2020 | McVerry et al. |
| 2020/0338240 | A1 | 10/2020 | Kaner et al. |
| 2020/0385506 | A1 | 12/2020 | McVerry et al. |
| 2021/0095122 | A1 | 4/2021 | Freeman et al. |
| 2021/0245111 | A1 | 8/2021 | Lee et al. |

FOREIGN PATENT DOCUMENTS

| | | |
|---|---|---|
| CN | 102099099 A | 6/2011 |
| CN | 103068476 A | 4/2013 |
| CN | 103582520 A | 2/2014 |
| CN | 104350081 A | 2/2015 |
| CN | 105854628 A | 8/2016 |
| CN | 105932317 A | 9/2016 |
| FR | 2989215 A1 | 10/2013 |
| JP | 56067848 A | 7/1981 |
| JP | 2007/527542 A | 9/2007 |
| JP | 2009/147369 A | 7/2009 |
| JP | 2010059346 A | 3/2010 |
| JP | 48-41863 B2 | 12/2011 |
| JP | 2012/055858 A | 3/2012 |
| JP | 2017/177754 A | 10/2017 |
| JP | 2017/185475 A | 10/2017 |
| JP | 2017177754 A | 10/2017 |
| KR | 2011/0031743 A | 3/2011 |
| TW | 201311750 A | 3/2013 |
| TW | 2017/20848 A | 6/2017 |
| WO | WO-9639821 A1 * | 12/1996 ............ A01N 25/10 |
| WO | WO-00/076641 A1 | 12/2000 |
| WO | WO-2004/100282 A2 | 11/2004 |
| WO | WO-2009/039467 A1 | 3/2009 |
| WO | WO-2009/099126 A1 | 8/2009 |
| WO | WO-2010/006196 A2 | 1/2010 |
| WO | WO-2010/036452 A2 | 4/2010 |
| WO | WO-2011/060202 A1 | 5/2011 |
| WO | WO-2012/010886 A1 | 1/2012 |
| WO | WO-2012/071461 A2 | 5/2012 |
| WO | WO-2013/109810 A1 | 7/2013 |
| WO | WO-2013109250 A1 * | 7/2013 ........... C09D 11/033 |
| WO | WO-2013112152 A1 * | 8/2013 ........... C09D 11/033 |
| WO | WO-2014/001795 A1 | 1/2014 |
| WO | WO-2014/032005 A1 | 2/2014 |
| WO | WO-2014/113618 A1 | 7/2014 |
| WO | WO-2016/083314 A1 | 6/2016 |
| WO | WO-2017170210 A1 | 10/2017 |
| WO | WO-2018/102517 A1 | 6/2018 |
| WO | WO-2018/213627 A1 | 11/2018 |
| WO | WO-2019/079765 A1 | 4/2019 |
| WO | WO-2019/094685 A1 | 5/2019 |
| WO | WO-2019/108871 A1 | 6/2019 |
| WO | WO-2020/247629 A1 | 12/2020 |

OTHER PUBLICATIONS

Extended European Search Report for EP Application No. 18882865.1 dated Jul. 23, 2021.
Anderson et al., "Conjugated Polymer Films for Gas Separations," Sci 252(5011):1412-1415 (1991).
Batool et al., "Fabrication of covalently bonded nanostructured thin films of epoxy resin and polydimethylsiloxane for oil adsorption," Polymer Bulletin, 74(12):4827-4840 (2017).
EIC search report for U.S. Appl. No. 16/404,372 (2020).
Extended European Search Report issued by the European Patent Office in corresponding Application No. EP 14753770, dated Oct. 24, 2016.
Extender European Search Report for EP Application No. 17876218.3 dated Mar. 24, 2020.
Freger et al., "TFC polyamide membranes modified by grafting of hydrophilic polymers: an FT-IR/AFM/TEM study," J Mem Sci, 209:283-292 (2002).
Gerard et al., "Surface modification of poly(butylene terephthalate) nonwoven by photochemistry and biofunctionalization with peptides for blood filtration," Polymer Chemistry, 49(23): 5087-5099 (2011).
International Search Report and Written Opinion for International Application No. PCT/US14/17758 dated May 30, 2014.
International Search Report and Written Opinion for International Application No. PCT/US17/63887 dated Jan. 26, 2018.
International Search Report and Written Opinion for International Application No. PCT/US2018/059967 dated Feb. 17, 2019.
International Search Report and Written Opinion for International Application No. PCT/US2018/063196 dated Mar. 10, 2019.
International Search Report and Written Opinion for International Application No. PCT/US2020/036121 dated Aug. 19, 2020.
Khong et al., "General Photo-Patterning of Polyelectrolyte Thin Films via Efficient Ionic Bis(Fluorinated Phenyl Azide) Photo-Crosslinkers and their Post-Deposition Modification," Advanced Functional Materials, 17(14): 2490-2499 (2007).
Khulbe et al., "The art of surface modification of synthetic polymeric membranes," J Appl Ploymer Sci, 115(2): 855-895 (2010).
Kuo et al., "Surface modification with poly(sulfobetaine methacrylate-co-acrylic acid) to reduce fibrinogen adsorption, platelet adhesion, and plasma coagulation," Biomacromolecules, 12(12):4348-4356 (2011).
Li et al., "Influence of polybenzimidazole main chain structure on H2/CO2 separation at elevated temperatures," Journal of Membrane Science, 461:59-68 (2014).
Liu et al., "Perfluorophenyl Azides: New Applications in Surface Functionalization and Nanomaterial Synthesis," Acc Chem Res, 43(11):1434-1443 (2010).

(56) References Cited

OTHER PUBLICATIONS

Liu et al., "Photoinitiated coupling of unmodified monosaccharides to iron oxide nanoparticles for sensing proteins and bacteria," Bioconjugate Chem, 20(7): 1349-1355 (2009).

Mandwar et al., "Perfluorophenyl azide immobilization chemistry for single molecule force spectroscopy of the concanavalin A/mannose interaction," Langmuir, 26(22): 16677-16680 (2010).

Mizutani et al., "Liquid, phenylazide-end-capped copolymers of epsilon-caprolactone and trimethylene carbonate: preparation, photocuring characteristics, and surface layering," Biomacromolecules, 3(4):668-675 (2002).

Mosnacek et al., "Photochemical grafting of polysulfobetaine onto polyethylene and polystyrene surfaces and investigation of long-term stability of the polysulfobetaine layer in seawater," Polymers for Advanced Technologies, 29(7):1930-1938 (2018).

Puleo et al., "Gas sorption and transport in substituted polystyrenes," Journal of Polymer Science Part B: Polymer Physics, 27(11):2385-2406 (1989).

Qureshi et al., "Nanoprotective layer-by-layer coatings with epoxy components for enhancing abrasion resistance: toward robust multimaterial nanoscale films," Acs Nano, 7(10):9336-9344 (2013).

Sakuragi et al., "A photoimmobilizable sulfobetaine-based polymer for a nonbiofouling surface," Materials Science and Engineering:C, 30(2):316-322 (2010).

Seo et al., "Simultaneous patterning of proteins and cells through bioconjugation with photoreactable phospholipid polymers," RSC Advances, 7(64):40669-40672 (2017).

Sivakumar et al., "Novel Microarrays for Simultaneous of Multiple Antiviral Antibodies," Plos One, 8(12):e81726/1-e81726/9 (2013).

Sundhoro et al., "Fabrication of carbohydrate microarrays on a poly (2-hydroxyethyl methacrylate)-based photoactive substrate," Organic & Biomolecular Chemistry, 14(3):1124-1130 (2015).

Sundhoro et al., "Poly(HEMA-co-HEMA-PFA): Synthesis and preparation of stable micelles encapsulating imaging nanoparticles," Journal of Colloid and Interface Science, 500:1-8 (2017).

Tanaka et al., "Synthesis and structures of zwitterionic polymers to induce electrostatic interaction with PDMS surface treated by air-plasma," Organic Chemistry, part ii:330-343 (2018).

Yuwen, "Polymer-based photoactive surface for the efficient immobilization of nanoparticles, polymers, graphene and; carbohydrates," PDXScholar, Dissertation, Portland State University (2011).

Seo "Simultaneous patterning of proteins and cells through bioconjugation with photoreactable phospholipid polymers," RSC Adv, 7: 40669-40672 (2017).

Extended European Search Report for European Patent Application No. 20819527.1 dated May 12, 2023.

* cited by examiner

PDMS    PSB

BIOFOULING RESISTANT COATINGS AND METHODS OF MAKING AND USING THE SAME

CROSS-REFERENCE

This application claims benefit of U.S. Provisional Patent Application No. 62/857,725, filed on Jun. 5, 2019, the contents of which are fully incorporated by reference herein.

BACKGROUND

Hospital acquired infections (HAIs) cause over 100,000 deaths per year and over $30 billion in direct healthcare cost. In some cases, medical devices implanted into the body are the source of the HAI. Planktonic bacteria adhere to the surface of the medical devices and begin to grow into resilient biofilms that become more resistant to antibiotics and disinfecting agents than in the planktonic state.

SUMMARY

Described herein, in certain embodiments, are compositions to use in biofouling-resistant coatings, biofouling-resistant coatings, methods of making biofouling-resistant coatings, biofouling-resistant devices, and methods of making biofouling-resistant devices.

In one aspect, described herein is a compound of Formula (I):

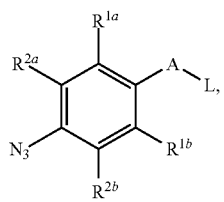

Formula (I)

wherein

A is selected from $-C(=O)-$, $-S(=O)-$, $-S(=O)_2-$, and $-S(=O)(-NR^3)-$;

L is selected from $-OQ$, $-NR^3Q$, and $-N(R^3)_2Q^+$;

Q is a structure represented by a formula:

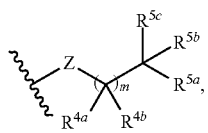

Z is selected from $-CR^{6a}R^{6b}-$, $-C(=O)-$, $-C(=NH)-$, and $-C(=NH)NR^7-$;

m is an integer selected from 0, 1, 2, 3, 4, 5, 6, 7, and 8;

each $R^{1a}$ and $R^{1b}$ is independently selected from hydrogen and halogen;

each $R^{2a}$ and $R^{2b}$ is independently selected from halogen, $-CN$, and optionally substituted $C_1$-$C_6$ fluoroalkyl;

each $R^3$ is independently selected from hydrogen, optionally substituted $C_1$-$C_4$ alkyl, $-X$-optionally substituted $C_1$-$C_4$ alkyl, optionally substituted aryl, and $-X$-optionally substituted aryl;

X is $-C(=O)-$, $-S(=O)-$, or $-S(=O)_2-$;

each $R^{4a}$, $R^{4b}$, $R^{5a}$, $R^{5c}$, $R^{6a}$, and $R^{6b}$ is independently selected from hydrogen, halogen, $-CN$, $-OH$, optionally substituted $C_1$-$C_4$ alkyl, optionally substituted $C_1$-$C_4$ fluoroalkyl, optionally substituted aryl, $-NR^{8a}R^{8b}$, $-NR^{8a}R^{8b}R^{8c}$, $-S(=O)_2O^-$, $-S(=O)_2OR^9$, $-C(=O)O^-$, and $-C(=O)OR^9$;

$R^{5b}$ is $-OR^{10b}$, $-NR^{10a}R^{10b}$, or $-NR^{10a}R^{10b}R^{10c+}$;

each $R^7$, $R^{8a}$, $R^{8b}$, $R^{8c}$, and $R^9$ is independently selected from hydrogen and optionally substituted $C_1$-$C_4$ alkyl, and optionally substituted aryl;

each $R^{10a}$ and $R^{10c}$ is independently selected from hydrogen, optionally substituted $C_1$-$C_4$ alkyl, optionally substituted aryl, -(optionally substituted $C_1$-$C_8$alkylene)S(=O)$_2$O$^-$, -(optionally substituted $C_1$-$C_8$alkylene)S(=O)$_2$OH, -(optionally substituted $C_1$-$C_8$alkylene)C(=O)O$^-$, and -(optionally substituted $C_1$-$C_8$alkylene)C(=O)OH; and $R^{10b}$ is $-C(=O)-C_2$-$C_6$alkenyl, $-S(=O)-C_2$-$C_6$alkenyl, or $-S(=O)_2-C_2$-$C_6$alkenyl;

provided that a compound of Formula (I) is not N-(2-((4-azido-2,3,5,6-tetrafluorophenyl)sulfonamido)ethyl)methacrylamide; N-(2-acrylamidoethyl)-4-azido-2,3,5,6-tetrafluorobenzamide; or 2-(methacryloyloxy)ethyl 4-azido-2,3,5,6-tetrafluorobenzoate.

In another aspect, described herein is a compound of Formula (II):

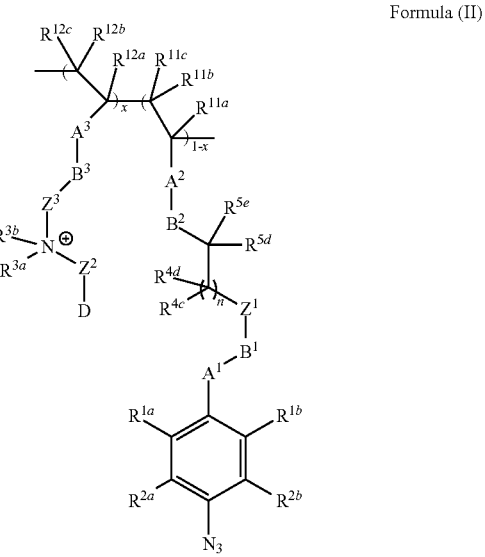

Formula (II)

wherein each $R^{1a}$ and $R^{1b}$ is independently selected from hydrogen and halogen;

each $R^{2a}$ and $R^{2b}$ is independently selected from halogen, $-CN$, and optionally substituted $C_1$-$C_6$ fluoroalkyl;

each $A^1$, $A^2$, and $A^3$ is independently selected from $-C(=O)-$, $-S(=O)-$, $-S(=O)_2-$, and $-S(=O)(=NR^{3c})-$;

each $B^1$, $B^2$, and $B^3$ is independently selected from $-O-$ and $-NR^{3c}-$;

D is $-S(=O)_2O^-$, $-S(=O)_2OR^{9a}$, $-C(=O)O^-$, or $-C(=O)OR^{9a}$;

$Z^1$ is $-(CR^{6c}R^{6d})_s-$;

$Z^2$ is $-(CR^{6c}R^{6d})_t-$;

$Z^3$ is $—(CR^{6c}R^{6d})_p$—;

each $R^{3a}$ and $R^{3b}$ is independently selected from hydrogen, optionally substituted $C_1$-$C_4$ alkyl, and optionally substituted benzyl;

each $R^{4c}$, $R^{4d}$, $R^{5d}$, $R^{5e}$, $R^{6c}$, and $R^{6d}$ is independently selected from hydrogen, halogen, —CN, —OH, optionally substituted $C_1$-$C_4$ alkyl, optionally substituted $C_1$-$C_4$ fluoroalkyl, optionally substituted $C_2$-$C_6$ alkenyl, —$NR^{3c}R^{3d}$, —$S(=O)_2O^-$, —$S(=O)_2OR^{9a}$, —$C(=O)O^-$, and —$C(=O)OR^{9a}$;

each $R^{3c}$ and $R^{3d}$ is independently selected from hydrogen, optionally substituted $C_1$-$C_4$ alkyl, —X-optionally substituted $C_1$-$C_4$ alkyl, optionally substituted $C_2$-$C_6$ alkenyl, and optionally substituted aryl;

X is —$C(=O)$—, —$S(=O)$—, or —$S(=O)_2$—;

each $R^{9a}$, $R^{11a}$, $R^{11b}$, $R^{11c}$, $R^{12a}$, $R^{12b}$, and $R^{12c}$ is independently selected from hydrogen, optionally substituted $C_1$-$C_4$ alkyl, and optionally substituted aryl;

n is an integer selected from 0, 1, 2, 3, 4, 5, 6, 7, and 8;
s is an integer selected from 1, 2, 3, 4, or 5;
t is an integer selected from 1, 2, 3, 4, or 5;
p is an integer selected from 1, 2, 3, 4, or 5;
x is 0.001-0.999; and wherein the compound of Formula (II) is charged or zwitterionic;

provided that a compound of Formula (II) is not

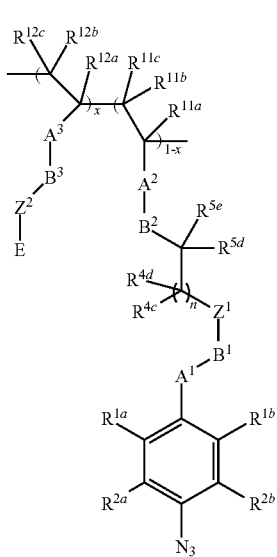

In another aspect, described herein is a compound of Formula (III):

Formula (III)

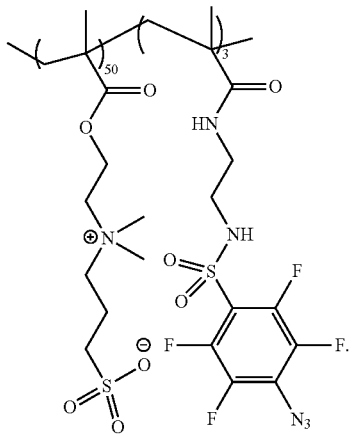

wherein each $R^{1a}$ and $R^{1b}$ is independently selected from hydrogen and halogen;

each $R^{2a}$ and $R^{2b}$ is independently selected from halogen, —CN, and optionally substituted $C_1$-$C_6$ fluoroalkyl;

each $A^1$, $A^2$, and $A^3$ is independently selected from —$C(=O)$—, —$S(=O)$—, —$S(=O)_2$—, and —$S(=O)(=NR^{3c})$—;

each $B^1$, $B^2$, and $B^3$ is independently selected from —O— and —$NR^{3c}$—;

$Z^1$ is —$(CR^{6c}R^{6d})_s$—;
$Z^2$ is —$(CR^{6c}R^{6d})_t$—;

E is —CN, —$OR^{9a}$, —$NR^{9a}R^{9b}$, —$NR^{9a}R^{9b}R^{9c+}$, optionally substituted $C_1$-$C_4$ alkyl, optionally substituted $C_1$-$C_6$ fluoroalkyl, —$S(=O)_2O^-$, —$S(=O)_2OR^{9a}$, —$C(=O)O^-$, or —$C(=O)OR^{9a}$;

each $R^{4c}$, $R^{4d}$, $R^{5d}$, $R^{5e}$, $R^{6c}$, and $R^{6d}$ is independently selected from hydrogen, halogen, —CN, —$OR^{9a}$, optionally substituted $C_1$-$C_4$ alkyl, optionally substituted $C_1$-$C_4$ fluoroalkyl, optionally substituted $C_2$-$C_6$ alkenyl, —$NR^{3c}R^{3d}$, —$S(=O)_2O^-$, —$S(=O)_2OR^{9a}$, —$C(=O)O^-$, and —$C(=O)OR^{9a}$;

each $R^{3c}$ and $R^{3d}$ is independently selected from hydrogen, optionally substituted $C_1$-$C_4$ alkyl, —X-optionally substituted $C_1$-$C_4$ alkyl, optionally substituted $C_2$-$C_6$ alkenyl, and optionally substituted aryl;

X is —$C(=O)$—, —$S(=O)$—, or —$S(=O)_2$—;

each $R^{9a}$, $R^{9b}$, $R^{9c}$, $R^{11a}$, $R^{11b}$, $R^{11c}$, $R^{12a}$, $R^{12b}$, and $R^{12c}$ is independently selected from hydrogen, optionally substituted $C_1$-$C_4$ alkyl, and optionally substituted aryl;

n is an integer selected from 0, 1, 2, 3, 4, 5, 6, 7, and 8;
s is an integer selected from 1, 2, 3, 4, or 5;
t is an integer selected from 1, 2, 3, 4, or 5; and
x is 0.001-0.999.

In another aspect, described herein is a copolymer comprising:

a) a repeating unit of Formula (VII):

Formula (VII)

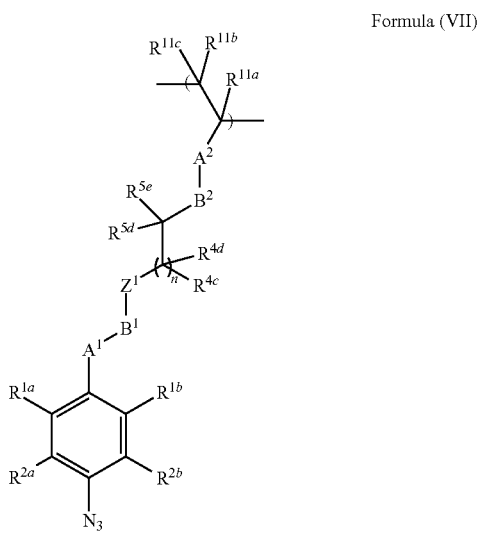

wherein, each $R^{1a}$ and $R^{1b}$ is independently selected from hydrogen and halogen;

each $R^{2a}$ and $R^{2b}$ is independently selected from halogen, —CN, and optionally substituted $C_1$-$C_6$ fluoroalkyl;

each $A^1$ and $A^2$ is independently selected from —C(=O)—, —S(=O)—, —S(=O)$_2$—, and —S(=O)(=NR$^{3c}$)—;

each $B^1$ and $B^2$ is independently selected from —O— and —NR$^{3c}$—;

$Z^1$ is —(CR$^{6c}$R$^{6d}$)$_s$—;

each $R^{4c}$, $R^{4d}$, $R^{5d}$, $R^{5e}$, $R^{6c}$, and $R^{6d}$ is independently selected from hydrogen, halogen, —CN, —OR$^{9a}$, optionally substituted C$_1$-C$_4$ alkyl, optionally substituted C$_1$-C$_4$ fluoroalkyl, optionally substituted C$_2$-C$_6$ alkenyl, —NR$^{3c}$R$^{3d}$, —S(=O)$_2$O$^-$, —S(=O)$_2$OR$^{9a}$, —C(=O)O$^-$, and —C(=O)OR$^{9a}$;

each $R^{3c}$ and $R^{3d}$ is independently selected from hydrogen, optionally substituted C$_1$-C$_4$ alkyl, —X-optionally substituted C$_1$-C$_4$ alkyl, optionally substituted C$_2$-C$_6$ alkenyl, and optionally substituted aryl;

X is —C(=O)—, —S(=O)—, or —S(=O)$_2$—;

each $R^{9a}$, $R^{11a}$, $R^{11b}$, and $R^{11c}$ is independently selected from hydrogen, optionally substituted C$_1$-C$_4$ alkyl, and optionally substituted aryl;

n is an integer selected from 0, 1, 2, 3, 4, 5, 6, 7, and 8; and s is an integer selected from 1, 2, 3, 4, and 5;

b) a repeating unit of Formula (VIII):

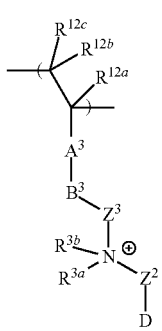

Formula (VIII)

wherein, $A^3$ is —C(=O)—, —S(=O)—, —S(=O)$_2$—, or —S(=O)(=NR$^{3c}$)—;

$B^3$ is —O— or —NR$^{3c}$—;

D is —S(=O)$_2$O$^-$, —S(=O)$_2$OR$^{9a}$, —C(=O)O$^-$, or —C(=O)OR$^{9a}$;

$Z^2$ is —(CR$^{6c}$R$^{6d}$)$_t$—;

$Z^3$ is —(CR$^{6c}$R$^{6d}$)$_p$—;

each $R^{3a}$ and $R^{3b}$ is independently selected from hydrogen, optionally substituted C$_1$-C$_4$ alkyl, and optionally substituted benzyl;

each $R^{6c}$ and $R^{6d}$ is independently selected from hydrogen, halogen, —CN, —OR$^{9a}$, optionally substituted C$_1$-C$_4$ alkyl, optionally substituted C$_1$-C$_4$ fluoroalkyl, optionally substituted C$_2$-C$_6$ alkenyl, —NR$^{3c}$R$^{3d}$, —S(=O)$_2$O$^-$, —S(=O)$_2$OR$^{9a}$, —C(=O)O$^-$, and —C(=O)OR$^{9a}$;

each $R^{3c}$ and $R^{3d}$ is independently selected from hydrogen, optionally substituted C$_1$-C$_4$ alkyl, —X-optionally substituted C$_1$-C$_4$ alkyl, optionally substituted C$_2$-C$_6$ alkenyl, and optionally substituted aryl;

X is —C(=O)—, —S(=O)—, or —S(=O)$_2$—;

each $R^{9a}$, $R^{12a}$, $R^{12b}$, and $R^{12c}$ is independently selected from hydrogen, optionally substituted C$_1$-C$_4$ alkyl, and optionally substituted aryl;

t is an integer selected from 1, 2, 3, 4, or 5;

p is an integer selected from 1, 2, 3, 4, or 5; and wherein the repeating unit of Formula (VIII) is charged or zwitterionic; and c) a repeating unit of Formula (IX):

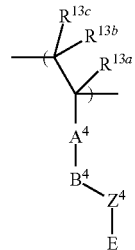

Formula (IX)

wherein, $A^4$ is —C(=O)—, —S(=O)—, —S(=O)$_2$—, or —S(=O)(=NR$^{3c}$)—;

$B^4$ is —O— or —NR$^{3c}$—;

$Z^4$ is —(CR$^{6c}$R$^{6d}$)$_k$—;

E is —CN, —OR$^{9a}$, —NR$^{9a}$R$^{9b}$, —NR$^{9a}$R$^{9b}$R$^{9c+}$, optionally substituted C$_1$-C$_4$ alkyl, optionally substituted C$_1$-C$_6$ fluoroalkyl, —S(=O)$_2$O$^-$, —S(=O)$_2$OR$^{9a}$, —C(=O)O$^-$, or —C(=O)OR$^{9a}$;

each $R^{6c}$, and $R^{6d}$ is independently selected from hydrogen, halogen, —CN, —OR$^{9a}$, optionally substituted C$_1$-C$_4$ alkyl, optionally substituted C$_1$-C$_4$ fluoroalkyl, optionally substituted C$_2$-C$_6$ alkenyl, —NR$^{3c}$R$^{3d}$, —S(=O)$_2$O$^-$, —S(=O)$_2$OR$^{9a}$, —C(=O)O$^-$, and —C(=O)OR$^{9a}$;

each $R^{3c}$ and $R^{3d}$ is independently selected from hydrogen, optionally substituted C$_1$-C$_4$ alkyl, —X-optionally substituted C$_1$-C$_4$ alkyl, optionally substituted C$_2$-C$_6$ alkenyl, and optionally substituted aryl;

X is —C(=O)—, —S(=O)—, or —S(=O)$_2$—;

each $R^{9a}$, $R^{9b}$, $R^{9c}$, $R^{13a}$, $R^{13b}$, and $R^{13c}$ is independently selected from hydrogen, optionally substituted C$_1$-C$_4$ alkyl, and optionally substituted aryl; and k is an integer selected from 1, 2, 3, 4, or 5.

Any combination of the groups described above or below for the various variables is contemplated herein. Throughout the specification, groups and substituents thereof are chosen by one skilled in the field to provide stable moieties and compounds.

In another aspect, described herein is a medical device coated with a compound of Formula (I), (II), or (III).

In another aspect, described herein is a medical device coated with a copolymer comprising a repeating unit of Formula (VII), (VIII), and (IX).

In another aspect, described herein is a biofouling-resistant medical device, wherein a surface of the medical device is coated with a phenyl azide-based copolymer having a number-average molecular weight of between about 10,000 and about 250,000.

In another aspect, described herein is a biofouling-resistant medical device, wherein a surface of the medical device is coated with a phenyl azide-based copolymer having a number-average molecular weight of between about 14,000 and about 21,000.

In another aspect, described herein is a biofouling-resistant medical device, wherein a surface of the medical device is coated with a phenyl azide-based copolymer having a polydispersity index (PDI) of between about 1 and 1.5.

In another aspect, described herein is a method of preparing a biofouling-resistant medical device, comprising:
  a) contacting a surface of a medical device with a mixture comprising a charged or zwitterion copolymer; and
  b) treating the surface of the medical device of step a) with a light source for a time sufficient to undergo photografting of the charged or zwitterion copolymer onto the surface of the medical device, thereby making the biofouling-resistant medical device;
  wherein the charged or zwitterion copolymer comprises a phenyl azide-based copolymer; and wherein the charged or zwitterion copolymer has a number-average molecular weight of between about 10,000 and about 250,000.

In another aspect, described herein is a method of preparing a biofouling-resistant medical device, comprising:
  a) contacting a surface of a medical device with a mixture (e.g., a solution) comprising a charged or zwitterion copolymer; and
  b) treating the surface of the medical device of step a) with a light source for a time sufficient to undergo photografting of the charged or zwitterion copolymer onto the surface of the medical device, thereby making the biofouling-resistant medical device;
  wherein the charged or zwitterion copolymer comprises a phenyl azide-based copolymer; and wherein the charged or zwitterion copolymer has a number-average molecular weight of between about 14,000 and about 21,000.

In another aspect, described herein is a method of preparing a charged or zwitterion copolymer modified biofouling-resistant device comprising:
  a) contacting a surface of a silicon-based device with a mixture (e.g., a solution) comprising a charged or zwitterion copolymer; and
  b) treating the surface of the device of step a) with a light source for a time sufficient to undergo photografting of the charged or zwitterion copolymer onto the surface of the silicon-based device, thereby generating the charged or zwitterion copolymer modified device;
  wherein the charged or zwitterion copolymer comprises a phenyl azide-based copolymer.

In another aspect, described herein is a method of preparing a charged or zwitterion copolymer modified biofouling-resistant device comprising:
  a) contacting a surface of a device with a mixture (e.g., a solution) comprising a charged or zwitterion copolymer; and
  b) treating the surface of the device of step a) with a light source for a time sufficient to undergo photografting of the charged or zwitterion copolymer onto the surface of the device, thereby generating the charged or zwitterion copolymer modified device;
  wherein the charged or zwitterion copolymer comprises a phenyl azide-based copolymer; and wherein the charged or zwitterion copolymer has a number-average molecular weight of between about 10,000 and about 250,000.

In another aspect, described herein is a method of preparing a charged or zwitterion copolymer modified biofouling-resistant device comprising:
  a) contacting a surface of a device with a mixture (e.g., a solution) comprising a charged or zwitterion copolymer; and
  b) treating the surface of the device of step a) with a light source for a time sufficient to undergo photografting of the charged or zwitterion copolymer onto the surface of the device, thereby generating the charged or zwitterion copolymer modified device;
  wherein the charged or zwitterion copolymer comprises a phenyl azide-based copolymer; and wherein the charged or zwitterion copolymer has a number-average molecular weight of between about 14,000 and about 21,000.

In yet another aspect, described herein is a method for synthesizing a compound of Formula (II) comprising: reacting a compound of Formula (IV) or a salt or solvate thereof with a compound of Formula (V):

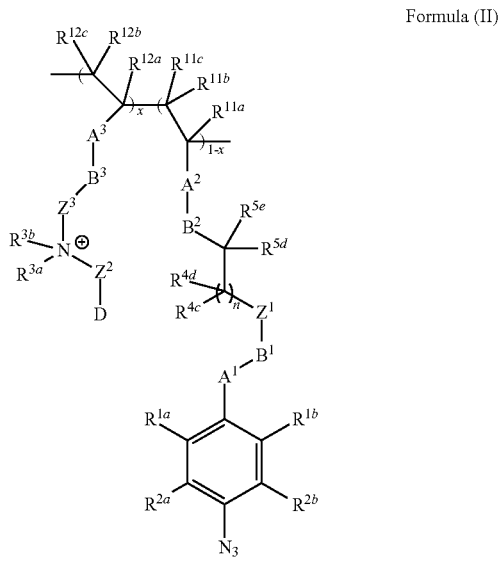

Formula (II)

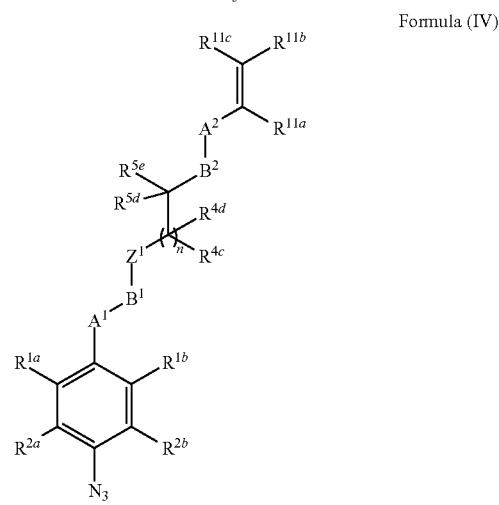

Formula (IV)

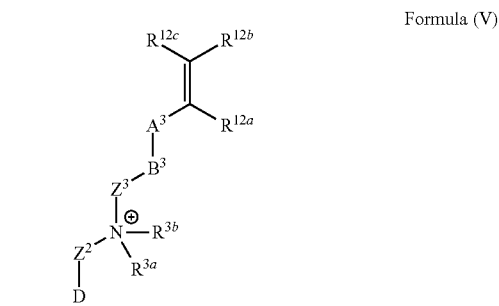

Formula (V)

wherein
each $R^{1a}$ and $R^{1b}$ is independently selected from hydrogen and halogen;
each $R^{2a}$ and $R^{2b}$ is independently selected from halogen, —CN, and optionally substituted $C_1$-$C_6$ fluoroalkyl;
each $A^1$, $A^2$, and $A^3$ is independently selected from —C(=O)—, —S(=O)—, —S(=O)$_2$—, and —S(=O)(=NR$^{3c}$)—;
each $B^1$, $B^2$, and $B^3$ is independently selected from —O— and —NR$^{3c}$—;
D is —S(=O)$_2$O$^-$, —S(=O)$_2$OR$^{9a}$, —C(=O)O$^-$, or —C(=O)OR$^{9a}$;
$Z^1$ is —(CR$^{6c}$R$^{6d}$)$_s$—;
$Z^2$ is —(CR$^{6c}$R$^{6d}$)$_t$—;
$Z^3$ is —(CR$^{6c}$R$^{6d}$)$_p$—;
each $R^{3a}$ and $R^{3b}$ is independently selected from hydrogen, optionally substituted $C_1$-$C_4$ alkyl, and optionally substituted benzyl;
each $R^{4c}$, $R^{4d}$, $R^{5d}$, $R^{5e}$, $R^{6c}$, and $R^{6d}$ is independently selected from hydrogen, halogen, —CN, —OH, optionally substituted $C_1$-$C_4$ alkyl, optionally substituted $C_1$-$C_4$ fluoroalkyl, optionally substituted $C_2$-$C_6$ alkenyl, —NR$^{3c}$R$^{3d}$, —S(=O)$_2$O$^-$, —S(=O)$_2$OR$^{9a}$, —C(=O)O$^-$, and —C(=O)OR$^{9a}$;
each $R^{3c}$ and $R^{3d}$ is independently selected from hydrogen, optionally substituted $C_1$-$C_4$ alkyl, —X-optionally substituted $C_1$-$C_4$ alkyl, optionally substituted $C_2$-$C_6$ alkenyl, and optionally substituted aryl;
X is —C(=O)—, —S(=O)—, or —S(=O)$_2$—;
each $R^{9a}$, $R^{11a}$, $R^{11b}$, $R^{11c}$, $R^{12a}$, $R^{12b}$, and $R^{12c}$ is independently selected from hydrogen, optionally substituted $C_1$-$C_4$ alkyl, and optionally substituted aryl;
n is an integer selected from 0, 1, 2, 3, 4, 5, 6, 7, and 8;
s is an integer selected from 1, 2, 3, 4, or 5;
t is an integer selected from 1, 2, 3, 4, or 5;
p is an integer selected from 1, 2, 3, 4, or 5;
x is 0.001-0.999; and
wherein the compounds of Formula (II) and Formula (V) are each independently charged or zwitterionic;
provided that a compound of Formula (II) is not

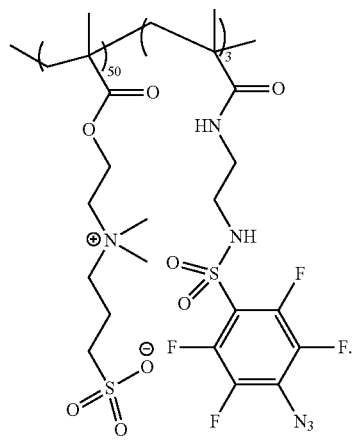

In another aspect, described herein is a method for synthesizing a compound of Formula (III) comprising: reacting a compound of Formula (IV) or a salt or solvate thereof with a compound of Formula (VI):

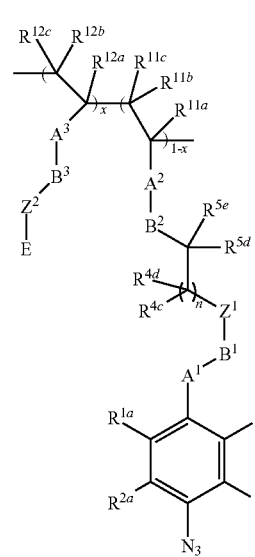

Formula (III)

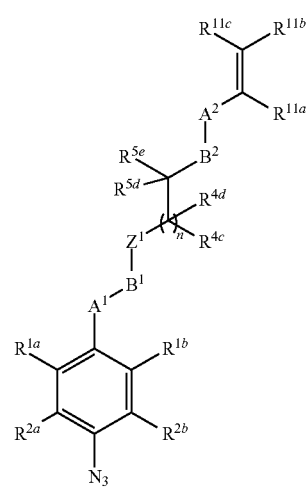

Formula (IV)

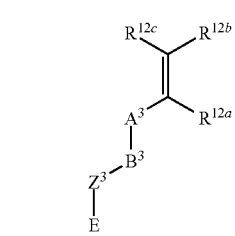

Formula (VI)

wherein
each $R^{1a}$ and $R^{1b}$ is independently selected from hydrogen and halogen;
each $R^{2a}$ and $R^{2b}$ is independently selected from halogen, —CN, and optionally substituted $C_1$-$C_6$ fluoroalkyl;
each $A^1$, $A^2$, and $A^3$ is independently selected from —C(=O)—, —S(=O)—, —S(=O)$_2$—, and —S(=O)(=NR$^{3c}$)—;
each $B^1$, $B^2$, and $B^3$ is independently selected from —O— and —NR$^{3c}$—;
$Z^1$ is —(CR$^{6c}$R$^{6d}$)$_s$—;
$Z^2$ is —(CR$^{6c}$R$^{6d}$)$_t$—;
E is —CN, —OR$^{9a}$, —NR$^{9a}$R$^{9b}$, —NR$^{9a}$R$^{9b}$R$^{9c+}$, optionally substituted $C_1$-$C_4$ alkyl, optionally substituted $C_1$-$C_6$ fluoroalkyl, —S(=O)$_2$O$^-$, —S(=O)$_2$OR$^{9a}$, —C(=O)O⁻, or —C(=O)OR$^{9a}$; each R$^{4c}$, R$^{4d}$, R$^{5d}$, R$^{5e}$, R$^{6c}$, and R$^{6d}$ is independently selected from hydrogen, halogen, —CN, —OR$^{9a}$, optionally substituted C$_1$-C$_4$ alkyl, optionally substituted C$_1$-C$_4$ fluoroalkyl, optionally substituted C$_2$-C$_6$ alkenyl, —NR$^{3c}$R$^{3d}$, —S(=O)$_2$O⁻, —S(=O)$_2$OR$^{9a}$, —C(=O)O⁻, and —C(=O)OR$^{9a}$;

each R$^{3c}$ and R$^{3d}$ is independently selected from hydrogen, optionally substituted C$_1$-C$_4$ alkyl, —X-optionally substituted C$_1$-C$_4$ alkyl, optionally substituted C$_2$-C$_6$ alkenyl, and optionally substituted aryl;

X is —C(=O)—, —S(=O)—, or —S(=O)$_2$—;

each R$^{9a}$, R$^{9b}$, R$^{9c}$, R$^{11a}$, R$^{11b}$, R$^{11c}$, R$^{12a}$, R$^{12b}$, and R$^{12c}$ is independently selected from hydrogen, optionally substituted C$_1$-C$_4$ alkyl, and optionally substituted aryl;

n is an integer selected from 0, 1, 2, 3, 4, 5, 6, 7, and 8;

s is an integer selected from 1, 2, 3, 4, or 5;

t is an integer selected from 1, 2, 3, 4, or 5; and x is 0.001-0.999.

In one aspect, also described herein is a charged or zwitterion copolymer modified biofouling-resistant device prepared by the method comprising:
  a) contacting a surface of a silicon-based device with a mixture (e.g., a solution) comprising a charged or zwitterion copolymer; and
  b) treating the surface of the device of step a) with a light source for a time sufficient to undergo photografting of the charged or zwitterion copolymer onto the surface of the silicon-based device, thereby generating the charged or zwitterion copolymer modified device;
  wherein the charged or zwitterion copolymer comprises a phenyl azide-based copolymer.

In another aspect, described herein is a charged or zwitterion copolymer modified biofouling-resistant device prepared by the method comprising:
  a) contacting a surface of a device with a mixture (e.g., a solution) comprising a charged or zwitterion copolymer; and
  b) treating the surface of the device of step a) with a light source for a time sufficient to undergo photografting of the charged or zwitterion copolymer onto the surface of the device, thereby generating the charged or zwitterion copolymer modified device;
  wherein the charged or zwitterion copolymer comprises a phenyl azide-based copolymer; and wherein the charged or zwitterion copolymer has a number-average molecular weight of between about 10,000 and about 250,000.

In another aspect, described herein is a charged or zwitterion copolymer modified biofouling-resistant device prepared by the method comprising:
  c) contacting a surface of a device with a mixture (e.g., a solution) comprising a charged or zwitterion copolymer; and
  d) treating the surface of the device of step a) with a light source for a time sufficient to undergo photografting of the charged or zwitterion copolymer onto the surface of the device, thereby generating the charged or zwitterion copolymer modified device;
  wherein the charged or zwitterion copolymer comprises a phenyl azide-based copolymer; and wherein the charged or zwitterion copolymer has a number-average molecular weight of between about 14,000 and about 21,000.

BRIEF DESCRIPTION OF THE FIGURES

The accompanying figures, which are incorporated in and constitute a part of this specification, illustrate several aspects and together with the description serve to explain and not to limit the scope of current disclosure.

Figure 1:
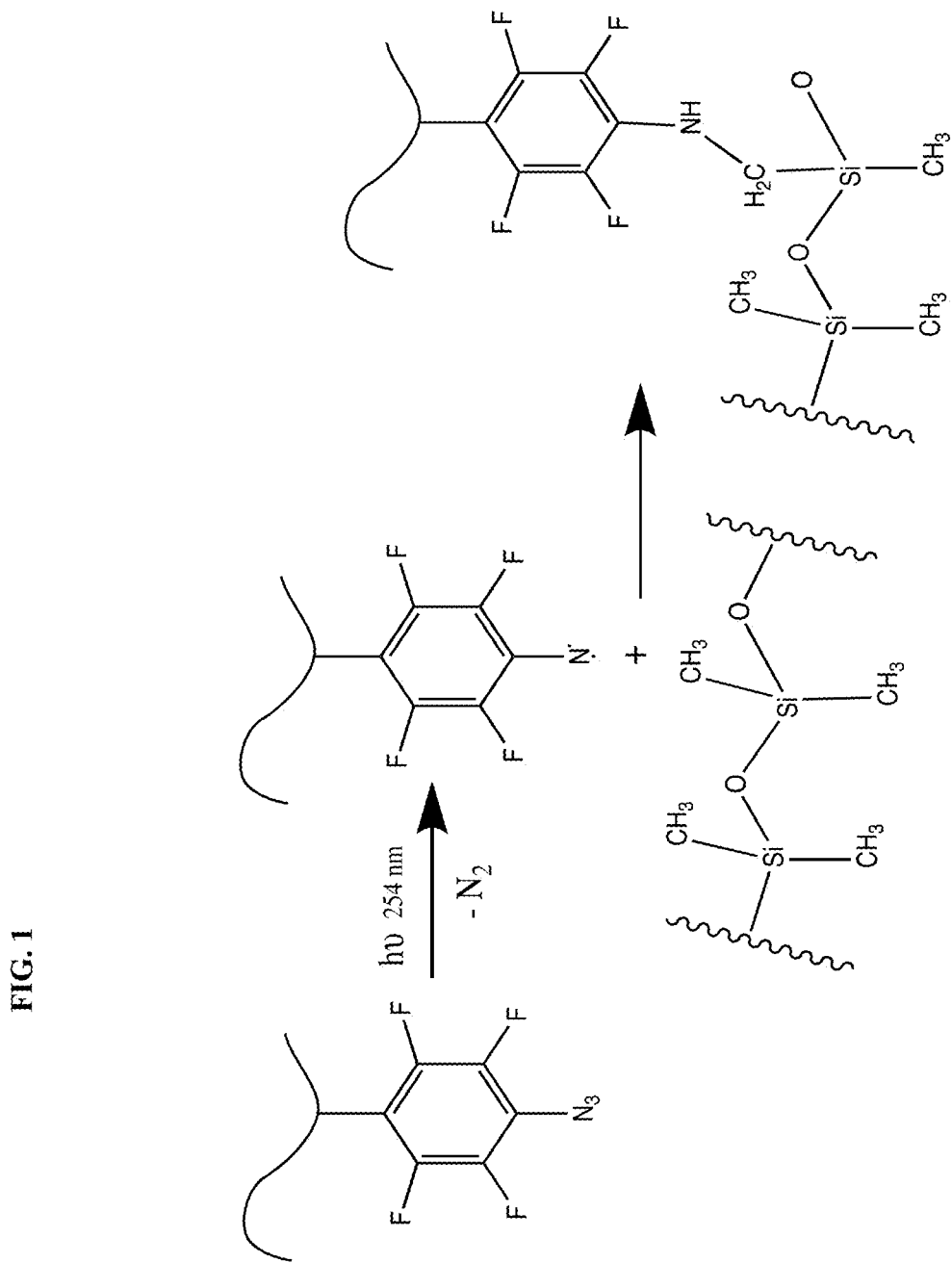
FIG. 1 illustrates representative photografting of poly (sulfobetaine methacrylate-co-perfluorophenylazide methacrylate) (PFPA-PSB copolymer) to a silicone surface.
Figure 2A:
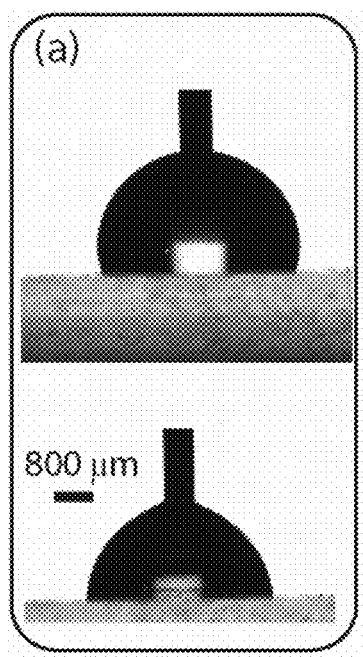
FIG. 2A illustrates representative water advancing contact angle (upper image) and receding contact angle (lower image) on an unmodified silicone surface and (b) PFPA-PSB copolymer modified silicone surface.
Figure 2B:
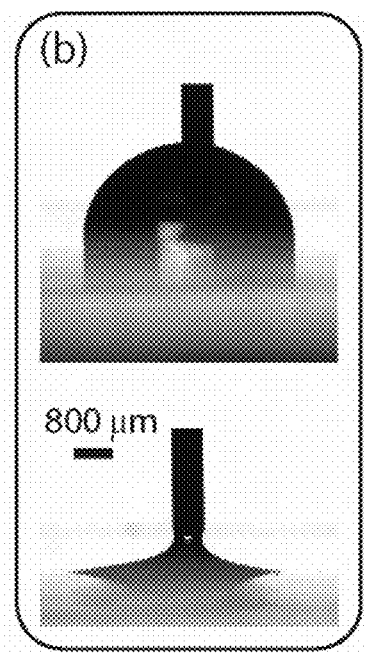
FIG. 2B illustrates representative water advancing contact angle (upper image) and receding contact angle (lower image) on a PFPA-PSB copolymer modified silicone surface.
Figure 3A:
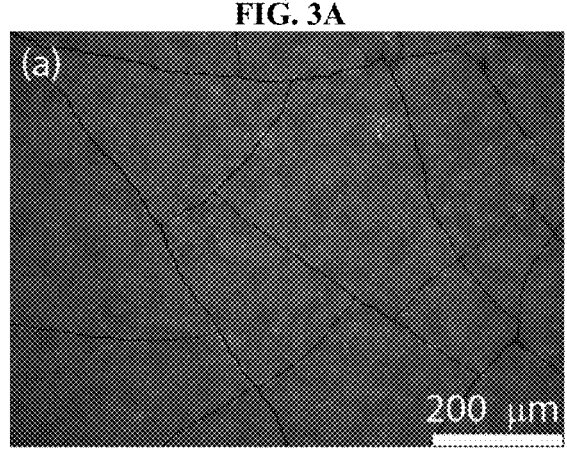
FIG. 3A illustrates high density of *Escherichia coli* adhesion to unmodified silicone surface forming an elastic film, which fractured upon surface drying.
Figure 3B:
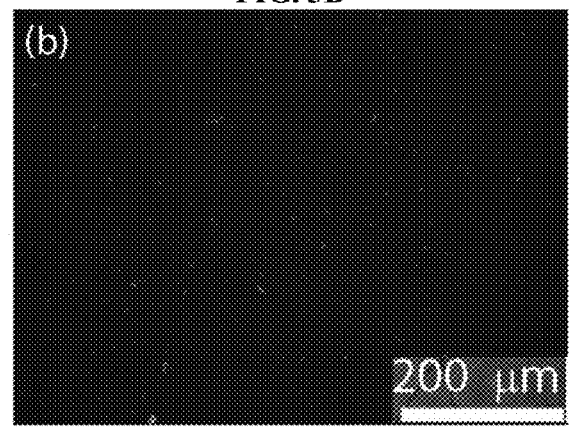
FIG. 3B illustrates very low density of *Escherichia coli* adhesion to poly(sulfobetaine methacrylate-co-perfluorophenylazide methacrylate)-modified silicone surface.
Figure 4:
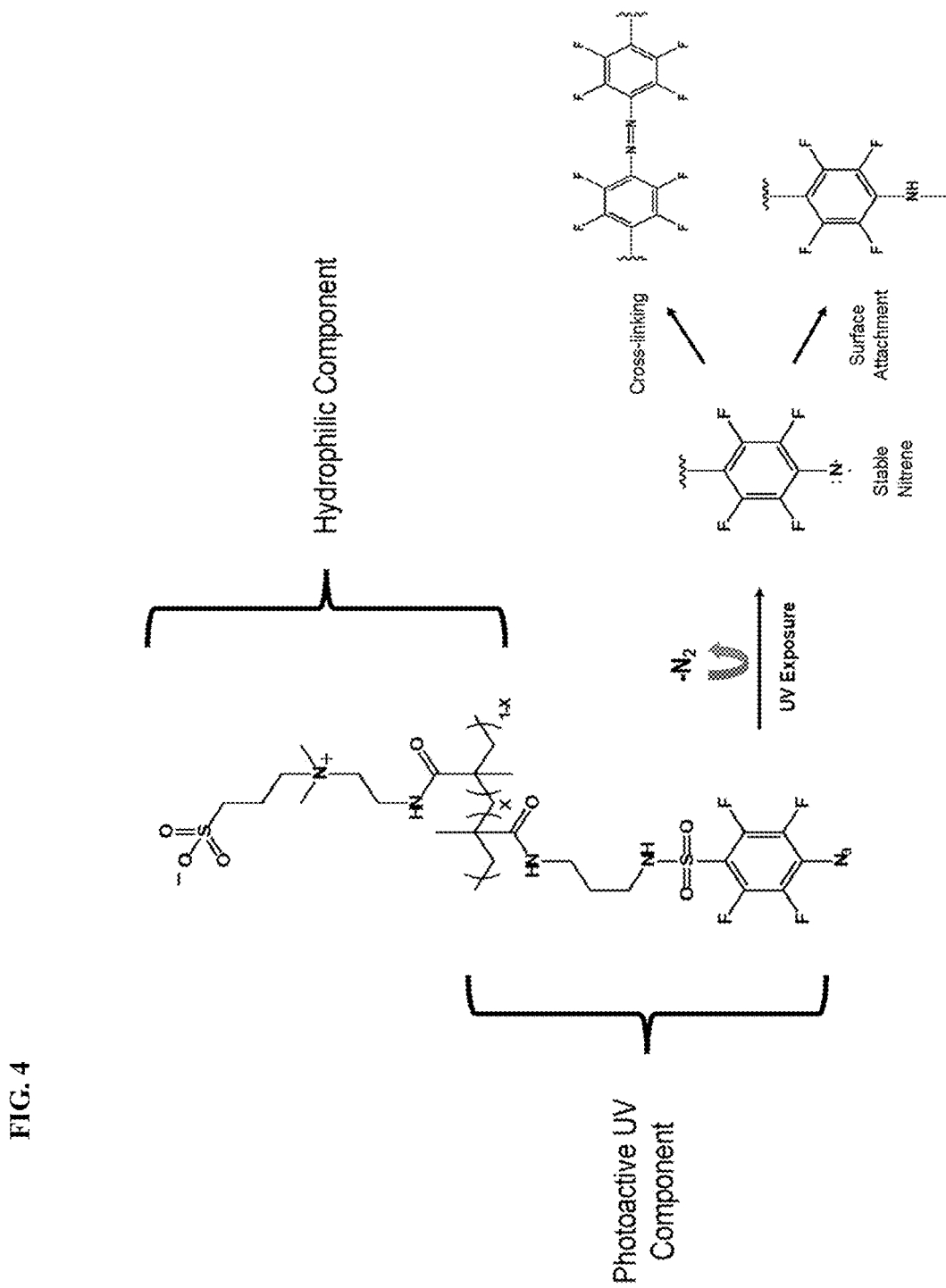
FIG. 4 illustrates the structure of PFPA-PSB copolymer.
Figure 5A:
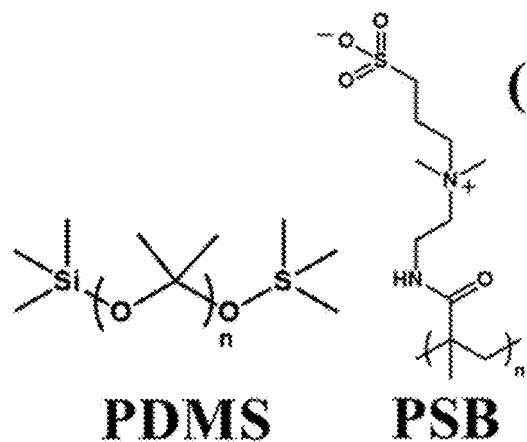
FIG. 5A illustrates chemical structure of polydimethylsiloxane and polysulfobetaine.
Figure 5B:
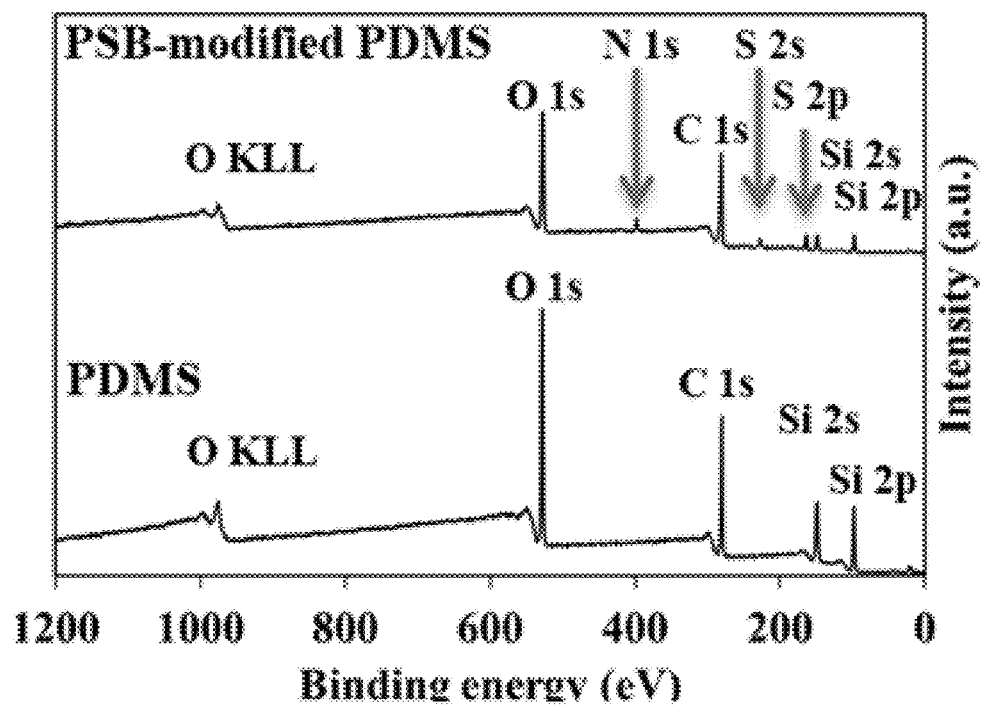
FIG. 5B illustrates XPS spectra of a PFPA-PSB modified PDMS substrate, showing the successful grafting of PSB on the organic substrate.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Hospital acquired infections (HAIs) cause over 100,000 deaths per year and over $30 billion in direct healthcare cost. Despite reduction of HAIs in recent years through improved antiseptic technique, surgical procedure, and diagnosis, HAIs declines are slowing down indicating the need for new preventative methods. In some instances, medical devices implanted into the body are the source of infection. It is estimated that 60-70% of HAIs are associated with the use of implantable medical devices. Planktonic bacteria adhere to the surface of the medical devices and begin to grow into resilient biofilms that become more resistant to antibiotics and disinfecting agents than in the planktonic state. As the biofilm grows and the cells continue to proliferate, the extracellular matrix scaffolding (made up of proteins and polysaccharides) bursts open, releasing more bacteria into the body. The body can no longer stave off infection and strong antibiotics must be used to fight the infectious cells. The use of strong antibiotics has led to the existence of antibiotic resistant bacteria, also known as superbugs, which can no longer be treated with conventional antibiotics.

Without the initial adhesion of planktonic cells to the surface of a material, the biofilm formation is prevented or reduced. Several researchers have identified the attractive forces that cause organic material to adhere to polymeric surfaces: hydrophobic interactions and electrostatic interactions (van der Waals forces) between the organic materials and polymer surface. Using self-assembled monolayers, Whitesides et al. surveyed several functional groups to determine surface functionalities that promote or hinder the non-specific adsorption of proteins. (Whitesides, G. M. A survey of structure-property relationships of surfaces that resist the adsorption of protein. *Langmuir,* 2001, 17 (18), pp 5605-5620). The functional groups that exhibited the lowest adhesion were electrostatically neutral hydrophilic moieties that contained hydrogen bond donating groups. From these design rules, many material coatings have been developed and shown to reduce adhesion of proteins and microorganisms. However, these coating are substrate dependent and/or require exotic reaction conditions that are not compatible for wide-scale use. In some cases, several polymers coatings and surface modifications have been developed to repel these interactions to reduce/prevent the formation of biofilms on surfaces. In some instances, the coating should have the following chemical requirements to be used as an anti-fouling surface: a) the coating should be hydrophilic; b) the coating should consist of mostly of hydrogen bond acceptors; and c) the coating should be electrostatically neutral. However, due to the water-solubility of hydrophilic coatings, the coating material should be covalently bound to the polymeric material for long-term effects.

In some instances, medical grade silicone is used in medical and health care industry. Its market currently undergoes a rapid growth and is projected to reach $7.23 billion by 2021. Medical grade silicone generally includes polydimethylsiloxane (PDMS) fluids and elastomers. Due to their good chemical stability, matching mechanical properties with human tissues, and no-requirements for plasticizers, PDMS elastomers generally have excellent biocompatibility, and are used in medical devices and biomedical implants such as catheters and pacemakers. PDMS elastomers also have high transparency and easy processability. Therefore, PDMS elastomers have found broad applications in fabricating microfluidic devices, which provide low-cost, simple, and robust systems for diagnosing diseases (Whitesides, G. M. The origins and the future of microfluidics. *Nature* 2006, 442 (7101), 368-373). However, PDMS elastomers also have a low surface energy of about 20 mN/m. Bacteria, platelets, proteins, and other biomolecules tend to adhere to the hydrophobic surfaces of PDMS elastomers (Hron, P. Hydrophilisation of silicone rubber for medical applications. *Polymer international* 2003, 52 (9), 1531-1539). For silicone medical implants, bacterial adhesion and biofilm formation may lead to the failure of medical devices, severe infection, and even death of patients. For disease diagnosis devices based on PDMS microfluidics, proteins and other biomolecules fouling on the PDMS surfaces can significantly reduce the sensitivity of these devices, and may even lead to complete device-failure if blocking of the microfluidic channels occurs (Zhou, J. et al. Recent developments in PDMS surface modification for microfluidic devices. *Electrophoresis* 2010, 31 (1), 2-16).

Hydrophilic treatment of the PDMS surfaces was found to be one of the strategies to alleviate or prevent the problem of biofouling (Keefe, A. J. et al. Suppressing surface reconstruction of superhydrophobic PDMS using a superhydrophilic zwitterionic polymer. *Biomacromolecules* 2012, 13 (5), 1683-1687). Some conventional methods of making PDMS surfaces hydrophilic include oxidation of the surfaces by oxygen plasma, UV-ozone, or corona discharge. However, these modifications are only temporary because PDMS has an extremely low glass transition temperature of about −120° C. and therefore the PDMS chains are highly mobile at room temperature. The PDMS chains are able to rearrange and recover the hydrophobic surface of PDMS elastomers within a time window of a few hours. In some cases, other methods seeking to make long-lasting hydrophilic PDMS surfaces take many steps and involve radical reaction or polymerization. These steps have to be performed in closed containers, and/or under the protection of inert gas. Due to the higher solubility of oxygen relative to nitrogen in PDMS, in some instances it takes long time to remove oxygen from PDMS so that the radical reaction can proceed efficiently. These strict reaction conditions significantly increase the cost and limit industrial applicability of these reactions.

In some embodiments, provided herein are biofouling-resistant coatings comprising charged or zwitterion compounds comprising phenyl-azide moieties. In some instances, biofouling comprises microfouling or macrofouling. Microfouling comprises formation of microorganism adhesion (e.g., bacteria adhesion) and/or biofilm. Biofilm is a group of microorganism which adheres to a surface. In some instances, the adhered microorganisms are further embedded in a self-produced matrix of extracellular polymeric substance, which comprises a polymeric conglomeration of extracellular DNA, protein, and polysaccharides. Macrofouling comprises attachment of larger organisms.

Charged and/or zwitterionic compounds bind water molecules via electrostatically induced hydration. In such cases, charged and/or zwitterionic materials exhibit surface resistance to protein/cell/bacterial adhesion, biofilm formation, and/or macrofouling. In some embodiments, the charged or zwitterion compounds comprise copolymers. In some embodiments, also provided herein are methods of making biofouling-resistant coatings comprising charged or zwitterion copolymers via polymerization reaction. In some embodiments, the polymerization reaction is addition polymerization, atomic transfer radical polymerization (ATRP), coordination polymerization, free-radical polymerization, nitroxide-mediated radical polymerization (NMP), reversible addition-fragmentation chain-transfer polymerization (RAFT), or ring-opening metathesis polymerization (ROMP). In some embodiments, the ionic polymerization is anionic polymerization or cationic polymerization. In some embodiments, the polymerization reaction is reversible-deactivation polymerization (RDP). In some embodiments, the polymerization reaction is free-radical polymerization. In some embodiments, the polymerization reaction is atomic transfer radical polymerization (ATRP). In some embodiments, biofouling-resistant coatings comprising charged or zwitterion copolymers are grafted onto a polymer surface of a device under a UV exposure. In some other embodiments, charged or zwitterion copolymers are grafted onto a silicone-comprising surface of a device under a UV exposure. In some embodiments, charged or zwitterion copolymers are grafted onto a surface of a medical device under a UV exposure. In some other embodiments, charged or zwitterion copolymers are grafted onto a silicone-comprising surface of a medical device under a UV exposure. In some embodiments, charged or zwitterion are grafted onto a polymer surface of a medical device under a UV exposure. In some other embodiments, charged or zwitterion copolymers are grafted onto a silicone-comprising polymer surface of a medical device under a UV exposure.

In some embodiments, a charged or zwitterion copolymer modified device comprises anti-fouling properties and is used to prevent and/or to reduce the development of biofouling. In some embodiments, a charged or zwitterion copolymer modified medical device comprises anti-fouling properties and is used to prevent and/or to reduce the development of biofouling. In some embodiments, the charged or zwitterion coatings prevent and/or reduce the attachment of microorganisms, plants, algae, or animals to a surface.

In additional embodiments, disclosed herein are compounds to be used to prepare charged or zwitterion copolymers of the disclosure as well as the charged or zwitterion copolymers themselves to be used within the methods disclosed herein.

I. Compounds

In one aspect, described herein is a compound that has the structure of Formula (I) or a salt or solvate thereof:

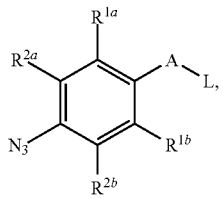

Formula (I)

wherein
A is selected from —C(=O)—, —S(=O)—, —S(=O)$_2$—, and —S(=O)(—NR$^3$)—;
L is selected from —OQ, —NR$^3$Q, and —N(R$^3$)$_2$Q$^+$;
Q is a structure represented by a formula:

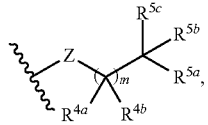

Z is selected from —CR$^{6a}$R$^{6b}$—, —C(=O)—, —C(=NH)—, and —C(=NH)NR$^7$—;
m is an integer selected from 0, 1, 2, 3, 4, 5, 6, 7, and 8;
each R$^{1a}$ and R$^{1b}$ is independently selected from hydrogen and halogen;
each R$^{2a}$ and R$^{2b}$ is independently selected from halogen, —CN, and optionally substituted C$_1$-C$_6$ fluoroalkyl;
each R$^3$ is independently selected from hydrogen, optionally substituted C$_1$-C$_4$ alkyl, —X-optionally substituted C$_1$-C$_4$ alkyl, optionally substituted aryl, and —X-optionally substituted aryl;
X is —C(=O)—, —S(=O)—, or —S(=O)$_2$—;
each R$^{4a}$, R$^{4b}$, R$^{5a}$, R$^{5c}$, R$^{6a}$ and R$^{6b}$ is independently selected from hydrogen, halogen, —CN, —OR$^9$, optionally substituted C$_1$-C$_4$ alkyl, optionally substituted C$_1$-C$_4$ fluoroalkyl, optionally substituted aryl, —NR$^{8a}$R$^{8b}$, —NR$^{8a}$R$^{8b}$R$^{8c}$, —S(=O)$_2$O$^-$, —S(=O)$_2$OR$^9$, —C(=O)O$^-$, and —C(=O)OR$^9$;
R$^{5b}$ is —OR$^{10b}$, —NR$^{10a}$R$^{10b}$, or —NR$^{10a}$R$^{10b}$R$^{10c+}$;
each R$^7$, R$^{8a}$, R$^{8b}$, R$^{8c}$, and R$^9$ is independently selected from hydrogen and optionally substituted C$_1$-C$_4$ alkyl, and optionally substituted aryl;
each R$^{10a}$ and R$^{10c}$ is independently selected from hydrogen, optionally substituted C$_1$-C$_4$ alkyl, optionally substituted aryl, -(optionally substituted C$_1$-C$_8$alkylene)S(=O)$_2$O$^-$, -(optionally substituted C$_1$-C$_8$alkylene)S(=O)$_2$OH, -(optionally substituted C$_1$-C$_8$alkylene)C(=O)O$^-$, and -(optionally substituted C$_1$-C$_8$alkylene)C(=O)OH; and R$^{10b}$ is —C(=O)—C$_2$-C$_6$alkenyl, —S(=O)—C$_2$-C$_6$alkenyl, or —S(=O)$_2$—C$_2$-C$_6$alkenyl.

In some embodiments, the compound of Formula (I) is not:
N-(2-((4-azido-2,3,5,6-tetrafluorophenyl)sulfonamido)ethyl)methacrylamide;
N-(2-acrylamidoethyl)-4-azido-2,3,5,6-tetrafluorobenzamide; or
2-(methacryloyloxy)ethyl 4-azido-2,3,5,6-tetrafluorobenzoate.

In some embodiments, N-(2-((4-azido-2,3,5,6-tetrafluorophenyl)sulfonamido)ethyl)methacrylamide has a structure of:

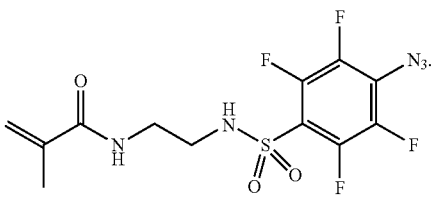 [SMILES: C=C(C)C(=O)NCCNS(=O)(=O)c1c(F)c(F)c(N=[N+]=[N-])c(F)c1F]

In some embodiments, N-(2-acrylamidoethyl)-4-azido-2,3,5,6-tetrafluorobenzamide has a structure of:

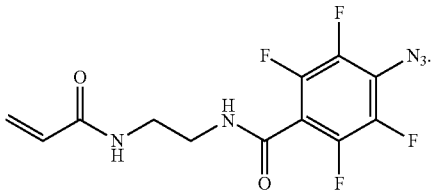 [SMILES: C=CC(=O)NCCNC(=O)c1c(F)c(F)c(N=[N+]=[N-])c(F)c1F]

In some embodiments, N-(2-acrylamidoethyl)-4-azido-2,3,5,6-tetrafluorobenzamide has a structure of:

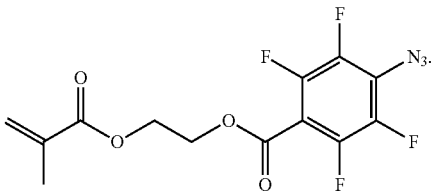 [SMILES: C=C(C)C(=O)OCCOC(=O)c1c(F)c(F)c(N=[N+]=[N-])c(F)c1F]

In some embodiments, the compound of Formula (I) has a structure selected from:

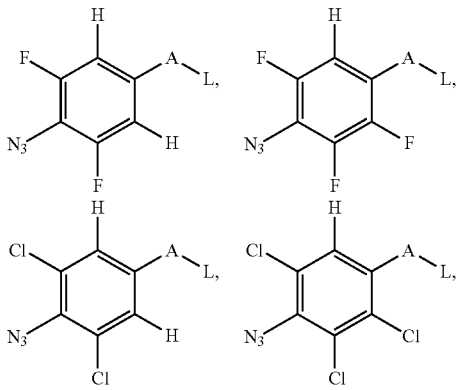

-continued
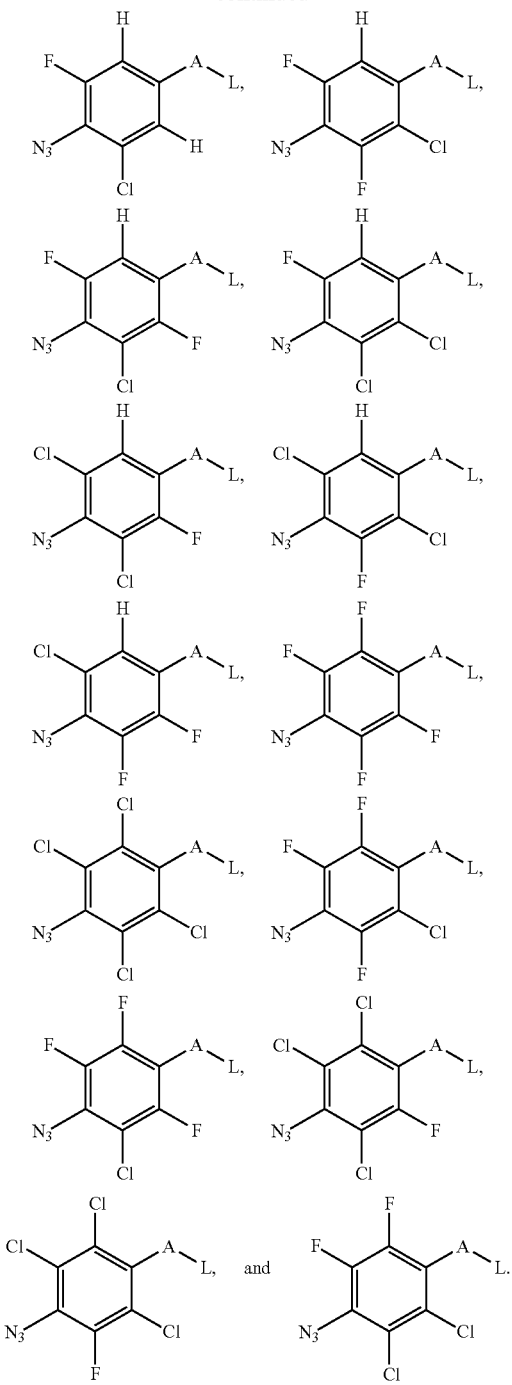
In some embodiments, the compound of Formula (I) has the following structure:
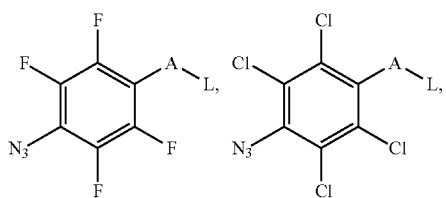
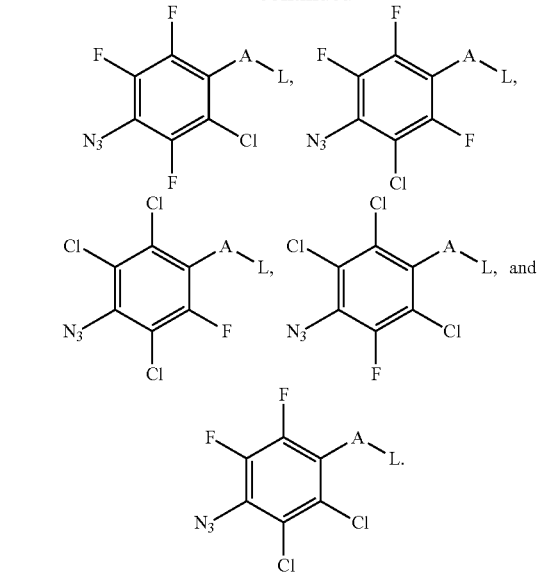
In some embodiments, the compound of Formula (I) has a structure selected from:
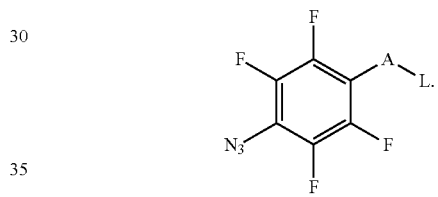
In some embodiments, the compound of Formula (I) has a structure selected from:
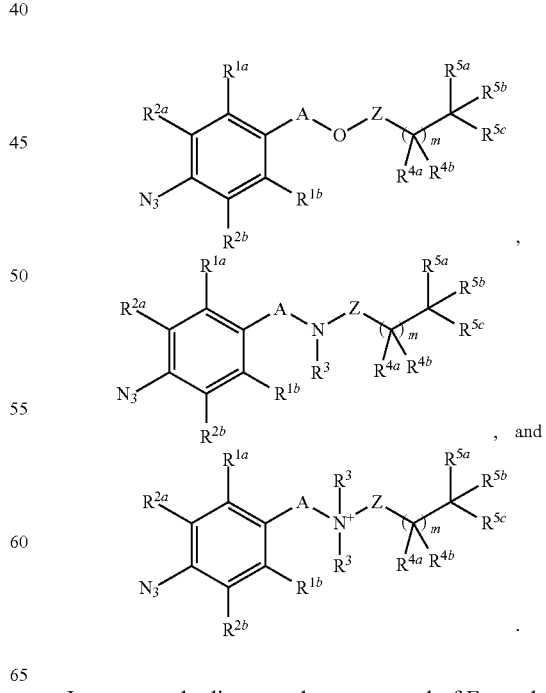
In some embodiments, the compound of Formula (I) has a structure selected from:

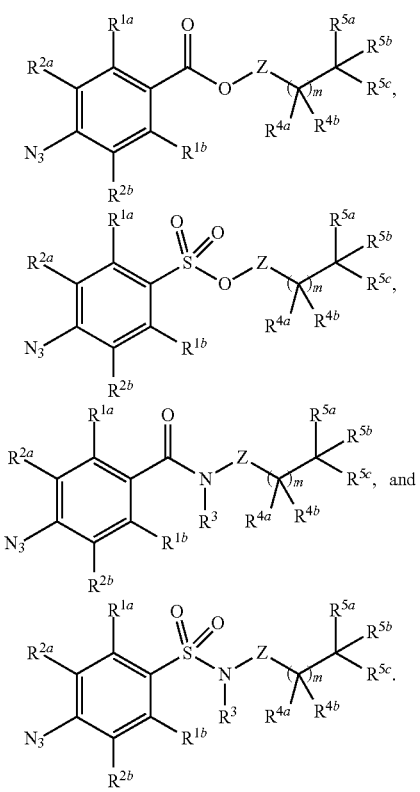

In some embodiments, each $R^{1a}$ and $R^{1b}$ is independently halogen. In some embodiments, each $R^{1a}$ and $R^{1b}$ is independently F or Cl. In some embodiments, each $R^{1a}$ and $R^{1b}$ is F. In some embodiments, each $R^{2a}$ and $R^{2b}$ is independently selected from halogen, —CN, and optionally substituted $C_1$-$C_6$ fluoroalkyl. In some embodiments, each $R^{2a}$ and $R^{2b}$ is independently selected from halogen, —CN, and —$CF_3$. In some embodiments, each $R^{2a}$ and $R^{2b}$ is independently selected from F, Cl, —CN, and —$CF_3$. In some embodiments, each $R^{2a}$ and $R^{2b}$ is independently halogen. In some embodiments, each $R^{2a}$ and $R^{2b}$ is F. In some embodiments, each $R^{2a}$ and $R^{2b}$ is —CN. In some embodiments, each $R^{2a}$ and $R^{2b}$ is independently $C_1$-$C_6$ fluoroalkyl. In some embodiments, each $R^{2a}$ and $R^{2b}$ is —$CF_3$.

In some embodiments, each $R^{1a}$, $R^{1b}$, $R^{2a}$, and $R^{2b}$ is F.

In some embodiments, Z is selected from —$CR^{6a}R^{6b}$—, —C(=O)—, —C(=NH)—, and —C(=NH)$NR^7$—. In some embodiments, Z is —$CR^{6a}R^{6b}$—. In some embodiments, Z is —C(=O)—. In some embodiments, Z is —C(=NH)—. In some embodiments, Z is —C(=NH)$NR^7$—.

In some embodiments, each $R^3$ is independently selected from hydrogen, optionally substituted $C_1$-$C_4$ alkyl, —X-optionally substituted $C_1$-$C_4$ alkyl, optionally substituted aryl, and —X-optionally substituted aryl. In some embodiments, $R^3$ is hydrogen. In some embodiments, $R^3$ is optionally substituted $C_1$-$C_4$ alkyl. In some embodiments, $R^3$ is —X-optionally substituted $C_1$-$C_4$ alkyl. In some embodiments, $R^3$ is optionally substituted aryl. In some embodiments, $R^3$ is —X-optionally substituted aryl.

In some embodiments, X is —C(=O)—, —S(=O)—, or —S(=O)$_2$—. In some embodiments, X is —C(=O)—. In some embodiments, X is —S(=O)—. In some embodiments, X is —S(=O)$_2$—.

In some embodiments, each $R^{6a}$ and $R^{6b}$ is hydrogen.
In some embodiments, m is 0, 1, 2, 3, 4, 5, or 6. In some embodiments, m is 0, 1, 2, 3, 4, or 5. In some embodiments, m is 0, 1, 2, or 3. In some embodiments, m is 0. In some embodiments, m is 1. In some embodiments, m is 2. In some embodiments, m is 3. In some embodiments, m is 4. In some embodiments, m is 5.

In some embodiments, $R^{5a}$ is hydrogen; $R^{5b}$ is —$NR^{10a}R^{10b}$; and $R^{5c}$ is hydrogen.

In some embodiments, $R^{5a}$ is hydrogen; $R^{5b}$ is —$OR^{10b}$; and $R^{5c}$ is hydrogen.

In some embodiments, $R^{4a}$ is hydrogen and $R^{4b}$ is hydrogen.

In some embodiments, the compound of Formula (I) has a structure of Formula (Ia):

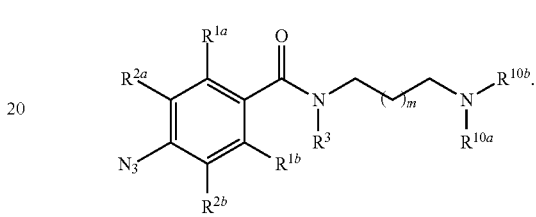

In some embodiments, the compound of Formula (I) has a structure of Formula (Ib):

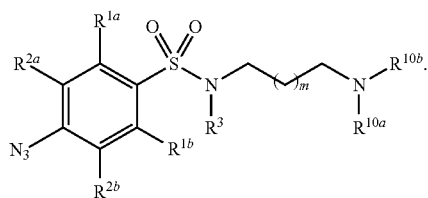

In some embodiments, the compound of Formula (I) has a structure of Formula (Ic):

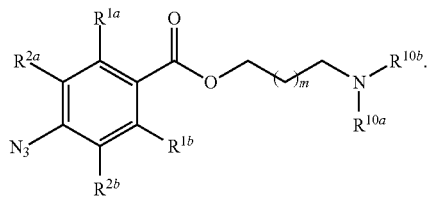

In some embodiments, the compound of Formula (I) has a structure of Formula (Id):

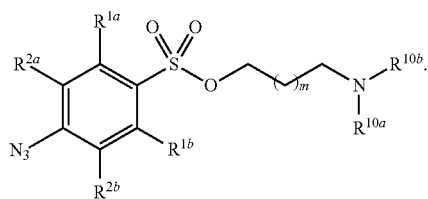

In some embodiments, $R^{10a}$ is hydrogen, optionally substituted $C_1$-$C_4$ alkyl, or optionally substituted aryl. In some embodiments, $R^{10a}$ is hydrogen. In some embodiments, $R^{10a}$ is optionally substituted $C_1$-$C_4$ alkyl. In some embodiments, $R^{10a}$ is $CH_3$. In some embodiments, $R^{10a}$ is $CH_2CH_3$. In some embodiments, $R^{10a}$ is optionally substituted aryl. In some embodiments, $R^{10a}$ is phenyl.

In some embodiments, the compound of Formula (I) has a structure of Formula (Ie):

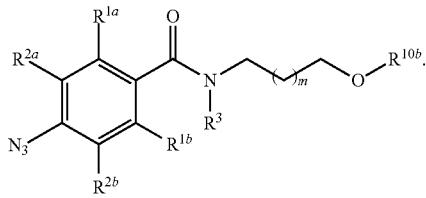

In some embodiments, the compound of Formula (I) has a structure of Formula (If):

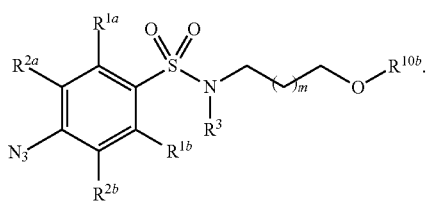

In some embodiments, the compound of Formula (I) has a structure of Formula (Ig):

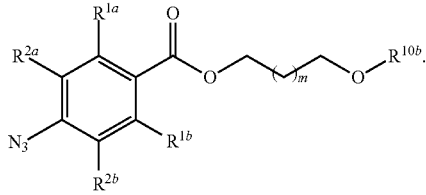

In some embodiments, the compound of Formula (I) has a structure of Formula (Ih):

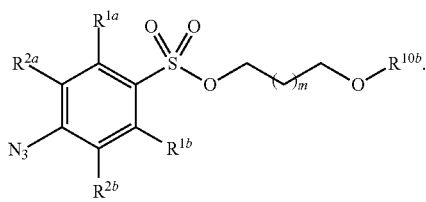

In some embodiments, $R^{10b}$ is —C(=O)—$C_2$-$C_6$alkenyl, —S(=O)—$C_2$-$C_6$alkenyl, or —S(=O)$_2$—$C_2$-$C_6$alkenyl. In some embodiments, $R^{10b}$ is —C(=O)—$C_2$-$C_6$alkenyl. In some embodiments, $R^{10b}$ is —(S=O)—$C_2$-$C_6$alkenyl. In some embodiments, $R^{10b}$ is —S(=O)$_2$—$C_2$-$C_6$alkenyl.

In some embodiments, the compound of Formula (I) is selected from:

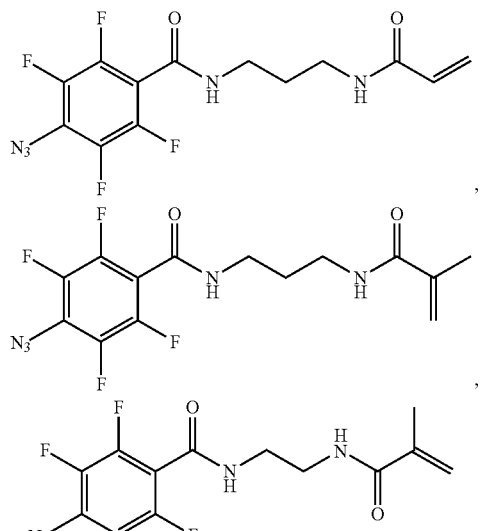

,

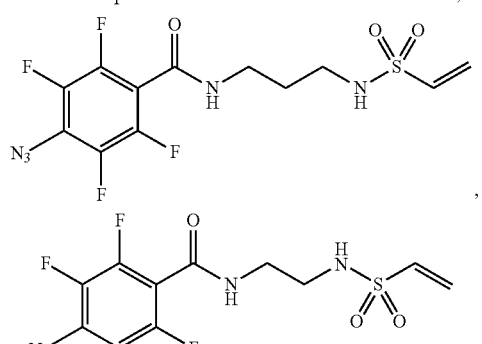

,

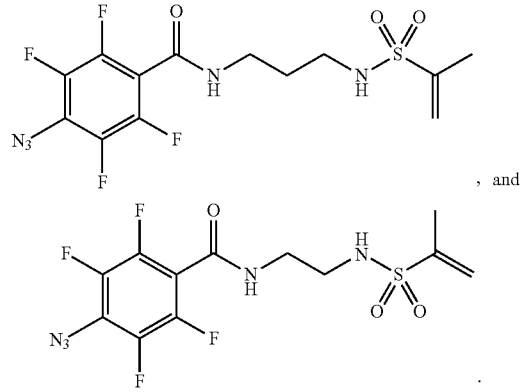

, and

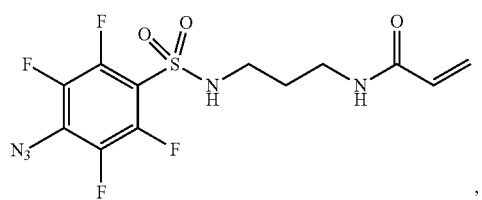

.

In some embodiments, the compound of Formula (I) is selected from:

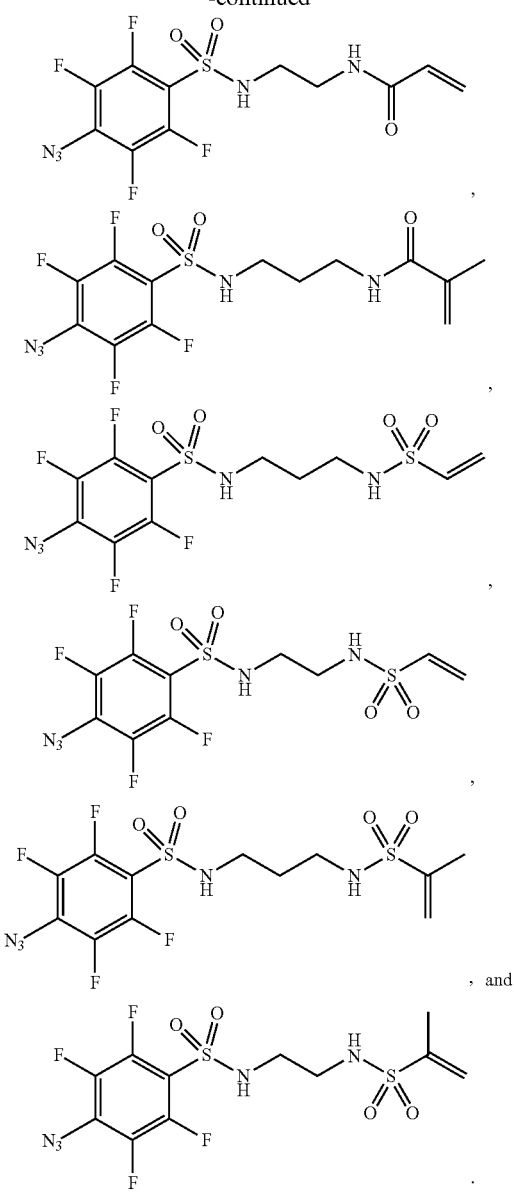
, 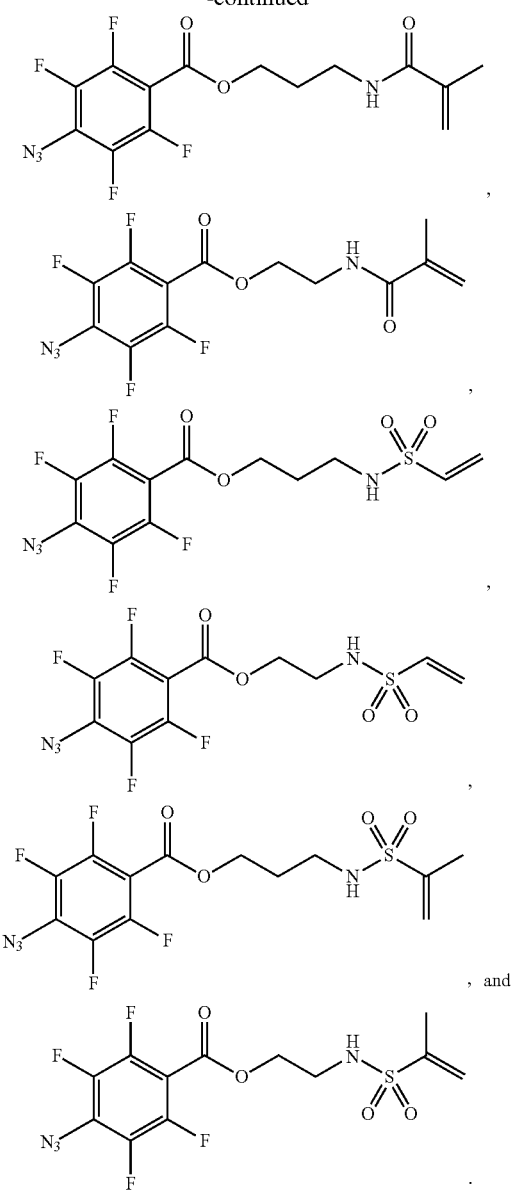
,
In some embodiments, the compound of Formula (I) is selected from:
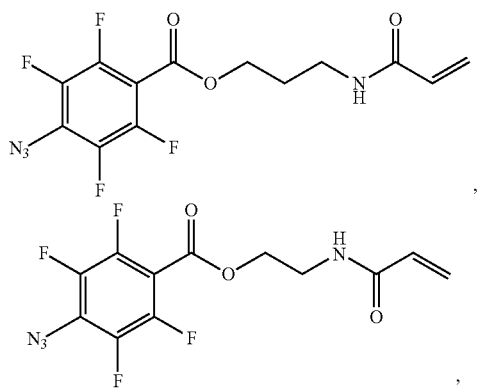
In some embodiments, the compound of Formula (I) is selected from:
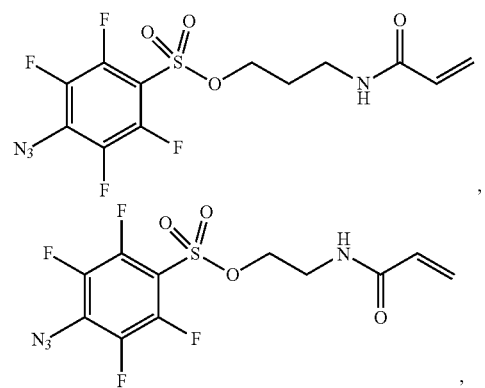

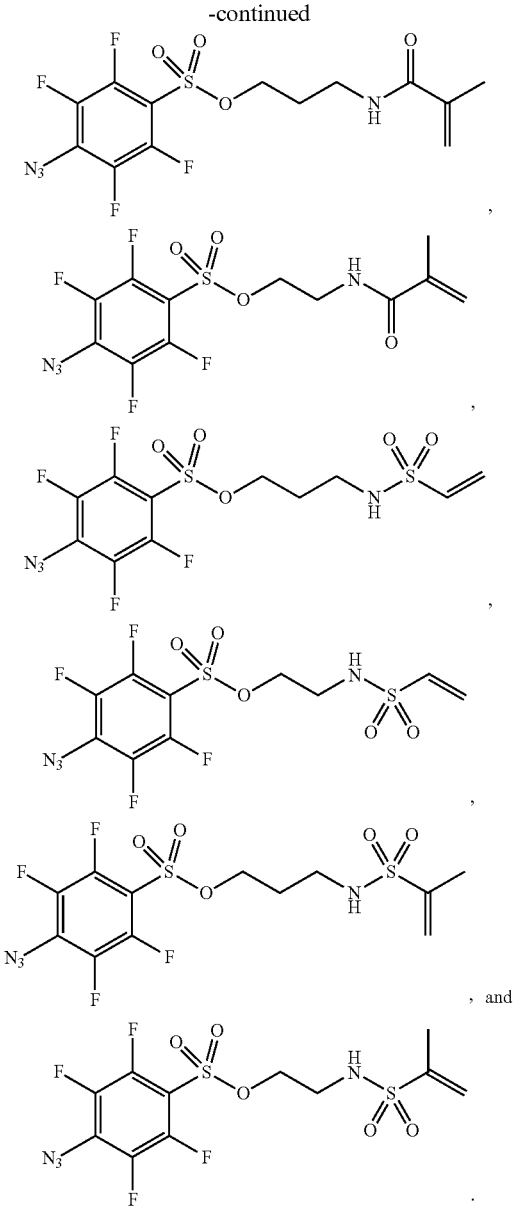
,
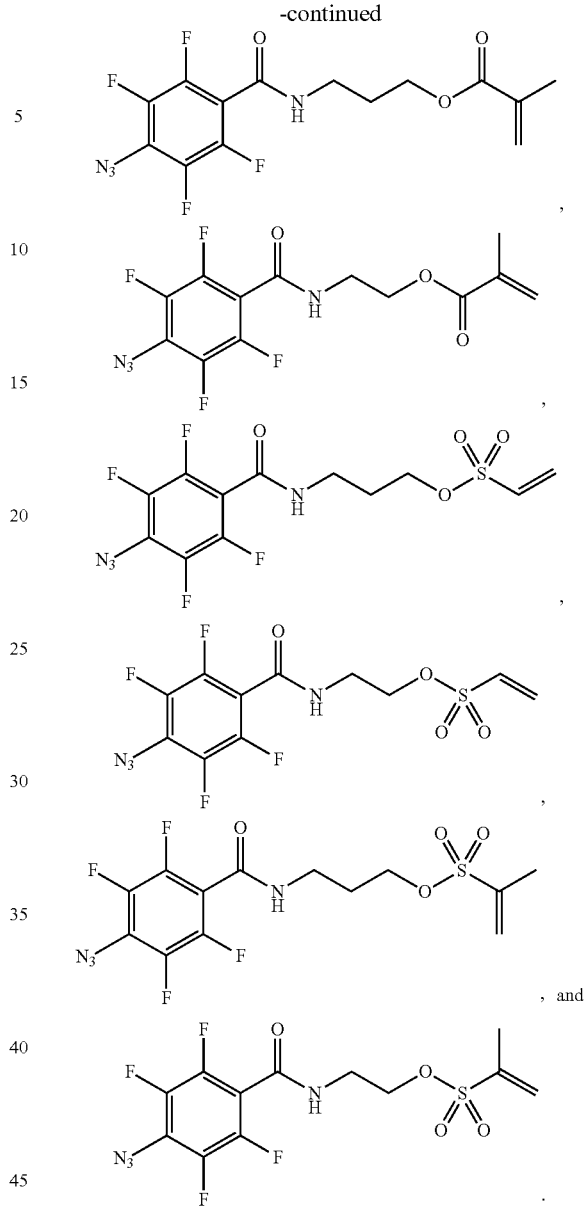
, and
In some embodiments, the compound of Formula (I) is selected from:
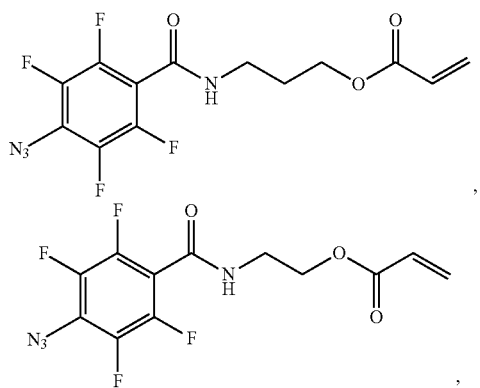
In some embodiments, the compound of Formula (I) is selected from:
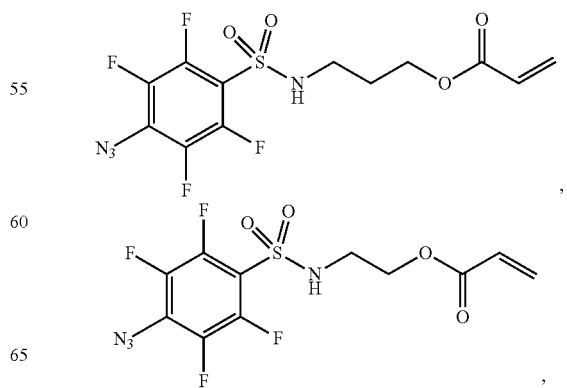

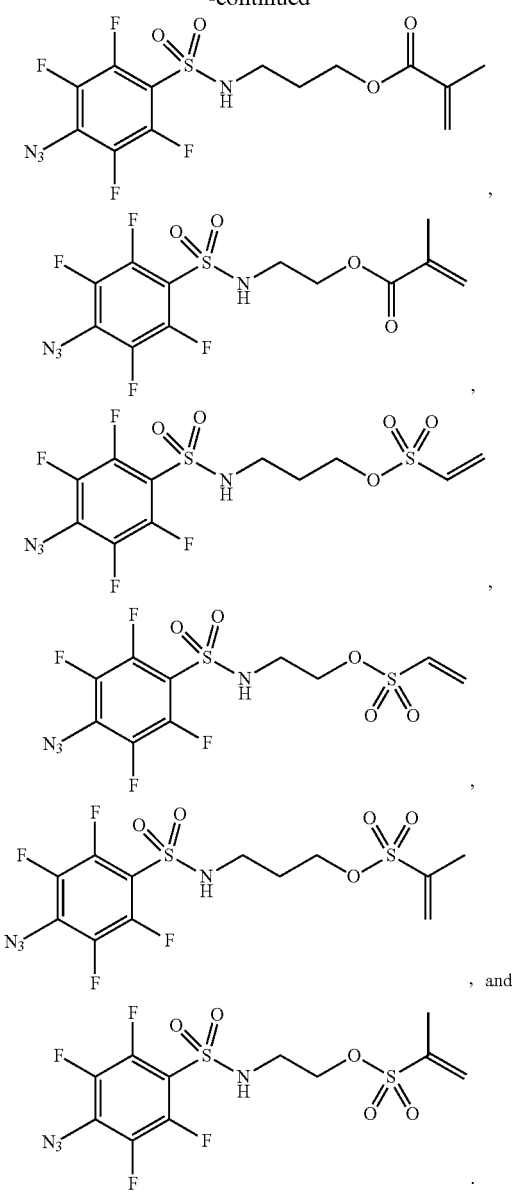
In some embodiments, the compound of Formula (I) is selected from:
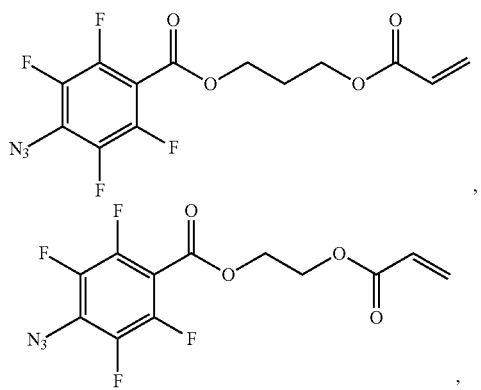
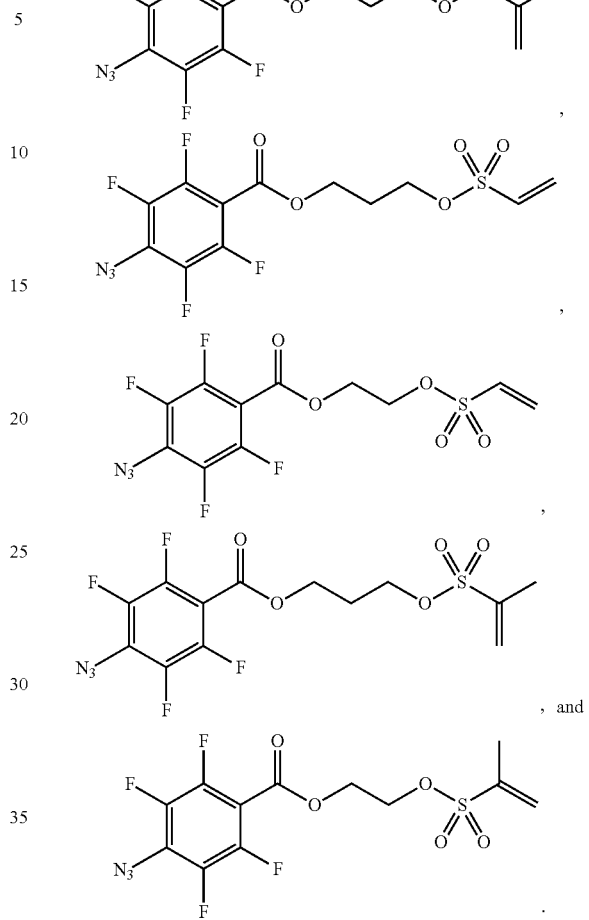
, and
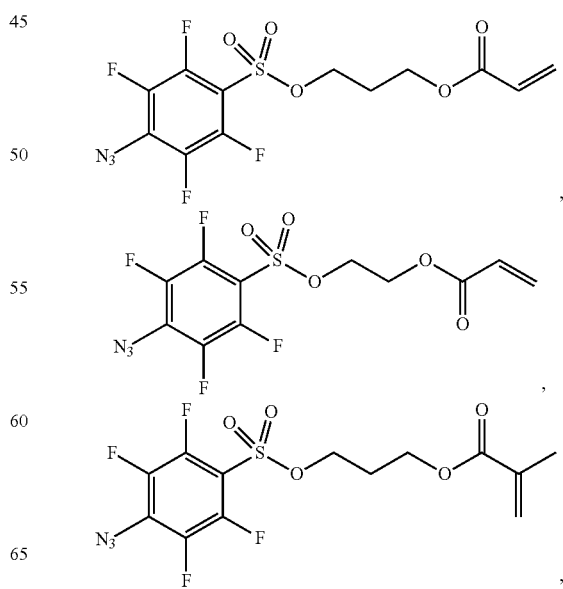
In some embodiments, the compound of Formula (I) is selected from:

-continued

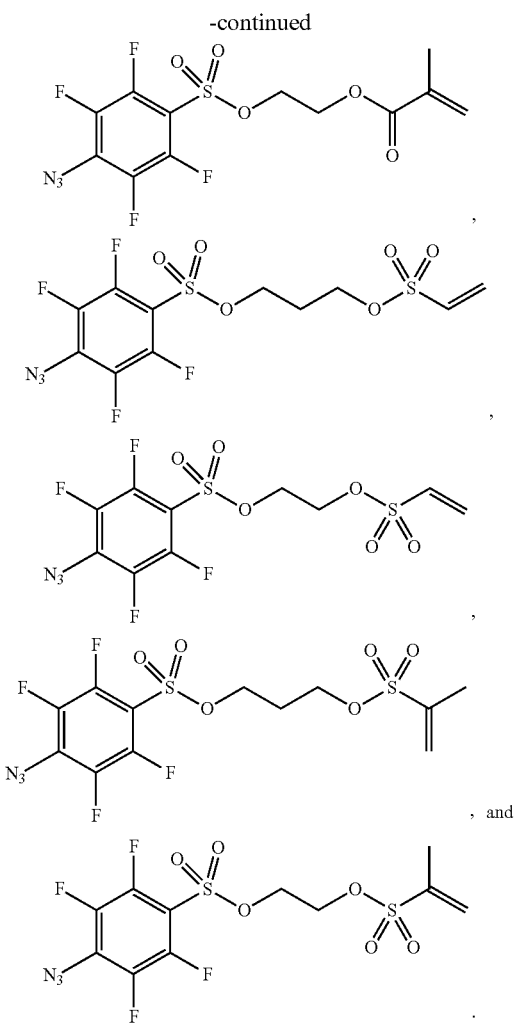
, and

.

In another aspect, described herein is a compound that has the structure of Formula (II) or a salt or solvate thereof:

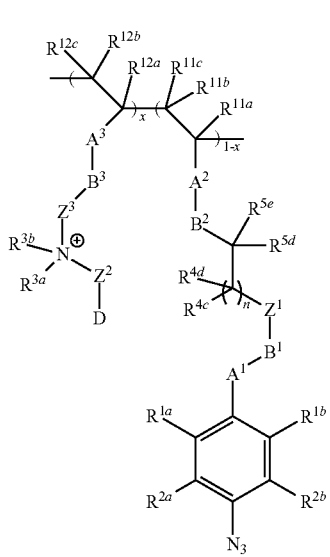

Formula (II)

wherein
each $R^{1a}$ and $R^{1b}$ is independently selected from hydrogen and halogen;
each $R^{2a}$ and $R^{2b}$ is independently selected from halogen, —CN, and optionally substituted $C_1$-$C_6$ fluoroalkyl;
each $A^1$, $A^2$, and $A^3$ is independently selected from —C(=O)—, —S(=O)—, —S(=O)$_2$—, and —S(=O)(=NR$^{3c}$)—;
each $B^1$, $B^2$, and $B^3$ is independently selected from —O— and —NR$^{3c}$—;
D is —S(=O)$_2$O$^-$, —S(=O)$_2$OR$^{9a}$, —C(=O)O$^-$, or —C(=O)OR$^{9a}$;
$Z^1$ is —(CR$^{6c}$R$^{6d}$)$_s$—;
$Z^2$ is —(CR$^{6c}$R$^{6d}$)$_t$—;
$Z^3$ is —(CR$^{6c}$R$^{6d}$)$_p$—;
each $R^{3a}$ and $R^{3b}$ is independently selected from hydrogen, optionally substituted $C_1$-$C_4$ alkyl, and optionally substituted benzyl;
each $R^{4c}$, $R^{4d}$, $R^{5d}$, $R^{5e}$, $R^{6c}$, and $R^{6d}$ is independently selected from hydrogen, halogen, —CN, —OR$^{9a}$, optionally substituted $C_1$-$C_4$ alkyl, optionally substituted $C_1$-$C_4$ fluoroalkyl, optionally substituted $C_2$-$C_6$ alkenyl, —NR$^{3c}$R$^{3d}$, —S(=O)$_2$O$^-$, —S(=O)$_2$OR$^{9a}$, —C(=O)O$^-$, and —C(=O)OR$^{9a}$;
each $R^{3c}$ and $R^{3d}$ is independently selected from hydrogen, optionally substituted $C_1$-$C_4$ alkyl, —X-optionally substituted $C_1$-$C_4$ alkyl, optionally substituted $C_2$-$C_6$ alkenyl, and optionally substituted aryl;
X is —C(=O)—, —S(=O)—, or —S(=O)$_2$—;
each $R^{9a}$, $R^{11a}$, $R^{11b}$, $R^{11c}$, $R^{12a}$, $R^{12b}$, and $R^{12c}$ is independently selected from hydrogen, optionally substituted $C_1$-$C_4$ alkyl, and optionally substituted aryl;
n is an integer selected from 0, 1, 2, 3, 4, 5, 6, 7, and 8;
s is an integer selected from 1, 2, 3, 4, or 5;
t is an integer selected from 1, 2, 3, 4, or 5;
p is an integer selected from 1, 2, 3, 4, or 5;
0<x<1; and
wherein the compound of Formula (II) is charged or zwitterionic.
In some embodiments, a compound of Formula (II) is not

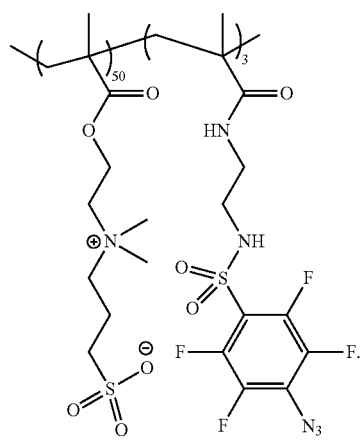

In some embodiments, x in Formula (II) is not about 0.9434.
In some embodiments, a compound of Formula (II) is not obtained by using 2 g sulfobetaine methacrylate monomer and 156 mg perfluorophenylazide methacrylamide monomer.
In some embodiments, each $R^{1a}$ and $R^{1b}$ is independently halogen. In some embodiments, each $R^{1a}$ and $R^{1b}$ is independently F or Cl. In some embodiments, each $R^{1a}$ and $R^{1b}$ is F. In some embodiments, each $R^{2a}$ and $R^{2b}$ is independently selected from halogen, —CN, and optionally substituted $C_1$-$C_6$ fluoroalkyl. In some embodiments, each $R^{2a}$ and $R^{2b}$ is independently selected from halogen, —CN, and —$CF_3$. In some embodiments, each $R^{2a}$ and $R^{2b}$ is independently selected from F, Cl, —CN, and —$CF_3$. In some embodiments, each $R^{2a}$ and $R^{2b}$ is independently halogen. In some embodiments, each $R^{2a}$ and $R^{2b}$ is F. In some embodiments, each $R^{2a}$ and $R^{2b}$ is —CN. In some embodiments, each $R^{2a}$ and $R^{2b}$ is independently $C_1$-$C_6$ fluoroalkyl. In some embodiments, each $R^{2a}$ and $R^{2b}$ is —$CF_3$.

In some embodiments, each $R^{1a}$, $R^{1b}$, $R^{2a}$, and $R^{2b}$ is F.

In some embodiments, A is —S(=O)$_2$—. In some embodiments, A is —C(=O)—.

In some embodiments, $A^2$ is —S(=O)$_2$—. In some embodiments, $A^2$ is —C(=O)—.

In some embodiments, $A^3$ is —S(=O)$_2$—. In some embodiments, $A^3$ is —C(=O)—.

In some embodiments, each $B^1$ and $B^2$ is —$NR^{3c}$—;

In some embodiments, each $R^{3c}$ is independently hydrogen, optionally substituted $C_1$-$C_4$ alkyl, or optionally substituted aryl. In some embodiments, $R^{3c}$ is hydrogen. In some embodiments, $R^{3c}$ is optionally substituted $C_1$-$C_4$ alkyl. In some embodiments, $R^{3c}$ is —$CH_3$. In some embodiments, $R^{3c}$ is optionally substituted aryl. In some embodiments, $R^{3c}$ is optionally substituted phenyl.

In some embodiments, $B^3$ is —O—.

In some embodiments, D is —S(=O)$_2$$OR^{9a}$ or —C(=O)$OR^{9a}$. In some embodiments, D is —S(=O)$_2$$OR^{9a}$. In some embodiments, D is —C(=O)$OR^{9a}$.

In some embodiments, $R^{9a}$ is hydrogen or —$CH_3$. In some embodiments, $R^{9a}$ is hydrogen. In some embodiments, $R^{9a}$ is —$CH_3$.

In some embodiments, D is —S(=O)$_2$O$^-$ or —C(=O)O$^-$. In some embodiments, D is —S(=O)$_2$O$^-$.

In some embodiments, D is —C(=O)O$^-$.

In some embodiments, each $R^{6a}$ and $R^{6d}$ is hydrogen.

In some embodiments, each $R^{3a}$ and $R^{3b}$ is independently hydrogen or $C_1$-$C_4$ alkyl. In some embodiments, each $R^{3a}$ and $R^{3b}$ is independently hydrogen or —$CH_3$. In some embodiments, each $R^{3a}$ and $R^{3b}$ is hydrogen. In some embodiments, each $R^{3a}$ and $R^{3b}$ is —$CH_3$.

In some embodiments, each $R^{4c}$ and $R^{4d}$ is independently is hydrogen or —$CH_3$. In some embodiments, each $R^{4c}$ and $R^{4d}$ is hydrogen. In some embodiments, each $R^{4c}$ and $R^{4d}$ is —$CH_3$. In some embodiments, $R^{4c}$ is hydrogen and $R^{4d}$ is —$CH_3$.

In some embodiments, each $R^{5d}$ and $R^{5e}$ is independently is hydrogen or —$CH_3$. In some embodiments, each $R^{5d}$ and $R^{5e}$ is hydrogen. In some embodiments, each $R^{5d}$ and $R^{5e}$ is —$CH_3$. In some embodiments, $R^{5d}$ is hydrogen and $R^{5e}$ is —$CH_3$.

In some embodiments, $R^{11a}$ is hydrogen or —$CH_3$. In some embodiments, $R^{11a}$ is hydrogen. In some embodiments, $R^{11a}$ is —$CH_3$.

In some embodiments, $R^{12a}$ is hydrogen or —$CH_3$. In some embodiments, $R^{12a}$ is hydrogen. In some embodiments, $R^{12a}$ is —$CH_3$.

In some embodiments, each $R^{11b}$, $R^{11c}$, $R^{2b}$, and $R^{12c}$ is hydrogen.

In some embodiments, n is 0, 1, 2, 3, 4, 5, or 6. In some embodiments, n is 0, 1, 2, 3, 4, or 5.

In some embodiments, n is 0. In some embodiments, n is 1. In some embodiments, n is 2. In some embodiments, n is 3. In some embodiments, n is 4. In some embodiments, n is 5.

In some embodiments, s is 1, 2, 3, or 4. In some embodiments, s is 1. In some embodiments, s is 2. In some embodiments, s is 3. In some embodiments, s is 4.

In some embodiments, t is 1, 2, 3, or 4. In some embodiments, t is 1. In some embodiments, t is 2. In some embodiments, t is 3. In some embodiments, t is 4.

In some embodiments, p is 1, 2, 3, or 4. In some embodiments, p is 1. In some embodiments, p is 2. In some embodiments, p is 3. In some embodiments, p is 4.

In some embodiments, x is more than 0. In some embodiments, x is less than 1. In some embodiments, x is 0.0000001-0.9999999. In some embodiments, x is 0.00001-0.99999. In some embodiments, x is 0.001-0.999. In some embodiments, x is 0.01-0.99. In some embodiments, x is 0.1-0.99. In some embodiments, x is 0.2-0.99. In some embodiments, x is 0.3-0.99. In some embodiments, x is 0.5-0.99. In some embodiments, x is 0.5-0.99. In some embodiments, x is 0.6-0.99. In some embodiments, x is 0.7-0.99. In some embodiments, x is 0.8-0.99. In some embodiments, x is 0.9-0.99. In some embodiments, x is 0.91-0.99. In some embodiments, x is 0.92-0.99.

In some embodiments, x is at least 0.0000001, at least 0.00001, at least 0.001, at least 0.01, at least 0.02, at least 0.03, at least 0.04, at least 0.05, at least 0.07, at least 0.09, at least 0.11, at least 0.15, at least 0.20, at least 0.23, at least 0.28, at least 0.35, at least 0.42, at least 0.5, at least 0.53, at least 0.58, at least 0.63, at least 0.67, at least 0.71, at least 0.75, at least 0.78, at least 0.79, at least 0.80, at least 0.81, at least 0.82, at least 0.83, at least 0.84, at least 0.85, at least 0.86, at least 0.87, at least 0.88, at least 0.89, at least 0.9, at least 0.91, at least 0.92, at least 0.93, at least 0.94, at least 0.95, at least 0.96, at least 0.97, at least 0.98, or at least 0.99.

In some embodiments, x is at most 0.9999999, at most 0.99999, at most 0.999, at most 0.99, at most 0.98, at most 0.97, at most 0.96, at most 0.95, at most 0.94, at most 0.93, at most 0.92, at most 0.91, at most 0.90, at most 0.89, at most 0.88, at most 0.87, at most 0.86, at most 0.85, at most 0.84, at most 0.83, at most 0.82, at most 0.81, at most 0.80, at most 0.79, at most 0.78, at most 0.77, at most 0.76, at most 0.75, at most 0.74, at most 0.70, at most 0.66, at most 0.62, at most 0.59, at most 0.56, at most 0.53, at most 0.50, at most 0.47, at most 0.43, at most 0.39, at most 0.34, at most 0.29, at most 0.25, at most 0.21, at most 0.18, at most 0.14, at most 0.10, at most 0.07, or at most 0.04.

In some embodiments, x is about 0.89 to about 0.999. In some embodiments, x is at least about 0.89. In some embodiments, x is at most about 0.999. In some embodiments, x is about 0.89 to about 0.9, about 0.89 to about 0.91, about 0.89 to about 0.92, about 0.89 to about 0.93, about 0.89 to about 0.94, about 0.89 to about 0.95, about 0.89 to about 0.96, about 0.89 to about 0.97, about 0.89 to about 0.98, about 0.89 to about 0.99, about 0.89 to about 0.999, about 0.9 to about 0.91, about 0.9 to about 0.92, about 0.9 to about 0.93, about 0.9 to about 0.94, about 0.9 to about 0.95, about 0.9 to about 0.96, about 0.9 to about 0.97, about 0.9 to about 0.98, about 0.9 to about 0.99, about 0.9 to about 0.999, about 0.91 to about 0.92, about 0.91 to about 0.93, about 0.91 to about 0.94, about 0.91 to about 0.95, about 0.91 to about 0.96, about 0.91 to about 0.97, about 0.91 to about 0.98, about 0.91 to about 0.99, about 0.91 to about 0.999, about 0.92 to about 0.93, about 0.92 to about 0.94, about 0.92 to about 0.95, about 0.92 to about 0.96, about 0.92 to about 0.97, about 0.92 to about 0.98, about 0.92 to about 0.99, about 0.92 to about 0.999, about 0.93 to about 0.94, about 0.93 to about 0.95, about 0.93 to about 0.96, about 0.93 to about 0.97, about 0.93 to about 0.98, about 0.93 to about 0.99, about 0.93 to about 0.999, about 0.94 to about 0.95, about 0.94 to about 0.96, about 0.94 to about 0.97, about 0.94 to about 0.98, about 0.94 to about 0.99, about 0.94 to about 0.999, about 0.95 to about 0.96, about 0.95 to about 0.97, about 0.95 to about 0.98, about 0.95 to about 0.99, about 0.95 to about 0.999, about 0.96 to about 0.97, about 0.96 to about 0.98, about 0.96 to about 0.99, about 0.96 to about 0.999, about 0.97 to about 0.98, about 0.97 to about 0.99, about 0.97 to about 0.999, about 0.98 to about 0.99, about 0.98 to about 0.999, or about 0.99 to about 0.999. In some embodiments, x is about 0.89, about 0.9, about 0.91, about 0.92, about 0.93, about 0.94, about 0.95, about 0.96, about 0.97, about 0.98, about 0.99, or about 0.999.

In another aspect, described herein is a compound that has the structure of Formula (III) or a salt or solvate thereof:

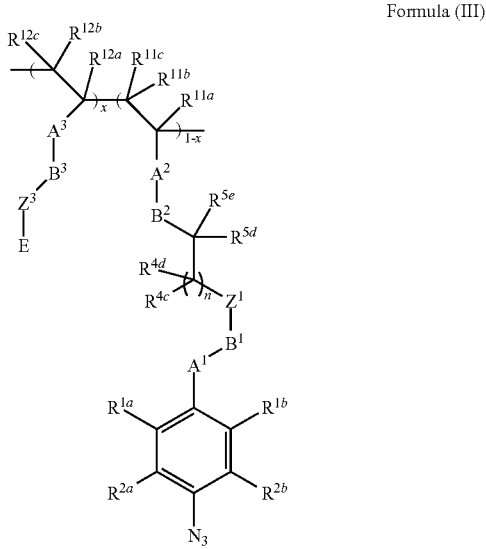

Formula (III)

wherein
each $R^{1a}$ and $R^{1b}$ is independently selected from hydrogen and halogen;
each $R^{2a}$ and $R^{2b}$ is independently selected from halogen, —CN, and optionally substituted $C_1$-$C_6$ fluoroalkyl;
each $A^1$, $A^2$, and $A^3$ is independently selected from —C(=O)—, —S(=O)—, —S(=O)$_2$—, and —S(=O)(=NR$^{3c}$)—;
each $B^1$, $B^2$, and $B^3$ is independently selected from —O— and —NR$^{3c}$—;
$Z^1$ is —(CR$^{6c}$R$^{6d}$)$_s$—;
$Z^2$ is —(CR$^{6c}$R$^{6d}$)$_t$—;
E is —CN, —OR$^{9a}$, —NR$^{9a}$R$^{9b}$, —NR$^{9a}$R$^{9b}$R$^{9c+}$ optionally substituted $C_1$-$C_4$ alkyl, optionally substituted $C_1$-$C_6$ fluoroalkyl, —S(=O)$_2$O$^-$, —S(=O)$_2$OR$^{9a}$, —C(=O)O$^-$, or —C(=O)OR$^{9a}$; each R$^{4c}$, R$^{4d}$, R$^{5d}$, R$^{5e}$, R$^{6c}$, and R$^{6d}$ is independently selected from hydrogen, halogen, —CN, —OR$^{9a}$, optionally substituted $C_1$-$C_4$ alkyl, optionally substituted $C_1$-$C_4$ fluoroalkyl, optionally substituted $C_2$-$C_6$ alkenyl, —NR$^{3c}$R$^{3d}$, —S(=O)$_2$O$^-$, —S(=O)$_2$OR$^{9a}$, —C(=O)O$^-$, and —C(=O)OR$^{9a}$;
each R$^{3c}$ and R$^{3d}$ is independently selected from hydrogen, optionally substituted $C_1$-$C_4$ alkyl, —X-optionally substituted $C_1$-$C_4$ alkyl, optionally substituted $C_2$-$C_6$ alkenyl, and optionally substituted aryl;

X is —C(=O)—, —S(=O)—, or —S(=O)$_2$—;
each R$^{9a}$, R$^{9b}$, R$^{9c}$, R$^{11a}$, R$^{11b}$, R$^{11c}$, R$^{12a}$, R$^{12b}$, and R$^{12c}$ is independently selected from hydrogen, optionally substituted $C_1$-$C_4$ alkyl, and optionally substituted aryl;
n is an integer selected from 0, 1, 2, 3, 4, 5, 6, 7, and 8;
s is an integer selected from 1, 2, 3, 4, or 5;
t is an integer selected from 1, 2, 3, 4, or 5; and
0<x<1.

In some embodiments, a compound of Formula (III) is charged or zwitterionic. In some embodiments, a compound of Formula (III) comprises a positively charged repeating unit. In some embodiments a compound of Formula (III) comprises a negatively charged repeating unit. In some embodiments, a compound of Formula (III) comprises positively charged repeating units and negatively charged repeating units. In some embodiments, the ratio of positively charged repeating units and negatively charged repeating units in a compound of Formula (III) is from about 10:1 to about 1:10. In some embodiments, the ratio of positively charged repeating units and negatively charged repeating units in a compound of Formula (III) is from about 5:1 to about 1:5 In some embodiments, the ratio of positively charged repeating units and negatively charged repeating units in a compound of Formula (III) is from about 2:1 to about 1:2. In some embodiments, the ratio of positively charged repeating units and negatively charged repeating units in a compound of Formula (III) is about 1:1.

In some embodiments, each $R^{1a}$ and $R^{1b}$ is independently halogen. In some embodiments, each $R^{1a}$ and $R^{1b}$ is independently F or Cl. In some embodiments, each $R^{1a}$ and $R^{1b}$ is F. In some embodiments, each $R^{2a}$ and $R^{2b}$ is independently selected from halogen, —CN, and optionally substituted $C_1$-$C_6$ fluoroalkyl. In some embodiments, each $R^{2a}$ and $R^{2b}$ is independently selected from halogen, —CN, and —CF$_3$. In some embodiments, each $R^{2a}$ and $R^{2b}$ is independently selected from F, Cl, —CN, and —CF$_3$. In some embodiments, each $R^{2a}$ and $R^{2b}$ is independently halogen. In some embodiments, each $R^{2a}$ and $R^{2b}$ is F. In some embodiments, each $R^{2a}$ and $R^{2b}$ is —CN. In some embodiments, each $R^{2a}$ and $R^{2b}$ is independently $C_1$-$C_6$ fluoroalkyl. In some embodiments, each $R^{2a}$ and $R^{2b}$ is —CF$_3$.

In some embodiments, each $R^{1a}$, $R^{1b}$, $R^{2a}$, and $R^{2b}$ is F.
In some embodiments, A is —S(=O)$_2$—. In some embodiments, A is —C(=O)—.
In some embodiments, $A^2$ is —S(=O)$_2$—. In some embodiments, $A^2$ is —C(=O)—.
In some embodiments, $A^3$ is —S(=O)$_2$—. In some embodiments, $A^3$ is —C(=O)—.
In some embodiments, each $B^1$, $B^2$, and $B^3$ is —NR$^{3c}$—.
In some embodiments, each R$^{3c}$ is independently hydrogen, optionally substituted $C_1$-$C_4$ alkyl, or optionally substituted aryl. In some embodiments, R$^{3c}$ is hydrogen. In some embodiments, R$^{3c}$ is optionally substituted $C_1$-$C_4$ alkyl. In some embodiments, R$^{3c}$ is —CH$_3$. In some embodiments, R$^{3c}$ is optionally substituted aryl. In some embodiments, R$^{3c}$ is optionally substituted phenyl.

In some embodiments, E is —NR$^{9a}$R$^{9b}$R$^{9c+}$ or —S(=O)$_2$OR$^{9a}$.
In some embodiments, E is —NR$^{9a}$R$^{9b}$R$^{9c+}$. In some embodiments, each R$^{9a}$, R$^{9b}$, and R$^{9c}$ is independently hydrogen or $C_1$-$C_4$ alkyl. In some embodiments, each R$^{9a}$, R$^{9b}$, and R$^{9c}$ is independently hydrogen or —CH$_3$. In some embodiments, R$^{9a}$ is hydrogen. In some embodiments, R$^{9a}$ is —CH$_3$. In some embodiments, R$^{9b}$ is hydrogen. In some embodiments, R$^{9b}$ is —CH$_3$. In some embodiments, R$^{9c}$ is hydrogen. In some embodiments, R$^{9c}$ is —CH$_3$.

In some embodiments, E is —S(=O)$_2$OR$^{9a}$. In some embodiments, each R$^{9a}$ is hydrogen or —CH$_3$. In some embodiments, R$^{9a}$ is hydrogen. In some embodiments, R$^{9a}$ is —CH$_3$.

In some embodiments, E is —S(=O)$_2$O$^-$ or —C(=O)O$^-$. In some embodiments, E is —S(=O)$_2$O$^-$.

In some embodiments, E is —C(=O)O$^-$.

In some embodiments, each R$^{6c}$ and R$^{6d}$ is independently selected from hydrogen and —CH$_3$.

In some embodiments, each R$^{6c}$ and R$^{6d}$ is hydrogen. In some embodiments, each R$^{6c}$ and R$^{6d}$ is —CH$_3$.

In some embodiments, each R$^{4c}$ and R$^{4d}$ is independently is hydrogen or —CH$_3$. In some embodiments, each R$^{4c}$ and R$^{4d}$ is hydrogen. In some embodiments, each R$^{4c}$ and R$^{4d}$ is —CH$_3$. In some embodiments, R$^{4c}$ is hydrogen and R$^{4d}$ is —CH$_3$.

In some embodiments, each R$^{5d}$ and R$^{5e}$ is independently is hydrogen or —CH$_3$. In some embodiments, each R$^{5d}$ and R$^{5e}$ is hydrogen. In some embodiments, each R$^{5d}$ and R$^{5e}$ is —CH$_3$. In some embodiments, R$^{5d}$ is hydrogen and R$^{5e}$ is —CH$_3$.

In some embodiments, R$^{11a}$ is hydrogen or —CH$_3$. In some embodiments, R$^{11a}$ is hydrogen. In some embodiments, R$^{11a}$ is —CH$_3$.

In some embodiments, R$^{12a}$ is hydrogen or —CH$_3$. In some embodiments, R$^{12a}$ is hydrogen. In some embodiments, R$^{12a}$ is —CH$_3$.

In some embodiments, each R$^{11b}$, R$^{11c}$, R$^{12b}$, and R$^{12c}$ is hydrogen.

In some embodiments, n is 0, 1, 2, 3, 4, 5, or 6. In some embodiments, n is 0, 1, 2, 3, 4, or 5.

In some embodiments, n is 0. In some embodiments, n is 1. In some embodiments, n is 2. In some embodiments, n is 3. In some embodiments, n is 4. In some embodiments, n is 5.

In some embodiments, s is 1, 2, 3, or 4. In some embodiments, s is 1. In some embodiments, s is 2. In some embodiments, s is 3. In some embodiments, s is 4.

In some embodiments, t is 1, 2, 3, or 4. In some embodiments, t is 1. In some embodiments, t is 2. In some embodiments, t is 3. In some embodiments, t is 4.

In some embodiments, x is more than 0. In some embodiments, x is less than 1. In some embodiments, x is 0.0000001-0.9999999. In some embodiments, x is 0.00001-0.99999. In some embodiments, x is 0.001-0.999. In some embodiments, x is 0.01-0.99. In some embodiments, x is 0.1-0.99. In some embodiments, x is 0.2-0.99. In some embodiments, x is 0.3-0.99. In some embodiments, x is 0.5-0.99. In some embodiments, x is 0.5-0.99. In some embodiments, x is 0.6-0.99. In some embodiments, x is 0.7-0.99. In some embodiments, x is 0.8-0.99. In some embodiments, x is 0.9-0.99. In some embodiments, x is 0.91-0.99. In some embodiments, x is 0.92-0.99.

In some embodiments, x is at least 0.0000001, at least 0.00001, at least 0.001, at least 0.01, at least 0.02, at least 0.03, at least 0.04, at least 0.05, at least 0.07, at least 0.09, at least 0.11, at least 0.15, at least 0.20, at least 0.23, at least 0.28, at least 0.35, at least 0.42, at least 0.5, at least 0.53, at least 0.58, at least 0.63, at least 0.67, at least 0.71, at least 0.75, at least 0.78, at least 0.79, at least 0.80, at least 0.81, at least 0.82, at least 0.83, at least 0.84, at least 0.85, at least 0.86, at least 0.87, at least 0.88, at least 0.89, at least 0.9, at least 0.91, at least 0.92, at least 0.93, at least 0.94, at least 0.95, at least 0.96, at least 0.97, at least 0.98, or at least 0.99.

In some embodiments, x is at most 0.9999999, at most 0.99999, at most 0.999, at most 0.99, at most 0.98, at most 0.97, at most 0.96, at most 0.95, at most 0.94, at most 0.93, at most 0.92, at most 0.91, at most 0.90, at most 0.89, at most 0.88, at most 0.87, at most 0.86, at most 0.85, at most 0.84, at most 0.83, at most 0.82, at most 0.81, at most 0.80, at most 0.79, at most 0.78, at most 0.77, at most 0.76, at most 0.75, at most 0.74, at most 0.70, at most 0.66, at most 0.62, at most 0.59, at most 0.56, at most 0.53, at most 0.50, at most 0.47, at most 0.43, at most 0.39, at most 0.34, at most 0.29, at most 0.25, at most 0.21, at most 0.18, at most 0.14, at most 0.10, at most 0.07, or at most 0.04.

In some embodiments, x is about 0.89 to about 0.999. In some embodiments, x is at least about 0.89. In some embodiments, x is at most about 0.999. In some embodiments, x is about 0.89 to about 0.9, about 0.89 to about 0.91, about 0.89 to about 0.92, about 0.89 to about 0.93, about 0.89 to about 0.94, about 0.89 to about 0.95, about 0.89 to about 0.96, about 0.89 to about 0.97, about 0.89 to about 0.98, about 0.89 to about 0.99, about 0.89 to about 0.999, about 0.9 to about 0.91, about 0.9 to about 0.92, about 0.9 to about 0.93, about 0.9 to about 0.94, about 0.9 to about 0.95, about 0.9 to about 0.96, about 0.9 to about 0.97, about 0.9 to about 0.98, about 0.9 to about 0.99, about 0.9 to about 0.999, about 0.91 to about 0.92, about 0.91 to about 0.93, about 0.91 to about 0.94, about 0.91 to about 0.95, about 0.91 to about 0.96, about 0.91 to about 0.97, about 0.91 to about 0.98, about 0.91 to about 0.99, about 0.91 to about 0.999, about 0.92 to about 0.93, about 0.92 to about 0.94, about 0.92 to about 0.95, about 0.92 to about 0.96, about 0.92 to about 0.97, about 0.92 to about 0.98, about 0.92 to about 0.99, about 0.92 to about 0.999, about 0.93 to about 0.94, about 0.93 to about 0.95, about 0.93 to about 0.96, about 0.93 to about 0.97, about 0.93 to about 0.98, about 0.93 to about 0.99, about 0.93 to about 0.999, about 0.94 to about 0.95, about 0.94 to about 0.96, about 0.94 to about 0.97, about 0.94 to about 0.98, about 0.94 to about 0.99, about 0.94 to about 0.999, about 0.95 to about 0.96, about 0.95 to about 0.97, about 0.95 to about 0.98, about 0.95 to about 0.99, about 0.95 to about 0.999, about 0.96 to about 0.97, about 0.96 to about 0.98, about 0.96 to about 0.99, about 0.96 to about 0.999, about 0.97 to about 0.98, about 0.97 to about 0.99, about 0.97 to about 0.999, about 0.98 to about 0.99, about 0.98 to about 0.999, or about 0.99 to about 0.999. In some embodiments, x is about 0.89, about 0.9, about 0.91, about 0.92, about 0.93, about 0.94, about 0.95, about 0.96, about 0.97, about 0.98, about 0.99, or about 0.999.

In another aspect, described herein is a copolymer comprising:

a) a repeating unit of Formula (VII):

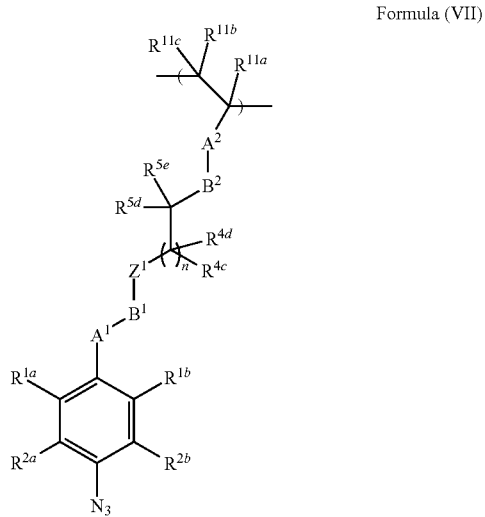

Formula (VII)

wherein
each $R^{1a}$ and $R^{1b}$ is independently selected from hydrogen and halogen;
each $R^{2a}$ and $R^{2b}$ is independently selected from halogen, —CN, and optionally substituted $C_1$-$C_6$ fluoroalkyl;
each $A^1$ and $A^2$ is independently selected from —C(=O)—, —S(=O)—, —S(=O)$_2$—, and —S(=O)(=NR$^{3c}$)—;
each $B^1$ and $B^2$ is independently selected from —O— and —NR$^{3c}$—;
$Z^1$ is —(CR$^{6c}$R$^{6d}$)$_s$—;
each $R^{4c}$, $R^{4d}$, $R^{5d}$, $R^{5e}$, $R^{6c}$, and $R^{6d}$ is independently selected from hydrogen, halogen, —CN, —OR$^{9a}$, optionally substituted $C_1$-$C_4$ alkyl, optionally substituted $C_1$-$C_4$ fluoroalkyl, optionally substituted $C_2$-$C_6$ alkenyl, —NR$^{3c}$R$^{3d}$, —S(=O)$_2$O$^-$, —S(=O)$_2$OR$^{9a}$, —C(=O)O$^-$, and —C(=O)OR$^{9a}$;
each $R^{3c}$ and $R^{3d}$ is independently selected from hydrogen, optionally substituted $C_1$-$C_4$ alkyl, —X-optionally substituted $C_1$-$C_4$ alkyl, optionally substituted $C_2$-$C_6$ alkenyl, and optionally substituted aryl;
X is —C(=O)—, —S(=O)—, or —S(=O)$_2$—;
each $R^{9a}$, $R^{11a}$, $R^{11b}$, and $R^{11c}$ is independently selected from hydrogen, optionally substituted $C_1$-$C_4$ alkyl, and optionally substituted aryl;
n is an integer selected from 0, 1, 2, 3, 4, 5, 6, 7, and 8; and
s is an integer selected from 1, 2, 3, 4, and 5;
b) a repeating unit of Formula (VIII):

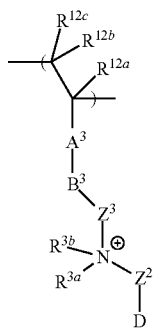

Formula (VIII)

wherein,
$A^3$ is —C(=O)—, —S(=O)—, —S(=O)$_2$—, or —S(=O)(=NR$^{3c}$)—;
$B^3$ is —O— or —NR$^{3c}$—;
D is —S(=O)$_2$O$^-$, —S(=O)$_2$OR$^{9a}$, —C(=O)O$^-$, or —C(=O)OR$^{9a}$;
$Z^2$ is —(CR$^{6c}$R$^{6d}$)$_t$—;
$Z^3$ is —(CR$^{6c}$R$^{6d}$)$_p$—;
each $R^{3a}$ and $R^{3b}$ is independently selected from hydrogen, optionally substituted $C_1$-$C_4$ alkyl, and optionally substituted benzyl;
each $R^{6c}$ and $R^{6d}$ is independently selected from hydrogen, halogen, —CN, —OR$^{9a}$, optionally substituted $C_1$-$C_4$ alkyl, optionally substituted $C_1$-$C_4$ fluoroalkyl, optionally substituted $C_2$-$C_6$ alkenyl, —NR$^{3c}$R$^{3d}$, —S(=O)$_2$O$^-$, —S(=O)$_2$OR$^{9a}$, —C(=O)O$^-$, and —C(=O)OR$^{9a}$;
each $R^{3c}$ and $R^{3d}$ is independently selected from hydrogen, optionally substituted $C_1$-$C_4$ alkyl, —X-optionally substituted $C_1$-$C_4$ alkyl, optionally substituted $C_2$-$C_6$ alkenyl, and optionally substituted aryl;

X is —C(=O)—, —S(=O)—, or —S(=O)$_2$—;
each $R^{9a}$, $R^{12a}$, $R^{12b}$, and $R^{12c}$ is independently selected from hydrogen, optionally substituted $C_1$-$C_4$ alkyl, and optionally substituted aryl;
t is an integer selected from 1, 2, 3, 4, or 5;
p is an integer selected from 1, 2, 3, 4, or 5; and
wherein the repeating unit of Formula (VIII) is charged or zwitterionic; and
c) a repeating unit of Formula (IX):

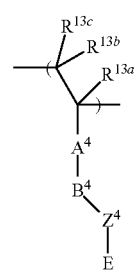

Formula (IX)

$A^4$ is —C(=O)—, —S(=O)—, —S(=O)$_2$—, or —S(=O)(=NR$^{3c}$)—;
$B^4$ is —O— or —NR$^{3c}$—;
$Z^4$ is —(CR$^{6c}$R$^{6d}$)$_k$—;
E is —CN, —OR$^{9a}$, —NR$^{9a}$R$^{9b}$, —NR$^{9a}$R$^{9b}$R$^{9c}$, optionally substituted $C_1$-$C_4$ alkyl, optionally substituted $C_1$-$C_6$ fluoroalkyl, —S(=O)$_2$O$^-$, —S(=O)$_2$OR$^{9a}$, —C(=O)O$^-$, or —C(=O)OR$^{9a}$;
each $R^{6c}$, and $R^{6d}$ is independently selected from hydrogen, halogen, —CN, —OR$^{9a}$, optionally substituted $C_1$-$C_4$ alkyl, optionally substituted $C_1$-$C_4$ fluoroalkyl, optionally substituted $C_2$-$C_6$ alkenyl, —NR$^{3c}$R$^{3d}$, —S(=O)$_2$O$^-$, —S(=O)$_2$OR$^{9a}$, —C(=O)O$^-$, and —C(=O)OR$^{9a}$;
each $R^{3c}$ and $R^{3d}$ is independently selected from hydrogen, optionally substituted $C_1$-$C_4$ alkyl, —X-optionally substituted $C_1$-$C_4$ alkyl, optionally substituted $C_2$-$C_6$ alkenyl, and optionally substituted aryl;
X is —C(=O)—, —S(=O)—, or —S(=O)$_2$—;
each $R^{9a}$, $R^{9b}$, $R^{9c}$, $R^{13a}$, $R^{13b}$, and $R^{13c}$ is independently selected from hydrogen, optionally substituted $C_1$-$C_4$ alkyl, and optionally substituted aryl; and
k is an integer selected from 1-10.

In some embodiments, the repeating unit of Formula (IX) is charged or zwitterionic.

In some embodiments, each $R^{1a}$ and $R^{1b}$ is independently halogen. In some embodiments, each $R^{1a}$ and $R^{1b}$ is independently F or Cl. In some embodiments, each $R^{1a}$ and $R^{1b}$ is F. In some embodiments, each $R^{2a}$ and $R^{2b}$ is independently selected from halogen, —CN, and optionally substituted $C_1$-$C_6$ fluoroalkyl. In some embodiments, each $R^{2a}$ and $R^{2b}$ is independently selected from halogen, —CN, and —CF$_3$. In some embodiments, each $R^{2a}$ and $R^{2b}$ is independently selected from F, Cl, —CN, and —CF$_3$. In some embodiments, each $R^{2a}$ and $R^{2b}$ is independently halogen. In some embodiments, each $R^{2a}$ and $R^{2b}$ is F. In some embodiments, each $R^{2a}$ and $R^{2b}$ is —CN. In some embodiments, each $R^{2a}$ and $R^{2b}$ is independently $C_1$-$C_6$ fluoroalkyl. In some embodiments, each $R^{2a}$ and $R^{2b}$ is —CF$_3$. In some embodiments, each $R^{1a}$, $R^{1b}$, $R^{2a}$, and $R^{2b}$ is F.

In some embodiments, A is —S(=O)$_2$—. In some embodiments, $A^2$ is —C(=O)—. In some embodiments, $A^2$ is —S(=O)$_2$—. In some embodiments, $A^2$ is —C(=O)—. In some embodiments, $A^3$ is —S(=O)$_2$—. In some embodiments, $A^3$ is —C(=O)—. In some embodiments, $A^4$ is —S(=O)$_2$—. In some embodiments, $A^4$ is —C(=O)—. In some embodiments, A is —S(=O)$_2$— and each $A^2$, $A^3$, and $A^4$ is —C(=O)—. In some embodiments, each $A^1$, $A^2$, $A^3$, and $A^4$ is —C(=O)—.

In some embodiments, each $B^1$, $B^2$, and $B^3$ is independently —O— or —NR$^{3c}$—. In some embodiments, $B^1$ is —O—. In some embodiments, $B^1$ is —NR$^{3c}$—. In some embodiments, $B^2$ is —O—. In some embodiments, $B^2$ is —NR$^{3c}$—. In some embodiments, $B^3$ is —O—. In some embodiments, $B^3$ is —NR$^{3c}$—. In some embodiments, $B^4$ is —O—. In some embodiments, $B^4$ is —NR$^{3c}$.

In some embodiments, each $R^{3c}$ is independently hydrogen, optionally substituted $C_1$-$C_4$ alkyl, or optionally substituted aryl. In some embodiments, $R^{3c}$ is hydrogen. In some embodiments, $R^{3c}$ is optionally substituted $C_1$-$C_4$ alkyl. In some embodiments, $R^{3c}$ is —CH$_3$. In some embodiments, each $R^{3c}$ is hydrogen or —CH$_3$. In some embodiments, $R^{3c}$ is optionally substituted aryl. In some embodiments, $R^{3c}$ is optionally substituted phenyl.

In some embodiments, D is —S(=O)$_2$OR$^{9a}$ or —C(=O)OR$^{9a}$. In some embodiments, D is —S(=O)$_2$OR$^{9a}$. In some embodiments, D is —C(=O)OR$^{9a}$. In some embodiments, $R^{9a}$ is hydrogen or —CH$_3$. In some embodiments, $R^{9a}$ is hydrogen. In some embodiments, $R^{9a}$ is —CH$_3$.

In some embodiments, D is —S(=O)$_2$O$^-$ or —C(=O)O$^-$. In some embodiments, D is —S(=O)$_2$O$^-$.

In some embodiments, D is —C(=O)O$^-$.

In some embodiments, E is —NR$^{9a}$R$^{9b}$R$^{9c+}$ or —S(=O)$_2$OR$^{9a}$. In some embodiments, E is —NR$^{9a}$R$^{9b}$R$^{9c+}$ or —C(=O)OR$^{9a}$.

In some embodiments, E is —NR$^{9a}$R$^{9b}$R$^{9c+}$. In some embodiments, each $R^{9a}$, $R^{9b}$, and $R^{9c}$ is independently hydrogen or $C_1$-$C_4$ alkyl. In some embodiments, each $R^{9a}$, $R^{9b}$, and $R^{9c}$ is independently hydrogen or —CH$_3$. In some embodiments, $R^{9a}$ is hydrogen. In some embodiments, $R^{9a}$ is —CH$_3$. In some embodiments, $R^{9b}$ is hydrogen. In some embodiments, $R^{9b}$ is —CH$_3$. In some embodiments, $R^{9c}$ is hydrogen. In some embodiments, $R^{9c}$ is —CH$_3$.

In some embodiments, E is —S(=O)$_2$OR$^{9a}$. In some embodiments, E is —C(=O)OR$^{9a}$. In some embodiments, each $R^{9a}$ is hydrogen or —CH$_3$. In some embodiments, $R^{9a}$ is hydrogen. In some embodiments, $R^{9a}$ is —CH$_3$.

In some embodiments, E is —S(=O)$_2$O$^-$ or —C(=O)O$^-$. In some embodiments, E is —S(=O)$_2$O$^-$.

In some embodiments, E is —C(=O)O$^-$.

In some embodiments, each $R^{3a}$ and $R^{3b}$ is independently hydrogen or $C_1$-$C_4$ alkyl. In some embodiments, each $R^{3a}$ and $R^{3b}$ is independently hydrogen or —CH$_3$. In some embodiments, each $R^{3a}$ and $R^{3b}$ is hydrogen. In some embodiments, each $R^{3a}$ and $R^{3b}$ is —CH$_3$.

In some embodiments, each $R^{4c}$ and $R^{4d}$ is independently selected from hydrogen and —CH$_3$.

In some embodiments, each $R^{4c}$ and $R^{4d}$ is hydrogen.

In some embodiments, each $R^{5d}$ and $R^{5e}$ is independently selected from hydrogen and —CH$_3$.

In some embodiments, each $R^{5d}$ and $R^{5e}$ is hydrogen.

In some embodiments, each $R^{4c}$, $R^{4d}$, $R^{5d}$, and $R^{5e}$ is independently hydrogen or —CH$_3$. In some embodiments, each $R^{4c}$, $R^{4d}$, $R^{5d}$, and $R^{5e}$ is hydrogen. In some embodiments, each $R^{4c}$, $R^{4d}$, $R^{5d}$, and $R^{5e}$ is —CH$_3$.

In some embodiments, each $R^{6c}$ and $R^{6d}$ is independently selected from hydrogen and —CH$_3$. In some embodiments, each $R^{6c}$ and $R^{6d}$ is hydrogen. In some embodiments, each $R^{6c}$ and $R^{6d}$ is —CH$_3$.

In some embodiments, each $R^{3c}$ and $R^{3d}$ is independently selected from hydrogen and —CH$_3$.

In some embodiments, each $R^{3c}$ and $R^{3d}$ is hydrogen.

In some embodiments, each $R^{3c}$, $R^{3d}$, $R^{6c}$, and $R^{6d}$ is independently hydrogen or —CH$_3$. In some embodiments, each $R^{3c}$, $R^{3d}$, $R^{6c}$, and $R^{6d}$ is hydrogen. In some embodiments, each $R^{3c}$, $R^{3d}$, $R^{6c}$, and $R^{6d}$ is —CH$_3$.

In some embodiments, $R^{11a}$ is hydrogen or —CH$_3$. In some embodiments, $R^{11a}$ is hydrogen. In some embodiments, $R^{11a}$ is —CH$_3$.

In some embodiments, $R^{12a}$ is hydrogen or —CH$_3$. In some embodiments, $R^{12a}$ is hydrogen. In some embodiments, $R^{12a}$ is —CH$_3$.

In some embodiments, $R^{13a}$ is hydrogen or —CH$_3$. In some embodiments, $R^{13a}$ is hydrogen. In some embodiments, $R^{13a}$ is —CH$_3$.

In some embodiments, each $R^{11a}$, $R^{12a}$, and $R^{13a}$ is independently hydrogen or —CH$_3$. In some embodiments, each $R^{11a}$, $R^{12a}$, and $R^{13a}$ is hydrogen. In some embodiments, each $R^{11a}$, $R^{12a}$, and $R^{13a}$ is —CH$_3$.

In some embodiments, each $R^{11b}$, $R^{12a}$, $R^{12b}$, $R^{12c}$, $R^{13b}$, and $R^{13c}$ is hydrogen.

In some embodiments, n is 0, 1, 2, 3, 4, 5, or 6. In some embodiments, n is 0, 1, 2, 3, 4, or 5.

In some embodiments, n is 0, 1, or 2. In some embodiments, n is 0. In some embodiments, n is 1. In some embodiments, n is 2. In some embodiments, n is 3. In some embodiments, n is 4. In some embodiments, n is 5.

In some embodiments, s is 1, 2, 3, or 4. In some embodiments, s is 1. In some embodiments, s is 2. In some embodiments, s is 3. In some embodiments, s is 4.

In some embodiments, t is 1, 2, 3, or 4. In some embodiments, t is 1. In some embodiments, t is 2. In some embodiments, t is 3. In some embodiments, t is 4.

In some embodiments, p is 1, 2, 3, or 4. In some embodiments, p is 1. In some embodiments, p is 2. In some embodiments, p is 3. In some embodiments, p is 4.

In some embodiments, k is 1, 2, 3, 4, or 5. In some embodiments, k is 1, 2, 3, or 4. In some embodiments, k is 2, 3, or 4. In some embodiments, k is 2 or 3. In some embodiments, k is 1. In some embodiments, k is 2. In some embodiments, k is 3. In some embodiments, k is 4.

In some embodiments, each s, t, p, and k is independently 1, 2, or 3. In some embodiments, each s, t, p, and k is independently 1 or 2. In some embodiments, each s, t, p, and k is independently 2 or 3.

In some embodiments, a repeating unit of Formula (IX) comprises a positively charged repeating unit of Formula (IX). In some embodiments, a repeating unit of Formula (IX) comprises a negatively charged repeating unit of Formula (IX). In some embodiments, a copolymer comprising repeating units of Formula (VII), (VIII), and (IX) comprises a positively charged repeating unit of Formula (IX) and a negatively charged repeating unit of Formula (IX). In some embodiments, the ratio of positively charged repeating units of Formula (IX) and negatively charged repeating units of Formula (IX) in a copolymer comprising repeating units of Formula (VII), (VIII), and (IX) is from about 10:1 to about 1:10. In some embodiments, the ratio of positively charged repeating units of Formula (IX) and negatively charged repeating units of Formula (IX) in a copolymer comprising repeating units of Formula (VII), (VIII), and (IX) is from about 5:1 to about 1:5. In some embodiments, the ratio of positively charged repeating units of Formula (IX) and negatively charged repeating units of Formula (IX) in a copolymer comprising repeating units of Formula (VII), (VIII), and (IX) is from about 2:1 to about 1:2. In some embodiments, the ratio of positively charged repeating units of Formula (IX) and negatively charged repeating units of Formula (IX) in a copolymer comprising repeating units of Formula (VII), (VIII), and (IX) is about 1:1.

In some embodiments, a copolymer comprising a repeating unit of Formula (VII), (VIII), and (IX) comprises the following number of monomer units: [(Formula (VII))a (Formula (VIII))b(Formula (IX))c], wherein each number a, b, and c is independently selected from 1 to 1000. In some embodiments, each number a, b, and c is independently selected from 1 to 100.

In some embodiments, a is from 1 to 10. In some embodiments, a is from 5 to 10. In some embodiments, a is from 5 to 20. In some embodiments, a is at least 1, at least 2, at least 3, at least 4, at least 5, at least 6, at least 7, at least 8, at least 9, at least 10, at least 12, at least 15, or at least 20. In some embodiments, a is at most 1, at most 2, at most 3, at most 4, at most 5, at most 6, at most 7, at most 8, at most 9, at most 10, at most 12, at most 15, or at most 20.

In some embodiments, b is from 5 to 75. In some embodiments, b is from 10 to 100. In some embodiments, b is from 20 to 250. In some embodiments, b is from 50 to 500. In some embodiments, b is from 100 to 1000. In some embodiments, b is at least 1, at least 5, at least 10, at least 25, at least 50, at least 100, at least 200, at least 300, at least 400, at least 500, at least 600, at least 700, at least 800, at least 900, or at least 1000. In some embodiments, b is at most 1, at most 5, at most 10, at most 25, at most 50, at most 100, at most 200, at most 300, at most 400, at most 500, at most 600, at most 700, at most 800, at most 900, or at most 1000.

In some embodiments, c is from 5 to 75. In some embodiments, c is from 10 to 100. In some embodiments, c is from 20 to 250. In some embodiments, c is from 50 to 500. In some embodiments, c is from 100 to 1000. In some embodiments, c is at least 1, at least 5, at least 10, at least 25, at least 50, at least 100, at least 200, at least 300, at least 400, at least 500, at least 600, at least 700, at least 800, at least 900, or at least 1000. In some embodiments, c is at most 1, at most 5, at most 10, at most 25, at most 50, at most 100, at most 200, at most 300, at most 400, at most 500, at most 600, at most 700, at most 800, at most 900, or at most 1000.

In some embodiments, the ratio of (b+c) to a is from 1:1000 to 1000:1. In some embodiments, the ratio of (b+c) to a is from 1:100 to 100:1. In some embodiments, the ratio of (b+c) to a is from 1:10 to 10:1. In some embodiments, the ratio of (b+c) to a is about 5:1, about 10:1, about 20:1, about 30:1, about 40:1, about 50:1, about 75:1, about 100:1, about 250:1, about 500:1, about 750:1, or about 1000:1.

In some embodiments, different variables of a compound of Formula (I), Formula (II), Formula (III), Formula (VII), Formula (VIII), and Formula (IX) as described above are applicable to the corresponding Formulas, compositions, membranes, devices, etc. disclosed throughout the application.

Any combination of the groups described above or below for the various variables is contemplated herein. Throughout the specification, groups and substituents thereof are chosen by one skilled in the field to provide stable moieties and compounds.

Further Forms of Compounds

In one aspect, the compound of Formula (I), (II), (III), (IV), (V), or (VI), or the copolymer comprising a repeating unit of Formula (VII), (VIII), and (IX) possesses one or more stereocenters and each stereocenter exists independently in either the R or S configuration. The compounds presented herein include all diastereomeric, enantiomeric, and epimeric forms as well as the appropriate mixtures thereof. The compounds and methods provided herein include all cis, trans, syn, anti, entgegen (E), and zusammen (Z) isomers as well as the appropriate mixtures thereof. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In one aspect, stereoisomers are obtained by stereoselective synthesis.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine and chlorine, such as, for example, $^2H$, $^3H$, $^{13}C$, $^{14}C$, $^{15}N$, $^{18}O$, $^{17}O$, $^{35}S$, $^{18}F$, $^{36}Cl$. In one aspect, isotopically-labeled compounds described herein, for example those into which radioactive isotopes such as $^3H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

Compounds described herein might be formed as, and/or used as, salts. The type of salts, include, but are not limited to: (1) acid addition salts, formed by reacting the free base form of the compound with: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g. lithium, sodium, potassium), an alkaline earth ion (e.g. magnesium, or calcium), or an aluminum ion. In some cases, compounds described herein may coordinate with an organic base, such as, but not limited to, ethanolamine, diethanolamine, triethanolamine, tromethamine, N-methylglucamine, dicyclohexylamine, tris(hydroxymethyl)methylamine. In other cases, compounds described herein may form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

It should be understood that a reference to a salt includes the solvent addition forms, particularly solvates. Solvates contain either stoichiometric or non-stoichiometric amounts of a solvent, such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

Synthesis of Compounds

Compounds described herein are synthesized using standard synthetic techniques or using methods known in the art in combination with methods described herein.

Unless otherwise indicated, conventional methods of mass spectroscopy, NMR, HPLC, protein chemistry, biochemistry, recombinant DNA techniques and pharmacology are employed.

Compounds are prepared using standard organic chemistry techniques such as those described in, for example, March's Advanced Organic Chemistry, 6th Edition, John Wiley and Sons, Inc. Alternative reaction conditions for the synthetic transformations described herein may be employed such as variation of solvent, reaction temperature, reaction time, as well as different chemical reagents and other reaction conditions. The starting materials are available from commercial sources or are readily prepared.

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3 527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

In the reactions described, it may be necessary to protect reactive functional groups, for example hydroxy, amino, imino, thio or carboxy groups, where these are desired in the final product, in order to avoid their unwanted participation in reactions. A detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure).

In some embodiments, compounds are synthesized as described in the Examples section.

II. Biofouling-Resistant Coatings

In one aspect, described herein is a biofouling-resistant coating comprising a compound of Formula (I):

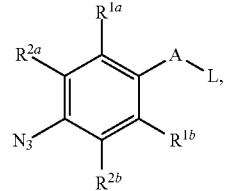

Formula (I)

wherein

A is selected from —C(=O)—, —S(=O)—, —S(=O)$_2$—, and —S(=O)(—NR$^3$)—;

L is selected from —OQ, —NR$^3$Q, and —N(R$^3$)$_2$Q$^+$;

Q is a structure represented by a formula:

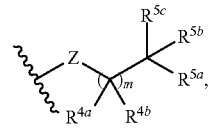

Z is selected from —CR$^{6a}$R$^{6b}$—, —C(=O)—, —C(=NH)—, and —C(=NH)NR$^7$—;

m is an integer selected from 0, 1, 2, 3, 4, 5, 6, 7, and 8;

each R$^{1a}$ and R$^{1b}$ is independently selected from hydrogen and halogen;

each R$^{2a}$ and R$^{2b}$ is independently selected from halogen, —CN, and optionally substituted C$_1$-C$_6$ fluoroalkyl;

each R$^3$ is independently selected from hydrogen, optionally substituted C$_1$-C$_4$ alkyl, —X-optionally substituted C$_1$-C$_4$ alkyl, optionally substituted aryl, and —X-optionally substituted aryl;

X is —C(=O)—, —S(=O)—, or —S(=O)$_2$—;

each R$^{4a}$, R$^{4b}$, R$^{5a}$, R$^{5c}$, R$^{6a}$, and R$^{6b}$ is independently selected from hydrogen, halogen, —CN, —OR$^9$, optionally substituted C$_1$-C$_4$ alkyl, optionally substituted C$_1$-C$_4$ fluoroalkyl, optionally substituted aryl, —NR$^{8a}$R$^{8b}$, —NR$^{8a}$R$^{8b}$R$^{8c+}$, —S(=O)$_2$O$^-$, —S(=O)$_2$OR$^9$, —C(=O)O$^-$, and —C(=O)OR$^9$;

R$^{5b}$ is —OR$^{10b}$, —NR$^{10a}$R$^{10b}$, or —NR$^{10a}$R$^{10b}$R$^{10c}$;

each R$^7$, R$^{8a}$, R$^{8b}$, R$^{8c}$, and R$^9$ is independently selected from hydrogen and optionally substituted C$_1$-C$_4$ alkyl, and optionally substituted aryl;

each R$^{10a}$ and R$^{10c}$ is independently selected from hydrogen, optionally substituted C$_1$-C$_4$ alkyl, optionally substituted aryl, -(optionally substituted C$_1$-C$_8$alkylene)S(=O)$_2$O$^-$, -(optionally substituted C$_1$-C$_8$alkylene)S(=O)$_2$OH, -(optionally substituted C$_1$-C$_8$alkylene)C(=O)O$^-$, and -(optionally substituted C$_1$-C$_8$alkylene)C(=O)OH; and R$^{10b}$ is —C(=O)—C$_2$-C$_6$alkenyl, —S(=O)—C$_2$-C$_6$alkenyl, or —S(=O)$_2$—C$_2$-C$_6$alkenyl.

In some embodiments, the compound of Formula (I) is not:

N-(2-((4-azido-2,3,5,6-tetrafluorophenyl)sulfonamido)ethyl)methacrylamide;

N-(2-acrylamidoethyl)-4-azido-2,3,5,6-tetrafluorobenzamide; or 2-(methacryloyloxy)ethyl 4-azido-2,3,5,6-tetrafluorobenzoate.

In some embodiments, the biofouling-resistant coating comprising a compound of Formula (I), comprises a residue of the compound of Formula (I). In some embodiments, the residue of a compound of Formula (I) comprises a singlet nitrene residue.

In some embodiments, the compound of Formula (I) has a structure as described above.

In some embodiments, different variables of a compound of Formula (I) are as described above.

In some embodiments, the compound of Formula (I) has a structure of Formula (Ia), Formula (Ib), Formula (Ic), Formula (Id), Formula (Ie), Formula (If), Formula (Ig), or Formula (Ih) as described above.

In some embodiments, the compound of Formula (I) is selected from compounds as described above.

In another aspect, described herein is a biofouling-resistant coating comprising a compound of Formula (II):

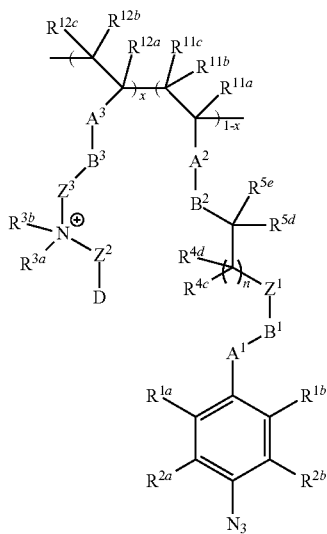

Formula (II)

wherein each R$^{1a}$ and R$^{1b}$ is independently selected from hydrogen and halogen;

each R$^{2a}$ and R$^{2b}$ is independently selected from halogen, —CN, and optionally substituted C$_1$-C$_6$ fluoroalkyl;

each A$^1$, A$^2$, and A$^3$ is independently selected from —C(=O)—, —S(=O)—, —S(=O)$_2$—, and —S(=O)(=NR$^{3c}$)—;

each B$^1$, B$^2$, and B$^3$ is independently selected from —O— and —NR$^{3c}$—;

D is —S(=O)$_2$O$^-$, —S(=O)$_2$OR$^{9a}$, —C(=O)O$^-$, or —C(=O)OR$^{9a}$;

Z$^1$ is —(CR$^{6c}$R$^{6d}$)$_s$—;

Z$^2$ is —(CR$^{6c}$R$^{6d}$)$_t$—;

Z$^3$ is —(CR$^{6c}$R$^{6d}$)$_p$—;

each R$^{3a}$ and R$^{3b}$ is independently selected from hydrogen, optionally substituted C$_1$-C$_4$ alkyl, and optionally substituted benzyl;

each R$^{4c}$, R$^{4d}$, R$^{5d}$, R$^{5e}$, R$^{6c}$, and R$^{6d}$ is independently selected from hydrogen, halogen, —CN, —OR$^{9a}$, optionally substituted C$_1$-C$_4$ alkyl, optionally substituted C$_1$-C$_4$ fluoroalkyl, optionally substituted C$_2$-C$_6$ alkenyl, —NR$^{3c}$R$^{3d}$, —S(=O)$_2$O$^-$, —S(=O)$_2$OR$^{9a}$, —C(=O)O$^-$, and —C(=O)OR$^{9a}$;

each R$^{3c}$ and R$^{3d}$ is independently selected from hydrogen, optionally substituted C$_1$-C$_4$ alkyl, —X-optionally substituted C$_1$-C$_4$ alkyl, optionally substituted C$_2$-C$_6$ alkenyl, and optionally substituted aryl;

X is —C(=O)—, —S(=O)—, or —S(=O)$_2$—;

each R$^{9a}$, R$^{11a}$, R$^{11b}$, R$^{11c}$, R$^{12a}$, R$^{12b}$, and R$^{12c}$ is independently selected from hydrogen, optionally substituted C$_1$-C$_4$ alkyl, and optionally substituted aryl;

n is an integer selected from 0, 1, 2, 3, 4, 5, 6, 7, and 8;

s is an integer selected from 1, 2, 3, 4, or 5;

t is an integer selected from 1, 2, 3, 4, or 5;

p is an integer selected from 1, 2, 3, 4, or 5;

0<x<1; and wherein the compound of Formula (II) is charged or zwitterionic.

In some embodiments, a compound of Formula (II) is not

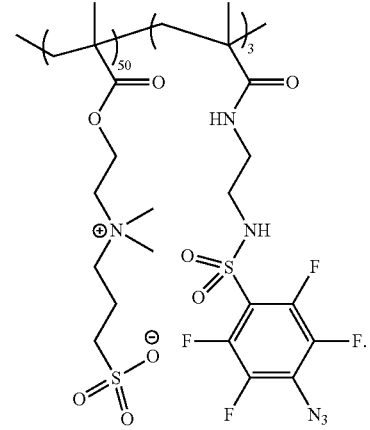

In some embodiments, x in Formula (II) is not about 0.9434.

In some embodiments, a compound of Formula (II) is not obtained by using 2 g sulfobetaine methacrylate monomer and 156 mg perfluorophenylazide methacrylamide monomer.

In some embodiments, different variables of a compound of Formula (II) are as described above.

In another aspect, described herein is a biofouling-resistant coating comprising a compound of Formula (III):

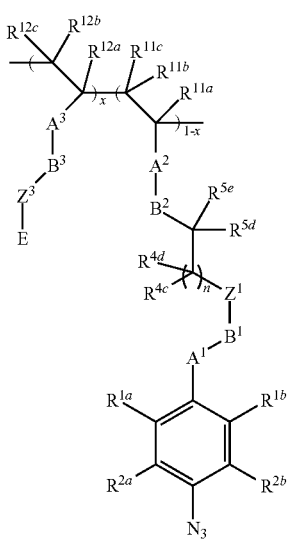

Formula (III)

wherein
each $R^{1a}$ and $R^{1b}$ is independently selected from hydrogen and halogen;
each $R^{2a}$ and $R^{2b}$ is independently selected from halogen, —CN, and optionally substituted $C_1$-$C_6$ fluoroalkyl;
each $A^1$, $A^2$, and $A^3$ is independently selected from —C(=O)—, —S(=O)—, —S(=O)$_2$—, and —S(=O)(=N$R^{3c}$)—;
each $B^1$, $B^2$, and $B^3$ is independently selected from —O— and —N$R^{3c}$—;
$Z^1$ is —(C$R^{6c}R^{6d}$)$_s$—;
$Z^2$ is —(C$R^{6c}R^{6d}$)$_t$—;
E is —CN, —O$R^{9a}$, —N$R^{9a}R^{9b}$, —N$R^{9a}R^{9b}R^{9c+}$ optionally substituted $C_1$-$C_4$ alkyl, optionally substituted $C_1$-$C_6$ fluoroalkyl, —S(=O)$_2$O$^-$, —S(=O)$_2$O$R^{9a}$, —C(=O)O$^-$, or —C(=O)O$R^{9a}$;
each $R^{4c}$, $R^{4d}$, $R^{5d}$, $R^{5e}$, $R^{6c}$, and $R^{6d}$ is independently selected from hydrogen, halogen, —CN, —O$R^{9a}$, optionally substituted $C_1$-$C_4$ alkyl, optionally substituted $C_1$-$C_4$ fluoroalkyl, optionally substituted $C_2$-$C_6$ alkenyl, —N$R^{3c}R^{3d}$, —S(=O)$_2$O$^-$, —S(=O)$_2$O$R^{9a}$, —C(=O)O$^-$, and —C(=O)O$R^{9a}$;
each $R^{3c}$ and $R^{3d}$ is independently selected from hydrogen, optionally substituted $C_1$-$C_4$ alkyl, —X-optionally substituted $C_1$-$C_4$ alkyl, optionally substituted $C_2$-$C_6$ alkenyl, and optionally substituted aryl;
X is —C(=O)—, —S(=O)—, or —S(=O)$_2$—;
each $R^{9a}$, $R^{9b}$, $R^{9c}$, $R^{11a}$, $R^{11b}$, $R^{11c}$, $R^{12a}$, $R^{12b}$, and $R^{12c}$, is independently selected from hydrogen, optionally substituted $C_1$-$C_4$ alkyl, and optionally substituted aryl;
n is an integer selected from 0, 1, 2, 3, 4, 5, 6, 7, and 8;
s is an integer selected from 1, 2, 3, 4, or 5;
t is an integer selected from 1, 2, 3, 4, or 5; and
$0 < x < 1$.

In some embodiments, a compound of Formula (III) is charged or zwitterionic. In some embodiments, a compound of Formula (III) comprises a positively charged repeating unit. In some embodiments a compound of Formula (III) comprises a negatively charged repeating unit. In some embodiments, a compound of Formula (III) comprises positively charged repeating units and negatively charged repeating units. In some embodiments, the ratio of positively charged repeating units and negatively charged repeating units in a compound of Formula (III) is from about 10:1 to about 1:10. In some embodiments, the ratio of positively charged repeating units and negatively charged repeating units in a compound of Formula (III) is from about 5:1 to about 1:5 In some embodiments, the ratio of positively charged repeating units and negatively charged repeating units in a compound of Formula (III) is from about 2:1 to about 1:2. In some embodiments, the ratio of positively charged repeating units and negatively charged repeating units in a compound of Formula (III) is about 1:1.

In some embodiments, different variables of a compound of Formula (III) are as described above.

In another aspect, described herein is a biofouling-resistant coating comprising a copolymer, comprising:
a) a repeating unit of Formula (VII):

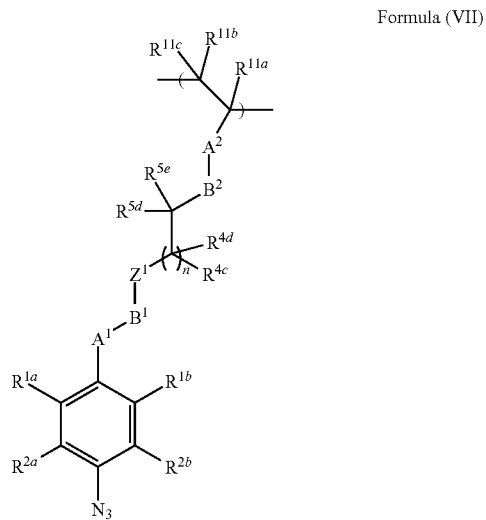

Formula (VII)

wherein
each $R^{1a}$ and $R^{1b}$ is independently selected from hydrogen and halogen;
each $R^{2a}$ and $R^{2b}$ is independently selected from halogen, —CN, and optionally substituted $C_1$-$C_6$ fluoroalkyl;
each $A^1$ and $A^2$ is independently selected from —C(=O)—, —S(=O)—, —S(=O)$_2$—, and —S(=O)(=N$R^{3c}$)—;
each $B^1$ and $B^2$ is independently selected from —O— and —N$R^{3c}$—;
$Z^1$ is —(C$R^{6c}R^{6d}$)$_s$—;
each $R^{4c}$, $R^{4d}$, $R^{5d}$, $R^{5e}$, $R^{6c}$, and $R^{6d}$ is independently selected from hydrogen, halogen, —CN, —O$R^{9a}$, optionally substituted $C_1$-$C_4$ alkyl, optionally substituted $C_1$-$C_4$ fluoroalkyl, optionally substituted $C_2$-$C_6$ alkenyl, —N$R^{3c}R^{3d}$, —S(=O)$_2$O$^-$, —S(=O)$_2$O$R^{9a}$, —C(=O)O$^-$, and —C(=O)O$R^{9a}$;
each $R^{3c}$ and $R^{3d}$ is independently selected from hydrogen, optionally substituted $C_1$-$C_4$ alkyl, —X-optionally substituted $C_1$-$C_4$ alkyl, optionally substituted $C_2$-$C_6$ alkenyl, and optionally substituted aryl;

X is —C(=O)—, —S(=O)—, or —S(=O)₂—;
each $R^{9a}$, $R^{11a}$, $R^{11b}$, and $R^{11c}$ is independently selected from hydrogen, optionally substituted $C_1$-$C_4$ alkyl, and optionally substituted aryl;
n is an integer selected from 0, 1, 2, 3, 4, 5, 6, 7, and 8; and
s is an integer selected from 1, 2, 3, 4, and 5;
b) a repeating unit of Formula (VIII):

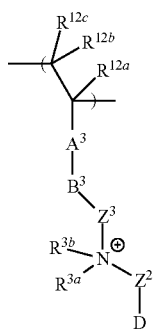

Formula (VIII)

wherein,
$A^3$ is —C(=O)—, —S(=O)—, —S(=O)₂—, or —S(=O)(=$NR^{3c}$)—;
$B^3$ is —O— or —$NR^{3c}$—;
D is —S(=O)₂O⁻, —S(=O)₂$OR^{9a}$, —C(=O)O⁻, or —C(=O)$OR^{9a}$;
$Z^2$ is —($CR^{6c}R^{6d}$)$_t$—;
$Z^3$ is —($CR^{6c}R^{6d}$)$_p$—;
each $R^{3a}$ and $R^{3b}$ is independently selected from hydrogen, optionally substituted $C_1$-$C_4$ alkyl, and optionally substituted benzyl;
each $R^{6c}$ and $R^{6d}$ is independently selected from hydrogen, halogen, —CN, —$OR^{9a}$, optionally substituted $C_1$-$C_4$ alkyl, optionally substituted $C_1$-$C_4$ fluoroalkyl, optionally substituted $C_2$-$C_6$ alkenyl, —$NR^{3c}R^{3d}$, —S(=O)₂O⁻, —S(=O)₂$OR^{9a}$, —C(=O)O⁻, and —C(=O)$OR^{9a}$;
each $R^{3c}$ and $R^{3d}$ is independently selected from hydrogen, optionally substituted $C_1$-$C_4$ alkyl, —X-optionally substituted $C_1$-$C_4$ alkyl, optionally substituted $C_2$-$C_6$ alkenyl, and optionally substituted aryl;
X is —C(=O)—, —S(=O)—, or —S(=O)₂—;
each $R^{9a}$, $R^{12a}$, $R^{12b}$, and $R^{12c}$ is independently selected from hydrogen, optionally substituted $C_1$-$C_4$ alkyl, and optionally substituted aryl;
t is an integer selected from 1, 2, 3, 4, or 5;
p is an integer selected from 1, 2, 3, 4, or 5; and
wherein the repeating unit of Formula (VIII) is charged or zwitterionic; and
c) a repeating unit of Formula (IX):

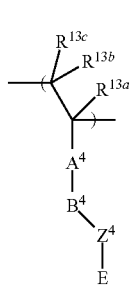

Formula (IX)

$A^4$ is —C(=O)—, —S(=O)—, —S(=O)₂—, or —S(=O)(=$NR^{3c}$)—;
$B^4$ is —O— or —$NR^{3c}$—;
$Z^4$ is —($CR^{6c}R^{6d}$)$_k$—;
E is —CN, —$OR^{9a}$, —$NR^{9a}R^{9b}$, —$NR^{9a}R^{9b}R^{9c+}$ optionally substituted $C_1$-$C_4$ alkyl, optionally substituted $C_1$-$C_6$ fluoroalkyl, —S(=O)₂O⁻, —S(=O)₂$OR^{9a}$, —C(=O)O⁻, or —C(=O)$OR^{9a}$;
each $R^{6c}$, and $R^{6d}$ is independently selected from hydrogen, halogen, —CN, —$OR^{9a}$, optionally substituted $C_1$-$C_4$ alkyl, optionally substituted $C_1$-$C_4$ fluoroalkyl, optionally substituted $C_2$-$C_6$ alkenyl, —$NR^{3c}R^{3d}$, —S(=O)₂O⁻, —S(=O)₂$OR^{9a}$, —C(=O)O⁻, and —C(=O)$OR^{9a}$;
each $R^{3c}$ and $R^{3d}$ is independently selected from hydrogen, optionally substituted $C_1$-$C_4$ alkyl, —X-optionally substituted $C_1$-$C_4$ alkyl, optionally substituted $C_2$-$C_6$ alkenyl, and optionally substituted aryl;
X is —C(=O)—, —S(=O)—, or —S(=O)₂—;
each $R^{9a}$, $R^{9b}$, $R^{9c}$, $R^{13a}$, $R^{13b}$, and $R^{13c}$ is independently selected from hydrogen, optionally substituted $C_1$-$C_4$ alkyl, and optionally substituted aryl; and
k is an integer selected from 1-10.

In some embodiments, the repeating unit of Formula (IX) is charged or zwitterionic.

In some embodiments, different variables of a compound of Formula (VII), Formula (VIII), and Formula (IX) are as described above.

Any combination of the groups described above or below for the various variables is contemplated herein. Throughout the specification, groups and substituents thereof are chosen by one skilled in the field to provide stable moieties and compounds.

In some embodiments, the biofouling-resistant coating described herein comprises one or more compounds of Formula (I), (II), or (III).

In some embodiments, the biofouling-resistant coating described herein comprises one or more copolymers of Formula (II) or (III). In some embodiments, the biofouling-resistant coating described herein comprises one or more copolymers comprising repeating units of Formula (VII), (VIII), and (IX).

In some embodiments, the biofouling-resistant coating comprising one or more compounds of Formula (I), (II), and (III) is applied onto a surface of the device. In some embodiments, the biofouling-resistant coating comprising one or more copolymers comprising repeating units of Formula (VII), (VIII), and (IX) is applied onto a surface of the device. In some embodiments, the surface of the device comprises a polymer. In some embodiments, the polymer is selected from polysiloxanes, polyurethanes, polyamides, polyimides, epoxy resins, polyesters, polyolefins, polysulfones, polycarbonates, polyvinylchloride, polyvinylidene difluoride, polyethers, polyether terpthalate, or a mixture thereof.

III. Devices

In certain embodiments, provided herein are devices coated by one or more compounds described herein. In some embodiments, the devices are medical devices. In some embodiments, the devices are non-medical devices. In some instances, provided herein are medical devices coated by one or more compounds described herein. In other instances, provided herein are non-medical devices coated by one or more compounds described herein. In additional instances, provided herein are devices coated by one or more compounds described herein in which the coated device reduces the potential for infection.

In some embodiments, the device comprises a polymer-based device. In some embodiments, the polymer-based device comprises a polyolefinic device. In some embodiments, the polyolefinic device comprises a device modified with polyethylene (PE), polypropylene (PP), polyamide (PA), polytetrafluoroethylene (PTFE), polyvinylidene fluoride (PVdF), polyvinyl chloride (PVC), or a combination thereof. In some embodiments, the device comprises a microporous device or a nonwoven device. In some embodiments, the device comprises a carbon-based device comprising a moiety capable of binding with a compound that has a structure of Formula (I), (II), or (III). In some embodiments, the device comprises a carbon-based device comprising a moiety capable of binding with a copolymer comprising a repeating unit of Formula (VII), (VIII), and (IX). In some embodiments, the carbon-based device comprises a polymer moiety. In some embodiments, the carbon-based device comprises a carbon-based polymer. In some embodiments, the carbon-based device comprises a polyolefin moiety. In some embodiments, the polyolefin moiety comprises a polyethylene (PE) moiety, a polypropylene (PP) moiety, a polyamide (PA) moiety, a polytetrafluoroethylene (PTFE) moiety, a polyvinylidene fluoride (PVdF) moiety, or a polyvinyl chloride (PVC) moiety.

In some embodiments, the device comprises a carbon-based device. In some embodiments, the carbon-based device comprises a carbon-based polymer. In some embodiments, the carbon-based device comprises a polyolefin moiety. In some embodiments, the polyolefin moiety comprises polyethylene moiety, polypropylene moiety, polyvinyl chloride moiety, polyvinylidene fluoride moiety, polytetrafluoroethylene moiety, polychlorotrifluoroethylene moiety, or polystyrene moiety.

In some embodiments, the carbon-based polymer comprises polyamide moiety, polyurethane moiety, phenol-formaldehyde resin moiety, polycarbonate moiety, polychloroprene moiety, polyacrylonitrile moiety, polyimide moiety, or polyester moiety. In some embodiments, the carbon-based polymer comprises nylon. In some embodiments, the carbon-based polymer comprises polyethylene terephthalate.

In some embodiments, the device comprises a silicon-based device. In some embodiments, the silicon-based device comprises a silicon-based polymer moiety. In some embodiments, the device comprises a silicon-based device comprising a moiety capable of binding with a compound that has a structure of Formula (I), (II), or (III). In some embodiments, the device comprises a silicon-based device comprising a moiety capable of binding with a copolymer comprising a repeating unit of Formula (VII), (VIII), and (IX). In some embodiments, the silicon-based device comprises a polymer moiety. In some embodiments, the silicon-based device comprises a siloxane polymer moiety, a sesquisiloxane polymer moiety, a siloxane-silarylene polymer moiety, a silalkylene polymer moiety, a polysilane moiety, a polysilylene moiety, or a polysilazane moiety.

In some embodiments, the silicon-based device comprises a siloxane polymer moiety. In some embodiments, the silicon-based device comprises silicone polymer. In some embodiments, the silicon-based device comprises a silicone-based device.

In some embodiments, the device comprises a carbon-based device or a silicon-based device.

In some embodiments, a device described herein coated by a compound described herein leads to a reduced potential for infection relative to a device not coated by the compound. In some instances, the reduced potential for infection is by about 10%, 20%, 30%, 40%, 50%, 60%, 70%, 80%, 90%, 95%, 99%, 99.5%, 99.9%, or more relative to a device not coated by the compound. In some instances, the reduced potential for infection is by about 10%, or more relative to a device not coated by the compound. In some instances, the reduced potential for infection is by about 20%, or more relative to a device not coated by the compound. In some instances, the reduced potential for infection is by about 30%, or more relative to a device not coated by the compound. In some instances, the reduced potential for infection is by about 40%, or more relative to a device not coated by the compound. In some instances, the reduced potential for infection is by about 50%, or more relative to a device not coated by the compound. In some instances, the reduced potential for infection is by about 60%, or more relative to a device not coated by the compound. In some instances, the reduced potential for infection is by about 70%, or more relative to a device not coated by the compound. In some instances, the reduced potential for infection is by about 80%, or more relative to a device not coated by the compound. In some instances, the reduced potential for infection is by about 90%, or more relative to a device not coated by the compound. In some instances, the reduced potential for infection is by about 95%, or more relative to a device not coated by the compound. In some instances, the reduced potential for infection is by about 99%, or more relative to a device not coated by the compound. In some instances, the reduced potential for infection is by about 99.5%, or more relative to a device not coated by the compound. In some instances, the reduced potential for infection is by about 99.9%, or more relative to a device not coated by the compound.

Medical Devices

In some embodiments, a device described herein is a medical device. In some cases, a medical device described herein comprises a dental instrument or a medical instrument. In some instances, a medical device comprises an implant, an IV, a prosthesis, a suturing material, a valve, a stent, a catheter, a rod, a shunt, a scope, a contact lens, a tubing, a wiring, an electrode, a clip, a fastener, a syringe, a container, or a combination thereof. In some embodiments, a medical device comprises an implant. In some embodiments, a medical device comprises an IV. In some embodiments, a medical device comprises a prosthesis. In some embodiments, a medical device comprises a suturing material. In some embodiments, a medical device comprises a valve. In some embodiments, a medical device comprises a stent. In some embodiments, a medical device comprises a catheter. In some embodiments, a medical device comprises a rod. In some embodiments, a medical device comprises a shunt. In some embodiments, a medical device comprises a scope. In some embodiments, a medical device comprises a contact lens. In some embodiments, a medical device comprises a tubing. In some embodiments, a medical device comprises a wiring. In some embodiments, a medical device comprises an electrode. In some embodiments, a medical device comprises a clip. In some embodiments, a medical device comprises a fastener. In some embodiments, a medical device comprises a syringe. In some embodiments, a medical device comprises a container. In some instances, a device described herein comprises a dental instrument or a medical instrument. In some instances, a device described herein comprises an implant, an IV, a prosthesis, a suturing material, a valve, a stent, a catheter, a rod, a shunt, a scope, a contact lens, a tubing, a wiring, an electrode, a clip, a fastener, a syringe, a container, or a combination thereof. In some embodiments, a device comprises an implant. In some embodiments, a device comprises an IV. In some embodiments, a device comprises a prosthesis. In some embodiments, a device comprises a suturing material. In some embodiments, a device comprises a valve. In some embodiments, a device comprises a stent. In some embodiments, a device comprises a catheter. In some embodiments, a device comprises a rod. In some embodiments, a device comprises a shunt. In some embodiments, a device comprises a scope. In some embodiments, a device comprises a contact lens. In some embodiments, a device comprises a tubing. In some embodiments, a device comprises a wiring. In some embodiments, a device comprises an electrode. In some embodiments, a device comprises a clip. In some embodiments, a device comprises a fastener. In some embodiments, a device comprises a syringe. In some embodiments, a device comprises a container.

In some embodiments, a compound described herein is coated onto a medical device. In some instances, a compound described herein is coated onto a medical device to prevent and/or reduce biofouling (e.g., microfouling such as bacteria adhesion or biofilm). In some instances, a compound described herein is coated onto a dental instrument or a medical instrument to prevent and/or reduce biofouling (e.g., microfouling such as bacteria adhesion or biofilm). In some instances, a compound described herein is coated onto an implant, an IV, a prosthesis, a suturing material, a valve, a stent, a catheter, a rod, a shunt, a scope, a contact lens, a tubing, a wiring, an electrode, a clip, a fastener, a syringe, a container, or a combination thereof to prevent and/or reduce biofouling (e.g., microfouling such as bacteria adhesion or biofilm).

In some cases, a device described herein comprises a catheter. In some cases, a catheter comprises an indwelling catheter. In some instances, a catheter comprises a permcath. In some instances, a catheter comprises a uretic catheter or a Foley catheter.

In some instances, a compound described herein is coated onto a catheter to prevent and/or reduce biofouling (e.g., microfouling such as bacteria adhesion or biofilm). In some instances, a compound described herein is coated onto an indwelling catheter to prevent and/or reduce biofouling (e.g., microfouling such as bacteria adhesion or biofilm). In some instances, a compound described herein is coated onto a permcath to prevent and/or reduce biofouling (e.g., microfouling such as bacteria adhesion or biofilm). In some instances, a compound described herein is coated onto a uretic catheter to prevent and/or reduce biofouling (e.g., microfouling such as bacteria adhesion or biofilm). In some instances, a compound described herein is coated onto a Foley catheter to prevent and/or reduce biofouling (e.g., microfouling such as bacteria adhesion or biofilm).

In some instances, a device described herein comprises an implant. In some instances, an implant comprises a dental implant or an orthopedic implant. In some cases, a device described herein comprises a dental implant. In other cases, a device described herein comprises an orthopedic implant.

In some instances, a compound described herein is coated onto an implant to prevent and/or reduce biofouling (e.g., microfouling such as bacteria adhesion or biofilm). In some instances, a compound described herein is coated onto a dental implant to prevent and/or reduce biofouling (e.g., microfouling such as bacteria adhesion or biofilm). In some instances, a compound described herein is coated onto an orthopedic implant to prevent and/or reduce biofouling (e.g., microfouling such as bacteria adhesion or biofilm).

In some embodiments, a device described herein comprises an IV. In some instances, a compound described herein is coated onto an IV to prevent and/or reduce biofouling (e.g., microfouling such as bacteria adhesion or biofilm).

In some embodiments, a device described herein comprises a prosthesis. In some cases, a prosthesis comprises an artificial bone, an artificial joint, an artificial organ, or a denture. In some cases, an artificial organ comprises an artificial pancreas, an artificial heart, an artificial limb, or a heart valve. In some embodiments, a device described herein comprises an artificial bone, an artificial joint, an artificial organ or a denture. In some embodiments, a device described herein comprises an artificial pancreas, an artificial heart, an artificial limb, or a heart valve.

In some instances, a compound described herein is coated onto prosthesis to prevent and/or reduce biofouling (e.g., microfouling such as bacteria adhesion or biofilm). In some instances, a compound described herein is coated onto an artificial bone, an artificial joint, an artificial organ, or a denture to prevent and/or reduce biofouling (e.g., microfouling such as bacteria adhesion or biofilm). In some instances, a compound described herein is coated onto an artificial pancreas, an artificial heart, an artificial limb, or a heart valve to prevent and/or reduce biofouling (e.g., microfouling such as bacteria adhesion or biofilm).

In some embodiments, a device described herein comprises a stent. In some instances, a stent is a small expandable tube used to the passageway of a blood vessel or duct remains open. In some cases, a stent comprises a coronary stent, a vascular stent, or a biliary stent. In some instances, a coronary stent is also referred to as a cardiac stent or a heart stent. In some embodiments, a device described herein comprises a coronary stent, a vascular stent, or a biliary stent.

In some instances, a compound described herein is coated onto stent to prevent and/or reduce biofouling (e.g., microfouling such as bacteria adhesion or biofilm). In some instances, a compound described herein is coated onto a coronary stent, a vascular stent, or a biliary stent to prevent and/or reduce biofouling (e.g., microfouling such as bacteria adhesion or biofilm).

In some instances, a device described herein comprises shunt. In some instances, a shunt is a hole or a small passage which allows fluid movement from one part of a body to another. In some instances, a shunt differs from a stent in that a shunt connects two previously unconnected portions.

In some instances, a shunt is an acquired shunt. In some cases, a shunt comprises a cardiac shunt, a cerebral shunt, a lumbar-peritoneal shunt, a peritoneovenous shunt, a pulmonary shunt, a portosystemic shunt (PSS), a portacaval shunt, or a vesico-amniotic shunt. In some cases, a cardiac shunt comprises a right-to-left, left-to-right, or bidirectional shunt. In some cases, a cerebral shunt comprises drainage of excess cerebrospinal fluid from the brain into the chest or abdomen cavity. In some cases, a lumbar-peritoneal shunt comprises channeling cerebrospinal fluid from the lumbar thecal sac into the peritoneal cavity. In some instances, a peritoneovenous shunt (also referred to as Denver shunt) drains peritoneal fluid from the peritoneum into the veins. In some cases, a portosystemic shunt (PSS) is a liver shunt which allows bypass of the liver by the circulatory system. In some cases, a portacaval shunt connects the portal vein with the inferior vena cava, for treatment of high blood pressure in the liver. In some cases, a vesico-amniotic shunt is for drainage of excess fluid in a fetus bladder into the surrounding area. In some cases, a device described herein comprises a cardiac shunt, a cerebral shunt, a lumbar-peritoneal shunt, a peritoneovenous shunt, a pulmonary shunt, a portosystemic shunt (PSS), a portacaval shunt, or a vesico-amniotic shunt.

In some instances, a compound described herein is coated onto shunt to prevent and/or reduce biofouling (e.g., microfouling such as bacteria adhesion or biofilm). In some instances, a compound described herein is coated onto a cardiac shunt, a cerebral shunt, a lumbar-peritoneal shunt, a peritoneovenous shunt, a pulmonary shunt, a portosystemic shunt (PSS), a portacaval shunt, or a vesico-amniotic shunt to prevent and/or reduce biofouling (e.g., microfouling such as bacteria adhesion or biofilm).

In some instances, a device described herein comprises a scope. In some cases, a scope is a medical instrument used in an image-guided surgery. In some cases, a scope comprises endoscope or laparoscope. Endoscopy is a medical procedure for examining the GI tract with the aid of an endoscope. In some cases, endoscopy further comprises sigmoidoscopy and colonoscopy.

Laparoscopy is a diagnostic procedure for examining internal organs utilizing a laparoscope. In some instances, a device described herein comprises a scope used in endoscopy. In other instances, a device described herein comprises a scope used in laparoscopy.

In some instances, a compound described herein is coated onto scope to prevent and/or reduce biofouling (e.g., microfouling such as bacteria adhesion or biofilm). In some instances, a compound described herein is coated onto endoscope to prevent and/or reduce biofouling (e.g., microfouling such as bacteria adhesion or biofilm). In some instances, a compound described herein is coated onto laparoscope to prevent and/or reduce biofouling (e.g., microfouling such as bacteria adhesion or biofilm).

In some embodiments, a device described herein comprises suturing material, valve, rod, tubing, wiring, electrode, clip, fastener, or a combination thereof. In some instances, a compound described herein is coated onto suturing material, valve, rod, tubing, wiring, electrode, clip, fastener, or a combination thereof to prevent and/or reduce biofouling (e.g., microfouling such as bacteria adhesion or biofilm).

In some embodiments, a device described herein comprises a syringe. In some cases, a syringe further comprises a needle. In some instances, a compound described herein is coated onto a syringe to prevent and/or reduce biofouling (e.g., microfouling such as bacteria adhesion or biofilm).

In some embodiments, a device described herein comprises a container, such as for storage of one or more medical devices. In some instances, a compound described herein is coated onto a container to prevent and/or reduce biofouling (e.g., microfouling such as bacteria adhesion or biofilm).

In some embodiments, a device described herein comprises a bandage or a patch. In some cases, a device described herein comprises a bandage. In other cases, a device described herein comprises a patch.

In some instances, a compound described herein is coated onto a bandage to prevent and/or reduce biofouling (e.g., microfouling such as bacteria adhesion or biofilm). In some instances, a compound described herein is coated onto patch to prevent and/or reduce biofouling (e.g., microfouling such as bacteria adhesion or biofilm).

In one aspect, described herein is a device coated by a compound of Formula (I):

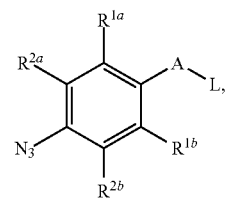

Formula (I)

wherein
A is selected from —C(=O)—, —S(=O)—, —S(=O)$_2$—, and —S(=O)(—NR$^3$)—;
L is selected from —OQ, —NR$^3$Q, and —N(R$^3$)$_2$Q$^+$;
Q is a structure represented by a formula:

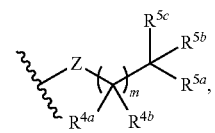

Z is selected from —CR$^{6a}$R$^{6b}$, —C(=O)—, —C(=NH)—, and —C(=NH)NR$^7$—;
m is an integer selected from 0, 1, 2, 3, 4, 5, 6, 7, and 8;
each R$^{1a}$ and R$^{1b}$ is independently selected from hydrogen and halogen;
each R$^{2a}$ and R$^{2b}$ is independently selected from halogen, —CN, and optionally substituted C$_1$-C$_6$ fluoroalkyl;
each R$^3$ is independently selected from hydrogen, optionally substituted C$_1$-C$_4$ alkyl, —X-optionally substituted C$_1$-C$_4$ alkyl, optionally substituted aryl, and —X-optionally substituted aryl;
X is —C(=O)—, —S(=O)—, or —S(=O)$_2$—;
each R$^{4a}$, R$^{4b}$, R$^{5a}$, R$^{5c}$, R$^{6a}$, and R$^{6b}$ is independently selected from hydrogen, halogen, —CN, —OR$^9$, optionally substituted C$_1$-C$_4$ alkyl, optionally substituted C$_1$-C$_4$ fluoroalkyl, optionally substituted aryl, —NR$^{8a}$R$^{8b}$, —NR$^{8a}$R$^{8b}$R$^{8c+}$, —S(=O)$_2$O$^-$, —S(=O)$_2$OR$^9$, —C(=O)O$^-$, and —C(=O)OR$^9$;
R$^{5b}$ is —OR$^{10b}$, —NR$^{10a}$R$^{10b}$, or —NR$^{10a}$R$^{10b}$R$^{10c+}$;
each R$^7$, R$^{8a}$, R$^{8b}$, R$^{8c}$, and R$^9$ is independently selected from hydrogen and optionally substituted C$_1$-C$_4$ alkyl, and optionally substituted aryl;
each R$^{10a}$ and R$^{10c}$ is independently selected from hydrogen, optionally substituted C$_1$-C$_4$ alkyl, optionally substituted aryl, -(optionally substituted C$_1$-C$_8$alkylene)S(=O)$_2$—, -(optionally substituted C$_1$-C$_8$alkylene)S(=O)$_2$OH, -(optionally substituted C$_1$-C$_8$alkylene)C(=O)O$^-$, and -(optionally substituted C$_1$-C$_8$alkylene)C(=O)OH; and
R$^{10b}$ is —C(=O)—C$_2$-C$_6$alkenyl, —S(=O)—C$_2$-C$_6$alkenyl, or —S(=O)$_2$—C$_2$-C$_6$alkenyl.

In some embodiments, the compound of Formula (I) is not:
N-(2-((4-azido-2,3,5,6-tetrafluorophenyl)sulfonamido)ethyl)methacrylamide;
N-(2-acrylamidoethyl)-4-azido-2,3,5,6-tetrafluorobenzamide; or
2-(methacryloyloxy)ethyl 4-azido-2,3,5,6-tetrafluorobenzoate.

In some embodiments, the device coated by a compound of Formula (I), comprises a residue of the compound of Formula (I). In some embodiments, the residue of a compound of Formula (I) comprises a singlet nitrene residue.

In some embodiments, the compound of Formula (I) has a structure as described above.

In some embodiments, different variables of a compound of Formula (I) are as described above.

In some embodiments, the compound of Formula (I) has a structure of Formula (Ia), Formula (Ib), Formula (Ic), Formula (Id), Formula (Ie), Formula (If), Formula (Ig), or Formula (Ih) as described above.

In some embodiments, the compound of Formula (I) is selected from compounds as described above.

In another aspect, described herein is a device coated by a compound of Formula (II):

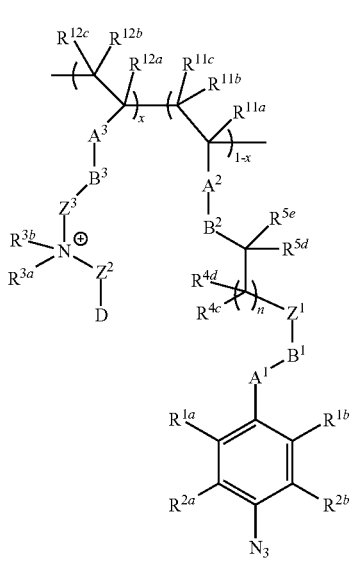

Formula (II)

wherein
each $R^{1a}$ and $R^{1b}$ is independently selected from hydrogen and halogen;
each $R^{2a}$ and $R^{2b}$ is independently selected from halogen, —CN, and optionally substituted $C_1$-$C_6$ fluoroalkyl;
each $A^1$, $A^2$, and $A^3$ is independently selected from —C(=O)—, —S(=O)—, —S(=O)$_2$—, and —S(=O)(=NR$^{3c}$)—;
each $B^1$, $B^2$, and $B^3$ is independently selected from —O— and —NR$^{3c}$—;
D is —S(=O)$_2$O$^-$, —S(=O)$_2$OR$^{9a}$, —C(=O)O$^-$, or —C(=O)OR$^{9a}$;
$Z^1$ is —(CR$^{6c}$R$^{6d}$)$_s$—;
$Z^2$ is —(CR$^{6c}$R$^{6d}$)$_t$—;
$Z^3$ is —(CR$^{6c}$R$^{6d}$)$_p$;
each $R^{3a}$ and $R^{3b}$ is independently selected from hydrogen, optionally substituted $C_1$-$C_4$ alkyl, and optionally substituted benzyl;
each $R^{4c}$, $R^{4d}$, $R^{5d}$, $R^{5e}$, $R^{6c}$, and $R^{6d}$ is independently selected from hydrogen, halogen, —CN, —OR$^{9a}$, optionally substituted $C_1$-$C_4$ alkyl, optionally substituted $C_1$-$C_4$ fluoroalkyl, optionally substituted $C_2$-$C_6$ alkenyl, —NR$^{3c}$R$^{3d}$, —S(=O)$_2$O$^-$, —S(=O)$_2$OR$^{9a}$, —C(=O)O$^-$, and —C(=O)OR$^{9a}$;
each $R^{3c}$ and $R^{3d}$ is independently selected from hydrogen, optionally substituted $C_1$-$C_4$ alkyl, —X-optionally substituted $C_1$-$C_4$ alkyl, optionally substituted $C_2$-$C_6$ alkenyl, and optionally substituted aryl;

X is —C(=O)—, —S(=O)—, or —S(=O)$_2$—;
each $R^{9a}$, $R^{11a}$, $R^{11b}$, $R^{11c}$, $R^{12a}$, $R^{12b}$, and $R^{12c}$ is independently selected from hydrogen, optionally substituted $C_1$-$C_4$ alkyl, and optionally substituted aryl;
n is an integer selected from 0, 1, 2, 3, 4, 5, 6, 7, and 8;
s is an integer selected from 1, 2, 3, 4, or 5;
t is an integer selected from 1, 2, 3, 4, or 5;
p is an integer selected from 1, 2, 3, 4, or 5;
0<x<1; and
wherein the compound of Formula (II) is charged or zwitterionic.

In some embodiments, a compound of Formula (II) is not

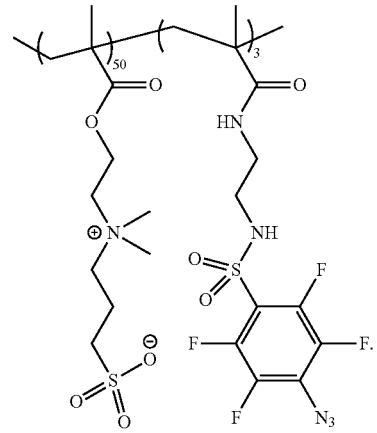

In some embodiments, x in Formula (II) is not about 0.9434.

In some embodiments, a compound of Formula (II) is not obtained by using 2 g sulfobetaine methacrylate monomer and 156 mg perfluorophenylazide methacrylamide monomer.

In some embodiments, different variables of a compound of Formula (II) are as described above.

In another aspect, described herein is a device coated by a compound of Formula (III):

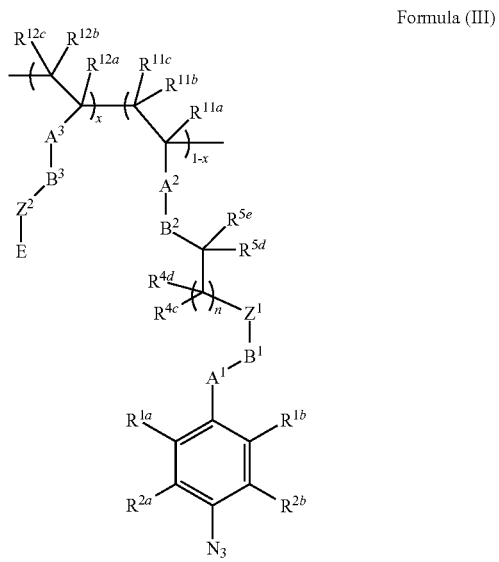

Formula (III)

wherein
each $R^{1a}$ and $R^{1b}$ is independently selected from hydrogen and halogen;
each $R^{2a}$ and $R^{2b}$ is independently selected from halogen, —CN, and optionally substituted $C_1$-$C_6$ fluoroalkyl;
each $A^1$, $A^2$, and $A^3$ is independently selected from —C(=O)—, —S(=O)—, —S(=O)$_2$—, and —S(=O)(=NR$^{3c}$)—;
each $B^1$, $B^2$, and $B^3$ is independently selected from —O— and —NR$^{3c}$—;
$Z^1$ is —(CR$^{6c}$R$^{6d}$)$_s$—;
$Z^2$ is —(CR$^{6c}$R$^{6d}$)$_t$—;
E is —CN, —OR$^{9a}$, —NR$^{9a}$R$^{9b}$, —NR$^{9a}$R$^{9b}$R$^{9c+}$, optionally substituted $C_1$-$C_4$ alkyl, optionally substituted $C_1$-$C_6$ fluoroalkyl, —S(=O)$_2$O$^-$, —S(=O)$_2$OR$^{9a}$, —C(=O)O$^-$, or —C(=O)OR$^{9a}$;
each $R^{4c}$, $R^{4d}$, $R^{5d}$, $R^{5e}$, $R^{6c}$, and $R^{6d}$ is independently selected from hydrogen, halogen, —CN, —OR$^{9a}$, optionally substituted $C_1$-$C_4$ alkyl, optionally substituted $C_1$-$C_4$ fluoroalkyl, optionally substituted $C_2$-$C_6$ alkenyl, —NR$^{3c}$R$^{3d}$, —S(=O)$_2$O$^-$, —S(=O)$_2$OR$^{9a}$, —C(=O)O$^-$, and —C(=O)OR$^{9a}$;
each $R^{3c}$ and $R^{3d}$ is independently selected from hydrogen, optionally substituted $C_1$-$C_4$ alkyl, —X-optionally substituted $C_1$-$C_4$ alkyl, optionally substituted $C_2$-$C_6$ alkenyl, and optionally substituted aryl;
X is —C(=O)—, —S(=O)—, or —S(=O)$_2$—;
each $R^{9a}$, $R^{9b}$, $R^{9c}$, $R^{11a}$, $R^{11b}$, $R^{11c}$, $R^{12a}$, $R^{12b}$, and $R^{12c}$ is independently selected from hydrogen, optionally substituted $C_1$-$C_4$ alkyl, and optionally substituted aryl;
n is an integer selected from 0, 1, 2, 3, 4, 5, 6, 7, and 8;
s is an integer selected from 1, 2, 3, 4, or 5;
t is an integer selected from 1, 2, 3, 4, or 5; and
0<x<1.

In some embodiments, a compound of Formula (III) is charged or zwitterionic. In some embodiments, a compound of Formula (III) comprises a positively charged repeating unit. In some embodiments a compound of Formula (III) comprises a negatively charged repeating unit. In some embodiments, a compound of Formula (III) comprises positively charged repeating units and negatively charged repeating units. In some embodiments, the ratio of positively charged repeating units and negatively charged repeating units in a compound of Formula (III) is from about 10:1 to about 1:10. In some embodiments, the ratio of positively charged repeating units and negatively charged repeating units in a compound of Formula (III) is from about 5:1 to about 1:5 In some embodiments, the ratio of positively charged repeating units and negatively charged repeating units in a compound of Formula (III) is from about 2:1 to about 1:2. In some embodiments, the ratio of positively charged repeating units and negatively charged repeating units in a compound of Formula (III) is about 1:1.

In some embodiments, different variables of a compound of Formula (III) are as described above.

In another aspect, described herein is a device coated by a copolymer, comprising:
a) a repeating unit of Formula (VII):

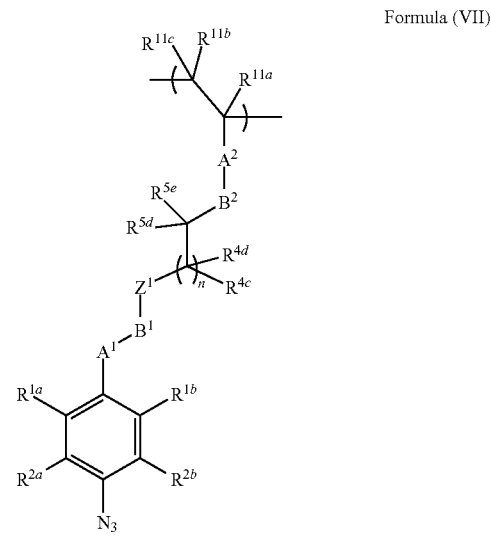

Formula (VII)

wherein
each $R^{1a}$ and $R^{1b}$ is independently selected from hydrogen and halogen;
each $R^{2a}$ and $R^{2b}$ is independently selected from halogen, —CN, and optionally substituted $C_1$-$C_6$ fluoroalkyl;
each $A^1$ and $A^2$ is independently selected from —C(=O)—, —S(=O)—, —S(=O)$_2$—, and —S(=O)(=NR$^{3c}$)—;
each $B^1$ and $B^2$ is independently selected from —O— and —NR$^{3c}$—;
$Z^1$ is —(CR$^{6c}$R$^{6d}$)$_s$—;
each $R^{4c}$, $R^{4d}$, $R^{5d}$, $R^{5e}$, $R^{6c}$, and $R^{6d}$ is independently selected from hydrogen, halogen, —CN, —OR$^{9a}$, optionally substituted $C_1$-$C_4$ alkyl, optionally substituted $C_1$-$C_4$ fluoroalkyl, optionally substituted $C_2$-$C_6$ alkenyl, —NR$^{3c}$R$^{3d}$, —S(=O)$_2$O$^-$, —S(=O)$_2$OR$^{9a}$, —C(=O)O$^-$, and —C(=O)OR$^{9a}$;
each $R^{3c}$ and $R^{3d}$ is independently selected from hydrogen, optionally substituted $C_1$-$C_4$ alkyl, —X-optionally substituted $C_1$-$C_4$ alkyl, optionally substituted $C_2$-$C_6$ alkenyl, and optionally substituted aryl;
X is —C(=O)—, —S(=O)—, or —S(=O)$_2$—;
each $R^{9a}$, $R^{11a}$, $R^{11b}$, and $R^{11c}$ is independently selected from hydrogen, optionally substituted $C_1$-$C_4$ alkyl, and optionally substituted aryl;
n is an integer selected from 0, 1, 2, 3, 4, 5, 6, 7, and 8; and
s is an integer selected from 1, 2, 3, 4, and 5;
b) a repeating unit of Formula (VIII):

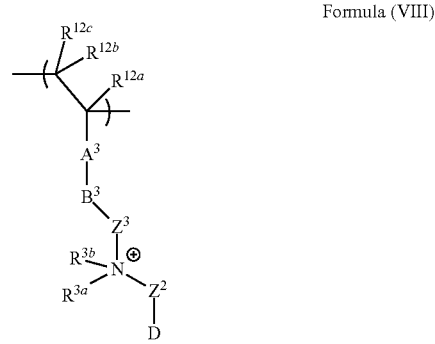

Formula (VIII)

wherein, $A^3$ is —C(=O)—, —S(=O)—, —S(=O)$_2$—, or —S(=O)(=NR$^{3c}$)—;

$B^3$ is —O— or —NR$^{3c}$—;

D is —S(=O)$_2$O$^-$, —S(=O)$_2$OR$^{9a}$, —C(=O)O$^-$, or —C(=O)OR$^{9a}$;

$Z^2$ is —(CR$^{6c}$R$^{6d}$)$_t$—;

$Z^3$ is —(CR$^{6c}$R$^{6d}$)$_p$;

each R$^{3a}$ and R$^{3b}$ is independently selected from hydrogen, optionally substituted C$_1$-C$_4$ alkyl, and optionally substituted benzyl;

each R$^{6c}$ and R$^{6d}$ is independently selected from hydrogen, halogen, —CN, —OR$^{9a}$, optionally substituted C$_1$-C$_4$ alkyl, optionally substituted C$_1$-C$_4$ fluoroalkyl, optionally substituted C$_2$-C$_6$ alkenyl, —NR$^{3c}$R$^{3d}$, —S(=O)$_2$O$^-$, —S(=O)$_2$OR$^{9a}$, —C(=O)O$^-$, and —C(=O)OR$^{9a}$;

each R$^{3c}$ and R$^{3d}$ is independently selected from hydrogen, optionally substituted C$_1$-C$_4$ alkyl, —X-optionally substituted C$_1$-C$_4$ alkyl, optionally substituted C$_2$-C$_6$ alkenyl, and optionally substituted aryl;

X is —C(=O)—, —S(=O)—, or —S(=O)$_2$—;

each R$^{9a}$, R$^{12a}$, R$^{12b}$, and R$^{12c}$ is independently selected from hydrogen, optionally substituted C$_1$-C$_4$ alkyl, and optionally substituted aryl;

t is an integer selected from 1, 2, 3, 4, or 5;

p is an integer selected from 1, 2, 3, 4, or 5; and wherein the repeating unit of Formula (VIII) is charged or zwitterionic; and c) a repeating unit of Formula (IX):

Formula (IX)

$A^4$ is —C(=O)—, —S(=O)—, —S(=O)$_2$—, or —S(=O)(=NR$^{3c}$)—;

$B^4$ is —O— or —NR$^{3c}$—;

$Z^4$ is —(CR$^{6c}$R$^{6d}$)$_k$—;

E is —CN, —OR$^{9a}$, —NR$^{9a}$R$^{9b}$, —NR$^{9a}$R$^{9b}$R$^{9c+}$ optionally substituted C$_1$-C$_4$ alkyl, optionally substituted C$_1$-C$_6$ fluoroalkyl, —S(=O)$_2$O$^-$, —S(=O)$_2$R$^{9a}$, —C(=O)O$^-$, or —C(=O)OR$^{9a}$;

each R$^{6c}$, and R$^{6d}$ is independently selected from hydrogen, halogen, —CN, —OR$^{9a}$, optionally substituted C$_1$-C$_4$ alkyl, optionally substituted C$_1$-C$_4$ fluoroalkyl, optionally substituted C$_2$-C$_6$ alkenyl, —NR$^{3c}$R$^{3d}$, —S(=O)$_2$O$^-$, —S(=O)$_2$OR$^{9a}$, —C(=O)O$^-$, and —C(=O)OR$^{9a}$;

each R$^{3c}$ and R$^{3d}$ is independently selected from hydrogen, optionally substituted C$_1$-C$_4$ alkyl, —X-optionally substituted C$_1$-C$_4$ alkyl, optionally substituted C$_2$-C$_6$ alkenyl, and optionally substituted aryl;

X is —C(=O)—, —S(=O)—, or —S(=O)$_2$—;

each R$^{9a}$, R$^{9b}$, R$^{9c}$, R$^{13a}$, R$^{13b}$, and R$^{13c}$, is independently selected from hydrogen, optionally substituted C$_1$-C$_4$ alkyl, and optionally substituted aryl; and k is an integer selected from 1-10.

In some embodiments, the repeating unit of Formula (IX) is charged or zwitterionic.

In some embodiments, different variables of a compound of Formula (VII), Formula (VIII), and Formula (IX) are as described above.

Biofouling-Resistant Medical Devices

In some embodiments, disclosed herein is a biofouling-resistant medical device, wherein a surface of the medical device is coated with one or more compounds of Formula (I), (II), or (III) described herein having a number-average molecular weight of between about 10,000 and about 250,000. In some embodiments, disclosed herein is a biofouling-resistant medical device, wherein a surface of the medical device is coated with one or more copolymers comprising repeating units of Formula (VII), (VIII), and (IX) described herein having a number-average molecular weight of between about 10,000 and about 250,000.

In some embodiments, the phenyl azide-based copolymer has a number-average molecular weight of at least about 10,000, about 20,000, about 30,000, about 40,000, about 50,000, about 60,000, about 70,000, about 80,000, about 90,000, about 100,000, about 110,000, about 120,000, about 130,000, about 140,000, about 150,000, about 160,000, about 170,000, about 180,000, about 190,000, or about 200,000. In some embodiments, the phenyl azide-based copolymer has a number-average molecular weight of no more than about 10,000, about 20,000, about 30,000, about 40,000, about 50,000, about 60,000, about 70,000, about 80,000, about 90,000, about 100,000, about 110,000, about 120,000, about 130,000, about 140,000, about 150,000, about 160,000, about 170,000, about 180,000, about 190,000, or about 200,000.

In some embodiments, the phenyl azide-based copolymer has a number-average molecular weight of between about 10,000 and about 20,000. In some embodiments, the phenyl azide-based copolymer has a number-average molecular weight of between about 10,000 and about 40,000. In some embodiments, the phenyl azide-based copolymer has a number-average molecular weight of between about 10,000 and about 60,000. In some embodiments, the phenyl azide-based copolymer has a number-average molecular weight of between about 10,000 and about 80,000. In some embodiments, the phenyl azide-based copolymer has a number-average molecular weight of between about 10,000 and about 100,000. In some embodiments, the phenyl azide-based copolymer has a number-average molecular weight of between about 10,000 and about 120,000. In some embodiments, the phenyl azide-based copolymer has a number-average molecular weight of between about 10,000 and about 140,000. In some embodiments, the phenyl azide-based copolymer has a number-average molecular weight of between about 10,000 and about 160,000. In some embodiments, the phenyl azide-based copolymer has a number-average molecular weight of between about 10,000 and about 200,000. In some embodiments, the phenyl azide-based copolymer has a number-average molecular weight of between about 20,000 and about 40,000. In some embodiments, the phenyl azide-based copolymer has a number-average molecular weight of between about 20,000 and about 60,000. In some embodiments, the phenyl azide-based copolymer has a number-average molecular weight of between about 20,000 and about 80,000. In some embodiments, the phenyl azide-based copolymer has a number-average molecular weight of between about 20,000 and about 100,000. In some embodiments, the phenyl azide-based copolymer has a number-average molecular weight of between about 20,000 and about 120,000. In some embodiments, the phenyl azide-based copolymer has a number-average molecular weight of between about 20,000 and about 140,000. In some embodiments, the phenyl azide-based copolymer has a number-average molecular weight of between about 20,000 and about 160,000. In some embodiments, the phenyl azide-based copolymer has a number-average molecular weight of between about 20,000 and about 200,000. In some embodiments, the phenyl azide-based copolymer has a number-average molecular weight of between about 20,000 and about 250,000. In some embodiments, the phenyl azide-based copolymer has a number-average molecular weight of between about 40,000 and about 60,000. In some embodiments, the phenyl azide-based copolymer has a number-average molecular weight of between about 40,000 and about 80,000. In some embodiments, the phenyl azide-based copolymer has a number-average molecular weight of between about 40,000 and about 100,000. In some embodiments, the phenyl azide-based copolymer has a number-average molecular weight of between about 40,000 and about 120,000. In some embodiments, the phenyl azide-based copolymer has a number-average molecular weight of between about 40,000 and about 140,000. In some embodiments, the phenyl azide-based copolymer has a number-average molecular weight of between about 40,000 and about 160,000. In some embodiments, the phenyl azide-based copolymer has a number-average molecular weight of between about 40,000 and about 200,000. In some embodiments, the phenyl azide-based copolymer has a number-average molecular weight of between about 40,000 and about 250,000. In some embodiments, the phenyl azide-based copolymer has a number-average molecular weight of between about 60,000 and about 80,000. In some embodiments, the phenyl azide-based copolymer has a number-average molecular weight of between about 60,000 and about 100,000. In some embodiments, the phenyl azide-based copolymer has a number-average molecular weight of between about 60,000 and about 120,000. In some embodiments, the phenyl azide-based copolymer has a number-average molecular weight of between about 60,000 and about 140,000. In some embodiments, the phenyl azide-based copolymer has a number-average molecular weight of between about 60,000 and about 160,000. In some embodiments, the phenyl azide-based copolymer has a number-average molecular weight of between about 60,000 and about 200,000. In some embodiments, the phenyl azide-based copolymer has a number-average molecular weight of between about 60,000 and about 250,000. In some embodiments, the phenyl azide-based copolymer has a number-average molecular weight of between about 80,000 and about 100,000. In some embodiments, the phenyl azide-based copolymer has a number-average molecular weight of between about 80,000 and about 120,000. In some embodiments, the phenyl azide-based copolymer has a number-average molecular weight of between about 80,000 and about 140,000. In some embodiments, the phenyl azide-based copolymer has a number-average molecular weight of between about 80,000 and about 160,000. In some embodiments, the phenyl azide-based copolymer has a number-average molecular weight of between about 80,000 and about 200,000. In some embodiments, the phenyl azide-based copolymer has a number-average molecular weight of between about 80,000 and about 250,000. In some embodiments, the phenyl azide-based copolymer has a number-average molecular weight of between about 100,000 and about 120,000. In some embodiments, the phenyl azide-based copolymer has a number-average molecular weight of between about 100,000 and about 140,000. In some embodiments, the phenyl azide-based copolymer has a number-average molecular weight of between about 100,000 and about 160,000. In some embodiments, the phenyl azide-based copolymer has a number-average molecular weight of between about 100,000 and about 200,000. In some embodiments, the phenyl azide-based copolymer has a number-average molecular weight of between about 100,000 and about 250,000. In some embodiments, the phenyl azide-based copolymer has a number-average molecular weight of between about 120,000 and about 140,000. In some embodiments, the phenyl azide-based copolymer has a number-average molecular weight of between about 120,000 and about 160,000. In some embodiments, the phenyl azide-based copolymer has a number-average molecular weight of between about 120,000 and about 200,000. In some embodiments, the phenyl azide-based copolymer has a number-average molecular weight of between about 120,000 and about 250,000. In some embodiments, the phenyl azide-based copolymer has a number-average molecular weight of between about 140,000 and about 160,000. In some embodiments, the phenyl azide-based copolymer has a number-average molecular weight of between about 140,000 and about 200,000. In some embodiments, the phenyl azide-based copolymer has a number-average molecular weight of between about 140,000 and about 250,000. In some embodiments, the phenyl azide-based copolymer has a number-average molecular weight of between about 160,000 and about 200,000. In some embodiments, the phenyl azide-based copolymer has a number-average molecular weight of between about 160,000 and about 250,000. In some embodiments, the phenyl azide-based copolymer has a number-average molecular weight of between about 200,000 and about 250,000. In some embodiments, the phenyl azide-based copolymer has a number-average molecular weight of about 10,000. In some embodiments, the phenyl azide-based copolymer has a number-average molecular weight of about 20,000. In some embodiments, the phenyl azide-based copolymer has a number-average molecular weight of about 40,000. In some embodiments, the phenyl azide-based copolymer has a number-average molecular weight of about 60,000. In some embodiments, the phenyl azide-based copolymer has a number-average molecular weight of about 80,000. In some embodiments, the phenyl azide-based copolymer has a number-average molecular weight of about 100,000. In some embodiments, the phenyl azide-based copolymer has a number-average molecular weight of about 120,000. In some embodiments, the phenyl azide-based copolymer has a number-average molecular weight of about 140,000. In some embodiments, the phenyl azide-based copolymer has a number-average molecular weight of about 160,000. In some embodiments, the phenyl azide-based copolymer has a number-average molecular weight of about 200,000. In some embodiments, the phenyl azide-based copolymer has a number-average molecular weight of about 250,000.

In some embodiments, disclosed herein is a biofouling-resistant medical device, wherein a surface of the medical device is coated with one or more compounds of Formula (I), (II), or (III) described herein having a number-average molecular weight of between about 14,000 and about 21,000. In some embodiments, disclosed herein is a biofouling-resistant medical device, wherein a surface of the medical device is coated with one or more copolymers comprising repeating units of Formula (VII), (VIII), and (IX) described herein having a number-average molecular weight of between about 14,000 and about 21,000.

In some embodiments, the phenyl azide-based copolymer has a number-average molecular weight of between about 14,000 and about 15,000. In some embodiments, the phenyl azide-based copolymer has a number-average molecular weight of between about 14,000 and about 16,000. In some embodiments, the phenyl azide-based copolymer has a number-average molecular weight of between about 14,000 and about 17,000. In some embodiments, the phenyl azide-based copolymer has a number-average molecular weight of between about 14,000 and about 18,000. In some embodiments, the phenyl azide-based copolymer has a number-average molecular weight of between about 14,000 and about 19,000. In some embodiments, the phenyl azide-based copolymer has a number-average molecular weight of between about 14,000 and about 20,000. In some embodiments, the phenyl azide-based copolymer has a number-average molecular weight of between about 15,000 and about 16,000. In some embodiments, the phenyl azide-based copolymer has a number-average molecular weight of between about 15,000 and about 17,000. In some embodiments, the phenyl azide-based copolymer has a number-average molecular weight of between about 15,000 and about 18,000. In some embodiments, the phenyl azide-based copolymer has a number-average molecular weight of between about 15,000 and about 19,000. In some embodiments, the phenyl azide-based copolymer has a number-average molecular weight of between about 15,000 and about 20,000. In some embodiments, the phenyl azide-based copolymer has a number-average molecular weight of between about 15,000 and about 21,000. In some embodiments, the phenyl azide-based copolymer has a number-average molecular weight of between about 16,000 and about 17,000. In some embodiments, the phenyl azide-based copolymer has a number-average molecular weight of between about 16,000 and about 18,000. In some embodiments, the phenyl azide-based copolymer has a number-average molecular weight of between about 16,000 and about 19,000. In some embodiments, the phenyl azide-based copolymer has a number-average molecular weight of between about 16,000 and about 20,000. In some embodiments, the phenyl azide-based copolymer has a number-average molecular weight of between about 16,000 and about 21,000. In some embodiments, the phenyl azide-based copolymer has a number-average molecular weight of between about 17,000 and about 18,000. In some embodiments, the phenyl azide-based copolymer has a number-average molecular weight of between about 17,000 and about 19,000. In some embodiments, the phenyl azide-based copolymer has a number-average molecular weight of between about 17,000 and about 20,000. In some embodiments, the phenyl azide-based copolymer has a number-average molecular weight of between about 17,000 and about 21,000. In some embodiments, the phenyl azide-based copolymer has a number-average molecular weight of between about 18,000 and about 19,000. In some embodiments, the phenyl azide-based copolymer has a number-average molecular weight of between about 18,000 and about 20,000. In some embodiments, the phenyl azide-based copolymer has a number-average molecular weight of between about 18,000 and about 21,000. In some embodiments, the phenyl azide-based copolymer has a number-average molecular weight of between about 19,000 and about 20,000. In some embodiments, the phenyl azide-based copolymer has a number-average molecular weight of between about 19,000 and about 21,000. In some embodiments, the phenyl azide-based copolymer has a number-average molecular weight of between about 20,000 and about 21,000. In some embodiments, the phenyl azide-based copolymer has a number-average molecular weight of about 14,000. In some embodiments, the phenyl azide-based copolymer has a number-average molecular weight of about 15,000. In some embodiments, the phenyl azide-based copolymer has a number-average molecular weight of about 16,000. In some embodiments, the phenyl azide-based copolymer has a number-average molecular weight of about 17,000. In some embodiments, the phenyl azide-based copolymer has a number-average molecular weight of about 18,000. In some embodiments, the phenyl azide-based copolymer has a number-average molecular weight of about 19,000. In some embodiments, the phenyl azide-based copolymer has a number-average molecular weight of about 20,000. In some embodiments, the phenyl azide-based copolymer has a number-average molecular weight of about 21,000.

In some embodiments, disclosed herein is a biofouling-resistant medical device, wherein a surface of the medical device is coated with one or more compounds of Formula (I), (II), or (III) described herein having a polydispersity index (PDI) of between about 1 and 1.5. In some embodiments, disclosed herein is a biofouling-resistant medical device, wherein a surface of the medical device is coated with one or more copolymers comprising repeating units of Formula (VII), (VIII), and (IX) described herein having a polydispersity index (PDI) of between about 1 and 1.5.

In some embodiments, the surface of the medical device is coated with a phenyl azide-based copolymer having a polydispersity index (PDI) of at least about 1, about 1.1, about 1.2, about 1.3, about 1.4, or about 1.5. In some embodiments, the surface of the medical device is coated with a phenyl azide-based copolymer having a polydispersity index (PDI) of no more than about 1, about 1.1, about 1.2, about 1.3, about 1.4, or about 1.5.

In some embodiments, the surface of the medical device is coated with a phenyl azide-based copolymer having a polydispersity index (PDI) of between about 1 and 1.1. In some embodiments, the surface of the medical device is coated with a phenyl azide-based copolymer having a polydispersity index (PDI) of between about 1 and 1.2. In some embodiments, the surface of the medical device is coated with a phenyl azide-based copolymer having a polydispersity index (PDI) of between about 1 and 1.3. In some embodiments, the surface of the medical device is coated with a phenyl azide-based copolymer having a polydispersity index (PDI) of between about 1 and 1.4. In some embodiments, the surface of the medical device is coated with a phenyl azide-based copolymer having a polydispersity index (PDI) of between about 1 and 1.5. In some embodiments, the surface of the medical device is coated with a phenyl azide-based copolymer having a polydispersity index (PDI) of between about 1.1 and 1.2. In some embodiments, the surface of the medical device is coated with a phenyl azide-based copolymer having a polydispersity index (PDI) of between about 1.1 and 1.3. In some embodiments, the surface of the medical device is coated with a phenyl azide-based copolymer having a polydispersity index (PDI) of between about 1.1 and 1.4. In some embodiments, the surface of the medical device is coated with a phenyl azide-based copolymer having a polydispersity index (PDI) of between about 1.1 and 1.5. In some embodiments, the surface of the medical device is coated with a phenyl azide-based copolymer having a polydispersity index (PDI) of between about 1.2 and 1.3. In some embodiments, the surface of the medical device is coated with a phenyl azide-based copolymer having a polydispersity index (PDI) of between about 1.2 and 1.4. In some embodiments, the surface of the medical device is coated with a phenyl azide-based copolymer having a polydispersity index (PDI) of between about 1.2 and 1.5. In some embodiments, the surface of the medical device is coated with a phenyl azide-based copolymer having a polydispersity index (PDI) of between about 1.3 and 1.4. In some embodiments, the surface of the medical device is coated with a phenyl azide-based copolymer having a polydispersity index (PDI) of between about 1.3 and 1.5. In some embodiments, the surface of the medical device is coated with a phenyl azide-based copolymer having a polydispersity index (PDI) of between about 1.4 and 1.5. In some embodiments, the PDI is about 1. In some embodiments, the PDI is about 1.1. In some embodiments, the PDI is about 1.2. In some embodiments, the PDI is about 1.3. In some embodiments, the PDI is about 1.4. In some embodiments, the PDI is about 1.5. In some embodiments, the PDI is about 1.11. In some embodiments, the PDI is about 1.12. In some embodiments, the PDI is about 1.13. In some embodiments, the PDI is about 1.14. In some embodiments, the PDI is about 1.15. In some embodiments, the PDI is about 1.16. In some embodiments, the PDI is about 1.17. In some embodiments, the PDI is about 1.18. In some embodiments, the PDI is about 1.19. In some embodiments, the PDI is about 1.21. In some embodiments, the PDI is about 1.22. In some embodiments, the PDI is about 1.23. In some embodiments, the PDI is about 1.24. In some embodiments, the PDI is about 1.25.

In some embodiments, the medical device comprises a dental instrument or a medical instrument. In some embodiments, the medical device comprises an implant, an IV, a prosthesis, a suturing material, a valve, a stent, a catheter, a rod, a shunt, a scope, a contact lens, a tubing, a wiring, an electrode, a clip, a fastener, a syringe, a container, or a combination thereof. In some embodiments, the medical device is a contact lens. In some embodiments, the medical device is a catheter. In some embodiments, the catheter is an indwelling catheter. In some embodiments, the catheter comprises a uretic catheter or a Foley catheter. In some embodiments, the medical device is a scope. In some embodiments, the scope comprises a scope utilized in an image-guided surgery. In some embodiments, the scope comprises a scope utilized in endoscopy or laparoscopy.

In some embodiments, the medical device comprises auditory prostheses, artificial larynx, dental implants, mammary implants, penile implants, cranio/facial tendons, tendons, ligaments, menisci, or disks. In some embodiments, the medical device comprises artificial bones, artificial joints, or artificial organs. In some embodiments, the artificial organs comprise artificial pancreas, artificial hearts, artificial limbs, or heart valves. In some embodiments, the medical device comprises a bandage or a patch.

In some embodiments, the copolymer comprises zwitterionic copolymer. In some embodiments, the zwitterionic copolymer comprises polysulfobetaine.

In some embodiments, the biofouling is produced by a bacterium, a virus, and/or a fungus.

Non-Medical Devices

In some embodiments, a device described herein comprises a non-medical device. In some instances, a non-medical device comprises a marine vessel or an underwater construction. In some cases, a surface of a non-medical device for coating a compound described herein comprises a surface that is immersed in water. In some cases, the immersion is an immersion of at least 30 minutes, 1 hour, 6 hours, 12 hours, 1 day, 2 days, 3 days, 4 days, 5 days, 6 days, 7 days, 8 days, 9 days, 10 days, 11 days, 12 days, 13 days, 14 days, 15 days, 30 days, 1 month, 2 months, 3 months, 4 months, 5 months, 6 months, 7 months, 8 months, 9 months, 10 months, 11 months, 1 year, 2 years, 3 years, 4 years, 5 years, 10 years, or more.

In some instances, a device described herein comprises a marine vessel. In some instances, a surface of a marine vessel comprises a surface that is immersed in water. In some cases, a surface of a marine vessel comprises a surface that is immersed in water for at least 30 minutes, 1 hour, 6 hours, 12 hours, 1 day, 2 days, 3 days, 4 days, 5 days, 6 days, 7 days, 8 days, 9 days, 10 days, 11 days, 12 days, 13 days, 14 days, 15 days, 30 days, 1 month, 2 months, 3 months, 4 months, 5 months, 6 months, 7 months, 8 months, 9 months, 10 months, 11 months, 1 year, 2 years, 3 years, 4 years, 5 years, 10 years, or more. In some instances, the surface of a device for coating a compound described herein comprises the hull of a marine vessel.

In some instances, a device described herein comprises an underwater construction. In some instances, an underwater construction comprises an underwater cable, a current measurement instrument, or an offshore oil platform. In some cases, a device described herein comprises an underwater cable. In some cases, a device described herein comprises a current measurement instrument. In other cases, a device described herein comprises an offshore oil platform.

In some cases, an underwater construction is a construction in which the construction is immersed in water for at least 30 minutes, 1 hour, 6 hours, 12 hours, 1 day, 2 days, 3 days, 4 days, 5 days, 6 days, 7 days, 8 days, 9 days, 10 days, 11 days, 12 days, 13 days, 14 days, 15 days, 30 days, 1 month, 2 months, 3 months, 4 months, 5 months, 6 months, 7 months, 8 months, 9 months, 10 months, 11 months, 1 year, 2 years, 3 years, 4 years, 5 years, or more. In some cases, a surface of an underwater construction is a construction in which the surface is immersed in water for at least 30 minutes, 1 hour, 6 hours, 12 hours, 1 day, 2 days, 3 days, 4 days, 5 days, 6 days, 7 days, 8 days, 9 days, 10 days, 11 days, 12 days, 13 days, 14 days, 15 days, 30 days, 1 month, 2 months, 3 months, 4 months, 5 months, 6 months, 7 months, 8 months, 9 months, 10 months, 11 months, 1 year, 2 years, 3 years, 4 years, 5 years, 10 years, or more. In some instances, a device described herein comprises an underwater construction in which the surface is immersed in water for at least 30 minutes, 1 hour, 6 hours, 12 hours, 1 day, 2 days, 3 days, 4 days, 5 days, 6 days, 7 days, 8 days, 9 days, 10 days, 11 days, 12 days, 13 days, 14 days, 15 days, 30 days, 1 month, 2 months, 3 months, 4 months, 5 months, 6 months, 7 months, 8 months, 9 months, 10 months, 11 months, 1 year, 2 years, 3 years, 4 years, 5 years, 10 years, or more.

In some embodiments, a compound described herein is coated onto a device (e.g., a medical device or a non-medical device). In some cases, a compound described herein is coated directly onto a device (e.g., a medical device or a non-medical device). In other instances, a compound described herein is coated indirectly onto a device (e.g., a medical device or a non-medical device). In some cases, the coating comprises dip-coating. In other cases, the coating comprises spray coating.

In some embodiments, a compound described herein is coated onto a device (e.g., a medical device or a non-medical device) to reduce the formation of biofouling. In some cases, the formation of biofouling is reduced by about 10%, 20%, 30%, 40%, 50%, 60%, 70%, 80%, 90%, 95%, 99%, 99.5%, 99.9%, or more relative to a device not coated with the compound. In some instances, the formation of biofouling is reduced by about 10%, or more relative to a device not coated with the compound. In some instances, the formation of biofouling is reduced by about 20%, or more relative to a device not coated with the compound. In some instances, the formation of biofouling is reduced by about 30%, or more relative to a device not coated with the compound. In some instances, the formation of biofouling is reduced by about 40%, or more relative to a device not coated with the compound. In some instances, the formation of biofouling is reduced by about 50%, or more relative to a device not coated with the compound. In some instances, the formation of biofouling is reduced by about 60%, or more relative to a device not coated with the compound. In some instances, the formation of biofouling is reduced by about 70%, or more relative to a device not coated with the compound. In some instances, the formation of biofouling is reduced by about 80%, or more relative to a device not coated with the compound. In some instances, the formation of biofouling is reduced by about 90%, or more relative to a device not coated with the compound. In some instances, the formation of biofouling is reduced by about 95%, or more relative to a device not coated with the compound. In some instances, the formation of biofouling is reduced by about 99%, or more relative to a device not coated with the compound. In some instances, the formation of biofouling is reduced by about 99.5%, or more relative to a device not coated with the compound. In some instances, the formation of biofouling is reduced by about 99.9%, or more relative to a device not coated with the compound.

IV. Methods of Making

In a further aspect, described herein is a method of preparing a biofouling-resistant device, comprising:
a) contacting a surface of a device with a mixture (e.g., a solution) comprising a copolymer; and
b) treating the surface of the device of step a) with a light source for a time sufficient to undergo photografting of the copolymer onto the surface of the device, thereby making the biofouling-resistant device;
wherein the copolymer comprises a phenyl azide-based copolymer; and wherein the copolymer has a number-average molecular weight of between about 10,000 and about 250,000.

In some embodiments, also described herein is a method of preparing a copolymer modified biofouling-resistant silicon-based device comprising:
a) contacting a surface of a silicon-based device with a mixture (e.g., a solution) comprising a charged or zwitterion copolymer; and
b) treating the surface of the device of step a) with a light source for a time sufficient to undergo photografting of the copolymer onto the surface of the silicon-based device, thereby generating the charged or zwitterion copolymer modified device;
wherein the charged or zwitterion copolymer comprises a phenyl azide-based copolymer.

In some embodiments, also described herein is a method of preparing a charged or zwitterion copolymer modified biofouling-resistant device comprising:
a) contacting a surface of a device with a mixture (e.g., a solution) comprising a charged or zwitterion copolymer; and
b) treating the surface of the device of step a) with a light source for a time sufficient to undergo photografting of the copolymer onto the surface of the device, thereby generating the charged or zwitterion copolymer modified device;
wherein the charged or zwitterion copolymer comprises a phenyl azide-based copolymer; and wherein the charged or zwitterion copolymer has a number-average molecular weight of between about 10,000 and about 250,000.

In some embodiments, the method comprises one-step grafting reaction that modifies the surface of a device.

In some embodiments, the device is a medical device described herein. In some embodiments, the device is a non-medical device described herein.

In some embodiments, the time sufficient to undergo photografting is at least 1 minute, at least 2 minutes, 3 minutes, 4 minutes, 5 minutes, 6 minutes, 7 minutes, 8 minutes, 9 minutes, 10 minutes, 15 minutes, 20 minutes, 25 minutes or 30 minutes.

In some embodiments, the light source is an ultraviolet light source. In some embodiments, the ultraviolet light source has an intensity of at least 500 $\mu W/cm^2$. In some embodiments, the ultraviolet light source has an intensity of at least 600 $\mu W/cm^2$. In some embodiments, the ultraviolet light source has an intensity of at least 700 $\mu W/cm^2$. In some embodiments, the ultraviolet light source has an intensity of at least 800 $\mu W/cm^2$. In some embodiments, the ultraviolet light source has an intensity of at least 900 $\mu W/cm^2$. In some embodiments, the ultraviolet light source has an intensity of at least 1000 $\mu W/cm^2$.

In some embodiments, the ultraviolet light source has a wavelength of between 240 nm and 280 nm, between 240 nm and 275 nm, between 240 nm and 270 nm, between 240 nm and 265 nm, between 240 nm and 260 nm, between 240 nm and 255 nm, between 240 nm and 250 nm, between 240 nm and 245 nm, between 250 nm and 280 nm, between 250 nm and 275 nm, between 250 nm and 270 nm, between 250 nm and 265 nm, between 250 nm and 260 nm, between 255 nm and 280 nm, between 255 nm and 275 nm, between 255 nm and 270 nm, between 255 nm and 265 nm, between 255 nm and 260 nm, between 260 nm and 280 nm, between 260 nm and 275 nm, between 260 nm and 270 nm, or between 270 nm and 280 nm.

In some embodiments, the ultraviolet light source has a wavelength of at least 240 nm, 245 nm, 250 nm, 251 nm, 252 nm, 253 nm, 254 nm, 255 nm, 256 nm, 257 nm, 258 nm, 259 nm, 260 nm, 261 nm, 262 nm, 263 nm, 264 nm, 265 nm, 266 nm, 267 nm, 268 nm, 269 nm, 270 nm, 275 nm or 280 nm. In some embodiments, the ultraviolet light source has a wavelength of no more than 240 nm, 245 nm, 250 nm, 251 nm, 252 nm, 253 nm, 254 nm, 255 nm, 256 nm, 257 nm, 258 nm, 259 nm, 260 nm, 261 nm, 262 nm, 263 nm, 264 nm, 265 nm, 266 nm, 267 nm, 268 nm, 269 nm, 270 nm, 275 nm or 280 nm.

In a further aspect, described herein is a method of preparing a biofouling-resistant device, comprising:
a) contacting a surface of a device with a mixture (e.g., a solution) comprising a copolymer; and
b) treating the surface of the device of step a) with a heat source for a time sufficient to undergo thermografting of the copolymer onto the surface of the device, thereby making the biofouling-resistant device;
wherein the copolymer comprises a phenyl azide-based copolymer; and wherein the copolymer has a number-average molecular weight of between about 10,000 and about 250,000.

In some embodiments, also described herein is a method of preparing a copolymer modified biofouling-resistant silicon-based device comprising:
  a) contacting a surface of a silicon-based device with a mixture (e.g., a solution) comprising a charged or zwitterion copolymer; and
  b) treating the surface of the device of step a) with a heat source for a time sufficient to undergo thermografting of the copolymer onto the surface of the silicon-based device, thereby generating the charged or zwitterion copolymer modified device;
  wherein the charged or zwitterion copolymer comprises a phenyl azide-based copolymer.

In some embodiments, also described herein is a method of preparing a charged or zwitterion copolymer modified biofouling-resistant device comprising:
  a) contacting a surface of a device with a mixture (e.g., a solution) comprising a charged or zwitterion copolymer; and
  b) treating the surface of the device of step a) with a heat source for a time sufficient to undergo thermografting of the copolymer onto the surface of the device, thereby generating the charged or zwitterion copolymer modified device;
  wherein the charged or zwitterion copolymer comprises a phenyl azide-based copolymer; and wherein the charged or zwitterion copolymer has a number-average molecular weight of between about 10,000 and about 250,000.

In some embodiments, the method comprises one-step grafting reaction that modifies the surface of a device.

In some embodiments, the device is a medical device described herein. In some embodiments, the device is a non-medical device described herein.

In some embodiments, the time sufficient to undergo thermografting is 1 minute, 2 minutes, 3 minutes, 4 minutes, 5 minutes, 6 minutes, 7 minutes, 8 minutes, 9 minutes, 10 minutes, 15 minutes, 20 minutes, 25 minutes, 30 minutes, 45 minutes, 1 hour, 1.5 hours, 2 hours, 3 hours, 4 hours, 5 hours, 6 hours, 9 hours, 12 hours, 18 hours, or 24 hours. In some embodiments, the time sufficient to undergo thermografting is at least 1 minute, at least 2 minutes, at least 3 minutes, at least 4 minutes, at least 5 minutes, at least 6 minutes, at least 7 minutes, at least 8 minutes, at least 9 minutes, at least 10 minutes, at least 15 minutes, at least 20 minutes, at least 25 minutes, at least 30 minutes, at least 45 minutes, at least 1 hour, at least 1.5 hours, at least 2 hours, at least 3 hours, at least 4 hours, at least 5 hours, at least 6 hours, at least 9 hours, at least 12 hours, or at least 18 hours. In some embodiments, the time sufficient to undergo thermografting is at most 2 minutes, at most 3 minutes, at most 4 minutes, at most 5 minutes, at most 6 minutes, at most 7 minutes, at most 8 minutes, at most 9 minutes, at most 10 minutes, at most 15 minutes, at most 20 minutes, at most 25 minutes, at most 30 minutes, at most 45 minutes, at most 1 hour, at most 1.5 hours, at most 2 hours, at most 3 hours, at most 4 hours, at most 5 hours, at most 6 hours, at most 9 hours, at most 12 hours, at most 18 hours, or at most 24 hours.

In some embodiments, the heat source provides a grafting temperature between 40 and 380 degree Celsius (° C.). In some embodiments, the heat source provides a grafting temperature between 40° C. and 360° C. In some embodiments, the heat source provides a grafting temperature between 60° C. and 320° C. In some embodiments, the heat source provides a grafting temperature between 80° C. and 260° C. In some embodiments, the heat source provides a grafting temperature between 100° C. and 220° C. In some embodiments, the heat source provides a grafting temperature between 120° C. and 220° C. In some embodiments, the heat source provides a grafting temperature between 40° C. and 60° C., between 60° C. and 80° C., between 80° C. and 100° C., between 100° C. and 120° C., between 120° C. and 140° C., between 140° C. and 160° C., between 160° C. and 180° C., between 180° C. and 200° C., between 200° C. and 220° C., between 220° C. and 240° C., between 240° C. and 260° C., between 260° C. and 280° C., between 280° C. and 300° C., between 300° C. and 320° C., between 320° C. and 340° C., or between 340° C. and 360° C. In some embodiments, the heat source provides a grafting temperature between 60° C. and 80° C., between 80° C. and 100° C., between 100° C. and 120° C., between 120° C. and 140° C., between 140° C. and 160° C., between 160° C. and 180° C., between 180° C. and 200° C., between 200° C. and 220° C., or between 220° C. and 240° C. In some embodiments, the heat source provides a grafting temperature of 60° C., 80° C., 100° C., 120° C., 140° C., 160° C., 180° C., 200° C., 220° C., 240° C., 260° C., 280° C., or 300° C. In some embodiments, the heat source provides a grafting temperature of 60° C., 80° C., 100° C., 120° C., 140° C., 160° C., 180° C., 200° C., or 220° C. In some embodiments, the heat source provides a grafting temperature of at least 60° C., at least 80° C., at least 100° C., at least 120° C., at least 140° C., at least 160° C., at least 180° C., at least 200° C., at least 220° C., at least 240° C., at least 260° C., or at least 280° C. In some embodiments, the heat source provides a grafting temperature of at most 80° C., at most 100° C., at most 120° C., at most 140° C., at most 160° C., at most 180° C., at most 200° C., at most 220° C., at most 240° C., at most 260° C., at most 280° C., or at most 300° C.

In some embodiments, the mixture of step a) is an aqueous solution, an aqueous colloid, or an aqueous suspension. In some embodiments, the mixture of step a) is a non-aqueous solution, an aqueous colloid, or an aqueous suspension.

In some embodiments, the phenyl azide-based copolymer is a compound of Formula (II) or (III) described herein.

In some embodiments, the mixture comprising a charged or zwitterion copolymer has a concentration of the charged or zwitterion copolymer in the mixture between 1 mg/mL and 30 mg/mL.

In some embodiments, the concentration of the charged or zwitterion copolymer in the mixture is between 0.1 mg/mL and 100 mg/mL, 0.5 mg/mL and 50 mg/mL, 1 mg/mL and 25 mg/mL, between 1 mg/mL and 20 mg/mL, between 1 mg/mL and 15 mg/mL, between 1 mg/mL and 10 mg/mL, between 1 mg/mL and 5 mg/mL, between 5 mg/mL and 30 mg/mL, between 5 mg/mL and 25 mg/mL, between 5 mg/mL and 20 mg/mL, between 5 mg/mL and 15 mg/mL, between 5 mg/mL and 10 mg/mL, between 10 mg/mL and 30 mg/mL, between 10 mg/mL and 25 mg/mL, between 10 mg/mL and 20 mg/mL, between 10 mg/mL and 15 mg/mL, between 15 mg/mL and 30 mg/mL, between 15 mg/mL and 25 mg/mL, between 15 mg/mL and 20 mg/mL, between 20 mg/mL and 30 mg/mL, or between 20 mg/mL and 25 mg/mL. In some embodiments, the concentration of the charged or zwitterion copolymer in the mixture is between 25 mg/mL and 30 mg/mL, between 30 mg/mL and 35 mg/mL, between 35 mg/mL and 40 mg/mL, between 40 mg/mL and 45 mg/mL, between 45 mg/mL and 50 mg/mL, between 50 mg/mL and 55 mg/mL, between 55 mg/mL and 60 mg/mL, between 60 mg/mL and 65 mg/mL, between 65 mg/mL and 70 mg/mL, between 70 mg/mL and 75 mg/mL, between 75 mg/mL and 80 mg/mL, between 80 mg/mL and 85 mg/mL, between 85 mg/mL and 90 mg/mL, between 90 mg/mL and 95 mg/mL, or between 95 mg/mL and 100 mg/mL.

In some embodiments, the concentration of the charged or zwitterion copolymer in the mixture is about 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 11 mg/mL, 12 mg/mL, 13 mg/mL, 14 mg/mL, 15 mg/mL, 16 mg/mL, 17 mg/mL, 18 mg/mL, 19 mg/mL, 20 mg/mL, 21 mg/mL, 22 mg/mL, 23 mg/mL, 24 mg/mL, 25 mg/mL, 26 mg/mL, 27 mg/mL, 28 mg/mL, 29 mg/mL, or 30 mg/mL. In some embodiments, the concentration of the charged or zwitterion copolymer in the mixture is about 31 mg/mL, 32 mg/mL, 33 mg/mL, 34 mg/mL, 35 mg/mL, 36 mg/mL, 37 mg/mL, 38 mg/mL, 39 mg/mL, 40 mg/mL, 41 mg/mL, 42 mg/mL, 43 mg/mL, 44 mg/mL, 45 mg/mL, 46 mg/mL, 47 mg/mL, 48 mg/mL, 49 mg/mL, 50 mg/mL, 51 mg/mL, 52 mg/mL, 53 mg/mL, 54 mg/mL, 55 mg/mL, 56 mg/mL, 57 mg/mL, 58 mg/mL, 59 mg/mL, or 60 mg/mL.

In some embodiments, the concentration of the charged or zwitterion copolymer is between 0.01 to 10 mg per square centimeter of the device. In some embodiments, the concentration of the charged or zwitterion copolymer is between 0.1 to 1 mg per square centimeter of the device. In some embodiments, the concentration of the charged or zwitterion copolymer is between 0.01 to 0.05, between 0.1 to 0.2, between 0.2 to 0.3, between 0.3 to 0.4, between 0.4 to 0.5, between 0.5 to 0.6, between 0.6 to 0.7, between 0.7 to 0.8, between 0.8 to 0.9, between 0.9 to 1, between 1 to 2, between 2 to 2, between 3 to 2, between 4 to 2, between 5 to 2, between 6 to 2, between 7 to 2, between 8 to 2, or between 9 to 10 per square centimeter of the device.

In some embodiments, the device comprises a polymer-based device. In some embodiments, the polymer-based device comprises a polyolefinic device. In some embodiments, the polyolefinic device comprises a device modified with polyethylene (PE), polypropylene (PP), polyamide (PA), polytetrafluoroethylene (PTFE), polyvinylidene fluoride (PVdF), polyvinyl chloride (PVC), or a combination thereof. In some embodiments, the device comprises a microporous device or a nonwoven device. In some embodiments, the device comprises a carbon-based device comprising a moiety capable of binding with a compound that has a structure of Formula (I), (II), or (III). In some embodiments, the device comprises a carbon-based device comprising a moiety capable of binding with a copolymer comprising a repeating unit of Formula (VII), (VIII), and (IX). In some embodiments, the carbon-based device comprises a polymer moiety. In some embodiments, the carbon-based device comprises a carbon-based polymer. In some embodiments, the carbon-based device comprises a polyolefin moiety. In some embodiments, the polyolefin moiety comprises a polyethylene (PE) moiety, a polypropylene (PP) moiety, a polyamide (PA) moiety, a polytetrafluoroethylene (PTFE) moiety, a polyvinylidene fluoride (PVdF) moiety, or a polyvinyl chloride (PVC) moiety.

In some embodiments, the device comprises a carbon-based device. In some embodiments, the carbon-based device comprises a carbon-based polymer. In some embodiments, the carbon-based device comprises a polyolefin moiety. In some embodiments, the polyolefin moiety comprises polyethylene moiety, polypropylene moiety, polyvinyl chloride moiety, polyvinylidene fluoride moiety, polytetrafluoroethylene moiety, polychlorotrifluoroethylene moiety, or polystyrene moiety. In some embodiments, the carbon-based polymer comprises polyamide moiety, polyurethane moiety, phenol-formaldehyde resin moiety, polycarbonate moiety, polychloroprene moiety, polyacrylonitrile moiety, polyimide moiety, or polyester moiety. In some embodiments, the carbon-based polymer comprises nylon. In some embodiments, the carbon-based polymer comprises polyethylene terephthalate.

In some embodiments, the device comprises a silicon-based device. In some embodiments, the silicon-based device comprises a silicon-based polymer moiety. In some embodiments, the device comprises a silicon-based device comprising a moiety capable of binding with a compound that has a structure of Formula (I), (II), or (III). In some embodiments, the device comprises a silicon-based device comprising a moiety capable of binding with a copolymer comprising a repeating unit of Formula (VII), (VIII), and (IX). In some embodiments, the silicon-based device comprises a polymer moiety. In some embodiments, the silicon-based device comprises a siloxane polymer moiety, a sesquisiloxane polymer moiety, a siloxane-silarylene polymer moiety, a silalkylene polymer moiety, a polysilane moiety, a polysilylene moiety, or a polysilazane moiety.

In some embodiments, the silicon-based device comprises a siloxane polymer moiety. In some embodiments, the silicon-based device comprises silicone polymer.

In some embodiments, the device comprises a carbon-based device or a silicon-based device.

In some embodiments, the copolymer comprises zwitterionic copolymer. In some embodiments, the zwitterionic copolymer comprises polysulfobetaine.

In some embodiments, the biofouling of the biofouling-resistant medical device described herein is produced by a bacterium, a virus, and/or a fungus.

V. Methods of Synthesis

Methods provided by the present disclosure also include methods of synthesizing a compound of Formula (II) comprising: reacting a compound of Formula (IV) or a salt or solvate thereof with a compound of Formula (V):

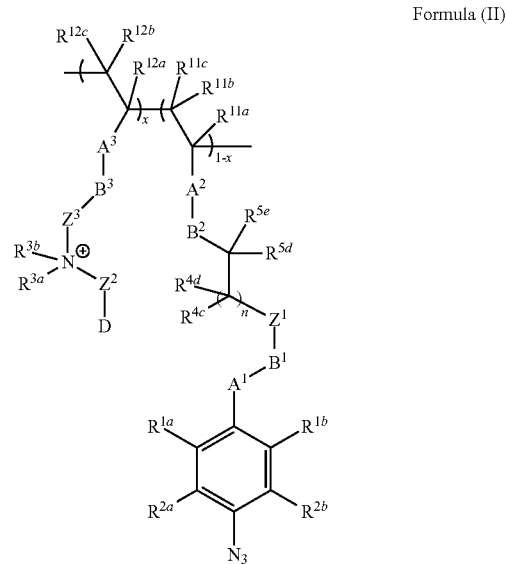

Formula (II)

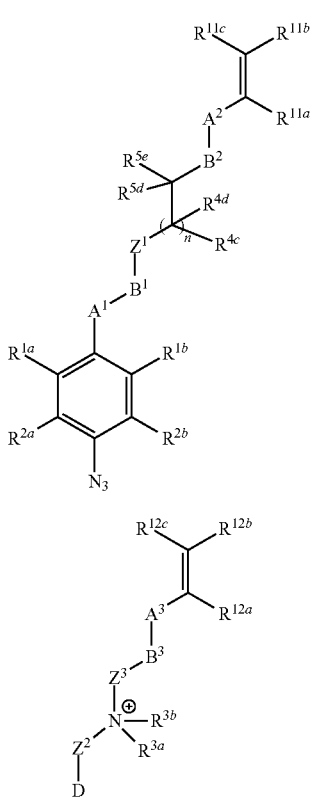

Formula (IV)

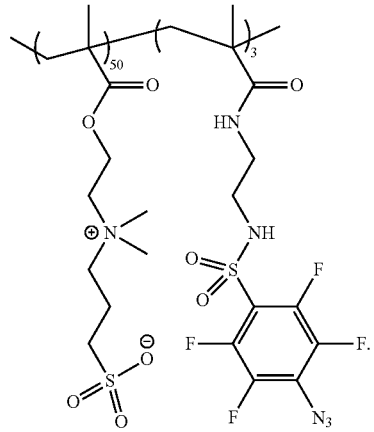

Formula (V)

wherein each $R^{1a}$ and $R^{1b}$ is independently selected from hydrogen and halogen;

each $R^{2a}$ and $R^{2b}$ is independently selected from halogen, —CN, and optionally substituted $C_1$-$C_6$ fluoroalkyl;

each $A^1$, $A^2$, and $A^3$ is independently selected from —C(=O)—, —S(=O)—, —S(=O)$_2$—, and —S(=O)(=NR$^{3c}$)—;

each $B^1$, $B^2$, and $B^3$ is independently selected from —O— and —NR$^{3c}$—;

D is —S(=O)$_2$O$^-$, —S(=O)$_2$OR$^{9a}$, —C(=O)O$^-$, or —C(=O)OR$^{5a}$;

$Z^1$ is —(CR$^{6c}$R$^{6d}$)$_s$—;

$Z^2$ is —(CR$^{6c}$R$^{6d}$)$_t$—;

$Z^3$ is —(CR$^{6c}$R$^{6d}$)$_p$;

each $R^{3a}$ and $R^{3b}$ is independently selected from hydrogen, optionally substituted $C_1$-$C_4$ alkyl, and optionally substituted benzyl;

each $R^{4c}$, $R^{4d}$, $R^{5d}$, $R^{5e}$, $R^{6c}$, and $R^{6d}$ is independently selected from hydrogen, halogen, —CN, —OH, optionally substituted $C_1$-$C_4$ alkyl, optionally substituted $C_1$-$C_4$ fluoroalkyl, optionally substituted $C_2$-$C_6$ alkenyl, —NR$^{3c}$R$^{3d}$, —S(=O)$_2$O$^-$, —S(=O)$_2$OR$^{9a}$, —C(=O)O$^-$, and —C(=O)OR$^{5a}$;

each $R^{3c}$ and $R^{3d}$ is independently selected from hydrogen, optionally substituted $C_1$-$C_4$ alkyl, —X-optionally substituted $C_1$-$C_4$ alkyl, optionally substituted $C_2$-$C_6$ alkenyl, and optionally substituted aryl;

X is —C(=O)—, —S(=O)—, or —S(=O)$_2$—;

each $R^{9a}$, $R^{11a}$, $R^{11b}$, $R^{11c}$, $R^{12a}$, $R^{12b}$, and $R^{12c}$ is independently selected from hydrogen, optionally substituted $C_1$-$C_4$ alkyl, and optionally substituted aryl;

n is an integer selected from 0, 1, 2, 3, 4, 5, 6, 7, and 8;

s is an integer selected from 1, 2, 3, 4, or 5;

t is an integer selected from 1, 2, 3, 4, or 5;

p is an integer selected from 1, 2, 3, 4, or 5;

$0 < x < 1$; and wherein the compounds of Formula (II) and Formula (V) are each charged or zwitterionic.

In some embodiments, a compound of Formula (II) is not

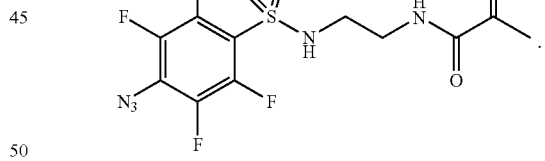

In some embodiments, x in Formula (II) is not about 0.9434.

In some embodiments, a compound of Formula (II) is not obtained by using 2 g sulfobetaine methacrylate monomer and 156 mg perfluorophenylazide methacrylamide monomer.

In some embodiments, different variables of a compound of Formula (II) are as described above.

In some embodiments, the compound of Formula (IV) has the structure of:

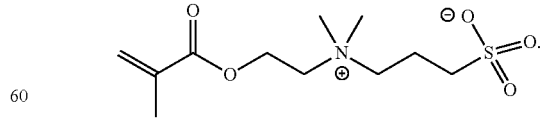

In some embodiments, the compound of Formula (V) has the structure of:

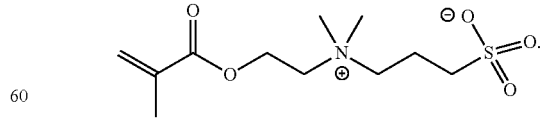

Methods provided by the present disclosure also include methods of synthesizing a compound of Formula (III) comprising: reacting a compound of Formula (IV) or a salt or solvate thereof with a compound of Formula (VI):

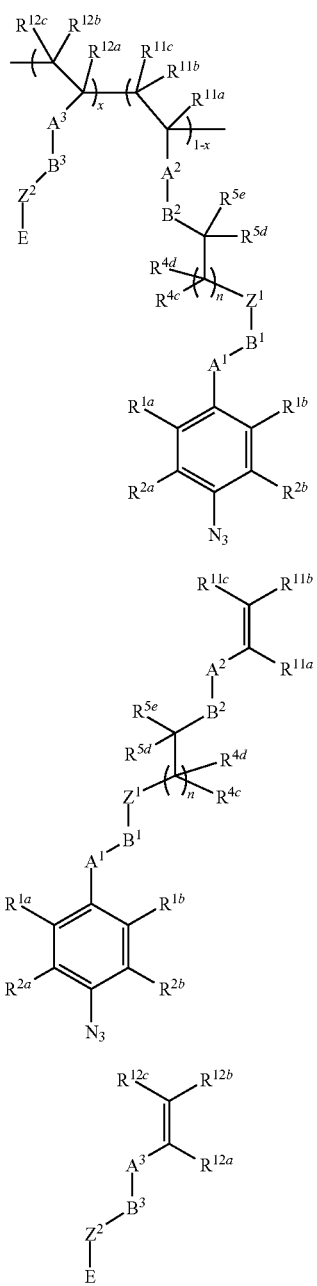

Formula (III)

Formula (IV)

Formula (VI)

wherein
each $R^{1a}$ and $R^{1b}$ is independently selected from hydrogen and halogen;
each $R^{2a}$ and $R^{2b}$ is independently selected from halogen, —CN, and optionally substituted $C_1$-$C_6$ fluoroalkyl;
each $A^1$, $A^2$, and $A^3$ is independently selected from —C(=O)—, —S(=O)—, —S(=O)$_2$—, and —S(=O)(=NR$^{3c}$)—;
each $B^1$, $B^2$, and $B^3$ is independently selected from —O— and —NR$^{3c}$—;
$Z^1$ is —(CR$^{6c}$R$^{6d}$)$_s$—;
$Z^2$ is —(CR$^{6c}$R$^{6d}$)$_t$—;
E is —CN, —OR$^{9a}$, —NR$^{9a}$R$^{9b}$, —NR$^{9a}$R$^{9b}$R$^{9c+}$ optionally substituted $C_1$-$C_4$ alkyl, optionally substituted $C_1$-$C_6$ fluoroalkyl, —S(=O)$_2$O$^-$, —S(=O)$_2$OR$^{9a}$, —C(=O)O$^-$, or —C(=O)OR$^{9a}$;

each $R^{4c}$, $R^{4d}$, $R^{5d}$, $R^{5e}$, $R^{6c}$, and $R^{6d}$ is independently selected from hydrogen, halogen, —CN, —OR$^{9a}$, optionally substituted $C_1$-$C_4$ alkyl, optionally substituted $C_1$-$C_4$ fluoroalkyl, optionally substituted $C_2$-$C_6$ alkenyl, —NR$^{3c}$R$^{3d}$, —S(=O)$_2$O$^-$, —S(=O)$_2$OR$^{9a}$, —C(=O)O$^-$, and —C(=O)OR$^{9a}$;
each $R^{3c}$ and $R^{3d}$ is independently selected from hydrogen, optionally substituted $C_1$-$C_4$ alkyl, —X-optionally substituted $C_1$-$C_4$ alkyl, optionally substituted $C_2$-$C_6$ alkenyl, and optionally substituted aryl;
X is —C(=O)—, —S(=O)—, or —S(=O)$_2$—;
each $R^{9a}$, $R^{9b}$, $R^{9c}$, $R^{11a}$, $R^{11b}$, $R^{11c}$, $R^{12a}$, $R^{12b}$, and $R^{12c}$ is independently selected from hydrogen, optionally substituted $C_1$-$C_4$ alkyl, and optionally substituted aryl;
n is an integer selected from 0, 1, 2, 3, 4, 5, 6, 7, and 8;
s is an integer selected from 1, 2, 3, 4, or 5;
t is an integer selected from 1, 2, 3, 4, or 5; and
$0 < x < 1$.

In some embodiments, the compounds of Formula (III) and Formula (VI) each charged or zwitterionic. In some embodiments, a compound of Formula (VI) comprises a positively charged compound of Formula (VI). In some embodiments a compound of Formula (VI) comprises a negatively charged compound of Formula (VI). In some embodiments, a compound of Formula (III) comprises positively charged repeating units. In some embodiments a compound of Formula (III) comprises negatively charged repeating units. In some embodiments, a compound of Formula (III) comprises positively charged repeating units and negatively charged repeating units. In some embodiments, the ratio of positively charged repeating units and negatively charged repeating units in a compound of Formula (III) is from about 10:1 to about 1:10. In some embodiments, the ratio of positively charged repeating units and negatively charged repeating units in a compound of Formula (III) is from about 5:1 to about 1:5 In some embodiments, the ratio of positively charged repeating units and negatively charged repeating units in a compound of Formula (III) is from about 2:1 to about 1:2. In some embodiments, the ratio of positively charged repeating units and negatively charged repeating units in a compound of Formula (III) is about 1:1.

In some embodiments, different variables of a compound of Formula (III) are as described above.

In some embodiments, the compound of Formula (IV) has the structure of:

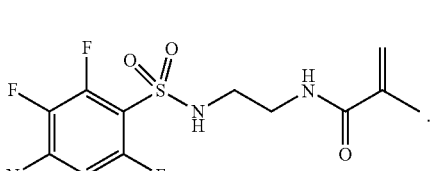

In some embodiments, the compound of Formula (VI) has the structure of:

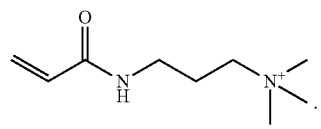

In some embodiments, the compound of Formula (VI) has the structure of:

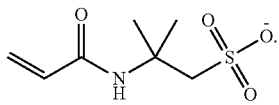

Any combination of the groups described above or below for the various variables is contemplated herein. Throughout the specification, groups and substituents thereof are chosen by one skilled in the field to provide stable moieties and compounds.

Properties of Biofouling-Resistant Coatings

In some embodiments, biofouling-resistant coatings disclosed herein have various properties that provide the superior function of the devices, including excellent flux, improved hydrophilicity, improved resistance to fouling, tunable surface charge properties, higher thermal stability, higher chemical stability, higher solvent stability, or a combination thereof. It is also understood that the coatings disclosed herein have other properties.

In some embodiments, a biofouling-resistant coating disclosed herein has a water receding angle of less than about 70°. In some embodiments, a biofouling-resistant coating disclosed herein has a water receding angle of less than about 65°. In some embodiments, a biofouling-resistant coating disclosed herein has a water receding angle of less than about 60°. In some embodiments, a biofouling-resistant coating disclosed herein has a water receding angle of less than about 55°. In some embodiments, a biofouling-resistant coating disclosed herein has a water receding angle of less than about 50°. In some embodiments, a biofouling-resistant coating disclosed herein has a water receding angle of less than about 45°. In some embodiments, a biofouling-resistant coating disclosed herein has a water receding angle of less than about 40°. In some embodiments, a biofouling-resistant coating disclosed herein has a water receding angle of less than about 35°. In some embodiments, a biofouling-resistant coating disclosed herein has a water receding angle of less than about 30°. In some embodiments, a biofouling-resistant coating disclosed herein has a water receding angle of less than about 25°. In some embodiments, a biofouling-resistant coating disclosed herein has a water receding angle of less than about 20°. In some embodiments, a biofouling-resistant coating disclosed herein has a water receding angle of less than about 15°. In some embodiments, a biofouling-resistant coating disclosed herein has a water receding angle of less than about 10°. In some embodiments, a biofouling-resistant coating disclosed herein has a water receding angle of less than about 5°. In some embodiments, a biofouling-resistant coating disclosed herein has a water receding angle of about 0°. In certain embodiments, the devices provided herein, coated by one or more biofouling-resistant coatings described herein have a high resistance of fouling.

In a further aspect, a biofouling-resistant coating disclosed herein exhibits an improvement in at least one property selected from resistance to fouling, hydrophilicity, surface charge, salt rejection, and roughness. In some embodiments, a biofouling-resistant coating disclosed herein demonstrates an improvement in at least one property selected from resistance to fouling, salt rejection, and hydrophilicity. In some embodiments, a biofouling-resistant coating disclosed herein demonstrates an improvement in resistance to fouling. In some embodiments, a biofouling-resistant coating disclosed herein demonstrates an improvement in hydrophilicity. In some embodiments, a biofouling-resistant coating disclosed herein demonstrates an improvement in surface charge. In some embodiments, a biofouling-resistant coating disclosed herein demonstrates an improvement in roughness. In some embodiments, a biofouling-resistant coating disclosed herein demonstrates reduced surface roughness. In some embodiments, a biofouling-resistant coating disclosed herein demonstrates an improvement in salt rejection.

In some embodiments, a biofouling-resistant coating disclosed herein comprising one or more compounds of Formula (I), (II), or (III) described herein prevents and/or reduces biofouling. In some embodiments, a biofouling-resistant coating disclosed herein comprising one or more copolymers comprising repeating units of Formula (VII), (VIII), and (IX) described herein prevents and/or reduces biofouling. In some instances, biofouling comprises microfouling or macrofouling. Microfouling comprises formation of microorganism adhesion (e.g., bacteria adhesion) and/or biofilm. Biofilm is a group of microorganism which adheres to a surface. In some instances, the adhered microorganisms are further embedded in a self-produced matrix of extracellular polymeric substance, which comprises a polymeric conglomeration of extracellular DNA, protein, and polysaccharides. Macrofouling comprises attachment of larger organism. In some instances a biofouling-resistant coating disclosed herein prevents and/or reduces microfouling. In some instances, a biofouling-resistant coating disclosed herein prevents and/or reduces bacterial adhesion. In some instances, a biofouling-resistant coating disclosed herein prevents and/or reduces biofilm. In other instances, a biofouling-resistant coating disclosed herein prevents and/or reduces macrofouling.

Microfouling

In some instances, microfouling is formed by bacteria or fungi. In some instances, microfouling is formed by bacteria. In some instances, a bacterium is a gram-positive bacterium or a gram-negative bacterium. In some cases, a bacterium is a marine bacterium.

In some cases, microfouling is formed by a gram-positive bacterium. Exemplary gram-positive bacteria include, but are not limited to, bacteria from the genus *Actinomyces, Arthrobacter, Bacillus, Clostridium, Corynebacterium, Enterococcus, Lactococcus, Listeria, Micrococcus, Mycobacterium, Staphylococcus,* or *Streptococcus*. In some instances, a gram-positive bacterium comprises *Actinomyces* spp., *Arthrobacter* spp., *Bacillus licheniformis, Clostridium difficile, Clostridium* spp., *Corynebacterium* spp., *Enterococcus faecalis, Lactococcus* spp., *Listeria monocytogenes, Micrococcus* spp., *Mycobacterium* spp., *Staphylococcus aureus, Staphylococcus epidermidis, Streptococcus pneumoniae,* or *Streptococcus pyogenes*.

In some instances, microfouling is formed by a gram-positive bacterium from the genus *Actinomyces, Arthrobacter, Bacillus, Clostridium, Corynebacterium, Enterococcus, Lactococcus, Listeria, Micrococcus, Mycobacterium, Staphylococcus,* or *Streptococcus*. In some instances, microfouling is formed by a gram-positive bacterium: *Actinomyces* spp., *Arthrobacter* spp., *Bacillus licheniformis, Clostridium difficile, Clostridium* spp., *Corynebacterium* spp., *Enterococcus faecalis, Lactococcus* spp., *Listeria monocytogenes, Micrococcus* spp., *Mycobacterium* spp., *Staphylococcus aureus, Staphylococcus epidermidis, Streptococcus pneumoniae,* or *Streptococcus pyogenes*.

In some instances, a biofouling-resistant coating disclosed herein is resistant to fouling. In some instances, a biofouling-resistant coating disclosed herein prevents and/or reduces microfouling on one or more of its surfaces. In some cases, a biofouling-resistant coating disclosed herein prevents and/or reduces microfouling formed by a gram-positive bacterium from the genus *Actinomyces, Arthrobacter, Bacillus, Clostridium, Corynebacterium, Enterococcus, Lactococcus, Listeria, Micrococcus, Mycobacterium, Staphylococcus,* or *Streptococcus.* In some cases, a biofouling-resistant coating disclosed herein prevents and/or reduces microfouling formed by a gram-positive bacterium: *Actinomyces* spp., *Arthrobacter* spp., *Bacillus licheniformis, Clostridium difficile, Clostridium* spp., *Corynebacterium* spp., *Enterococcus faecalis, Lactococcus* spp., *Listeria monocytogenes, Micrococcus* spp., *Mycobacterium* spp., *Staphylococcus aureus, Staphylococcus epidermidis, Streptococcus pneumoniae,* or *Streptococcus pyogenes.*

In some cases, microfouling comprises bacteria adhesion. In some instances, a biofouling-resistant coating disclosed herein prevents and/or reduces bacteria adhesion. In some cases, a biofouling-resistant coating disclosed herein prevents and/or reduces bacteria adhesion formed by a gram-positive bacterium from the genus *Actinomyces, Arthrobacter, Bacillus, Clostridium, Corynebacterium, Enterococcus, Lactococcus, Listeria, Micrococcus, Mycobacterium, Staphylococcus,* or *Streptococcus.* In some cases, a biofouling-resistant coating disclosed herein coated onto a material prevents and/or reduces bacteria adhesion formed by a gram-positive bacterium: *Actinomyces* spp., *Arthrobacter* spp., *Bacillus licheniformis, Clostridium difficile, Clostridium* spp., *Corynebacterium* spp., *Enterococcus faecalis, Lactococcus* spp., *Listeria monocytogenes, Micrococcus* spp., *Mycobacterium* spp., *Staphylococcus aureus, Staphylococcus epidermidis, Streptococcus pneumoniae,* or *Streptococcus pyogenes.*

In some cases, microfouling comprises biofilm. In some instances, a biofouling-resistant coating disclosed herein coated onto a material prevents and/or reduces biofilm. In some cases, a biofouling-resistant coating disclosed herein coated onto a material prevents and/or reduces biofilm formed by a gram-positive bacterium from the genus *Actinomyces, Arthrobacter, Bacillus, Clostridium, Corynebacterium, Enterococcus, Lactococcus, Listeria, Micrococcus, Mycobacterium, Staphylococcus,* or *Streptococcus.* In some cases, a biofouling-resistant coating disclosed herein coated onto a material prevents and/or reduces biofilm formed by a gram-positive bacterium: *Actinomyces* spp., *Arthrobacter* spp., *Bacillus licheniformis, Clostridium difficile, Clostridium* spp., *Corynebacterium* spp., *Enterococcus faecalis, Lactococcus* spp., *Listeria monocytogenes, Micrococcus* spp., *Mycobacterium* spp., *Staphylococcus aureus, Staphylococcus epidermidis, Streptococcus pneumoniae,* or *Streptococcus pyogenes.*

In some cases, microfouling is formed by a gram-negative bacterium. Exemplary gram-negative bacteria include, but are not limited to, bacteria from the genus *Alteromonas, Aeromonas, Desulfovibrio, Escherichia, Fusobacterium, Geobacter, Haemophilus, Klebsiella, Legionella, Porphyromonas, Proteus, Pseudomonas, Serratia, Shigella, Salmonella,* or *Vibrio.* In some instances, a gram-negative bacterium comprises *Alteromonas* spp., *Aeromonas* spp., *Desulfovibrio* spp., *Escherichia coli, Fusobacterium nucleatum, Geobacter* spp., *Haemophilus* spp., *Klebsiella* spp., *Legionella pneumophila, Porphyromonas* spp., *Pseudomonas aeruginosa, Proteus vulgaris, Proteus mirabilis, Proteus penneri, Serratia* spp., *Shigella dysenteriae, Shigella flexneri, Shigella boydii, Shigella sonnei, Salmonella bongori, Salmonella enterica,* or *Vibrio Cholerae.*

In some instances, microfouling is formed by a gram-negative bacterium from the genus *Alteromonas, Aeromonas, Desulfovibrio, Escherichia, Fusobacterium, Geobacter, Haemophilus, Klebsiella, Legionella, Porphyromonas, Proteus, Pseudomonas, Serratia, Shigella, Salmonella,* or *Vibrio.* In some instances, microfouling is formed by a gram-negative bacterium: *Alteromonas* spp., *Aeromonas* spp., *Desulfovibrio* spp., *Escherichia coli, Fusobacterium nucleatum, Geobacter* spp., *Haemophilus* spp., *Klebsiella* spp., *Legionella pneumophila, Porphyromonas* spp., *Pseudomonas aeruginosa, Proteus vulgaris, Proteus mirabilis, Proteus penneri, Serratia* spp., *Shigella dysenteriae, Shigella flexneri, Shigella boydii, Shigella sonnei, Salmonella bongori, Salmonella enterica,* or *Vibrio Cholerae.*

In some embodiments, a biofouling-resistant coating disclosed herein prevents and/or reduces microfouling formed by a gram-negative bacterium from the genus *Alteromonas, Aeromonas, Desulfovibrio, Escherichia, Fusobacterium, Geobacter, Haemophilus, Klebsiella, Legionella, Porphyromonas, Proteus, Pseudomonas, Serratia, Shigella, Salmonella,* or *Vibrio.* In some instances, a biofouling-resistant coating disclosed herein prevents and/or reduces microfouling formed by a gram-negative bacterium: *Alteromonas* spp., *Aeromonas* spp., *Desulfovibrio* spp., *Escherichia coli, Fusobacterium nucleatum, Geobacter* spp., *Haemophilus* spp., *Klebsiella* spp., *Legionella pneumophila, Porphyromonas* spp., *Pseudomonas aeruginosa, Proteus vulgaris, Proteus mirabilis, Proteus penneri, Serratia* spp., *Shigella dysenteriae, Shigella flexneri, Shigella boydii, Shigella sonnei, Salmonella bongori, Salmonella enterica,* or *Vibrio Cholerae.*

In some embodiments, microfouling comprises bacteria adhesion. In some embodiments, a biofouling-resistant coating disclosed herein prevents and/or reduces bacteria adhesion formed by a gram-negative bacterium from the genus *Alteromonas, Aeromonas, Desulfovibrio, Escherichia, Fusobacterium, Geobacter, Haemophilus, Klebsiella, Legionella, Porphyromonas, Proteus, Pseudomonas, Serratia, Shigella, Salmonella,* or *Vibrio.* In some instances, a biofouling-resistant coating disclosed herein prevents and/or reduces bacteria adhesion formed by a gram-negative bacterium: *Alteromonas* spp., *Aeromonas* spp., *Desulfovibrio* spp., *Escherichia coli, Fusobacterium nucleatum, Geobacter* spp., *Haemophilus* spp., *Klebsiella* spp., *Legionella pneumophila, Porphyromonas* spp., *Pseudomonas aeruginosa, Proteus vulgaris, Proteus mirabilis, Proteus penneri, Serratia* spp., *Shigella dysenteriae, Shigella flexneri, Shigella boydii, Shigella sonnei, Salmonella bongori, Salmonella enterica,* or *Vibrio Cholerae.*

In some instances, microfouling comprises biofilm. In some embodiments, a biofouling-resistant coating disclosed herein prevents and/or reduces biofilm formed by a gram-negative bacterium from the genus *Alteromonas, Aeromonas, Desulfovibrio, Escherichia, Fusobacterium, Geobacter, Haemophilus, Klebsiella, Legionella, Porphyromonas, Proteus, Pseudomonas, Serratia, Shigella, Salmonella,* or *Vibrio.* In some instances, a biofouling-resistant coating disclosed herein prevents and/or reduces biofilm formed by a gram-negative bacterium: *Alteromonas* spp., *Aeromonas* spp., *Desulfovibrio* spp., *Escherichia coli, Fusobacterium nucleatum, Geobacter* spp., *Haemophilus* spp., *Klebsiella* spp., *Legionella pneumophila, Porphyromonas* spp., *Pseudomonas aeruginosa, Proteus vulgaris, Proteus mirabilis, Proteus penneri, Serratia* spp., *Shigella dysenteriae, Shigella flexneri, Shigella boydii, Shigella sonnei, Salmonella bongori, Salmonella enterica,* or *Vibrio Cholerae.*

In some cases, microfouling is formed by a marine bacterium. In some instances, a marine bacterium comprises *Pseudoalteromonas* spp. or *Shewanella* spp. In some cases, microfouling is formed by *Pseudoalteromonas* spp. or *Shewanella* spp.

In some embodiments, a biofouling-resistant coating disclosed herein prevents and/or reduces microfouling formed by a marine bacterium. In some cases, a biofouling-resistant coating disclosed herein prevents and/or reduces microfouling formed by *Pseudoalteromonas* spp. or *Shewanella* spp.

In some instances, microfouling comprises bacteria adhesion. In some embodiments, a biofouling-resistant coating disclosed herein prevents and/or reduces bacteria adhesion formed by a marine bacterium. In some cases, a biofouling-resistant coating disclosed herein prevents and/or reduces bacteria adhesion formed by *Pseudoalteromonas* spp. or *Shewanella* spp.

In some instances, microfouling comprises biofilm. In some embodiments, a biofouling-resistant coating disclosed herein prevents and/or reduces biofilm formed by a marine bacterium. In some cases, a biofouling-resistant coating disclosed herein prevents and/or reduces biofilm formed by *Pseudoalteromonas* spp. or *Shewanella* spp.

In some embodiments, microfouling is formed by a fungus. Exemplary fungus includes, but is not limited to, *Candida albicans, Candida glabrata, Candida rugose, Candida parapsilosis, Candida tropicalis, Candida dubliniensis*, or *Hormoconis resinae*. In some cases, microfouling is formed by *Candida albicans, Candida glabrata, Candida rugose, Candida parapsilosis, Candida tropicalis, Candida dubliniensis*, or *Hormoconis resinae*.

In some embodiments, a biofouling-resistant coating disclosed herein prevents and/or reduces microfouling formed by a fungus. In some cases, a biofouling-resistant coating disclosed herein prevents and/or reduces microfouling formed by *Candida albicans, Candida glabrata, Candida rugose, Candida parapsilosis, Candida tropicalis, Candida dubliniensis*, or *Hormoconis resinae*.

In some instances, microfouling comprises bacteria adhesion. In some embodiments, a biofouling-resistant coating disclosed herein prevents and/or reduces bacteria adhesion formed by a fungus. In some cases, a biofouling-resistant coating disclosed herein prevents and/or reduces bacteria adhesion formed by *Candida albicans, Candida glabrata, Candida rugose, Candida parapsilosis, Candida tropicalis, Candida dubliniensis*, or *Hormoconis resinae*.

In some instances, microfouling comprises biofilm. In some embodiments, a biofouling-resistant coating disclosed herein prevents and/or reduces biofilm formed by a fungus. In some cases, a biofouling-resistant coating disclosed herein prevents and/or reduces biofilm formed by *Candida albicans, Candida glabrata, Candida rugose, Candida parapsilosis, Candida tropicalis, Candida dubliniensis*, or *Hormoconis resinae*.

Macrofouling

In some embodiments, macrofouling comprises calcareous fouling organism or non-calcareous fouling organism. A calcareous fouling organism is an organism with a hard body. In some cases, calcareous fouling organisms comprise barnacle, bryozoan, mollusk, polychaete, tube worm, or zebra mussel. A non-calcareous fouling organism comprises a soft body. Non-calcareous fouling organism comprises seaweed, hydroids, or algae.

In some instances, macrofouling is formed by a calcareous fouling organism. In some cases, macrofouling is formed by barnacle, bryozoan, mollusk, polychaete, tube worm, or zebra mussel.

In some embodiments, a biofouling-resistant coating disclosed herein prevents and/or reduces macrofouling formed by a calcareous fouling organism. In some instances, a biofouling-resistant coating disclosed herein prevents and/or reduces macrofouling formed by barnacle, bryozoan, mollusk, polychaete, tube worm, or zebra mussel.

In some cases, macrofouling is formed by a non-calcareous fouling organism. In some cases, macrofouling is formed by seaweed, hydroids, or algae.

In some embodiments, also disclosed herein are biofouling-resistant coating preventing and/or reducing macrofouling formed by a non-calcareous fouling organism. In some instances, a biofouling-resistant coating disclosed herein prevents and/or reduces macrofouling formed by seaweed, hydroids, or algae.

In some embodiments, a biofouling-resistant coating disclosed herein reduces the formation of biofouling on its surface. In some cases, the formation of biofouling on a surface of a device modified with a compound of Formula (I), (II), or (III) is reduced by about 10%, 20%, 30%, 40%, 50%, 60%, 70%, 80%, 90%, 95%, 99%, 99.5%, 99.9%, or more relative to the unmodified surface of a device. In some cases, the formation of biofouling on a surface of a device modified with a copolymer comprising a repeating unit of Formula (VII), (VIII), and (IX) is reduced by about 10%, 20%, 30%, 40%, 50%, 60%, 70%, 80%, 90%, 95%, 99%, 99.5%, 99.9%, or more relative to the unmodified surface of a device. In some instances, the formation of biofouling is reduced by at least about 10%, 20%, 30%, 40%, 50%, 60%, 70%, 80%, 90%, 95%, 99%, 99.5%, 99.9%, or more relative to the unmodified surface of a device. In some instances, the formation of biofouling relative to the unmodified surface of a device is determined by comparing the amount of biofouling following a period of time of storage, use, and/or testing of the device(s). For example, the devices may be tested by exposing them to conditions conducive of biofouling formation (e.g., in vitro biofouling testing techniques known and practiced in the art). In some instances, the formation of biofouling is reduced by about 10%, or more relative to the unmodified surface of a device. In some instances, the formation of biofouling is reduced by about 20%, or more relative to the unmodified surface of a device. In some instances, the formation of biofouling is reduced by about 30%, or more relative to the unmodified surface of a device. In some instances, the formation of biofouling is reduced by about 40%, or more relative to the unmodified surface of a device. In some instances, the formation of biofouling is reduced by about 50%, or more relative to the unmodified surface of a device. In some instances, the formation of biofouling is reduced by about 60%, or more relative to the unmodified surface of a device. In some instances, the formation of biofouling is reduced by about 70%, or more relative to the unmodified surface of a device. In some instances, the formation of biofouling is reduced by about 80%, or more relative to the unmodified surface of a device. In some instances, the formation of biofouling is reduced by about 90%, or more relative to the unmodified surface of a device. In some instances, the formation of biofouling is reduced by about 95%, or more relative to the unmodified surface of a device. In some instances, the formation of biofouling is reduced by about 99%, or more relative to the unmodified surface of a device. In some instances, the formation of biofouling is reduced by about 99.5%, or more relative to the unmodified surface of a device. In some instances, the formation of biofouling is reduced by about 99.9%, or more relative to the unmodified surface of a device.

In some embodiments, a biofouling-resistant coating disclosed herein is further coated with an additional agent. In some instances, the additional agent is an antimicrobial agent. Exemplary antimicrobial agent comprises quaternary ammonium salts or tertiary amines. In some instances, the additional agent is a chemical disinfectant. Exemplary chemical disinfectant comprises sodium hypochlorite, sodium hydroxide, and benzalkonium chloride.

Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a component," "a polymer," or "a particle" includes mixtures of two or more such components, polymers, or particles, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. In some embodiments, the term "about" includes an amount that would be expected to be within experimental error. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that throughout the application, data is provided in a number of different formats and that this data represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance may or may not occur, and that the description includes instances where said event or circumstance occurs and instances where it does not.

As used herein, the terms "effective amount" and "amount effective" refer to an amount that is sufficient to achieve the desired result or to have an effect on an undesired condition.

The term "stable", as used herein, refers to compositions that are not substantially altered when subjected to conditions to allow for their production, detection, and, in certain aspects, their recovery, purification, and use for one or more of the purposes disclosed herein.

As used herein, the term "polymer" refers to a relatively high molecular weight organic compound, natural or synthetic, whose structure can be represented by a repeated small unit, the monomer (e.g., polyethylene, rubber, cellulose). Synthetic polymers are typically formed by addition or condensation polymerization of monomers. Unless indicated otherwise, polymer molecular weights are given in Daltons.

As used herein, the term "homopolymer" refers to a polymer formed from a single type of repeating unit (monomer residue).

As used herein, the term "copolymer" refers to a polymer formed from two or more different repeating units (monomer residues). By way of example and without limitation, a copolymer can be an alternating copolymer, a random copolymer, a block copolymer, or a graft copolymer. It is also contemplated that, in certain aspects, various block segments of a block copolymer can themselves comprise copolymers. In some embodiments, the terms "copolymer" and "compound" are used interchangeably throughout the specification.

As used herein, the term "oligomer" refers to a relatively low molecular weight polymer in which the number of repeating units is between two and ten, for example, from two to eight, from two to six, or form two to four. In one aspect, a collection of oligomers can have an average number of repeating units of from about two to about ten, for example, from about two to about eight, from about two to about six, or form about two to about four.

As used herein, the term "cross-linked polymer" refers to a polymer having bonds linking one polymer chain to another.

As used herein, the term "porogen composition" or "porogen(s)" refers to any structured material that can be used to create a porous material.

"Oxo" refers to the =O substituent.

"Benzyl" refers to the —$CH_2(C_6H_5)$ substituent.

"Alkyl" refers to a straight or branched hydrocarbon chain radical, having from one to twenty carbon atoms, and which is attached to the rest of the molecule by a single bond. An alkyl comprising up to 10 carbon atoms is referred to as a $C_1$-$C_{10}$ alkyl, likewise, for example, an alkyl comprising up to 6 carbon atoms is a $C_1$-$C_6$ alkyl. Alkyls (and other moieties defined herein) comprising other numbers of carbon atoms are represented similarly. Alkyl groups include, but are not limited to, $C_1$-$C_{10}$ alkyl, $C_1$-$C_9$ alkyl, $C_1$-$C_8$ alkyl, $C_1$-$C_7$ alkyl, $C_1$-$C_6$ alkyl, $C_1$—C alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl. Representative alkyl groups include, but are not limited to, methyl, ethyl, n-propyl, 1-methylethyl (i-propyl), n-butyl, i-butyl, s-butyl, n-pentyl, 1,1-dimethylethyl (t-butyl), 3-methylhexyl, 2-methylhexyl, 1-ethyl-propyl, and the like. In some embodiments, the alkyl is methyl or ethyl. In some embodiments, the alkyl is —CH(CH$_3$)$_2$ or —C(CH$_3$)$_3$. Unless stated otherwise specifically in the specification, an alkyl group may be optionally substituted as described below.

"Alkylene" or "alkylene chain" refers to a straight or branched divalent hydrocarbon chain linking the rest of the molecule to a radical group. In some embodiments, the alkylene is —CH$_2$—, —CH$_2$CH$_2$—, or —CH$_2$CH$_2$CH$_2$—. In some embodiments, the alkylene is —CH$_2$—. In some embodiments, the alkylene is —CH$_2$CH$_2$—. In some embodiments, the alkylene is —CH$_2$CH$_2$CH$_2$—. In some embodiments, the alkylene is —CH$_2$C(CH$_3$)CH$_2$—.

"Alkoxy" refers to a radical of the formula —OR where R is an alkyl radical as defined. Unless stated otherwise specifically in the specification, an alkoxy group may be optionally substituted as described below. Representative alkoxy groups include, but are not limited to, methoxy, ethoxy, propoxy, butoxy, pentoxy. In some embodiments, the alkoxy is methoxy. In some embodiments, the alkoxy is ethoxy.

"Alkenyl" refers to a type of alkyl group in which at least one carbon-carbon double bond is present. In one embodiment, an alkenyl group has the formula —C(R$^a$)═C(R$^a$)$_2$, wherein each R$^a$ refers to the remaining portions of the alkenyl group, which may be the same or different. In some embodiments, each R$^a$ is hydrogen or an alkyl group. In some embodiments, an alkenyl is selected from ethenyl (i.e., vinyl), propenyl (i.e., allyl), butenyl, pentenyl, pentadienyl, and the like. Non-limiting examples of an alkenyl group include —CH═CH$_2$, —C(CH$_3$)═CH$_2$, —CH═CHCH$_3$, —C(CH$_3$)═CHCH$_3$, and —CH$_2$CH═CH$_2$.

"Heteroalkylene" refers to an alkyl radical as described above where one or more carbon atoms of the alkyl is replaced with a O, N or S atom. "Heteroalkylene" or "heteroalkylene chain" refers to a straight or branched divalent heteroalkyl chain linking the rest of the molecule to a radical group. Unless stated otherwise specifically in the specification, the heteroalkyl or heteroalkylene group may be optionally substituted as described below. Representative heteroalkyl groups include, but are not limited to —OCH$_2$OMe, —OCH$_2$CH$_2$OMe, or —OCH$_2$CH$_2$OCH$_2$CH$_2$NH$_2$. Representative heteroalkylene groups include, but are not limited to —OCH$_2$CH$_2$O—, —OCH$_2$CH$_2$OCH$_2$CH$_2$O—, or —OCH$_2$CH$_2$OCH$_2$CH$_2$OCH$_2$CH$_2$O—.

"Alkylamino" refers to a radical of the formula —NHR or —NRR where each R is, independently, an alkyl radical as defined above. Unless stated otherwise specifically in the specification, an alkylamino group may be optionally substituted as described below.

The term "aromatic" refers to a planar ring having a delocalized 7-electron system containing 4n+2 π electrons, where n is an integer. Aromatics can be optionally substituted. The term "aromatic" includes both aryl groups (e.g., phenyl, naphthalenyl) and heteroaryl groups (e.g., pyridinyl, quinolinyl).

"Aryl" refers to an aromatic ring wherein each of the atoms forming the ring is a carbon atom. Aryl groups can be optionally substituted. Examples of aryl groups include, but are not limited to phenyl, and naphthyl. In some embodiments, the aryl is phenyl. Depending on the structure, an aryl group can be a monoradical or a diradical (i.e., an arylene group). Unless stated otherwise specifically in the specification, the term "aryl" or the prefix "ar-" (such as in "aralkyl") is meant to include aryl radicals that are optionally substituted.

"Carboxy" refers to —CO$_2$H. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to:

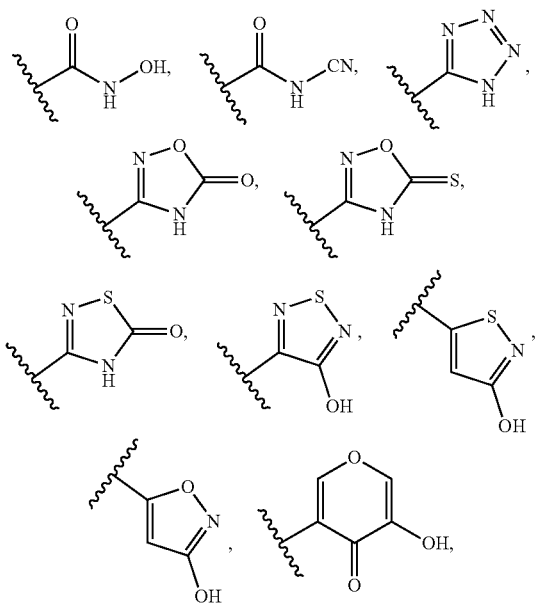

and the like.

"Cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. Cycloalkyls may be fused with an aromatic ring (in which case the cycloalkyl is bonded through a non-aromatic ring carbon atom). Cycloalkyl groups include groups having from 3 to 10 ring atoms. Representative cycloalkyls include, but are not limited to, cycloalkyls having from three to ten carbon atoms, from three to eight carbon atoms, from three to six carbon atoms, or from three to five carbon atoms. Monocyclic cycloalkyl radicals include, for example, cyclopropyl, cyclobutyl, cyclopentyl, cyclohexyl, cycloheptyl, and cyclooctyl. In some embodiments, the monocyclic cycloalkyl is cyclopropyl, cyclobutyl, cyclopentyl or cyclohexyl. In some embodiments, the monocyclic cycloalkyl is cyclopentyl. Polycyclic radicals include, for example, adamantyl, norbornyl, decalinyl, and 3,4-dihydronaphthalen-1(2H)-one. Unless otherwise stated specifically in the specification, a cycloalkyl group may be optionally substituted.

"Fluoroalkyl" refers to an alkyl in which one or more hydrogen atoms are replaced by a fluorine atom. In one aspect, a fluoroalkyl is a $C_1$-$C_6$ fluoroalkyl. In some embodiments, a fluoroalkyl is selected from trifluoromethyl, difluoromethyl, fluoromethyl, 2,2,2-trifluoroethyl, 1-fluoromethyl-2-fluoroethyl, and the like.

"Fused" refers to any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Haloalkoxy" refers to an alkoxy radical, as defined above, that is substituted by one or more halo radicals, as defined above, e.g., trifluoromethoxy, difluoromethoxy, fluoromethoxy, trichloromethoxy, 2,2,2-trifluoroethoxy, 1,2-difluoroethoxy, 3-bromo-2-fluoropropoxy, 1,2-dibromoethoxy, and the like. Unless stated otherwise specifically in the specification, a haloalkoxy group may be optionally substituted.

"Heterocycloalkyl" or "heterocyclyl" or "heterocyclic ring" refers to a stable 3- to 14-membered non-aromatic ring radical comprising 2 to 10 carbon atoms and from one to 4 heteroatoms selected from the group consisting of nitrogen, oxygen, and sulfur. Unless stated otherwise specifically in the specification, the heterocycloalkyl radical may be a monocyclic, or bicyclic ring system, which may include fused (when fused with an aryl or a heteroaryl ring, the heterocycloalkyl is bonded through a non-aromatic ring atom) or bridged ring systems. The nitrogen, carbon or sulfur atoms in the heterocyclyl radical may be optionally oxidized. The nitrogen atom may be optionally quaternized. The heterocycloalkyl radical is partially or fully saturated. Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl. The term heterocycloalkyl also includes all ring forms of carbohydrates, including but not limited to monosaccharides, disaccharides and oligosaccharides. Unless otherwise noted, heterocycloalkyls have from 2 to 10 carbons in the ring. In some embodiments, heterocycloalkyls have from 2 to 8 carbons in the ring. In some embodiments, heterocycloalkyls have from 2 to 8 carbons in the ring and 1 or 2 N atoms. In some embodiments, heterocycloalkyls have from 2 to 10 carbons, 0-2 N atoms, 0-2 O atoms, and 0-1 S atoms in the ring. In some embodiments, heterocycloalkyls have from 2 to 10 carbons, 1-2 N atoms, 0-1 O atoms, and 0-1 S atoms in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group may be optionally substituted.

"Heteroaryl" refers to an aryl group that includes one or more ring heteroatoms selected from nitrogen, oxygen and sulfur. The heteroaryl is monocyclic or bicyclic. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, furazanyl, indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Illustrative examples of bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, heteroaryl is pyridinyl, pyrazinyl, pyrimidinyl, thiazolyl, thienyl, thiadiazolyl or furyl.

In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a C1-C9heteroaryl. In some embodiments, monocyclic heteroaryl is a C1-C5heteroaryl. In some embodiments, monocyclic heteroaryl is a 5-membered or 6-membered heteroaryl. In some embodiments, a bicyclic heteroaryl is a C6-C9heteroaryl.

The term "optionally substituted" or "substituted" means that the referenced group may be substituted with one or more additional group(s) individually and independently selected from alkyl, haloalkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkyne, $C_1$-$C_6$alkylalkyne, halogen, acyl, acyloxy, —$CO_2H$, —$CO_2$alkyl, nitro, and amino, including mono- and di-substituted amino groups (e.g. —$NH_2$, —NHR, —$N(R)_2$), and the protected derivatives thereof. In some embodiments, optional substituents are independently selected from alkyl, alkoxy, haloalkyl, cycloalkyl, halogen, —CN, —$NH_2$, —$NH(CH_3)$, —$N(CH_3)_2$, —OH, —$CO_2H$, and —$CO_2$alkyl. In some embodiments, optional substituents are independently selected from fluoro, chloro, bromo, iodo, —$CH_3$, —$CH_2CH_3$, —$CF_3$, —$OCH_3$, and —$OCF_3$. In some embodiments, substituted groups are substituted with one or two of the preceding groups. In some embodiments, an optional substituent on an aliphatic carbon atom (acyclic or cyclic, saturated or unsaturated carbon atoms, excluding aromatic carbon atoms) includes oxo (=O). Compounds described herein can contain one or more double bonds and, thus, potentially give rise to cis/trans (E/Z) isomers, as well as other conformational isomers. Unless stated to the contrary, the compounds disclosed herein include all such possible isomers, as well as mixtures of such isomers.

In some embodiments, PSB and PFPA-PSB are used interchangeably and refer to poly(sulfobetaine methacrylate-co-perfluorophenylazide methacrylate).

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplemental volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Examples

The following examples are provided for illustrative purposes only, and are intended to be purely exemplary of the disclosure and are not intended to limit the scope of the claims provided herein. Efforts have been made to ensure accuracy with respect to numbers (e.g., amounts, temperature, etc.), but some errors and deviations should be accounted for.

Materials

α-Bromoisobutyryl bromide, N-Boc-ethanolamine, Trifluoroacetic acid, 1,1,4,7,10,10-Hexamethyltriethylenetramine (97%), [2-(Methacryloyloxy)ethyl]dimethyl-(3-sulfopropyl)ammonium hydroxide, tetrabutylammonium chloride, and cupper(I) chloride are used as received from Sigma Aldrich. Sodium bicarbonate, methylene chloride, magnesium sulfate, and 2,2,2-trifluoroethanol are purchased from Alfa Aesar. Sylgard 184 kit (Dow Corning) is obtained from Fisher Chemical.

The zwitterionic polymer, polysulfobetaine (PSB), is selected as an antifouling component of the coating. By adsorbing water electrostatically, PSB coatings form a thin hydration barrier that prevents organic material from adhering to its surface. Commonly used approaches to attach PSB coatings to surfaces such as radical-initiated graft polymerizations of PSB-methacrylate necessitate the use of oxygen-free conditions, preconditioning steps, or long reaction times that do not meet the scalability requirements. To circumvent the use of air-free graft polymerizations, we employ perfluorophenylazide (PFPA) as a molecular anchor to graft the PSB coating to the surface of polymeric materials under ambient conditions. When triggered with UV-light, PFPA moieties generate a highly reactive nitrene that forms covalent bonds with materials containing amines, C=C double bonds, and C—H bonds. With this method, it is surprisingly found that PSB is rapidly coated to a variety of substrates using UV light under ambient conditions with no preconditioning steps needed. In addition, it is unexpectedly found that water provides an optimal solvent for photografting of PFPA-PSB coating and that photografting of PFPA-PSB does not proceed well in the presence of organic solvents.

Example 1. Synthesis of ATRP Initiator 2-Aminoethyl 2-Bromoisobutyrate

ATRP initiator 2-aminoethyl 2-bromoisobutyrate is synthesized according to the following procedure. 5 g of 2-bromoisobutyryl bromide is added to a solution of 3.8 g of t-Boc-aminoethyl alcohol and 2.5 g of triethylamine in 12 ml methylene chloride in an ice bath. After 16 h, the salts are filtered off and the filtrate is extracted with saturated sodium bicarbonate solution. Methylene chloride phase is dried over magnesium sulfate and evaporated. The resulting t-Boc-aminoethyl 2-bromoisobutyrate is treated by 15 ml trifluoroacetic acid (TFA) for 2 h and crystallized upon addition of ethyl ether.

Example 2. Synthesis of PFPAS-Methacrylate/acrylate

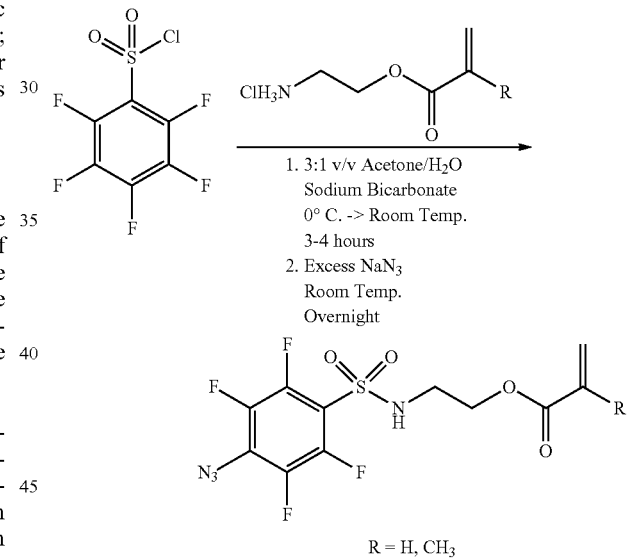

2-Aminoethyl methacrylate/acrylate hydrochloride is dissolved in DI Water at a concentration of 0.56M. 2 equivalents of sodium bicarbonate is added dropwise to the solution. In a separate vial, 1 equivalent of pentafluorobenzene sulfonyl chloride is dissolved in acetone at a concentration of 0.186M. Both solutions are cooled to 4° C. The solution containing 2-aminoethyl methacrylate/acrylate and sodium bicarbonate is added to the pentafluorobenzenesulfonyl chloride solution dropwise on ice. The reaction is stirred and gradually warmed up to room temperature. After 3 hours, 3 equivalents of sodium azide is added to the solution and the reaction is stirred for another 18 hours at room temperature. After, the acetone is removed under reduced pressure. Three times the reaction volume of methyl tert-butyl ether is added to the crude mixture and poured into a separatory funnel. DI water is added three times to wash the organic layer. The methyl tert-butyl ether is removed under reduced pressure to give the desired product.

Example 3. Synthesis of PFPAA-Methacrylate/methacrylamide/acrylate/acrylamide

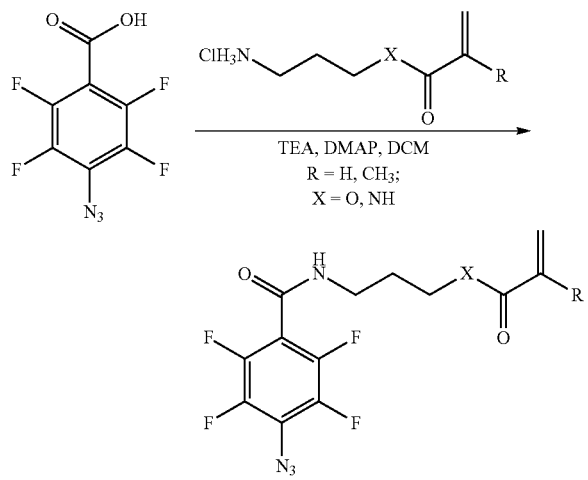

4-azidotetrafluorobenzoic acid was prepared according a published procedure by Keana et al. (*J. Org. Chem.* 1990, 55(11), 3640-7). To prepare the PFPAA-methacrylate: N-3-aminopropylmethacrylate hydrochloride and triethylamine are dissolved in dichloromethane to a concentration of 0.31M each. This solution is allowed to stir for 3 hours. The 4-azidotetrafluorobenzoic acid is then dissolved at a concentration of 0.235M. 4-dimethylaminopyridine is then added to the solution containing the 4-azidotetrafluorobenzoic acid (0.26M). A second portion of triethylamine is added so that the final concentration of triethylamine in the reaction is 0.56M. The reaction is then stirred for 48 hours, washed 3× with DI water, and the organic layer evaporated under reduced pressure to give the desired product. This procedure is used to prepare different PFPA amide—methacrylate/methacrylamide/acrylate/acrylamide compounds.

Example 4. Synthesis of PFPAE-methaerylate/niethacrylamide/acrylate/acrylamide

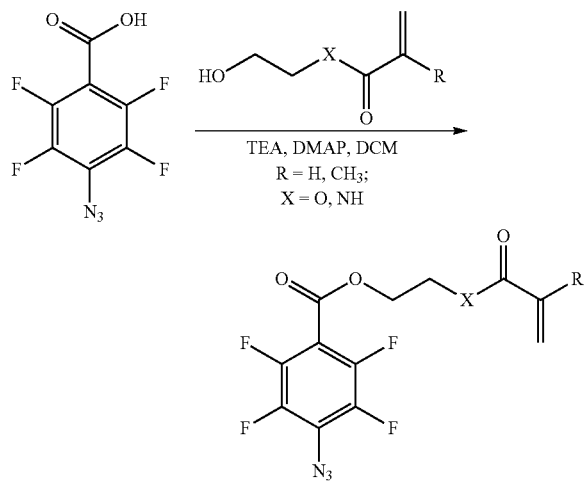

4-azidotetrafluorobenzoic acid was prepared according a published procedure by Keana et al. (*J. Org. Chem.* 1990, 55(11), 3640-7). To prepare the PFPAE-methacrylamide: 2-Hydroxyethyl methacrylamide and triethylamine are dissolved in dichloromethane to a concentration of 0.31M each. This solution is allowed to stir for 3 hours. The 4-azidotetrafluorobenzoic acid is then dissolved at a concentration of 0.235M. 4-dimethylaminopyridine is then added to the solution containing the 4-azidotetrafluorobenzoic acid (0.26M). A second portion of triethylamine is added so that the final concentration of triethylamine in the reaction is 0.56M. The reaction is then stirred for 48 hours, washed 3× with DI water, and the organic layer evaporated under reduced pressure to give the desired product. This procedure is used to prepare different PFPA ester—methacrylate/methacrylamide/acrylate/acrylamide compounds.

Example 5. Copolymer Formation by Polymerization of Sulfobetaine Methacrylate and Perfluorophenylazide

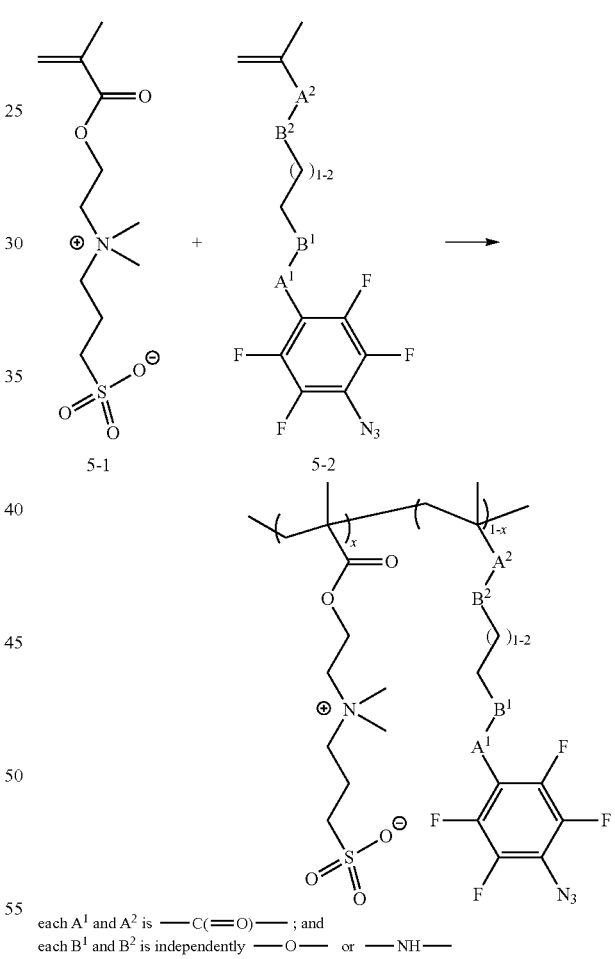

each $A^1$ and $A^2$ is —C(=O)—; and
each $B^1$ and $B^2$ is independently —O— or —NH—

The copolymer is synthesized as follows: 2 g sulfobetaine methacrylate monomer 5-1, 100 mg, 150 mg, or 200 mg of perfluorophenylazide monomer 5-2, and 2 g tetrabutylammonium chloride are dissolved in 30 mL trifluoroethanol in a Schlenk flask and undergo two vacuum-argon cycles. Then, 14 mg Cu(I)Cl and 76 µL 1,1,4,7,10,10-hexamethyl-triethylenetetramine are added. The Schlenk flask is sealed with a rubber septum and another two vacuum-argon cycles are performed. Finally, 44 mg TFA protected 2-aminoethyl 2-bromoisobutyrate as ATRP initiator is dissolved in a small amount of trifluoroethanol (~0.5 mL) and syringe-injected into the Schlenk flask, followed by two additional vacuum-argon cycles. Polymerization is carried out at 60° C. under argon. After 24 h, the reaction mixture is cooled down to room temperature and the copolymer is purified by performing membrane dialysis using a membrane with cut off molecular weight of 1000 Dalton. The resulting copolymer is freeze-dried before further use.

NMR spectra are recorded on a Bruker DPX300 spectrometer. Chemical shifts are calibrated to residual solvent signals. Molecular weights and dispersities are measured by gel permeation chromatography on a Shimadzu HPLC system with a refractive index detector S3 RID-10A, one Tosoh TSKGel guard column, and one Tosoh TSKGel G4000PW column. Eluent is 0.1 M NaNO$_3$+20 mM phosphate buffer pH 7+20% MeCN at 25° C. (flow rate 0.7 mL/min). Calibration is performed using near-monodisperse PEG standards from Polymer Laboratories. Light scattering is used to obtain the absolute molecular weight.

Example 6. Synthesis of Mixed Charged Copolymers

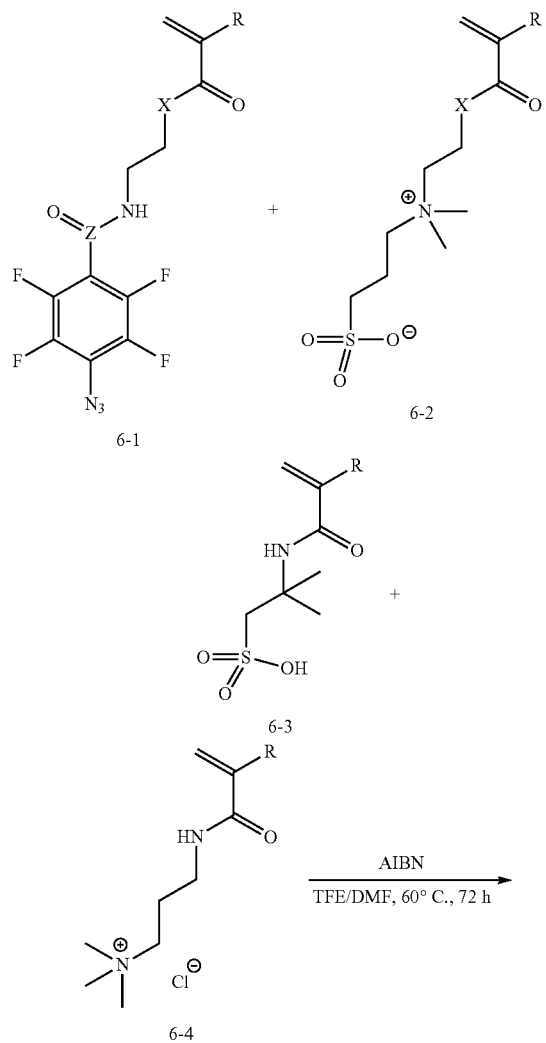

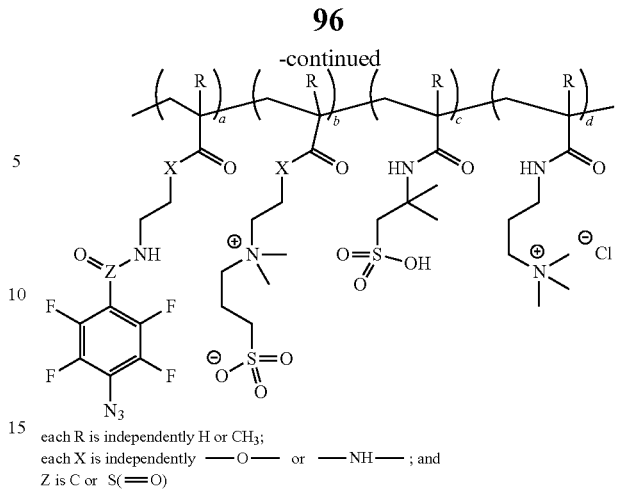

each R is independently H or CH$_3$;
each X is independently —O— or —NH—; and
Z is C or S(═O)

Monomers 6-2, 6-3, and 6-4 are dissolved in different molar ratios in a solution of 4:1 TFE:DMF at a total concentration of 0.37M. 6-1 is added at a concentration of 0.022M and the radical initiator (AIBN) is added at a concentration of 0.0037M. The reaction is performed protected under argon gas using common Schlenk line technique. The oxygen is removed under reduced pressure and back-filled with argon gas three times. The reaction is stirred by mechanical stir bar and is heated to 60° C. using oil bath. After 72 h, the reaction solvent is removed under reduced pressure with a rotary evaporator to ¼th of the original reaction volume. Once concentrated, the polymer crude mixture is diluted with 10 times its volume with DI water. Residual monomers and oligomers are removed by pipetting the crude polymer reaction mixture into cellulose dialysis bags, with a 10,000 Dalton molecular weight cut-off, and placing the filled dialysis bag into a large water bath. The water bath is replenished with fresh deionized water continuously over 7 days. The purified polymer solution, now dispersed in water inside the dialysis bags, are freeze-dried to remove the water to yield a white powder. To synthesize mixed charged copolymers of different isoelectric points, the molar ratios of 6-2, 6-3, and 6-4 can be modified.

Example 7. Synthesis of Mixed Charged Copolymers

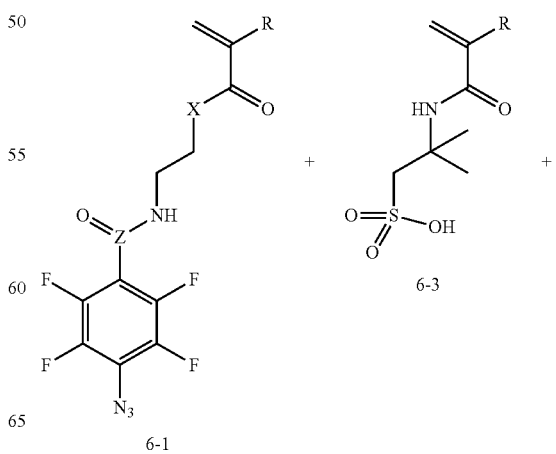

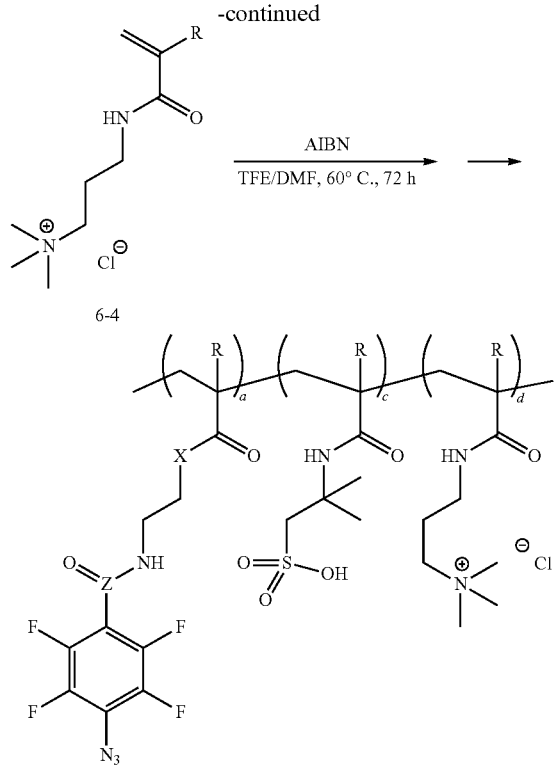

each R is independently H or CH₃;
each X is independently —O— or —NH—; and
Z is C or S(=O)

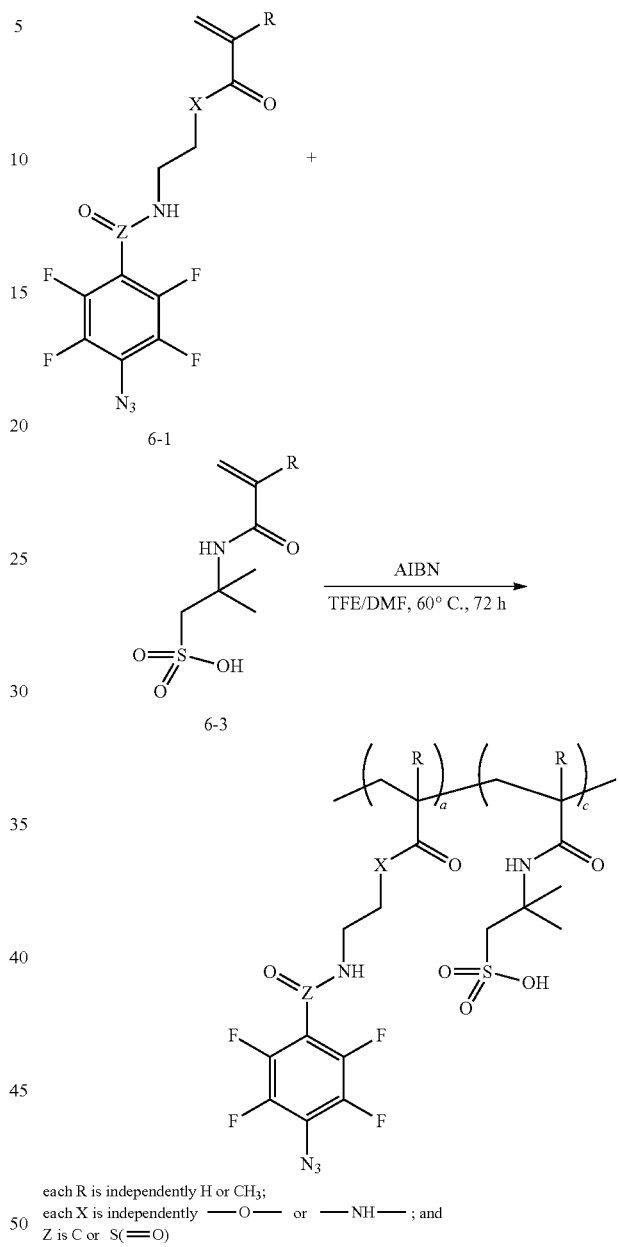

each R is independently H or CH₃;
each X is independently —O— or —NH—; and
Z is C or S(=O)

Monomers 6-3 and 6-4 are dissolved in different molar ratios in a solution of 4:1 TFE:DMF at a total concentration of 0.37M. 6-1 is added at a concentration of 0.022M and the radical initiator (AIBN) is added at a concentration of 0.0037M. The reaction is performed protected under argon gas using common Schlenk line technique. The oxygen is removed under reduced pressure and back-filled with argon gas three times. The reaction is stirred by mechanical stir bar and is heated to 60° C. using oil bath. After 72 h, the reaction solvent is removed under reduced pressure with a rotary evaporator to ¼th of the original reaction volume. Once concentrated, the polymer crude mixture is diluted with 10 times its volume with DI water. Residual monomers and oligomers are removed by pipetting the crude polymer reaction mixture into cellulose dialysis bags, with a 10,000 Dalton molecular weight cut-off, and placing the filled dialysis bag into a large water bath. The water bath is replenished with fresh deionized water continuously over 7 days. The purified polymer solution, now dispersed in water inside the dialysis bags, are freeze-dried to remove the water to yield a white powder. To synthesize mixed charged copolymers of different isoelectric points, the molar ratios of 6-3 and 6-4 can be modified.

Example 8. Synthesis of PFPA-Positive and PFPA-Negative Charged Copolymers

A surface containing a 1:1 molar ratio of positive and negative moieties is hypothesized to possess great antifouling properties. To achieve the 1:1 molar ratio of positive and negative moieties on the surface, two separate copolymers can be polymerized, each copolymer containing either positive charged moieties or negative charged moieties, and then blending them together in a 1:1 molar ratio in solution. An example of this is demonstrated below.

To synthesize a negatively charged PFPA-sulfonic acid copolymer, monomer 6-3 is dissolved in a solution of 4:1 TFE:DMF at a concentration of 0.37M. 6-1 is added at a concentration of 0.022M and the radical initiator (AIBN) is added at a concentration of 0.0037M. The reaction is performed protected under argon gas using common Schlenk line technique. The oxygen is removed under reduced pressure and back-filled with argon gas three times. The reaction is stirred by mechanical stir bar and is heated to 60° C. using oil bath. After 72 h, the reaction solvent is removed under reduced pressure with a rotary evaporator to ¼th of the original reaction volume. Once concentrated, the polymer crude mixture is diluted with 10 times its volume with Deionized water. Residual monomers and oligomers are removed by pipetting the crude polymer reaction mixture into cellulose dialysis bags, with a 10,000 Dalton molecular weight cut-off, and placing the filled dialysis bag into a large water bath. The water bath is replenished with fresh deionized water continuously over 7 days. The purified polymer solution, now dispersed in water inside the dialysis bags, are freeze-dried to remove the water to yield a white powder.

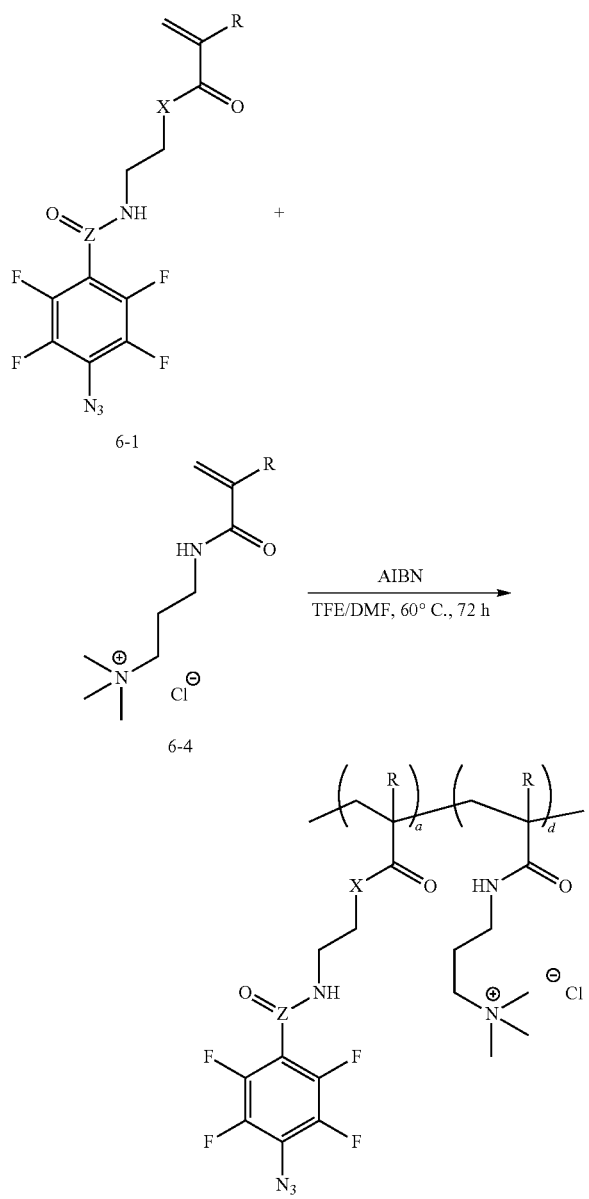

each R is independently H or CH$_3$;
each X is independently —O— or —NH—; and
Z is C or S(=O)

To synthesize a positively charged PFPA-quaternary ammonium copolymer, monomer 6-4 is dissolved in a solution of 4:1 TFE:DMF at a concentration of 0.37M. 6-1 is added at a concentration of 0.022M and the radical initiator (AIBN) is added at a concentration of 0.0037M. The reaction is performed protected under argon gas using common Schlenk line technique. The oxygen is removed under reduced pressure and back-filled with argon gas three times. The reaction is stirred by mechanical stir bar and is heated to 60° C. using oil bath. After 72 h, the reaction solvent is removed under reduced pressure with a rotary evaporator to ¼th of the original reaction volume. Once concentrated, the polymer crude mixture is diluted with 10 times its volume with Deionized water. Residual monomers and oligomers are removed by pipetting the crude polymer reaction mixture into cellulose dialysis bags, with a 10,000 Dalton molecular weight cut-off, and placing the filled dialysis bag into a large water bath. The water bath is replenished with fresh deionized water continuously over 7 days. The purified polymer solution, now dispersed in water inside the dialysis bags, are freeze-dried to remove the water to yield a white powder.

Once powders of each of the positively charged copolymer and negatively charged copolymer are obtained, they can be each added into a suitable solvent (H$_2$O, DMF, 2,2,2-trifluoroethanole, DMSO, DMAc, etc) to make a 1:1 molar ratio of sulfonic acid moieties and quaternary ammonium moieties. The resulting mixture is used to modify a surface.

Example 9. UV Light Silicone Surface Modification and Characterization

Copolymer of Example 5 or 6 is dissolved or suspended in DI water to prepare 2-20 mg/mL aqueous mixture. Silicone elastomer films are prepared by mixing 10:1 (by weight) base:crosslinker (Sylgard 184), followed by degassing under vacuum and subsequently crosslinking at 70° C. for 8 h. For anti-biofouling experiments, 2 mg/mL of copolymer aqueous mixture is spread onto a cured silicone elastomer surface and exposed to 254 nm UV light irradiation for 10 mins. Then the silicone elastomer surface is rinsed with large amounts of DI water to remove unreacted and physically adsorbed copolymer molecules from the surface and stored underneath a layer of water before further use.

Contact angles of deionized water (18 MΩ/cm, Millipore) on polymer coatings are measured using a rame-hart Model 590 goniometer. Advancing angles ($\theta_{adv}$) are measured as water is supplied via a syringe, while receding angles ($\theta_{rec}$) are measured as water is removed via a syringe. The total drop volume is about 5 µL, and the pump dispensing speed is about 0.2 µL/s. Measurements are taken over three or more different locations on each surface, and the reported values are in the format of average standard deviation.

For surface modification, the following photoreaction takes place. First, PFPA decomposes by releasing N$_2$ to give the singlet phenylnitrene upon activation of the compound by UV light. The singlet phenylnitrene further undergoes C—H or N—H insertion, and C=C addition reactions which contributes to the covalent bond formation with the target surfaces (Liu, L.-H. et al. Perfluorophenyl azides: new applications in surface functionalization and nanomaterial synthesis. *Accounts of Chemical Research* 2010, 43 (11), 1434-1443). In this process, "the singlet phenylnitrene" reaction intermediate is a strong nucleophile and its stability is not affected by the existence of oxygen and water molecules.

Example 10. Silicone Surface Heat Modification and Characterization

Four 2 cm segments of a catheter (16 fr) were immersed in a 10 mg/mL solution of PFPA-PSB copolymer dissolved in DI water in a sealed flask and subjected to a 1 h heating period at various temperatures (80° C., 100° C., 120° C., 140° C., 160° C., 180° C., 200° C., or 220° C.). The catheter segments were then removed from the solution and rinsed by slowly dipping twice in fresh DI water and blotted on a paper towel to remove any liquid from the interior lumens of the samples. The catheters were then allowed to dry A dye solution of 3 mg/mL Crystal Violet-HCl solution in DI water was stirred overnight. The modified catheter segments and an analogous set of unmodified catheter segments were immersed individually in the crystal violet solution for 1 minute and then rinsed by dipping twice in fresh DI water blotted on a paper towel to remove any liquid from the interior lumens of the samples. The catheter segments were then placed into scintillation vials.

10 mL of a 2:1 solution of DI Water: Acetic Acid was then added to each vial. Each vial was shaken vigorously for 30 seconds to remove all adsorbed crystal violet from the catheters. 2 mL of solution was removed from each tube, placed into a cuvette, and the absorbance at 580 nm was taken. Because the initial readings were too high, each solution was then diluted by a factor of 2. The absorbance measurement at 580 nm for the unmodified (control) and modified catheters by thermal treatment at different temperatures are listed in Table E-10 below.

TABLE E-10

| T, °C. | Absorbances at 580 nm |
|---|---|
| N/A | 0.104 (control) |
| 80 | 0.296 |
| 100 | 0.347 |
| 120 | 0.492 |
| 140 | 0.458 |
| 160 | 0.615 |
| 180 | 0.685 |
| 200 | 0.652 |
| 220 | 1.486 |

Example 11. Substrates Modification and Characterization

Coating substrates with PSB: PDMS substrates are prepared by mixing a 10:1 ratio of elastomer to curing agent, followed by curing at 80° C. for 1 h. The PDMS disks are cut with a laser cutter into 3 mm diameter disks. 30 µL of coating (PSB) mixture with concentrations 2, 5, or 10 mg mL$^{-1}$ is placed and spread out on the surface of each disk. The PSB is then crosslinked on the discs by exposing them to 254 nm UV light for 10 min under sterile conditions, followed by rinsing with Milli-Q water and drying with air.

Contact angle visualization and measurement: Water contact angle on various substrates, such as PDMS, Nylon 66, polystyrene, polyvinyl chloride, and polyethylene is visualized by placing 17 µL of Milli-Q water on the flat substrates at room temperature followed by imaging them. The images are analyzed using Fta32 version 2.1 software to measure the contact angle. To study the recovery of water contact angle on PDMS substrates, they are divided into two groups: (i) uncoated PDMS sheets, which are treated using 02 plasma (Plasma Etch PE25-JW Plasma Cleaner, Nev., US) for 1 min, followed by measuring water contact angle after 1, 2, 4, 7, and 10 days, and (ii) PDMS sheets that are coated with PSB, and the contact angle is similarly measured over time.

XPS studies are carried out on a Kratos AXIS Ultra DLD with a monochromatic Al Kα X-ray source operating at 10 mA and 15 kV. Survey spectra and individual high-resolution spectra are collected using pass energies of 160 and 20 eV, respectively. Data processing are performed using CasaXPS 2.3 software, and spectra binding energies are calibrated by assigning the hydrocarbon peak in the C1s high-resolution spectra to 284.6 eV Cell culture: NIH/3T3 fibroblast cells are cultured in cell culture flasks containing DMEM with 10% FBS and 1% P/S and passaged twice a week. For this purpose, a standard cell culture incubator (Thermo Fisher Scientific, PA, USA) is used to provide 5% $CO_2$ atmosphere and temperature=37° C. To conduct cell studies, 0.5% trypsin-EDTA is used to trypsinize fibroblast cells and count them using a hemocytometer, followed by seeding them on desirable substrates.

Cell adhesion: Trypsinized fibroblasts cells are seeded on PSB-coated 96-well plates by placing 100 µL of the cell suspension (cell density~$1\times10^5$ in 1 mL media) on the treated well plates, cultured for 24 h. Uncoated well plates are used as a control.

Cytotoxicity evaluation: To assess the cytotoxicity of un-crosslinked PSB, trypsinized fibroblasts cells are seeded on 96-well plates by placing 100 µL of the cell suspension (cell density~$1\times10^5$ in 1 mL media) and cultured for 24 h, followed by adding a desired amount of un-crosslinked PSB to the media and further culturing for 72 h. The cytotoxicity of crosslinked PSB is evaluated by seeding 500 µL of cell suspension (cell density~$2\times10^5$ in 1 mL media) in 24-well plates, culturing for 24 h, followed by placing PSB coated PDMS discs (diameter~6 mm, height 3 mm) in the medium and further culturing for 72 h.

Metabolic activity assessment: MTT ((3-(4,5-Dimethylthiazol-2-yl)-2,5-Diphenyltetrazolium Bromide) (Thermo Fisher Scientific) stain solutions are prepared at a concentration~5 mg mL$^{-1}$ in DPBS. Cell culture media are removed from the well plates, followed by one time rinsing with DPBS. The wells are then loaded with fresh media and MTT solution at a ratio of 9:1. The well plates are wrapped with aluminum foil and incubated for 4 h at 37° C. and 5% $CO_2$. After 4 h, the wells are aspirated with a pipette and 200 or 500 µL of DMSO is added for 96- and 24-well plates, respectively. The well plates are wrapped with aluminum foil again and left on a rotator for 30 min, after which absorbance is recorded at 570 nm using a microplate reader (Synergy HTX multi-mode reader, BioTek, VT, USA).

Live/Dead assay: To assess the cell viability, a live/dead fluorescence assay is used. The staining solution is prepared by adding ethidium homodimer-1 (20 µL) and calcein AM (5 µL) to DPBS (10 mL). To perform the assay, the cells are incubated with 1 mL of the staining solution for approximately 20 min and imaged using a fluorescent microscope (Axio Observer 5, Zeiss, Germany) at excitation/emission wavelengths 494/515 nm for calcein and 528/617 nm for ethidium homodimer-1.

Protein adsorption: The protein adsorption is assessed by incubating 100 µg of 50 µg mL of Alexa Fluor™ 488 (AF)-conjugated BSA on each PDMS substrate for 1 h at 37° C. To inhibit the photodegradation of AF, aluminum foil is used to wrap the substrates. Then, the PDMS substrates are gently rinsed with Milli-Q water and imaged at a constant exposure time 1.13 ms using a fluorescent microscope (Axio Observer 5, Zeiss, Germany) at excitation/emission wavelengths 488/517 nm. ImageJ (National Institutes of Health, US) is used to quantify the emitted fluorescence via the mean gray value analysis tool. The average pixel brightness indirectly reflects the amount of protein adsorbed to the substrates. Background autofluorescence is eliminated using AF-free samples as control.

Bacterial culture: Bacterial species, E. coli, S. epidermidis, S. aureus Rosenbach, S. aureus (MRSA), P. aeruginosa, and C. albicans are used in this work. All strains are incubated at 30° C. at 150 rpm until a mid-exponential phase is reached, at which time the cells are harvested by centrifugation at 3800×g for 8 min. *E. coli* is grown on a Luria-Bertani (LB) broth, *S. epidermidis, P. aeruginosa*, and *S. aureus* Rosenbach are grown on nutrient broth; *S. aureus* (MRSA) is grown on a trypticase soy broth (TSB); and *C. albicans* is grown on a yeast mold (YM) broth. These initial cultures are then adjusted to an optical density of 1 at 600 nm and had an initial total cell number ranging from $1\times10^7$ cells per mL to $1\times10^8$ cells per mL.

Bacterial adhesion: 55 mm diameter Petri dishes are filled with a 10:1 elastomer to curing agent (Sylgard 184) and allowed to cure at room temperature for at least 48 hours to form a 3 mm thick PDMS film on the bottom of the dishes. Modified plates are coated with a solution containing PFPA-PSB and irradiated with 254 nm UV light. Each modified and unmodified PDMS-lined dish is inoculated with 4 mL of bacterial or fungal suspension and incubated for 24-72 hours (shaken at 25 rpm) at 35° C. The bacterial or fungal suspension is then removed and stored for further microscopy. The Petri dishes are gently rinsed with sterile, deionized water using a Pasteur pipette, and covered in 4 mL of a dye solution (SYTO 9 live/dead Baclight Bacterial Viability Kit L13152, Molecular Probes) for 15 min. The SYTO 9 solution is prepared by dissolving the contents of component A of the kit in 30 mL of sterile, deionized water. After the staining is complete, the Petri dishes are gently rinsed with deionized water and imaged using a 4×CCD camera (Axiocam MRm System) attached to a Zeiss Axioskop 2 microscope with a 10× objective, 40× objective, a fluorescent lamp, and a blue excitation filter. During observation, the images are taken at an excitation range of 450-490 nm. The number of attached microorganisms on all fluorescent images are determined using ImageJ software.

Statistical analysis: The data are reported as mean values standard deviation of at least triplicate experiments. The one-way analysis of variance (ANOVA) and Tukey's multiple comparisons are used, and statistically significant differences are identified for p-values lower than 0.05 (*p<0.05), 0.01 (p<0.01), 0.001 (*p<0.001), and 0.0001 (****p<0.0001).

*Escherichia coli* is used as the model bacteria for this test. Pure bacterial cell cultures are suspended in Luria-Bertani (LB) broth and grown at 35° C. while being shaken at 150 rpm and incubated until a mid-exponential phase is reached, at which time the cells are harvested by centrifugation at 3800×g for 8 min. The cells are then re-suspended with fresh LB medium to a concentration of $4\times10^7$ cells/mL. Membrane coupons, of approximately 1 cm², are incubated in this bacterial suspension for 24 hr at 25 rpm and 35° C. The coupons are then removed from the suspension and gently rinsed with fresh LB broth using a Pasteur pipette. Once rinsed, the coupons are immersed in a dye solution (SYTO 9 live/dead Baclight Bacterial Viability Kit L13152, Molecular Probes) for 15 min. The SYTO 9 solution is prepared by dissolving the contents of component A of the kit in 30 mL of sterile distillated water. After the staining is complete, the coupons are gently rinsed with fresh LB broth and imaged using a microscope (Olympus BX51 microscope) equipped with a fluorescent lamp and green/red fluorescence filters and a 4×CCD camera attachment (FVIEW-II, Soft Imaging System, USA).

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

Numbered Embodiments

Embodiment 1 is a compound that has the structure of Formula (I):

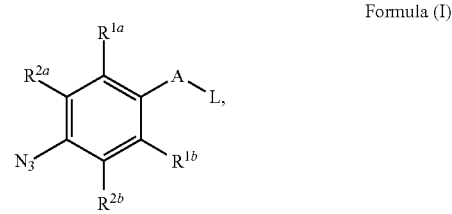

Formula (I)

wherein

A is selected from —C(=O)—, —S(=O)—, —S(=O)$_2$—, and —S(=O)(—NR$^3$)—;

L is selected from —OQ, —NR$^3$Q, and —N(R$^3$)$_2$Q$^+$;

Q is a structure represented by a formula:

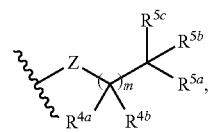

Z is selected from —CR$^{6a}$R$^{6b}$—, —C(=O)—, —C(=NH)—, and —C(=NH)NR$^7$—;

m is an integer selected from 0, 1, 2, 3, 4, 5, 6, 7, and 8;

each R$^{1a}$ and R$^{1b}$ is independently selected from hydrogen and halogen;

each R$^{2a}$ and R$^{2b}$ is independently selected from halogen, —CN, and optionally substituted C$_1$-C$_6$ fluoroalkyl;

each R$^3$ is independently selected from hydrogen, optionally substituted C$_1$-C$_4$ alkyl, —X-optionally substituted C$_1$-C$_4$ alkyl, optionally substituted aryl, and —X-optionally substituted aryl;

X is —C(=O)—, —S(=O)—, or —S(=O)$_2$—;

each R$^{4a}$, R$^{4b}$, R$^{5a}$, R$^{5c}$, R$^{6a}$, and R$^{6b}$ is independently selected from hydrogen, halogen, —CN, —OH, optionally substituted C$_1$-C$_4$ alkyl, optionally substituted C$_1$-C$_4$ fluoroalkyl, optionally substituted aryl, —NR$^{8a}$R$^{8b}$, —NR$^{8a}$R$^{8b}$R$^{8c+}$, —S(=O)$_2$O$^-$, —S(=O)$_2$OR$^9$, —C(=O)O$^-$, and —C(=O)OR$^9$;

R$^{5b}$ is —OR$^{10b}$, —NR$^{10a}$R$^{10b}$, or —NR$^{10a}$R$^{10b}$R$^{10c+}$;

each R$^7$, R$^{8a}$, R$^{8b}$, R$^{8c}$, and R$^9$ is independently selected from hydrogen and optionally substituted C1-C$_4$ alkyl, and optionally substituted aryl;

each R$^{10a}$ and R$^{10c}$ is independently selected from hydrogen, optionally substituted C$_1$-C$_4$ alkyl, optionally substituted aryl, -(optionally substituted C$_1$-C$_8$alkylene)S(=O)$_2$O$^-$, -(optionally substituted C$_1$-C$_8$alkylene)S(=O)$_2$OH, -(optionally substituted C$_1$-C$_8$alkylene)C(=O)O$^-$, and -(optionally substituted C$_1$-C$_8$alkylene)C(=O)OH; and $R^{10b}$ is —C(=O)—$C_2$-$C_6$alkenyl, —S(=O)—$C_2$-$C_6$alkenyl, or —S(=O)$_2$—$C_2$-$C_6$alkenyl; provided that a compound of Formula (I) is not N-(2-((4-azido-2,3,5,6-tetrafluorophenyl)sulfonamido)ethyl) methacrylamide;

N-(2-acrylamidoethyl)-4-azido-2,3,5,6-tetrafluorobenzamide; or 2-(methacryloyloxy)ethyl 4-azido-2,3,5,6-tetrafluorobenzoate.

Embodiment 2 is the compound of embodiment 1, wherein the compound has a structure selected from:

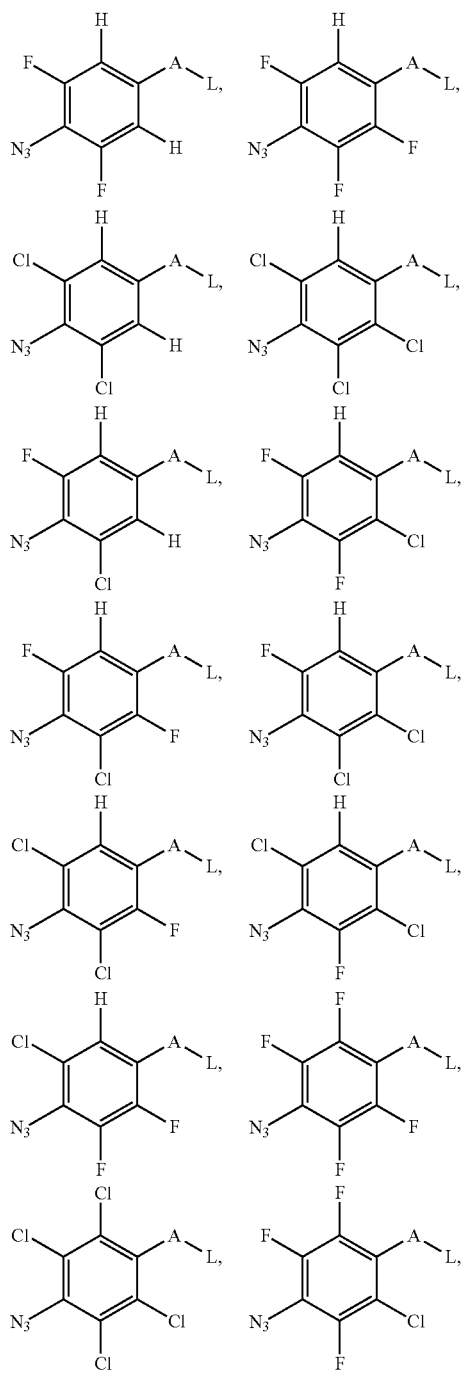

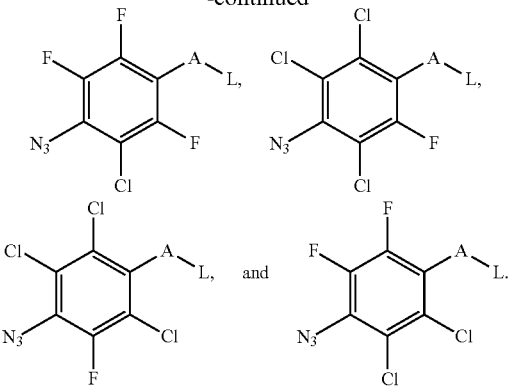

Embodiment 3 is the compound of embodiment 1 or 2, wherein the compound has a structure selected from:

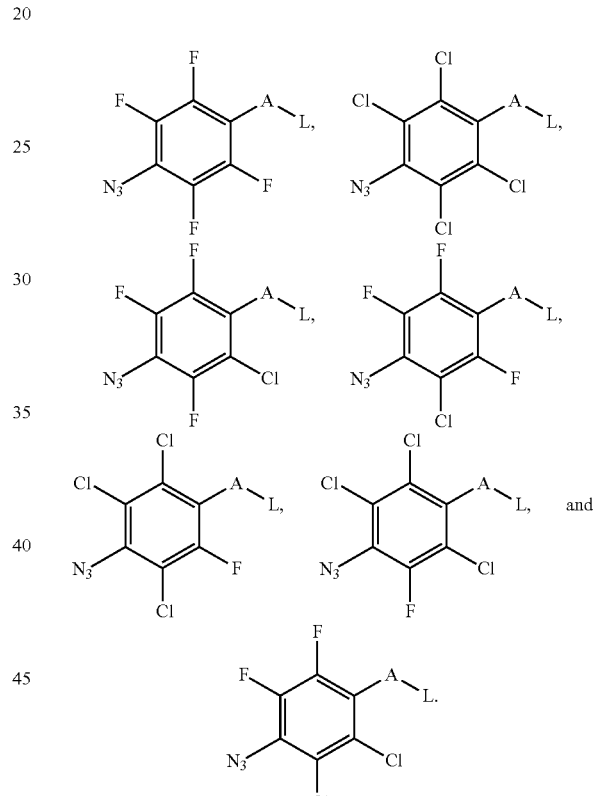

Embodiment 4 is the compound of any one of embodiments 1-3, wherein the compound has a structure selected from:

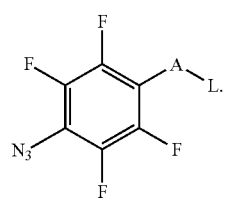

Embodiment 5 is the compound of embodiment 1, wherein the compound has the structure selected from:

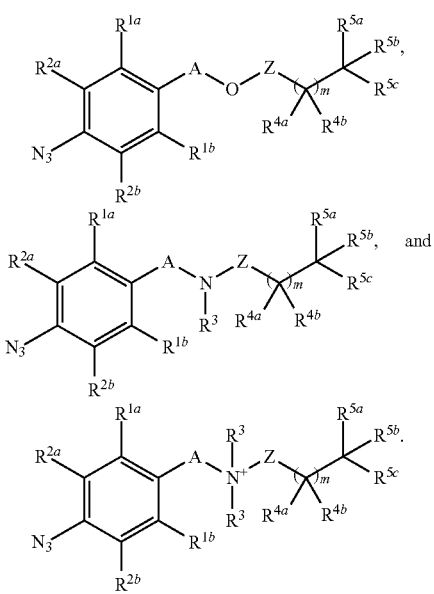

Embodiment 6 is the compound of embodiment 1, wherein the compound has the following structure:

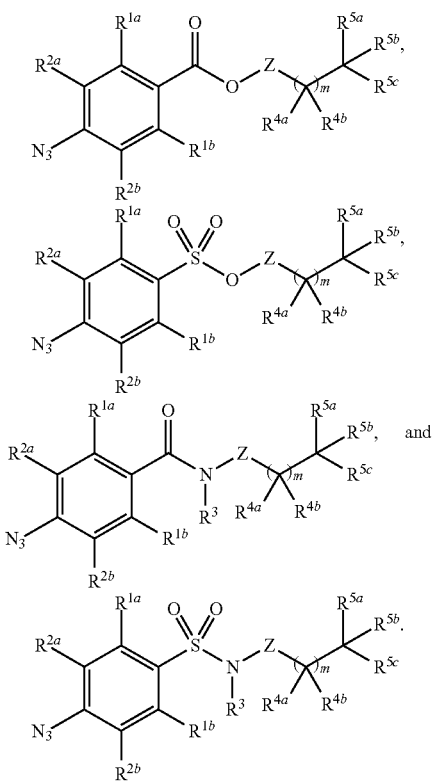

Embodiment 7 is the compound of embodiment 5 or 6, wherein $R^{1a}$, $R^{1b}$, $R^{2a}$, and $R^{2b}$ are each —F.

Embodiment 8 is the compound of any one of embodiments 1-7, wherein Z is —$CR^{6a}R^{6b}$—.

Embodiment 9 is the compound of embodiment 8, wherein $R^{6a}$ and $R^{6b}$ are each hydrogen.

Embodiment 10 is the compound of any one of embodiments 1-9, wherein m is 0, 1, 2, or 3.

Embodiment 11 is the compound of embodiment 10, wherein m is 0.

Embodiment 12 is the compound of any one of embodiments 1-11, wherein $R^{5a}$ is hydrogen; $R^{5b}$ is —$NR^{10a}R^{10b}$; and $R^{5c}$ is hydrogen.

Embodiment 13 is the compound of any one of embodiments 1-11, wherein $R^{5a}$ is hydrogen; $R^{5b}$ is —$OR^{10b}$; and $R^{5c}$ is hydrogen.

Embodiment 14 is the compound of embodiment 1, wherein the compound has the structure of Formula (Ia):

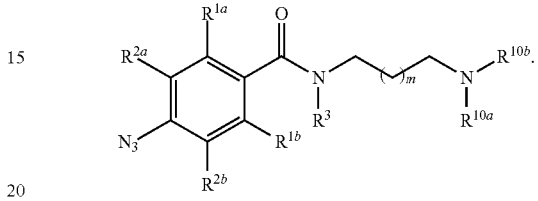

Embodiment 15 is the compound of embodiment 1, wherein the compound has the structure of Formula (Ib):

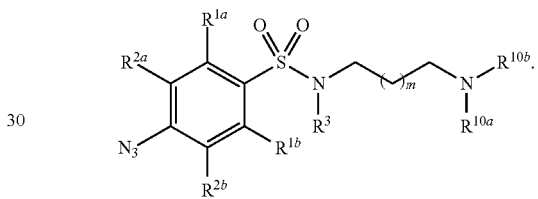

Embodiment 16 is the compound of embodiment 1, wherein the compound of Formula (I) has a structure of Formula (Ic):

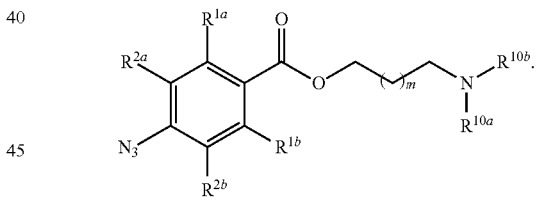

Embodiment 17 is the compound of embodiment 1, wherein the compound of Formula (I) has a structure of Formula (Id):

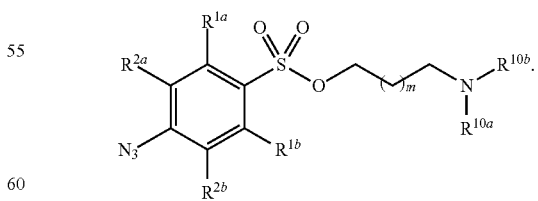

Embodiment 18 is the compound of any one of embodiments 1-17, wherein $R^{10a}$ is hydrogen.

Embodiment 19 is the compound of embodiment 1, wherein the compound of Formula (I) has a structure of Formula (Ie):

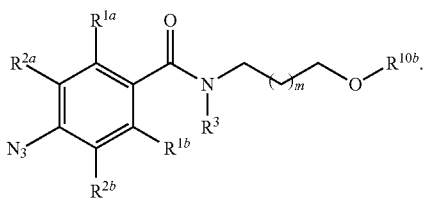

Embodiment 20 is the compound of embodiment 1, wherein the compound of Formula (I) has a structure of Formula (If):

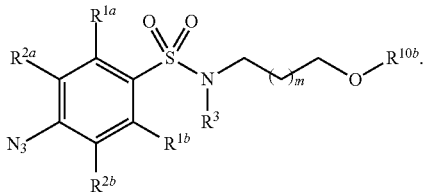

Embodiment 21 is the compound of embodiment 1, wherein the compound of Formula (I) has a structure of Formula (Ig):

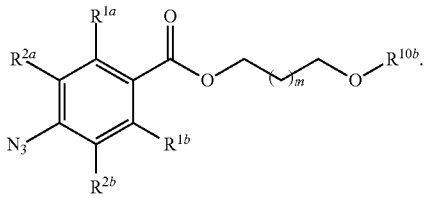

Embodiment 22 is the compound of embodiment 1, wherein the compound of Formula (I) has a structure of Formula (Ih):

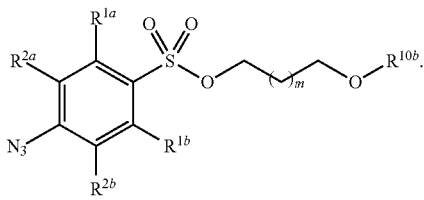

Embodiment 23 is the compound of any one of embodiments 1-15, 19, or 20, wherein $R^3$ is hydrogen.

Embodiment 24 is a compound that has the structure of Formula (II):

Formula (II)

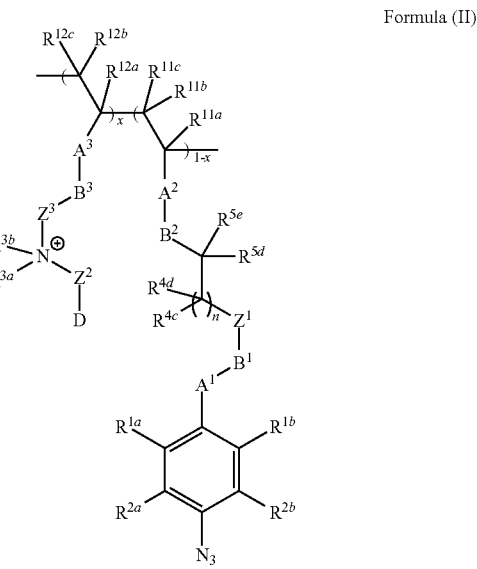

wherein
each $R^{1a}$ and $R^{1b}$ is independently selected from hydrogen and halogen;
each $R^{2a}$ and $R^{2b}$ is independently selected from halogen, —CN, and optionally substituted C1-C6fluoroalkyl;
each $A^1$, $A^2$, and $A^3$ is independently selected from —C(=O)—, —S(=O)—, —S(=O)$_2$—, and —S(=O)(=NR$^{3c}$)—;
each $B^1$, $B^2$, and $B^3$ is independently selected from —O— and —NR$^{3c}$—;
D is —S(=O)$_2$O$^-$, —S(=O)$_2$OR$^{9a}$, —C(=O)O$^-$, or —C(=O)OR$^{9a}$;
$Z^1$ is —(CR$^{6c}$R$^{6d}$)$_s$—;
$Z^2$ is —(CR$^{6c}$R$^{6d}$)$_t$—;
$Z^3$ is —(CR$^{6c}$R$^{6d}$)$_p$;
each $R^{3c}$ and $R^{3b}$ is independently selected from hydrogen, optionally substituted $C_1$-$C_4$ alkyl, and optionally substituted benzyl;
each $R^{4c}$, $R^{4d}$, $R^{5d}$, $R^{5e}$, $R^{6c}$, and $R^{6d}$ is independently selected from hydrogen, halogen, —CN, —OH, optionally substituted $C_1$-$C_4$ alkyl, optionally substituted $C_1$-$C_4$ fluoroalkyl, optionally substituted $C_2$-$C_6$ alkenyl, —NR$^{3c}$R$^{3d}$, —S(=O)$_2$O$^-$, —S(=O)$_2$OR$^{9a}$, —C(=O)O$^-$, and —C(=O)OR$^{9a}$;
each $R^{3c}$ and $R^{3d}$ is independently selected from hydrogen, optionally substituted $C_1$-$C_4$ alkyl, —X-optionally substituted $C_1$-$C_4$ alkyl, optionally substituted $C_2$-$C_6$ alkenyl, and optionally substituted aryl;
X is —C(=O)—, —S(=O)—, or —S(=O)$_2$—;
each $R^{9a}$, $R^{11a}$, $R^{11b}$, $R^{11c}$, $R^{12a}$, $R^{12b}$, and $R^{12c}$ is independently selected from hydrogen, optionally substituted $C_1$-$C_4$ alkyl, and optionally substituted aryl;
n is an integer selected from 0, 1, 2, 3, 4, 5, 6, 7, and 8;
s is an integer selected from 1, 2, 3, 4, or 5;
t is an integer selected from 1, 2, 3, 4, or 5;
p is an integer selected from 1, 2, 3, 4, or 5;
x is 0.001-0.999; and
wherein the compounds of Formula (II) is charged or zwitterionic;

provided that a compound of Formula (II) is not

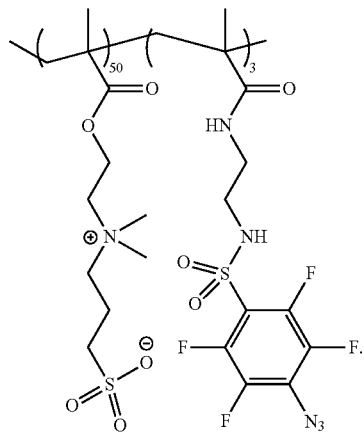

Embodiment 25 is the compound of embodiment 24, wherein each $R^{1a}$ and $R^{1b}$ is independently halogen.

Embodiment 26 is the compound of embodiment 24 or 25, wherein each $R^{1a}$ and $R^{1b}$ is independently F or Cl.

Embodiment 27 is the compound of any one of embodiments 24-26, wherein $R^{1a}$ and $R^{1b}$ are each F.

Embodiment 28 is the compound of any one of embodiments 24-27, wherein each $R^{2a}$ and $R^{2b}$ is independently selected from halogen, —CN, and —CF$_3$;

Embodiment 29 is the compound of any one of embodiments 24-28, wherein each $R^{2a}$ and $R^{2b}$ is independently selected from F, Cl, —CN, and —CF$_3$;

Embodiment 30 is the compound of any one of embodiments 24-29, wherein $R^{2a}$ and $R^{2b}$ are each F.

Embodiment 31 is the compound of any one of embodiments 24-30, wherein A is —S(=O)$_2$—; $A^2$ is —C(=O)—; and $A^3$ is —C(=O)—.

Embodiment 32 is the compound of any one of embodiments 24-31, wherein $B^1$ and $B^2$ are each —NR$^{3c}$—.

Embodiment 33 is the compound of embodiment 32, wherein $R^{3c}$ is hydrogen or —CH$_3$.

Embodiment 34 is the compound of embodiment 33, wherein $R^{3c}$ is hydrogen.

Embodiment 35 is the compound of any one of embodiments 24-34, wherein $B^3$ is —O—.

Embodiment 36 is the compound of any one of embodiments 24-35, wherein D is —S(=O)$_2$OR$^{9a}$ or —C(=O)OR$^{9a}$.

Embodiment 37 is the compound of embodiment 36 wherein $R^{9a}$ is hydrogen or —CH$_3$.

Embodiment 38 is the compound of any one of embodiments 24-35, wherein D is —S(=O)$_2$O— or —C(=O)O—.

Embodiment 39 is the compound of embodiment 38, wherein D is —S(=O)$_2$O$^-$.

Embodiment 40 is the compound of any one of embodiments 24-39, wherein each $R^{6c}$ and $R^{6d}$ is hydrogen.

Embodiment 41 is the compound of any one of embodiments 24-40, wherein each $R^{3a}$ and $R^{3b}$ is —CH$_3$.

Embodiment 42 is the compound of any one of embodiments 24-41, wherein $R^{11a}$ is hydrogen or —CH$_3$.

Embodiment 43 is the compound of embodiment 42, wherein $R^{11a}$ is —CH$_3$.

Embodiment 44 is the compound of any one of embodiments 24-43, wherein $R^{12a}$ is hydrogen or —CH$_3$.

Embodiment 45 is the compound of embodiment 44, wherein $R^{12a}$ is —CH$_3$.

Embodiment 46 is the compound of any one of embodiments 24-45, wherein each $R^{11b}$, $R^{11c}$, $R^{12b}$, and $R^{12c}$ is hydrogen.

Embodiment 47 is a compound that has the structure of Formula (III):

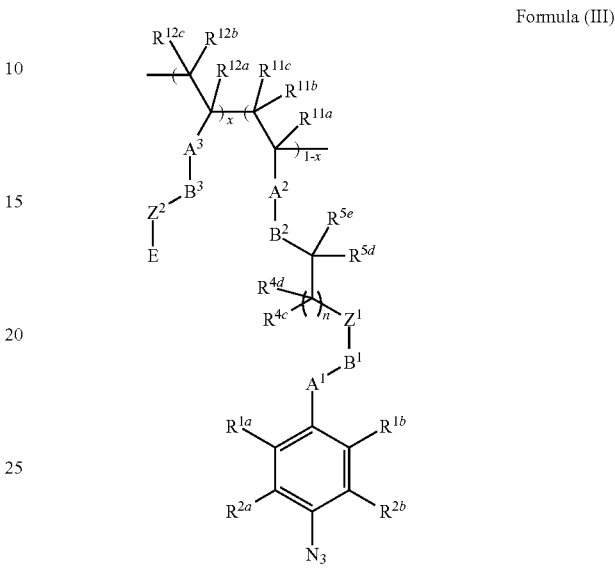

Formula (III)

wherein
each $R^{1a}$ and $R^{1b}$ is independently selected from hydrogen and halogen;
each $R^{2a}$ and $R^{2b}$ is independently selected from halogen, —CN, and optionally substituted $C_1$-$C_6$ fluoroalkyl;
each $A^1$, $A^2$, and $A^3$ is independently selected from —C(=O)—, —S(=O)—, —S(=O)$_2$—, and —S(=O)(=NR$^{3c}$)—;
each $B^1$, $B^2$, and $B^3$ is independently selected from —O— and —NR$^{3c}$—;
$Z^1$ is —(CR$^{6c}$R$^{6d}$)$_s$—;
$Z^2$ is —(CR$^{6c}$R$^{6d}$)$_t$—;
E is —CN, —OR$^{9a}$, —NR$^{9a}$R$^{9b}$, —NR$^{9a}$R$^{9b}$R$^{9c+}$ optionally substituted $C_1$-$C_4$ alkyl, optionally substituted $C_1$-$C_6$ fluoroalkyl, —S(=O)$_2$O$^-$, —S(=O)$_2$OR$^{9a}$, —C(=O)O$^-$, or —C(=O)OR$^{9a}$;
each $R^{4c}$, $R^{4d}$, $R^{5d}$, $R^{5e}$, $R^{6c}$, and $R^{6d}$ is independently selected from hydrogen, halogen, —CN, —OR$^{9a}$, optionally substituted $C_1$-$C_4$ alkyl, optionally substituted $C_1$-$C_4$ fluoroalkyl, optionally substituted $C_2$-$C_6$ alkenyl, —NR$^{3c}$R$^{3d}$, —S(=O)$_2$O$^-$, —S(=O)$_2$OR$^{9a}$, —C(=O)O$^-$, and —C(=O)OR$^{9a}$;
each $R^{3c}$ and $R^{3d}$ is independently selected from hydrogen, optionally substituted $C_1$-$C_4$ alkyl, —X-optionally substituted $C_1$-$C_4$ alkyl, optionally substituted $C_2$-$C_6$ alkenyl, and optionally substituted aryl;
X is —C(=O)—, —S(=O)—, or —S(=O)$_2$—;
each $R^{9a}$, $R^{9b}$, $R^{9c}$, $R^{11a}$, $R^{11b}$, $R^{11c}$, $R^{12a}$, $R^{12b}$, and $R^{12c}$ is independently selected from hydrogen, optionally substituted $C_1$-$C_4$ alkyl, and optionally substituted aryl;
n is an integer selected from 0, 1, 2, 3, 4, 5, 6, 7, and 8
s is an integer selected from 1, 2, 3, 4, or 5;
t is an integer selected from 1, 2, 3, 4, or 5; and
x is 0.001-0.999.

Embodiment 48 is the compound of embodiment 47, wherein each $R^{1a}$ and $R^{1b}$ is independently halogen.

Embodiment 49 is the compound of embodiment 47 or 48, wherein each $R^{1a}$ and $R^{1b}$ is independently F or Cl.

Embodiment 50 is the compound of any one of embodiments 47-49, wherein $R^{1a}$ and $R^{1b}$ are each F.

Embodiment 51 is the compound of any one of embodiments 47-50, wherein each $R^{2a}$ and $R^{2b}$ is independently selected from halogen, —CN, and —CF$_3$;

Embodiment 52 is the compound of any one of embodiments 47-51, wherein each $R^{2a}$ and $R^{2b}$ is independently selected from F, Cl, —CN, and —CF$_3$;

Embodiment 53 is the compound of any one of embodiments 47-52, wherein $R^{2a}$ and $R^{2b}$ are each F.

Embodiment 54 is the compound of any one of embodiments 47-53, wherein A is —S(=O)$_2$—; $A^2$ is —C(=O)—; and $A^3$ is —C(=O)—.

Embodiment 55 is the compound of any one of embodiments 47-54, wherein $B^1$ and $B^2$ are each —NR$^{3c}$—.

Embodiment 56 is the compound of embodiment 55, wherein $R^{3c}$ is hydrogen or —CH$_3$.

Embodiment 57 is the compound of embodiment 56, wherein $R^{3c}$ is hydrogen.

Embodiment 58 is the compound of any one of embodiments 47-57, wherein $B^3$ is —NR$^{3c}$—.

Embodiment 59 is the compound of embodiment 58, wherein $R^{3c}$ is hydrogen.

Embodiment 60 is the compound of any one of embodiments 47-59, wherein E is —NR$^{9a}$R$^{9b}$R$^{9c+}$ or —S(=O)$_2$OR$^{9a}$.

Embodiment 61 is the compound of embodiment 60, wherein E is —NR$^{9a}$R$^{9b}$R$^{9c+}$.

Embodiment 62 is the compound of embodiment 61, wherein each $R^{9a}$, $R^{9b}$, and $R^{9c}$ is hydrogen or —CH$_3$.

Embodiment 63 is the compound of embodiment 62, wherein each $R^{9a}$, $R^{9b}$, and $R^{9c}$ is hydrogen.

Embodiment 64 is the compound of embodiment 62, wherein each $R^{9a}$, $R^{9b}$, and $R^{9c}$ is —CH$_3$.

Embodiment 65 is the compound of embodiment 60, wherein E is —S(=O)$_2$OR$^{9a}$.

Embodiment 66 is the compound of embodiment 65, wherein $R^{9a}$ is hydrogen or —CH$_3$.

Embodiment 67 is the compound of embodiment 66, wherein each $R^{9a}$ is hydrogen.

Embodiment 68 is the compound of embodiment 66, wherein each $R^{9a}$ is —CH$_3$.

Embodiment 69 is the compound of any one of embodiments 47-68, wherein each $R^{6c}$ and $R^{6d}$ is independently selected from hydrogen and —CH$_3$.

Embodiment 70 is the compound of any one of embodiments 47-69, wherein each $R^{3a}$ and $R^{3b}$ is —CH$_3$.

Embodiment 71 is the compound of any one of embodiments 47-70, wherein $R^{11a}$ is hydrogen or —CH$_3$.

Embodiment 72 is the compound of embodiment 71, wherein $R^{11a}$ is —CH$_3$.

Embodiment 73 is the compound of any one of embodiments 47-72, wherein $R^{12a}$ is hydrogen or —CH$_3$.

Embodiment 74 is the compound of embodiment 73, wherein $R^{12a}$ is —CH$_3$.

Embodiment 75 is the compound of any one of embodiments 47-74, wherein each $R^{11b}$, $R^{11c}$, $R^{12b}$, and $R^{12c}$ is hydrogen.

Embodiment 76 is a copolymer comprising:
a) a repeating unit of Formula (VII):

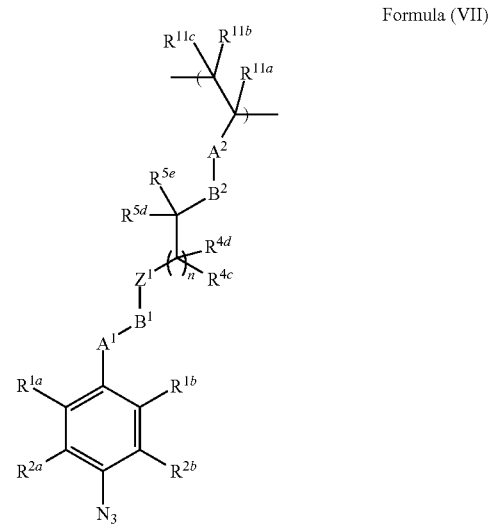

Formula (VII)

wherein
each $R^{1a}$ and $R^{1b}$ is independently selected from hydrogen and halogen;
each $R^{2a}$ and $R^{2b}$ is independently selected from halogen, —CN, and optionally substituted C$_1$-C$_6$ fluoroalkyl;
each $A^1$ and $A^2$ is independently selected from —C(=O)—, —S(=O)—, —S(=O)$_2$—, and —S(=O)(=NR$^{3c}$)—;
each $B^1$ and $B^2$ is independently selected from —O— and —NR$^{3c}$—;
$Z^1$ is —(CR$^{6c}$R$^{6d}$)$_n$—;
each $R^{4c}$, $R^{4d}$, $R^{5d}$, $R^{5e}$, $R^{6c}$, and $R^{6d}$ is independently selected from hydrogen, halogen, —CN, —OR$^{9a}$, optionally substituted C$_1$-C$_4$ alkyl, optionally substituted C$_1$-C$_4$ fluoroalkyl, optionally substituted C$_2$-C$_6$ alkenyl, —NR$^{3c}$R$^{3d}$, —S(=O)$_2$O$^-$, —S(=O)$_2$OR$^{9a}$, —C(=O)O$^-$, and —C(=O)OR$^{9a}$;
each $R^{3c}$ and $R^{3d}$ is independently selected from hydrogen, optionally substituted C$_1$-C$_4$ alkyl, —X-optionally substituted C$_1$-C$_4$ alkyl, optionally substituted C$_2$-C$_6$ alkenyl, and optionally substituted aryl;
X is —C(=O)—, —S(=O)—, or —S(=O)$_2$—;
each $R^{9a}$, $R^{11a}$, $R^{11b}$, and $R^{11c}$ is independently selected from hydrogen, optionally substituted C$_1$-C$_4$ alkyl, and optionally substituted aryl;
n is an integer selected from 0, 1, 2, 3, 4, 5, 6, 7, and 8; and
s is an integer selected from 1, 2, 3, 4, and 5;
b) a repeating unit of Formula (VIII):

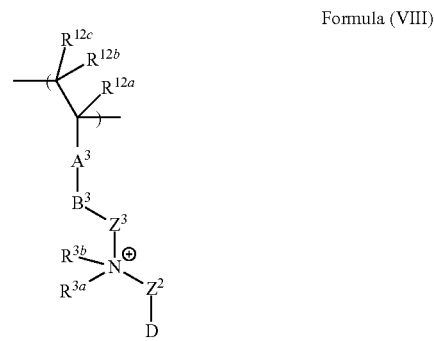

Formula (VIII)

wherein,
A³ is —C(=O)—, —S(=O)—, —S(=O)₂—, or —S(=O)(=NR³ᶜ)—;
B³ is —O— or —NR³ᶜ—;
D is —S(=O)₂O⁻, —S(=O)₂OR⁹ᵃ, —C(=O)O⁻, or —C(=O)OR⁹ᵃ;
Z² is —(CR⁶ᶜR⁶ᵈ)$_t$—;
Z³ is —(CR⁶ᶜR⁶ᵈ)$_p$—;
each R³ᵃ and R³ᵇ is independently selected from hydrogen, optionally substituted C₁-C₄ alkyl, and optionally substituted benzyl;
each R⁶ᶜ and R⁶ᵈ is independently selected from hydrogen, halogen, —CN, —OR⁹ᵃ, optionally substituted C₁-C₄ alkyl, optionally substituted C₁-C₄ fluoroalkyl, optionally substituted C₂-C₆ alkenyl, —NR³ᶜR³ᵈ, —S(=O)₂O⁻, —S(=O)₂OR⁹ᵃ, —C(=O)O⁻, and —C(=O)OR⁹ᵃ;
each R³ᶜ and R³ᵈ is independently selected from hydrogen, optionally substituted C₁-C₄ alkyl, —X-optionally substituted C₁-C₄ alkyl, optionally substituted C₂-C₆ alkenyl, and optionally substituted aryl;
X is —C(=O)—, —S(=O)—, or —S(=O)₂—;
each R⁹ᵃ, R¹²ᵃ, R¹²ᵇ, and R¹²ᶜ is independently selected from hydrogen, optionally substituted C₁-C₄ alkyl, and optionally substituted aryl;
t is an integer selected from 1, 2, 3, 4, or 5;
p is an integer selected from 1, 2, 3, 4, or 5; and
wherein the repeating unit of Formula (VIII) is charged or zwitterionic; and
c) a repeating unit of Formula (IX):

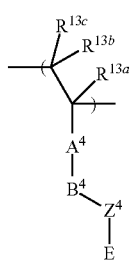

Formula (IX)

A⁴ is —C(=O)—, —S(=O)—, —S(=O)₂—, or —S(=O)(=NR³ᶜ)—;
B⁴ is —O— or —NR³ᶜ—;
Z⁴ is —(CR⁶ᶜR⁶ᵈ)$_k$—;
E is —CN, —OR⁹ᵃ, —NR⁹ᵃR⁹ᵇ, —NR⁹ᵃR⁹ᵇR⁹ᶜ⁺ optionally substituted C₁-C₄ alkyl, optionally substituted C₁-C₆ fluoroalkyl, —S(=O)₂O⁻, —S(=O)₂OR⁹ᵃ, —C(=O)O⁻, or —C(=O)OR⁹ᵃ;
each R⁶ᶜ, and R⁶ᵈ is independently selected from hydrogen, halogen, —CN, —OR⁹ᵃ, optionally substituted C₁-C₄ alkyl, optionally substituted C₁-C₄ fluoroalkyl, optionally substituted C₂-C₆ alkenyl, —NR³ᶜR³ᵈ, —S(=O)₂O⁻, —S(=O)₂OR⁹ᵃ, —C(=O)O⁻, and —C(=O)OR⁹ᵃ;
each R³ᶜ and R³ᵈ is independently selected from hydrogen, optionally substituted C₁-C₄ alkyl, —X-optionally substituted C₁-C₄ alkyl, optionally substituted C₂-C₆ alkenyl, and optionally substituted aryl;
X is —C(=O)—, —S(=O)—, or —S(=O)₂—;
each R⁹ᵃ, R⁹ᵇ, R⁹ᶜ, R¹³ᵃ, R¹³ᵇ and R¹³ᶜ is independently selected from hydrogen, optionally substituted C₁-C₄ alkyl, and optionally substituted aryl; and
k is an integer selected from 1, 2, 3, 4, or 5.

Embodiment 77 is the copolymer of embodiment 76, wherein each R¹ᵃ and R¹ᵇ is independently halogen.

Embodiment 78 is the copolymer of embodiment 76 or 77, wherein each R¹ᵃ and R¹ᵇ is independently F or Cl.

Embodiment 79 is the copolymer of any one of embodiments 76-78, wherein each R¹ᵃ and R¹ᵇ is F.

Embodiment 80 is the copolymer of any one of embodiments 76-79, wherein each R²ᵃ and R²ᵇ is independently selected from halogen, —CN, and —CF₃.

Embodiment 81 is the copolymer of any one of embodiments 76-80, wherein each R²ᵃ and R²ᵇ is independently selected from F, Cl, —CN, and —CF₃.

Embodiment 82 is the copolymer of any one of embodiments 76-81, wherein each R²ᵃ and R²ᵇ is F.

Embodiment 83 is the copolymer of any one of embodiments 76-82, wherein A is —S(=O)₂— and each A², A³, and A⁴ is —C(=O)—.

Embodiment 84 is the copolymer of any one of embodiments 76-83, wherein each B¹, B², and B³ is independently —O— or —NR³ᶜ—.

Embodiment 85 is the copolymer of any one of embodiments 76-84, wherein each R³ᶜ is hydrogen or —CH₃.

Embodiment 86 is the copolymer of any one of embodiments 76-85, wherein D is —S(=O)₂O⁻ or —C(=O)O⁻.

Embodiment 87 is the copolymer of any one of embodiments 76-86, wherein E is —NR⁹ᵃR⁹ᵇR⁹ᶜ⁺ or —S(=O)₂OR⁹ᵃ.

Embodiment 88 is the copolymer of any one of embodiments 76-87, wherein each R⁹ᵃ, R⁹ᵇ, and R⁹ᶜ is independently hydrogen or C₁-C₄ alkyl.

Embodiment 89 is the copolymer of any one of embodiments 76-88, wherein each R³ᵃ and R³ᵇ is —CH₃.

Embodiment 90 is the copolymer of any one of embodiments 76-89, wherein each R⁴ᶜ, R⁴ᵈ, R⁵ᵈ, and R⁵ᵉ is hydrogen.

Embodiment 91 is the copolymer of any one of embodiments 76-90, wherein each R³ᶜ, R³ᵈ, R⁶ᶜ, and R⁶ᵈ is hydrogen.

Embodiment 92 is the copolymer of any one of embodiments 76-91, wherein each R¹¹ᵃ, R¹²ᵃ, and R¹³ᵃ is hydrogen or —CH₃.

Embodiment 93 is the copolymer of any one of embodiments 76-92, wherein each R¹¹ᵇ, R¹¹ᶜ, R¹²ᵇ, R¹²ᶜ, R¹³ᵇ, and R¹³ᶜ is hydrogen.

Embodiment 94 is the copolymer of any one of embodiments 76-93, wherein n is 0, 1, or 2.

Embodiment 95 is the copolymer of any one of embodiments 76-94, wherein each s, t, p, and k is independently 1, 2 or 3.

Embodiment 96 is a medical device coated with a compound of any one of embodiments 1-95.

Embodiment 97 is a biofouling-resistant medical device, wherein a surface of the medical device is coated with a phenyl azide-based copolymer having a number-average molecular weight of between about 10,000 and about 250,000.

Embodiment 98 is the biofouling-resistant medical device of embodiment 97, wherein the phenyl azide-based copolymer has a number-average molecular weight of between about 10,000 and about 20,000.

Embodiment 99 is the biofouling-resistant medical device of embodiment 97, wherein the phenyl azide-based copolymer has a number-average molecular weight of between about 10,000 and about 40,000.

Embodiment 100 is the biofouling-resistant medical device of embodiment 97, wherein the phenyl azide-based copolymer has a number-average molecular weight of between about 20,000 and about 60,000.

Embodiment 101 is the biofouling-resistant medical device of embodiment 97, wherein the phenyl azide-based copolymer has a number-average molecular weight of between about 40,000 and about 100,000.

Embodiment 102 is the biofouling-resistant medical device of embodiment 97, wherein the phenyl azide-based copolymer has a number-average molecular weight of between about 80,000 and about 160,000.

Embodiment 103 is the biofouling-resistant medical device of embodiment 97, wherein the phenyl azide-based copolymer has a number-average molecular weight of between about 120,000 and about 200,000.

Embodiment 104 is the biofouling-resistant medical device of embodiment 97, wherein the phenyl azide-based copolymer has a number-average molecular weight of between about 14,000 and about 21,000.

Embodiment 105 is the biofouling-resistant medical device of embodiment 97, wherein the phenyl azide-based copolymer has a number-average molecular weight of between about 15,000 and about 18,000.

Embodiment 106 is the biofouling-resistant medical device of any one of embodiments 97-105, wherein the phenyl azide-based copolymer is a compound of any one of embodiments 24-75 or a copolymer of any one of embodiments 76-95.

Embodiment 107 is a biofouling-resistant medical device, wherein a surface of the medical device is coated with a phenyl azide-based copolymer having a polydispersity index (PDI) of between about 1 and 1.5.

Embodiment 108 is the biofouling-resistant medical device of embodiment 107, wherein the PDI is about 1.4, 1.3, 1.2, or 1.1.

Embodiment 109 is the biofouling-resistant medical device of embodiment 107, wherein the PDI is about 1.19.

Embodiment 110 is the biofouling-resistant medical device of any one of embodiments 97-109, wherein the medical device comprises a dental instrument or a medical instrument.

Embodiment 111 is the biofouling-resistant medical device of any one of embodiments 97-110, wherein the medical device comprises an implant, an IV, a prosthesis, suturing material, valve, stent, catheter, rod, shunt, scope, a contact lens, tubing, wiring, electrode, clip, fastener, syringe, container, or a combination thereof.

Embodiment 112 is the biofouling-resistant medical device of embodiment 111, wherein the medical device is a contact lens.

Embodiment 113 is the biofouling-resistant medical device of embodiment 111, wherein the medical device is catheter.

Embodiment 114 is the biofouling-resistant medical device of embodiment 113, wherein the catheter is an indwelling catheter.

Embodiment 115 is the biofouling-resistant medical device of embodiment 113, wherein the catheter comprises an uretic catheter or a Foley catheter.

Embodiment 116 is the biofouling-resistant medical device of embodiment 111, wherein the medical device is scope.

Embodiment 117 is the biofouling-resistant medical device of embodiment 116, wherein the scope comprises a scope utilized in an image-guided surgery.

Embodiment 118 is the biofouling-resistant medical device of embodiment 116, wherein the scope comprises a scope utilized in endoscopy or laparoscopy.

Embodiment 119 is the biofouling-resistant medical device of embodiment 110 or 111, wherein the medical device comprises auditory prostheses, artificial larynx, dental implants, mammary implants, penile implants, cranio/facial tendons, tendons, ligaments, menisci, or disks.

Embodiment 120 is the biofouling-resistant medical device of any one of embodiments 110, 111, or 119, wherein the medical device comprises artificial bones, artificial joints, or artificial organs.

Embodiment 121 is the biofouling-resistant medical device of embodiment 120, wherein the artificial organs comprise artificial pancreas, artificial hearts, artificial limbs, or heart valves.

Embodiment 122 is the biofouling-resistant medical device of any one of embodiments 97-109, wherein the medical device comprises a bandage or a patch.

Embodiment 123 is the biofouling-resistant medical device of any one of embodiments 107-122, wherein the phenyl azide-based copolymer comprises a compound of any one of embodiments 1-75 or a copolymer of any one of embodiments 76-95.

Embodiment 124 is the biofouling-resistant medical device of any one of embodiments 107-122, wherein the copolymer comprises zwitterionic copolymer.

Embodiment 125 is the biofouling-resistant medical device of embodiment 124, wherein the zwitterionic copolymer is polysulfobetaine.

Embodiment 126 is the biofouling-resistant medical device of any one of embodiments 107-125, wherein the biofouling is produced by a bacterium, a virus, and/or a fungus.

Embodiment 127 is a method of making a biofouling-resistant medical device, comprising:
  a) contacting a surface of a medical device with a solution or suspension comprising a charged or zwitterion copolymer; and
  b) treating the surface of the medical device of step a) with a light source for a time sufficient to undergo photografting of the charged or zwitterion copolymer onto the surface of the medical device, thereby making the biofouling-resistant medical device;
wherein the charged or zwitterion copolymer comprises a phenyl azide-based copolymer; and
  wherein the charged or zwitterion copolymer having a number-average molecular weight of between about 10,000 and about 250,000.

Embodiment 128 is a method of making a charged or zwitterion copolymer modified biofouling-resistant device comprising:
  a) contacting a surface of a silicon-based device with a solution or suspension comprising a charged or zwitterion copolymer; and
  b) treating the surface of the device of step a) with a light source for a time sufficient to undergo photografting of the charged or zwitterion copolymer onto the surface of the silicon-based device, thereby generating the charged or zwitterion copolymer modified device;
wherein the charged or zwitterion copolymer comprises a phenyl azide-based copolymer.

Embodiment 129 is a method of making a charged or zwitterion copolymer modified biofouling-resistant device comprising:
  a) contacting a surface of a device with a solution or suspension comprising a charged or zwitterion copolymer; and
  b) treating the surface of the device of step a) with a light source for a time sufficient to undergo photografting of the charged or zwitterion copolymer onto the surface of the device, thereby generating the charged or zwitterion copolymer modified device;

wherein the charged or zwitterion copolymer comprises a phenyl azide-based copolymer; and wherein the charged or zwitterion copolymer having a number-average molecular weight of between about 10,000 and about 250,000.

Embodiment 130 is the method of any one of embodiments 127-129, wherein the time sufficient to undergo photografting is at least 1 minute, at least 2 minutes, 3 minutes, 4 minutes, 5 minutes, 6 minutes, 7 minutes, 8 minutes, 9 minutes, 10 minutes, 15 minutes, 20 minutes, 25 minutes or 30 minutes.

Embodiment 131 is the method of any one of embodiments 127-130, wherein the light source is an ultraviolet light source.

Embodiment 132 is the method of embodiment 131, wherein the ultraviolet light source has an intensity of at least 900 µW/cm$^2$.

Embodiment 133 is the method of embodiment 131 or 132, wherein the ultraviolet light source has a wavelength of between 240 nm and 280 nm, between 240 nm and 275 nm, between 240 nm and 270 nm, between 240 nm and 265 nm, between 240 nm and 260 nm, between 240 nm and 255 nm, between 240 nm and 250 nm, between 240 nm and 245 nm, between 250 nm and 280 nm, between 250 nm and 275 nm, between 250 nm and 270 nm, between 250 nm and 265 nm, between 250 nm and 260 nm, between 255 nm and 280 nm, between 255 nm and 275 nm, between 255 nm and 270 nm, between 255 nm and 265 nm, between 255 nm and 260 nm, between 260 nm and 280 nm, between 260 nm and 275 nm, between 260 nm and 270 nm, or between 270 nm and 280 nm.

Embodiment 134 is the method of embodiment 131 or 132, wherein the ultraviolet light source has a wavelength of at least 240 nm, 245 nm, 250 nm, 251 nm, 252 nm, 253 nm, 254 nm, 255 nm, 256 nm, 257 nm, 258 nm, 259 nm, 260 nm, 261 nm, 262 nm, 263 nm, 264 nm, 265 nm, 266 nm, 267 nm, 268 nm, 269 nm, 270 nm, 275 nm or 280 nm.

Embodiment 135 is the method of any one of embodiments 127-134, wherein the solution or suspension of step a) is an aqueous solution or suspension.

Embodiment 136 is the method of any one of embodiments 127-135, wherein photografting of step b) is not affected by the presence of oxygen.

Embodiment 137 is the method of any one of embodiments 127-136, wherein the charged or zwitterion copolymer is a compound of any one of embodiments 24-75 or a copolymer of any one of embodiments 76-95.

Embodiment 138 is the method of any one of the embodiments 127-137, wherein the solution or suspension comprising a charged or zwitterion copolymer has a concentration of the charged or zwitterion copolymer in the solution or suspension between 1 mg/mL and 30 mg/mL.

Embodiment 139 is the method of embodiment 138, wherein the concentration of the charged or zwitterion copolymer in the solution or suspension is between 1 mg/mL and 25 mg/mL, between 1 mg/mL and 20 mg/mL, between 1 mg/mL and 15 mg/mL, between 1 mg/mL and 10 mg/mL, between 1 mg/mL and 5 mg/mL, between 5 mg/mL and 30 mg/mL, between 5 mg/mL and 25 mg/mL, between 5 mg/mL and 20 mg/mL, between 5 mg/mL and 15 mg/mL, between 5 mg/mL and 10 mg/mL, between 10 mg/mL and 30 mg/mL, between 10 mg/mL and 25 mg/mL, between 10 mg/mL and 20 mg/mL, between 10 mg/mL and 15 mg/mL, between 15 mg/mL and 30 mg/mL, between 15 mg/mL and 25 mg/mL, between 15 mg/mL and 20 mg/mL, between 20 mg/mL and 30 mg/mL, or between 20 mg/mL and 25 mg/mL.

Embodiment 140 is the method of embodiment 138, wherein the concentration of the charged or zwitterion copolymer in the solution or suspension is about 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 11 mg/mL, 12 mg/mL, 13 mg/mL, 14 mg/mL, 15 mg/mL, 16 mg/mL, 17 mg/mL, 18 mg/mL, 19 mg/mL, 20 mg/mL, 21 mg/mL, 22 mg/mL, 23 mg/mL, 24 mg/mL, 25 mg/mL, 26 mg/mL, 27 mg/mL, 28 mg/mL, 29 mg/mL, or 30 mg/mL.

Embodiment 141 is the method of any one of embodiments 127-140, wherein the concentration of the charged or zwitterion copolymer is between 0.1 to 1 mg per square centimeter of the device.

Embodiment 142 is the method of embodiment 128, wherein the charged or zwitterion copolymer has a number-average molecular weight of between about 10,000 and about 250,000

Embodiment 143 is the method of any one of embodiments 127 or 129-142, wherein the charged or zwitterion copolymer has a number-average molecular weight of between about 10,000 and about 20,000.

Embodiment 144 is the method of any one of embodiments 127 or 129-142, wherein the charged or zwitterion copolymer has a number-average molecular weight of between about 10,000 and about 40,000.

Embodiment 145 is the method of any one of embodiments 127 or 129-142, wherein the charged or zwitterion copolymer has a number-average molecular weight of between about 20,000 and about 60,000.

Embodiment 146 is the method of any one of embodiments 127 or 129-142, wherein the charged or zwitterion copolymer has a number-average molecular weight of between about 40,000 and about 100,000.

Embodiment 147 is the method of any one of embodiments 127 or 129-142, wherein the charged or zwitterion copolymer has a number-average molecular weight of between about 80,000 and about 160,000.

Embodiment 148 is the method of any one of embodiments 127 or 129-142, wherein the charged or zwitterion copolymer has a number-average molecular weight of between about 120,000 and about 200,000.

Embodiment 149 is the method of any one of embodiments 127 or 129-142, wherein the charged or zwitterion copolymer has a number-average molecular weight of between about 14,000 and about 21,000.

Embodiment 150 is the method of any one of embodiments 127 or 129-142, wherein the charged or zwitterion copolymer has a number-average molecular weight of between about 15,000 and about 18,000.

Embodiment 151 is the method of embodiment 127 or 129, wherein the device comprises a carbon-based device or a silicon-based device.

Embodiment 152 is the method of embodiment 151, wherein the device comprises a silicon-based device.

Embodiment 153 is the method of embodiment 128 or 152, wherein the silicon-based device comprises a silicon-based polymer moiety.

Embodiment 154 is the method of embodiment 153, wherein the silicon-based polymer moiety comprises siloxane polymer moiety, sesquisiloxane polymer moiety, siloxane-silarylene polymer moiety, silalkylene polymer moiety, polysilane moiety, polysilylene moiety, or polysilazane moiety.

Embodiment 155 is the method of embodiment 154, wherein the silicon-based device comprises siloxane polymer moiety.

Embodiment 156 is the method of embodiment 151, wherein the device comprises a carbon-based device.

Embodiment 157 is the method of embodiment 156, wherein the carbon-based device comprises a carbon-based polymer.

Embodiment 158 is the method of embodiment 156, wherein the carbon-based device comprises a polyolefin moiety.

Embodiment 159 is the method of embodiment 158, wherein the polyolefin moiety comprises polyethylene moiety, polypropylene moiety, polyvinyl chloride moiety, polyvinylidene fluoride moiety, polytetrafluoroethylene moiety, polychlorotrifluoroethylene moiety, or polystyrene moiety.

Embodiment 160 is the method of embodiment 157, wherein the carbon-based polymer comprises polyamide moiety, polyurethane moiety, phenol-formaldehyde resin moiety, polycarbonate moiety, polychloroprene moiety, polyacrylonitrile moiety, polyimide moiety, or polyester moiety.

Embodiment 161 is the method of embodiment 157, wherein the carbon-based polymer comprises nylon.

Embodiment 162 is the method of embodiment 157, wherein the carbon-based polymer comprises polyethylene terephthalate.

Embodiment 163 is the method of any one of embodiments 127-162, wherein the copolymer comprises zwitterionic copolymer.

Embodiment 164 is the method of embodiment 163, wherein the zwitterionic copolymer is polysulfobetaine.

Embodiment 165 is the method of any one of embodiments 127-164, wherein the biofouling is produced by a bacterium, a virus, and/or a fungus.

Embodiment 166 is a method for synthesizing a compound of Formula (II) comprising: reacting a compound of Formula (IV) or a salt or solvate thereof with a compound of Formula (V):

Formula (II)

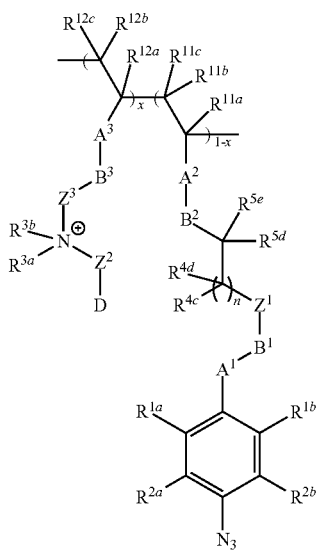

Formula (IV)

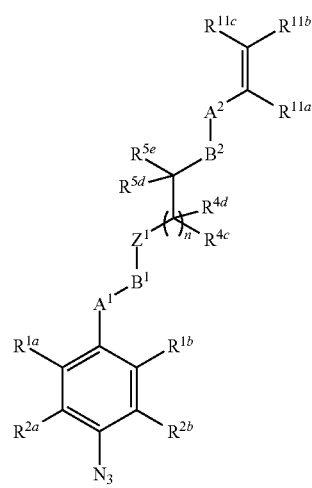

Formula (V)

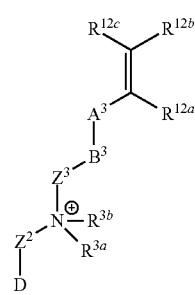

wherein each $R^{1a}$ and $R^{1b}$ is independently selected from hydrogen and halogen;

each $R^{2a}$ and $R^{2b}$ is independently selected from halogen, —CN, and optionally substituted $C_1$-$C_6$ fluoroalkyl;

each $A^1$, $A^2$, and $A^3$ is independently selected from —C(=O)—, —S(=O)—, —S(=O)$_2$—, and —S(=O)(=NR$^{3c}$)—;

each $B^1$, $B^2$, and $B^3$ is independently selected from —O— and —NR$^{3c}$—;

D is —S(=O)$_2$O$^-$, —S(=O)$_2$OR$^{9a}$, —C(=O)O$^-$, or —C(=O)OR$^{9a}$;

$Z^1$ is —(CR$^{6c}$R$^{6d}$)$_s$—;

$Z^2$ is —(CR$^{6c}$R$^{6d}$)$_t$—;

$Z^3$ is —(CR$^{6c}$R$^{6d}$)$_p$;

each $R^{3a}$ and $R^{3b}$ is independently selected from hydrogen, optionally substituted $C_1$-$C_4$ alkyl, and optionally substituted benzyl;

each $R^{4c}$, $R^{4d}$, $R^{5d}$, $R^{5e}$, $R^{6c}$, and $R^{6d}$ is independently selected from hydrogen, halogen, —CN, —OH, optionally substituted $C_1$-$C_4$ alkyl, optionally substituted $C_1$-$C_4$ fluoroalkyl, optionally substituted $C_2$-$C_6$ alkenyl, —NR$^{3c}$R$^{3d}$, —S(=O)$_2$O$^-$, —S(=O)$_2$OR$^{9a}$, —C(=O)O$^-$, and —C(=O)OR$^{9a}$;

each $R^{3c}$ and $R^{3d}$ is independently selected from hydrogen, optionally substituted $C_1$-$C_4$ alkyl, —X-optionally substituted $C_1$-$C_4$ alkyl, optionally substituted $C_2$-$C_6$ alkenyl, and optionally substituted aryl;

X is —C(=O)—, —S(=O)—, or —S(=O)$_2$—;

each $R^{9a}$, $R^{11a}$, $R^{11b}$, $R^{11c}$, $R^{12a}$, $R^{12b}$, and $R^{12c}$ is independently selected from hydrogen, optionally substituted $C_1$-$C_4$ alkyl, and optionally substituted aryl;

n is an integer selected from 0, 1, 2, 3, 4, 5, 6, 7, and 8;

s is an integer selected from 1, 2, 3, 4, or 5;

t is an integer selected from 1, 2, 3, 4, or 5;
p is an integer selected from 1, 2, 3, 4, or 5;
x is 0.001-0.999; and
wherein the compounds of Formula (II) and Formula (V) are each independently charged or zwitterionic; provided that a compound of Formula (II) is not

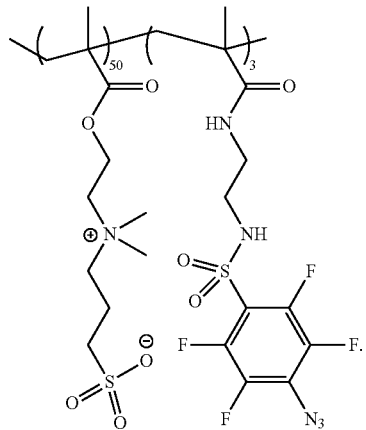

Embodiment 167 is the method of embodiment 166, wherein each $R^{1a}$ and $R^{1b}$ is independently halogen.

Embodiment 168 is the method of embodiment 166 or 167, wherein each $R^{1a}$ and $R^{1b}$ is independently F or Cl.

Embodiment 169 is the method of any one of embodiments 166-168, wherein $R^{1a}$ and $R^{1b}$ are each F.

Embodiment 170 is the method of any one of embodiments 166-169, wherein each $R^{2a}$ and $R^{2b}$ is independently selected from halogen, —CN, and —CF$_3$;

Embodiment 171 is the method of any one of embodiments 166-170, wherein each $R^{2a}$ and $R^{2b}$ is independently selected from F, Cl, —CN, and —CF$_3$;

Embodiment 172 is the method of any one of embodiments 166-171, wherein $R^{2a}$ and $R^{2b}$ are each F.

Embodiment 173 is the method of any one of embodiments 166-172, wherein A is —S(=O)$_2$—; $A^2$ is —C(=O)—; and $A^3$ is —C(=O)—.

Embodiment 174 is the method of any one of embodiments 166-173, wherein $B^1$ and $B^2$ are each —NR$^{3c}$—.

Embodiment 175 is the method of embodiment 174, wherein $R^{3c}$ is hydrogen or —CH$_3$.

Embodiment 176 is the method of embodiment 175, wherein $R^{3c}$ is hydrogen.

Embodiment 177 is the method of any one of embodiments 166-176, wherein $B^3$ is —O—.

Embodiment 178 is the method of any one of embodiments 166-177, wherein D is —S(=O)$_2$OR$^{9a}$ or —C(=O)OR$^{9a}$.

Embodiment 179 is the method of embodiment 178, wherein $R^{9a}$ is hydrogen or —CH$_3$.

Embodiment 180 is the method of any one of embodiments 166-177, wherein D is —S(=O)$_2$O$^-$ or —C(=O)O$^-$.

Embodiment 181 is the method of embodiment 180, wherein D is —S(=O)$_2$O$^-$.

Embodiment 182 is the method of any one of embodiments 166-181, wherein each $R^{6c}$ and $R^{6d}$ is hydrogen.

Embodiment 183 is the method of any one of embodiments 166-182, wherein each $R^{3a}$ and $R^{3b}$ is —CH$_3$.

Embodiment 184 is the method of any one of embodiments 166-183, wherein $R^{11a}$ is hydrogen or —CH$_3$.

Embodiment 185 is the method of embodiment 184, wherein $R^{11a}$ is —CH$_3$.

Embodiment 186 is the method of any one of embodiments 166-185, wherein $R^{12a}$ is hydrogen or —CH$_3$.

Embodiment 187 is the method of embodiment 186, wherein $R^{12a}$ is —CH$_3$.

Embodiment 188 is the method of any one of embodiments 166-187, wherein each $R^{11b}$, $R^{11c}$, $R^{12b}$, and $R^{12C}$ is hydrogen.

Embodiment 189 is a method for synthesizing a compound of Formula (III) comprising: reacting a compound of Formula (IV) or a salt or solvate thereof with a compound of Formula (VI):

Formula (III)

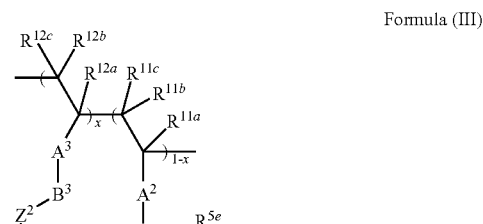

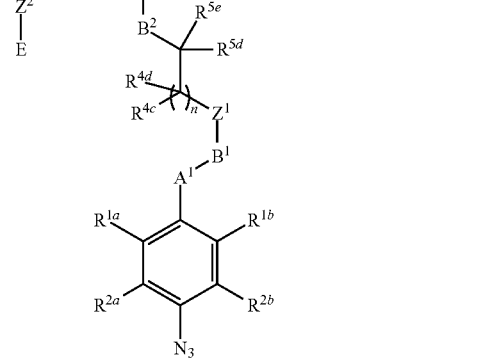

Formula (IV)

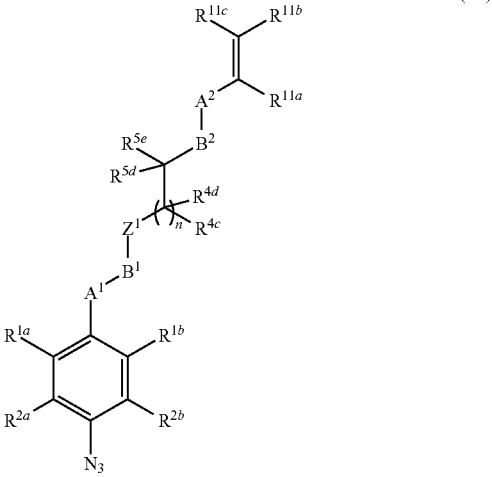

Formula (VI)

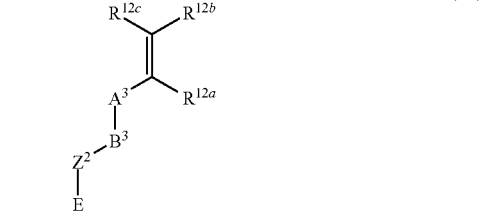

wherein
   each $R^{1a}$ and $R^{1b}$ is independently selected from hydrogen and halogen;
   each $R^{2a}$ and $R^{2b}$ is independently selected from halogen, —CN, and optionally substituted $C_1$-$C_6$ fluoroalkyl;
   each $A^1$, $A^2$, and $A^3$ is independently selected from —C(=O)—, —S(=O)—, —S(=O)$_2$—, and —S(=O)(=$NR^{3c}$)—;
   each $B^1$, $B^2$, and $B^3$ is independently selected from —O— and —$NR^{3c}$—;
   $Z^1$ is —$(CR^{6c}R^{6d})_s$—;
   $Z^2$ is —$(CR^{6c}R^{6d})_t$—;
   E is —CN, —$OR^{9a}$, —$NR^{9a}R^{9b}$, —$NR^{9a}R^{9b}R^{9c+}$ optionally substituted $C_1$-$C_4$ alkyl, optionally substituted $C_1$-$C_6$ fluoroalkyl, —S(=O)$_2$O$^-$, —S(=O)$_2$$OR^{9a}$, —C(=O)O$^-$, or —C(=O)$OR^{9a}$;
   each $R^{4c}$, $R^{4d}$, $R^{5d}$, $R^{5e}$, $R^{6c}$, and $R^{6d}$ is independently selected from hydrogen, halogen, —CN, —$OR^{9a}$, optionally substituted $C_1$-$C_4$ alkyl, optionally substituted $C_1$-$C_4$ fluoroalkyl, optionally substituted $C_2$-$C_6$ alkenyl, —$NR^{3c}R^{3d}$, —S(=O)$_2$O$^-$, —S(=O)$_2$$OR^{9a}$, —C(=O)O$^-$, and —C(=O)$OR^{9a}$;
   each $R^{3c}$ and $R^{3d}$ is independently selected from hydrogen, optionally substituted $C_1$-$C_4$ alkyl, —X-optionally substituted $C_1$-$C_4$ alkyl, optionally substituted $C_2$-$C_6$ alkenyl, and optionally substituted aryl;
   X is —C(=O)—, —S(=O)—, or —S(=O)$_2$—;
   each $R^{9a}$, $R^{9b}$, $R^{9c}$, $R^{11a}$, $R^{11b}$, $R^{11c}$, $R^{12a}$, $R^{12b}$, and $R^{12c}$ is independently selected from hydrogen, optionally substituted $C_1$-$C_4$ alkyl, and optionally substituted aryl;
   n is an integer selected from 0, 1, 2, 3, 4, 5, 6, 7, and 8
   s is an integer selected from 1, 2, 3, 4, or 5;
   t is an integer selected from 1, 2, 3, 4, or 5; and
   x is 0.001-0.999.

Embodiment 190 is the method of embodiment 189, wherein each $R^{1a}$ and $R^{1b}$ is independently halogen.

Embodiment 191 is the method of embodiment 189 or 190, wherein each $R^{1a}$ and $R^{1b}$ is independently F or Cl.

Embodiment 192 is the method of any one of embodiments 189-191, wherein $R^{1a}$ and $R^{1b}$ are each F.

Embodiment 193 is the method of any one of embodiments 189-192, wherein each $R^{2a}$ and $R^{2b}$ is independently selected from halogen, —CN, and —CF$_3$;

Embodiment 194 is the method of any one of embodiments 189-193, wherein each $R^{2a}$ and $R^{2b}$ is independently selected from F, Cl, —CN, and —CF$_3$;

Embodiment 195 is the method of any one of embodiments 189-194, wherein $R^{2a}$ and $R^{2b}$ are each F.

Embodiment 196 is the method of any one of embodiments 189-195, wherein A is —S(=O)$_2$—; $A^2$ is —C(=O)—; and $A^3$ is —C(=O)—.

Embodiment 197 is the method of any one of embodiments 189-196, wherein $B^1$ and $B^2$ are each —$NR^{3c}$—.

Embodiment 198 is the method of embodiment 197 wherein $R^{3c}$ is hydrogen or —CH$_3$.

Embodiment 199 is the method of embodiment 198, wherein $R^{3c}$ is hydrogen.

Embodiment 200 is the method of any one of embodiments 189-199, wherein $B^3$ is —$NR^{3c}$—.

Embodiment 201 is the method of embodiment 200, wherein $R^{3c}$ is hydrogen.

Embodiment 202 is the method of any one of embodiments 189-201, wherein E is —$NR^{9a}R^{9b}R^{9c+}$ or —S(=O)$_2$$OR^{9a}$.

Embodiment 203 is the method of embodiment 202, wherein E is —$NR^{9a}R^{9b}R^{9c+}$.

Embodiment 204 is the method of embodiment 203, wherein each $R^{9a}$, $R^{9b}$, and $R^{9c}$ is hydrogen or —CH$_3$.

Embodiment 205 is the method of embodiment 204, wherein each $R^{9a}$, $R^{9b}$, and $R^{9c}$ is hydrogen.

Embodiment 206 is the method of embodiment 204, wherein each $R^{9a}$, $R^{9b}$, and $R^{9c}$ is —CH$_3$.

Embodiment 207 is the method of embodiment 202, wherein E is —S(=O)$_2$$OR^{9a}$.

Embodiment 208 is the method of embodiment 207, wherein $R^{9a}$ is hydrogen or —CH$_3$.

Embodiment 209 is the method of embodiment 208, wherein each $R^{9a}$ is hydrogen.

Embodiment 210 is the method of embodiment 208, wherein each $R^{9a}$ is —CH$_3$.

Embodiment 211 is the method of any one of embodiments 189-210, wherein each $R^{6c}$ and $R^{6d}$ is independently selected from hydrogen and —CH$_3$.

Embodiment 212 is the method of any one of embodiments 189-211, wherein each $R^{3a}$ and $R^{3b}$ is —CH$_3$.

Embodiment 213 is the method of any one of embodiments 189-212, wherein $R^{11a}$ is hydrogen or —CH$_3$.

Embodiment 214 is the method of embodiment 213, wherein $R^{11a}$ is —CH$_3$.

Embodiment 215 is the method of any one of embodiments 189-214, wherein $R^{12a}$ is hydrogen or —CH$_3$.

Embodiment 216 is the method of embodiment 215, wherein $R^{12a}$ is —CH$_3$.

Embodiment 217 is the method of any one of embodiments 189-216, wherein each $R^{11b}$, $R^{11c}$, $R^{12b}$, and $R^{12c}$ is hydrogen.

Embodiment 218 is a charged or zwitterion copolymer modified biofouling-resistant device prepared by the method comprising:
   a) contacting a surface of a silicon-based device with a solution or suspension comprising a charged or zwitterion copolymer; and
   b) treating the surface of the device of step a) with a light source for a time sufficient to undergo photografting of the charged or zwitterion copolymer onto the surface of the silicon-based device, thereby generating the charged or zwitterion copolymer modified device;
wherein the charged or zwitterion copolymer comprises a phenyl azide-based copolymer.

Embodiment 219 is a charged or zwitterion copolymer modified biofouling-resistant device prepared by the method comprising:
   a) contacting a surface of a device with a solution or suspension comprising a charged or zwitterion copolymer; and
   b) treating the surface of the device of step a) with a light source for a time sufficient to undergo photografting of the charged or zwitterion copolymer onto the surface of the device, thereby generating the charged or zwitterion copolymer modified device;
wherein the charged or zwitterion copolymer comprises a phenyl azide-based copolymer; and
   wherein the charged or zwitterion copolymer having a number-average molecular weight of between about 10,000 and about 250,000.

Embodiment 220 is the device of embodiment 218 or 219, wherein the time sufficient to undergo photografting is at least 1 minute, at least 2 minutes, 3 minutes, 4 minutes, 5 minutes, 6 minutes, 7 minutes, 8 minutes, 9 minutes, 10 minutes, 15 minutes, 20 minutes, 25 minutes or 30 minutes.

Embodiment 221 is the device of any one of embodiments 218-220, wherein the light source is an ultraviolet light source.

Embodiment 222 is the device of embodiment 221, wherein the ultraviolet light source has an intensity of at least 900 µW/cm².

Embodiment 223 is the device of embodiment 221 or 222, wherein the ultraviolet light source has a wavelength of between 240 nm and 280 nm, between 240 nm and 275 nm, between 240 nm and 270 nm, between 240 nm and 265 nm, between 240 nm and 260 nm, between 240 nm and 255 nm, between 240 nm and 250 nm, between 240 nm and 245 nm, between 250 nm and 280 nm, between 250 nm and 275 nm, between 250 nm and 270 nm, between 250 nm and 265 nm, between 250 nm and 260 nm, between 255 nm and 280 nm, between 255 nm and 275 nm, between 255 nm and 270 nm, between 255 nm and 265 nm, between 255 nm and 260 nm, between 260 nm and 280 nm, between 260 nm and 275 nm, between 260 nm and 270 nm, or between 270 nm and 280 nm.

Embodiment 224 is the device of embodiment 221 or 222, wherein the ultraviolet light source has a wavelength of at least 240 nm, 245 nm, 250 nm, 251 nm, 252 nm, 253 nm, 254 nm, 255 nm, 256 nm, 257 nm, 258 nm, 259 nm, 260 nm, 261 nm, 262 nm, 263 nm, 264 nm, 265 nm, 266 nm, 267 nm, 268 nm, 269 nm, 270 nm, 275 nm or 280 nm.

Embodiment 225 is the device of any one of embodiments 218-224, wherein the solution or suspension of step a) is an aqueous solution or suspension.

Embodiment 226 is the device of any one of embodiments 218-225, wherein photografting of step b) is not affected by the presence of oxygen.

Embodiment 227 is the device of any one of embodiments 218-226, wherein the charged or zwitterion compound comprises a compound of any one of embodiments 1-75 or a copolymer of any one of embodiments 76-95.

Embodiment 228 is the device of any one of the embodiments 218-227, wherein the solution or suspension comprising a charged or zwitterion compound has a concentration of the charged or zwitterion compound in the solution or suspension between 1 mg/mL and 30 mg/mL.

Embodiment 229 is the device of embodiment 228, wherein the concentration of the charged or zwitterion compound in the solution or suspension is between 1 mg/mL and 25 mg/mL, between 1 mg/mL and 20 mg/mL, between 1 mg/mL and 15 mg/mL, between 1 mg/mL and 10 mg/mL, between 1 mg/mL and 5 mg/mL, between 5 mg/mL and 30 mg/mL, between 5 mg/mL and 25 mg/mL, between 5 mg/mL and 20 mg/mL, between 5 mg/mL and 15 mg/mL, between 5 mg/mL and 10 mg/mL, between 10 mg/mL and 30 mg/mL, between 10 mg/mL and 25 mg/mL, between 10 mg/mL and 20 mg/mL, between 10 mg/mL and 15 mg/mL, between 15 mg/mL and 30 mg/mL, between 15 mg/mL and 25 mg/mL, between 15 mg/mL and 20 mg/mL, between 20 mg/mL and 30 mg/mL, or between 20 mg/mL and 25 mg/mL.

Embodiment 230 is the device of embodiment 228, wherein the concentration of the charged or zwitterion compound in the solution or suspension is about 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 11 mg/mL, 12 mg/mL, 13 mg/mL, 14 mg/mL, 15 mg/mL, 16 mg/mL, 17 mg/mL, 18 mg/mL, 19 mg/mL, 20 mg/mL, 21 mg/mL, 22 mg/mL, 23 mg/mL, 24 mg/mL, 25 mg/mL, 26 mg/mL, 27 mg/mL, 28 mg/mL, 29 mg/mL, or 30 mg/mL.

Embodiment 231 is the device of any one of embodiments 218-230, wherein the concentration of the charged or zwitterion compound is between 0.1 to 1 mg per square centimeter of the device.

Embodiment 232 is the device of embodiment 218, wherein the charged or zwitterion copolymer has a number-average molecular weight of between about 10,000 and about 250,000

Embodiment 233 is the device of any one of embodiments 219-232, wherein the charged or zwitterion copolymer has a number-average molecular weight of between about 10,000 and about 20,000.

Embodiment 234 is the device of any one of embodiments 219-232, wherein the charged or zwitterion copolymer has a number-average molecular weight of between about 10,000 and about 40,000.

Embodiment 235 is the device of any one of embodiments 219-232, wherein the charged or zwitterion copolymer has a number-average molecular weight of between about 20,000 and about 60,000.

Embodiment 236 is the device of any one of embodiments 219-232, wherein the charged or zwitterion copolymer has a number-average molecular weight of between about 40,000 and about 100,000.

Embodiment 237 is the device of any one of embodiments 219-232, wherein the charged or zwitterion copolymer has a number-average molecular weight of between about 80,000 and about 160,000.

Embodiment 238 is the device of any one of embodiments 219-232, wherein the charged or zwitterion copolymer has a number-average molecular weight of between about 120,000 and about 200,000.

Embodiment 239 is the device of any one of embodiments 219-232, wherein the charged or zwitterion copolymer has a number-average molecular weight of between about 14,000 and about 21,000.

Embodiment 240 is the device of any one of embodiments 219-232, wherein the charged or zwitterion copolymer has a number-average molecular weight of between about 15,000 and about 18,000.

Embodiment 241 is the device of embodiment 219, wherein the device comprises a carbon-based device or a silicon-based device containing a moiety capable of binding with the phenyl azide-zwitterion compound of any one of embodiments 24-75 or a copolymer of any one of embodiments 76-95.

Embodiment 242 is the device of embodiment 241, wherein the device comprises a silicon-based device.

Embodiment 243 is the device of embodiment 218 or 242, wherein the silicon-based device comprises a polymer moiety.

Embodiment 244 is the device of embodiment 243, wherein the silicon-based device comprises a siloxane polymer moiety, a sesquisiloxane polymer moiety optionally having a ladder structure, a siloxane-silarylene polymer moiety, a silalkylene polymer moiety, a polysilane moiety, a polysilylene moiety, or a polysilazane moiety.

Embodiment 245 is the device of embodiment 244, wherein the silicon-based device comprises a siloxane polymer moiety.

Embodiment 246 is the device of embodiment 241, wherein the device comprises a carbon-based device.

Embodiment 247 is the device of embodiment 246, wherein the carbon-based device comprises a carbon-based polymer.

Embodiment 248 is the device of embodiment 246, wherein the carbon-based device comprises a polyolefin moiety.

Embodiment 249 is the device of embodiment 248, wherein the polyolefin moiety comprises polyethylene moiety, polypropylene moiety, polyvinyl chloride moiety, polyvinylidene fluoride moiety, polytetrafluoroethylene moiety, polychlorotrifluoroethylene moiety, or polystyrene moiety.

Embodiment 250 is the device of embodiment 247, wherein the carbon-based polymer comprises polyamide moiety, polyurethane moiety, phenol-formaldehyde resin moiety, polycarbonate moiety, polychloroprene moiety, polyacrylonitrile moiety, polyimide moiety, or polyester moiety.

Embodiment 251 is the device of embodiment 247, wherein the carbon-based polymer comprises nylon.

Embodiment 252 is the device of embodiment 247, wherein the carbon-based polymer comprises polyethylene terephthalate.

Embodiment 253 is the device of any one of embodiments 218-252, wherein the device is resistant to fouling.

Embodiment 254 is the device of embodiment 253, wherein the device prevents and/or reduces biofouling.

Embodiment 255 is the device of embodiment 254, wherein biofouling comprises microfouling or macrofouling.

Embodiment 256 is the device of embodiment 255, wherein microfouling comprises biofilm and bacterial adhesion.

Embodiment 257 is the device of embodiment 255 or 256, wherein microfouling is formed by a bacterium or a fungus.

Embodiment 258 is the device of any one of embodiments 255-257, wherein microfouling is formed by a gram-positive bacterium.

Embodiment 259 is the device of embodiment 258, wherein the gram-positive bacterium comprises a bacterium from the genus *Actinomyces, Arthrobacter, Bacillus, Clostridium, Corynebacterium, Enterococcus, Lactococcus, Listeria, Micrococcus, Mycobacterium, Staphylococcus,* or *Streptococcus.*

Embodiment 260 is the device of embodiment 258 or 259, wherein the gram-positive bacterium comprises *Actinomyces* spp., *Arthrobacter* spp., *Bacillus licheniformis, Clostridium difficile, Clostridium* spp., *Corynebacterium* spp., *Enterococcus faecalis, Lactococcus* spp., *Listeria monocytogenes, Micrococcus* spp., *Mycobacterium* spp., *Staphylococcus aureus, Staphylococcus epidermidis, Streptococcus pneumoniae,* or *Streptococcus pyogenes.*

Embodiment 261 is the device of any one of embodiments 255-257, wherein microfouling is formed by a gram-negative bacterium.

Embodiment 262 is the device of embodiment 261, wherein the gram-negative bacterium comprises a bacterium from the genus *Alteromonas, Aeromonas, Desulfovibrio, Escherichia, Fusobacterium, Geobacter, Haemophilus, Klebsiella, Legionella, Porphyromonas, Proteus, Pseudomonas, Serratia, Shigella, Salmonella,* or *Vibrio.*

Embodiment 263 is the device of embodiment 261 or 262, wherein the gram-negative bacterium comprises *Alteromonas* spp., *Aeromonas* spp., *Desulfovibrio* spp., *Escherichia coli, Fusobacterium nucleatum, Geobacter* spp., *Haemophilus* spp., *Klebsiella* spp., *Legionella pneumophila, Porphyromonas* spp., *Pseudomonas aeruginosa, Proteus vulgaris, Proteus mirabilis, Proteus penneri, Serratia* spp., *Shigella dysenteriae, Shigella flexneri, Shigella boydii, Shigella sonnei, Salmonella bongori, Salmonella enterica,* or *Vibrio Cholerae.*

Embodiment 264 is the device of embodiment 257, wherein the bacterium is a marine bacterium.

Embodiment 265 is the device of embodiment 264, wherein the marine bacterium comprises *Pseudoalteromonas* spp. or *Shewanella* spp.

Embodiment 266 is the device of any one of embodiments 255-257, wherein microfouling is formed by a fungus.

Embodiment 267 is the device of embodiment 266, wherein the fungus comprises *Candida albicans, Candida glabrata, Candida rugose, Candida parapsilosis, Candida tropicalis, Candida dubliniensis,* or *Hormoconis resinae.*

Embodiment 268 is the device of embodiment 255, wherein macrofouling comprises calcareous fouling organism or non-calcareous fouling organism.

Embodiment 269 is the device of embodiment 268, wherein calcareous fouling organism comprises barnacle, bryozoan, mollusk, polychaete, tube worm, or zebra mussel.

Embodiment 270 is the device of embodiment 268, wherein non-calcareous fouling organism comprises seaweed, hydroids, or algae.

Embodiment 271 is the device of any one of embodiments 218-270, wherein the formation of biofouling on a surface of a device is reduced by about 10%, 20%, 30%, 40%, 50%, 60%, 70%, 80%, 90%, 95%, 99%, 99.5%, 99.9%, or more relative to unmodified surface of a device.

Embodiment 272 is the device of any one of embodiments 218-271, wherein the device is further coated with an additional agent.

Embodiment 273 is the device of embodiment 272, wherein the additional agent is an antimicrobial agent.

Embodiment 274 is the device of embodiment 272, wherein the additional agent is a chemical disinfectant.

Embodiment I is a copolymer comprising:
a) a repeating unit of Formula (VII):

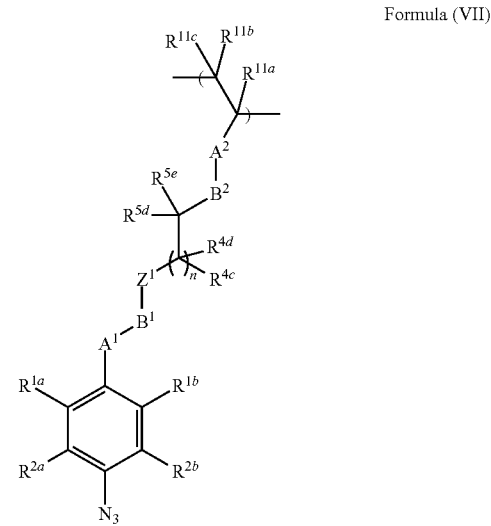

Formula (VII)

wherein
each $R^{1a}$ and $R^{1b}$ is independently selected from hydrogen and halogen;
each $R^{2a}$ and $R^{2b}$ is independently selected from halogen, —CN, and optionally substituted $C_1$-$C_6$ fluoroalkyl;
each $A^1$ and $A^2$ is independently selected from —C(=O)—, —S(=O)—, —S(=O)$_2$—, and —S(=O)(=NR$^{3c}$)—;
each $B^1$ and $B^2$ is independently selected from —O— and —NR$^{3c}$—; $Z^1$ is —(CR$^{6c}$R$^{6d}$)$_s$—;
each $R^{4c}$, $R^{4d}$, $R^{5d}$, $R^{5e}$, $R^{6c}$, and $R^{6d}$ is independently selected from hydrogen, halogen, —CN, —OR$^{9a}$, optionally substituted $C_1$-$C_4$ alkyl, optionally substituted $C_1$-$C_4$ fluoroalkyl, optionally substituted $C_2$-$C_6$ alkenyl, $-NR^{3c}R^{3d}$, $-S(=O)_2O^-$, $-S(=O)_2OR^{9a}$, $-C(=O)O^-$, and $-C(=O)OR^{9a}$;

each $R^{3c}$ and $R^{3d}$ is independently selected from hydrogen, optionally substituted $C_1$-$C_4$ alkyl, —X-optionally substituted $C_1$-$C_4$ alkyl, optionally substituted $C_2$-$C_6$ alkenyl, and optionally substituted aryl;

X is $-C(=O)-$, $-S(=O)-$, or $-S(=O)_2-$;

each $R^{9a}$, $R^{11a}$, $R^{11b}$, and $R^{11c}$ is independently selected from hydrogen, optionally substituted $C_1$-$C_4$ alkyl, and optionally substituted aryl;

n is an integer selected from 0, 1, 2, 3, 4, 5, 6, 7, and 8; and s is an integer selected from 1, 2, 3, 4, and 5;

b) a repeating unit of Formula (VIII):

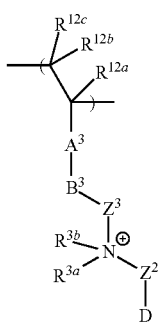

Formula (VIII)

wherein, $A^3$ is $-C(=O)-$, $-S(=O)-$, $-S(=O)_2-$, or $-S(=O)(=NR^{3c})-$;

$B^3$ is $-O-$ or $-NR^{3c}-$;

D is $-S(=O)_2O^-$, $-S(=O)_2OR^{9a}$, $-C(=O)O^-$, or $-C(=O)OR^{9a}$;

$Z^2$ is $-(CR^{6c}R^{6d})_t-$;

$Z^3$ is $-(CR^{6c}R^{6d})_p-$;

each $R^{3a}$ and $R^{3b}$ is independently selected from hydrogen, optionally substituted $C_1$-$C_4$ alkyl, and optionally substituted benzyl;

each $R^{6c}$ and $R^{6d}$ is independently selected from hydrogen, halogen, —CN, $-OR^{9a}$, optionally substituted $C_1$-$C_4$ alkyl, optionally substituted $C_1$-$C_4$ fluoroalkyl, optionally substituted $C_2$-$C_6$ alkenyl, $-NR^{3c}R^{3d}$, $-S(=O)_2O^-$, $-S(=O)_2OR^{9a}$, $-C(=O)O^-$, and $-C(=O)OR^{9a}$;

each $R^{3c}$ and $R^{3d}$ is independently selected from hydrogen, optionally substituted $C_1$-$C_4$ alkyl, —X-optionally substituted $C_1$-$C_4$ alkyl, optionally substituted $C_2$-$C_6$ alkenyl, and optionally substituted aryl;

X is $-C(=O)-$, $-S(=O)-$, or $-S(=O)_2-$;

each $R^{9a}$, $R^{12a}$, $R^{12b}$, and $R^{12c}$ is independently selected from hydrogen, optionally substituted $C_1$-$C_4$ alkyl, and optionally substituted aryl;

t is an integer selected from 1, 2, 3, 4, or 5;

p is an integer selected from 1, 2, 3, 4, or 5; and wherein the repeating unit of Formula (VIII) is charged or zwitterionic; and c) a repeating unit of Formula (IX):

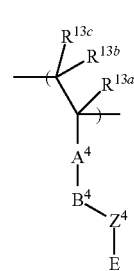

Formula (IX)

$A^4$ is $-C(=O)-$, $-S(=O)-$, $-S(=O)_2-$, or $-S(=O)(=NR^{3c})-$;

$B^4$ is $-O-$ or $-NR^{3c}-$;

$Z^4$ is $-(CR^{6c}R^{6d})_k-$;

E is —CN, $-OR^{9a}$, $-NR^{9a}R^{9b}$, $-NR^{9a}R^{9b}R^{9c+}$ optionally substituted $C_1$-$C_4$ alkyl, optionally substituted $C_1$-$C_6$ fluoroalkyl, $-S(=O)_2O^-$, $-S(=O)_2OR^{9a}$, $-C(=O)O^-$, or $-C(=O)OR^{9a}$;

each $R^{6c}$, and $R^{6d}$ is independently selected from hydrogen, halogen, —CN, $-OR^{9a}$, optionally substituted $C_1$-$C_4$ alkyl, optionally substituted $C_1$-$C_4$ fluoroalkyl, optionally substituted $C_2$-$C_6$ alkenyl, $-NR^{3c}R^{3d}$, $-S(=O)_2O^-$, $-S(=O)_2OR^{9a}$, $-C(=O)O^-$, and $-C(=O)OR^{9a}$;

each $R^{3c}$ and $R^{3d}$ is independently selected from hydrogen, optionally substituted $C_1$-$C_4$ alkyl, —X-optionally substituted $C_1$-$C_4$ alkyl, optionally substituted $C_2$-$C_6$ alkenyl, and optionally substituted aryl;

X is $-C(=O)-$, $-S(=O)-$, or $-S(=O)_2-$;

each $R^{9a}$, $R^{9b}$, $R^{9c}$, $R^{13a}$, $R^{13b}$, and $R^{13c}$ is independently selected from hydrogen, optionally substituted $C_1$-$C_4$ alkyl, and optionally substituted aryl; and k is an integer selected from 1, 2, 3, 4, or 5.

Embodiment II is the copolymer of embodiment I, wherein each $R^{1a}$, $R^{1b}$, $R^{2a}$, and $R^{2b}$ is F.

Embodiment III is the copolymer of embodiment I or II, wherein $A^1$ is $-S(=O)_2-$ and each $A^2$, $A^3$, and $A^4$ is $-C(=O)-$.

Embodiment IV is the copolymer of any one of embodiments I-III, wherein each $B^1$, $B^2$, and $B^3$ is independently $-O-$ or $-NR^{3c}-$.

Embodiment V is the copolymer of any one of embodiments I-IV, wherein each $R^{3c}$ is hydrogen or $-CH_3$.

Embodiment VI is the copolymer of any one of embodiments I-V, wherein D is $-S(=O)_2O-$ or $-C(=O)O^-$.

Embodiment VII is the copolymer of any one of embodiments I-VI, wherein E is $-NR^{9a}R^{9b}R^{9c+}$ or $-S(=O)_2OR^{9a}$.

Embodiment VIII is the copolymer of any one of embodiments I-VII, wherein each $R^{9a}$, $R^{9b}$, and $R^{9c}$ is independently hydrogen or $C_1$-$C_4$ alkyl.

Embodiment IX is the copolymer of any one of embodiments I-VIII, wherein each $R^{3a}$ and $R^{3b}$ is $-CH_3$.

Embodiment X is the copolymer of any one of embodiments I-IX, wherein each $R^{3c}$, $R^{3d}$, $R^{4c}$, $R^{4d}$, $R^{5d}$, $R^{5e}$, $R^{6c}$, and $R^{6d}$ is hydrogen.

Embodiment XI is the copolymer of any one of embodiments I-X, wherein each $R^{11a}$, $R^{12a}$, and $R^{13a}$ is hydrogen or $-CH_3$.

Embodiment XII is the copolymer of any one of embodiments I-XI, wherein each $R^{11b}$, $R^{11c}$, $R^{12b}$, $R^{12c}$, $R^{13b}$, and $R^{13c}$ is hydrogen.

Embodiment XIII is the copolymer of any one of embodiments I-XII, wherein n is 0, 1, or 2.

Embodiment XIV is the copolymer of any one of embodiments I-XIII, wherein each s, t, p, and k is independently 1, 2 or 3.

Embodiment XV is a medical device coated with a compound of any one of embodiments I-XIV.

Embodiment XVI is a biofouling-resistant medical device, wherein a surface of the medical device is coated with a compound of any one of embodiments I-XIV.

Embodiment XVII is the biofouling-resistant medical device of embodiment XVI, wherein the medical device comprises an implant, an IV, a prosthesis, suturing material, valve, stent, catheter, rod, shunt, scope, a contact lens, tubing, wiring, electrode, clip, fastener, syringe, container, or a combination thereof.

Embodiment XVIII is the biofouling-resistant medical device of embodiment XVI or XVII, wherein the medical device is a catheter.

Embodiment XIX is the biofouling-resistant medical device of any one of embodiments XVI-XVIII, wherein the biofouling is produced by a bacterium, a virus, and/or a fungus.

Embodiment XX is a method of making a biofouling-resistant medical device, comprising:
a) contacting a surface of a device with a mixture comprising a charged or zwitterion copolymer; and
b) treating the surface of the device of step a) with a heat source for a time sufficient to undergo thermografting of the copolymer onto the surface of the device, thereby making the biofouling-resistant device;
wherein the charged or zwitterion copolymer comprises a phenyl azide-based copolymer; and wherein the charged or zwitterion copolymer having a number-average molecular weight of between about 10,000 and about 250,000.

Embodiment XXI is the method of any one of embodiments XX, wherein the time sufficient to undergo thermografting is 1 minute, 2 minutes, 3 minutes, 4 minutes, 5 minutes, 6 minutes, 7 minutes, 8 minutes, 9 minutes, 10 minutes, 15 minutes, 20 minutes, 25 minutes, 30 minutes, 45 minutes, 1 hour, 1.5 hours, 2 hours, 3 hours, 4 hours, 5 hours, 6 hours, 9 hours, 12 hours, 18 hours, or 24 hours.

Embodiment XXII is the method of embodiment XX or XXI, wherein the heat source provides a grafting temperature between 60° C. and 80° C., between 80° C. and 100° C., between 100° C. and 120° C., between 120° C. and 140° C., between 140° C. and 160° C., between 160° C. and 180° C., between 180° C. and 200° C., between 200° C. and 220° C., or between 220° C. and 240° C.

Embodiment XXIII is the method of any one of embodiments XX-XXII, wherein the solution or suspension of step a) is an aqueous solution or suspension.

Embodiment XXIV is the method of any one of embodiments XX-XXIII, wherein thermografting of step b) is not affected by the presence of oxygen.

Embodiment XXV is the method of any one of embodiments XX-XXIV, wherein the charged or zwitterion copolymer is a copolymer of any one of embodiments 1-14.

Embodiment XXVI is the method of any one of embodiments XX-XXV, wherein the solution or suspension comprising a charged or zwitterion copolymer has a concentration of the charged or zwitterion copolymer in the solution or suspension between 1 mg/mL and 30 mg/mL.

Embodiment XXVII is the method of any one of embodiments XX-XXV, wherein the concentration of the charged or zwitterion copolymer in the solution or suspension is between 1 mg/mL and 25 mg/mL, between 1 mg/mL and 20 mg/mL, between 1 mg/mL and 15 mg/mL, between 1 mg/mL and 10 mg/mL, between 1 mg/mL and 5 mg/mL, between 5 mg/mL and 30 mg/mL, between 5 mg/mL and 25 mg/mL, between 5 mg/mL and 20 mg/mL, between 5 mg/mL and 15 mg/mL, between 5 mg/mL and 10 mg/mL, between 10 mg/mL and 30 mg/mL, between 10 mg/mL and 25 mg/mL, between 10 mg/mL and 20 mg/mL, between 10 mg/mL and 15 mg/mL, between 15 mg/mL and 30 mg/mL, between 15 mg/mL and 25 mg/mL, between 15 mg/mL and 20 mg/mL, between 20 mg/mL and 30 mg/mL, or between 20 mg/mL and 25 mg/mL.

Embodiment XXVIII is the method of any one of embodiments XX-XXVII, wherein the device comprises a carbon-based device or a silicon-based device.

Embodiment XXIX is the method of any one of embodiments XX-XXVIII, wherein the device comprises a silicon-based device, wherein the silicon-based device comprises a silicon-based polymer moiety.

Embodiment XXX is the method of any one of embodiments XX-XXIX, wherein the biofouling is produced by a bacterium, a virus, and/or a fungus.

The invention claimed is:

1. A copolymer comprising:
a) a repeating unit of Formula (VII):

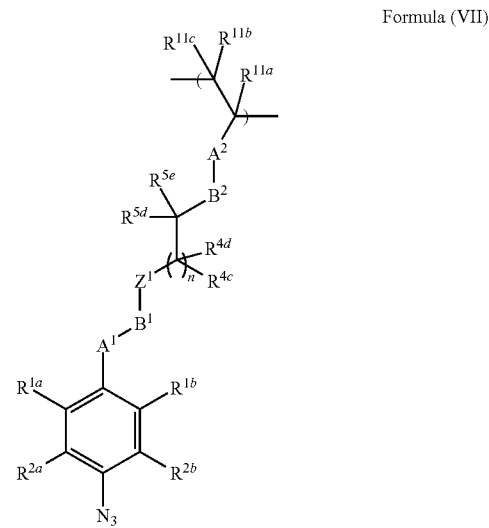

Formula (VII)

wherein
each $R^{1a}$ and $R^{1b}$ is independently selected from hydrogen and halogen;
each $R^{2a}$ and $R^{2b}$ is independently selected from halogen, —CN, and optionally substituted $C_1$-$C_6$ fluoroalkyl;
each $A^1$ and $A^2$ is independently selected from —C(=O)—, —S(=O)—, —S(=O)$_2$—, and —S(=O)(=NR$^{3c}$)—;
each $B^1$ and $B^2$ is independently selected from —O— and —NR$^{3c}$—;
$Z^1$ is —(CR$^{6c}$R$^{6d}$)$_s$—;
each $R^{4c}$, $R^{4d}$, $R^{5d}$, $R^{5e}$, $R^{6c}$, and $R^{6d}$ is independently selected from hydrogen, halogen, —CN, —OR$^{9a}$, optionally substituted $C_1$-$C_4$ alkyl, optionally substituted $C_1$-$C_4$ fluoroalkyl, optionally substituted $C_2$-$C_6$ alkenyl, —NR$^{3c}$R$^{3d}$, —S(=O)$_2$O$^-$, —S(=O)$_2$OR$^{9a}$, —C(=O)O$^-$, and —C(=O)OR$^{9a}$;
each $R^{3c}$ and $R^{3d}$ is independently selected from hydrogen, optionally substituted $C_1$-$C_4$ alkyl, —X-optionally substituted $C_1$-$C_4$ alkyl, optionally substituted $C_2$-$C_6$ alkenyl, and optionally substituted aryl;

X is —C(=O)—, —S(=O)—, or —S(=O)$_2$—;

each $R^{9a}$, $R^{11a}$, $R^{11b}$, and $R^{11c}$ is independently selected from hydrogen, optionally substituted $C_1$-$C_4$ alkyl, and optionally substituted aryl;

n is an integer selected from 0, 1, 2, 3, 4, 5, 6, 7, and 8; and s is an integer selected from 1, 2, 3, 4, and 5;

b) a repeating unit of Formula (VIII):

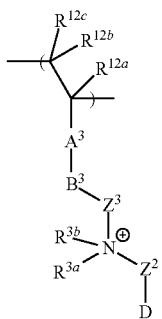

Formula (VIII)

wherein, $A^3$ is —C(=O)—, —S(=O)—, —S(=O)$_2$—, or —S(=O)(=NR$^{3c}$)—;

$B^3$ is —O— or —NR$^{3c}$—;

D is —S(=O)$_2$O$^-$, —S(=O)$_2$OR$^{9a}$, —C(=O)O$^-$, or —C(=O)OR$^{9a}$;

$Z^2$ is —(CR$^{6c}$R$^{6d}$)$_t$—;

$Z^3$ is —(CR$^{6c}$R$^{6d}$)$_p$—;

each $R^{3a}$ and $R^{3b}$ is independently selected from hydrogen, optionally substituted $C_1$-$C_4$ alkyl, and optionally substituted benzyl;

each $R^{6c}$ and $R^{6d}$ is independently selected from hydrogen, halogen, —CN, —OR$^{9a}$, optionally substituted $C_1$-$C_4$ alkyl, optionally substituted $C_1$-$C_4$ fluoroalkyl, optionally substituted $C_2$-$C_6$ alkenyl, —NR$^{3c}$R$^{3d}$, —S(=O)$_2$O$^-$, —S(=O)$_2$OR$^{9a}$, —C(=O)O$^-$, and —C(=O)OR$^{9a}$;

each $R^{3c}$ and $R^{3d}$ is independently selected from hydrogen, optionally substituted $C_1$-$C_4$ alkyl, —X-optionally substituted $C_1$-$C_4$ alkyl, optionally substituted $C_2$-$C_6$ alkenyl, and optionally substituted aryl;

X is —C(=O)—, —S(=O)—, or —S(=O)$_2$—;

each $R^{9a}$, $R^{12a}$, $R^{12b}$, and $R^{12c}$ is independently selected from hydrogen, optionally substituted $C_1$-$C_4$ alkyl, and optionally substituted aryl;

t is an integer selected from 1, 2, 3, 4, or 5;

p is an integer selected from 1, 2, 3, 4, or 5; and wherein the repeating unit of Formula (VIII) is charged or zwitterionic; and c) a repeating unit of Formula (IX):

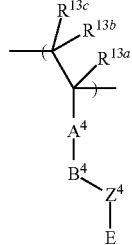

Formula (IX)

$A^4$ is —C(=O)—, —S(=O)—, —S(=O)$_2$—, or —S(=O)(=NR$^{3c}$)—;

$B^4$ is —O— or —NR$^{3c}$—;

$Z^4$ is —(CR$^{6c}$R$^{6d}$)$_k$—;

E is —CN, —OR$^{9a}$, —NR$^{9a}$R$^{9b}$, —NR$^{9a}$R$^{9b}$R$^{9c+}$, optionally substituted $C_1$-$C_4$ alkyl, optionally substituted $C_1$-$C_6$ fluoroalkyl, —S(=O)$_2$O$^-$, —S(=O)$_2$OR$^{9a}$, —C(=O)O$^-$, or —C(=O)OR$^{9a}$;

each $R^{6c}$, and $R^{6d}$ is independently selected from hydrogen, halogen, —CN, —OR$^{9a}$, optionally substituted $C_1$-$C_4$ alkyl, optionally substituted $C_1$-$C_4$ fluoroalkyl, optionally substituted $C_2$-$C_6$ alkenyl, —NR$^{3c}$R$^{3d}$, —S(=O)$_2$O$^-$, —S(=O)$_2$OR$^{9a}$, —C(=O)O$^-$, and —C(=O)OR$^{9a}$;

each $R^{3c}$ and $R^{3d}$ is independently selected from hydrogen, optionally substituted $C_1$-$C_4$ alkyl, —X-optionally substituted $C_1$-$C_4$ alkyl, optionally substituted $C_2$-$C_6$ alkenyl, and optionally substituted aryl;

X is —C(=O)—, —S(=O)—, or —S(=O)$_2$—;

each $R^{9a}$, $R^{9b}$, $R^{9c}$, $R^{13a}$, $R^{13b}$, and $R^{13c}$ is independently selected from hydrogen, optionally substituted $C_1$-$C_4$ alkyl, and optionally substituted aryl; and k is an integer selected from 1, 2, 3, 4, or 5.

2. The copolymer of claim 1, wherein each $R^{1a}$, $R^{1b}$, $R^{2a}$, and $R^{2b}$ is F.

3. The copolymer of claim 1, wherein $A^1$ is —S(=O)$_2$— and each $A^2$, $A^3$, and $A^4$ is —C(=O)—.

4. The copolymer of claim 1, wherein each $B^1$, $B^2$, and $B^3$ is independently —O— or —NR$^{3c}$—.

5. The copolymer of claim 4, wherein each $R^{3c}$ is hydrogen or —CH$_3$.

6. The copolymer of claim 1, wherein D is —S(=O)$_2$O$^-$ or —C(=O)O$^-$.

7. The copolymer of claim 1, wherein E is —NR$^{9a}$R$^{9b}$R$^{9c+}$ or —S(=O)$_2$OR$^{9a}$.

8. The copolymer of claim 7, wherein each $R^{9a}$, $R^{9b}$, and $R^{9c}$ is independently hydrogen or $C_1$-$C_4$ alkyl.

9. The copolymer of claim 1, wherein each $R^{3a}$ and $R^{3b}$ is —CH$_3$.

10. The copolymer of claim 1, wherein each $R^{3c}$, $R^{3d}$, $R^{4c}$, $R^{4d}$, $R^{5d}$, $R^{5e}$, $R^{6c}$, and $R^{6d}$ is hydrogen.

11. The copolymer of claim 1, wherein each $R^{11a}$, $R^{12a}$, and $R^{13a}$ is hydrogen or —CH$_3$.

12. The copolymer of claim 1, wherein each $R^{11b}$, $R^{11c}$, $R^{12b}$, $R^{12c}$, $R^{13b}$, and $R^{13c}$ is hydrogen.

13. The copolymer of claim 1, wherein n is 0, 1, or 2.

14. The copolymer of claim 1, wherein each s, t, p, and k is independently 1, 2 or 3.

* * * * *